US012662490B2

(12) United States Patent
Kroll et al.

(10) Patent No.: US 12,662,490 B2
(45) Date of Patent: Jun. 23, 2026

(54) HETEROCYCLIC COMPOUNDS

(71) Applicant: Hoffmann-La Roche Inc., Little Falls, NJ (US)

(72) Inventors: Carsten Kroll, Basel (CH); Flore Reggiani, Ranspach le Haut (FR); Miroslav Kosar, Urdorf (CH); Maurice Biedermann, Zurich (CH); Bernd Kuhn, Reinach (CH); Benoit Hornsperger, Altkirch (FR); Uwe Grether, Efringen-Kirchen (DE); Fionn O'Hara, Basel (CH); Hans Richter, Grenzach-Wyhlen (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 1172 days.

(21) Appl. No.: 17/569,749

(22) Filed: Jan. 6, 2022

(65) Prior Publication Data

US 2022/0242876 A1 Aug. 4, 2022

Related U.S. Application Data

(63) Continuation of application No. PCT/EP2020/069074, filed on Jul. 7, 2020.

(30) Foreign Application Priority Data

Jul. 9, 2019 (EP) .................................... 19185088

(51) Int. Cl.
*C07D 498/04* (2006.01)
*C07D 513/04* (2006.01)
*C07D 519/00* (2006.01)

(52) U.S. Cl.
CPC ......... *C07D 498/04* (2013.01); *C07D 513/04* (2013.01); *C07D 519/00* (2013.01)

(58) Field of Classification Search
CPC ... C07D 498/04; C07D 513/04; C07D 519/00
See application file for complete search history.

(56) References Cited

U.S. PATENT DOCUMENTS 4,391,978 A 7/1983 Imhof et al.
4,454,130 A 6/1984 Tominaga et al.
4,632,925 A 12/1986 Mullin, Jr. et al.
4,956,359 A 9/1990 Taylor, Jr. et al.
6,673,908 B1 1/2004 Stanton, Jr.
7,488,737 B2 2/2009 Xie et al.
8,614,209 B2 12/2013 Webster et al.
10,106,556 B2 10/2018 Ikeda et al.
10,610,520 B2 4/2020 Ikeda et al.
11,390,610 B2 7/2022 Benz et al.
11,420,961 B2 8/2022 Benz et al.
11,608,347 B2 3/2023 Petersen et al.
11,802,133 B2 10/2023 Bell et al.
11,814,375 B2 11/2023 Benz et al.
11,981,661 B2 5/2024 Benz et al.
2015/0018335 A1 1/2015 Cisar et al.
2020/0255439 A1 8/2020 Kamata et al.
2020/0299277 A1 9/2020 Benz et al.
2020/0308158 A1 10/2020 Bell et al.
2020/0308190 A1 10/2020 Bell et al.
2020/0392125 A1 12/2020 Benz et al.
2021/0024546 A1 1/2021 Petersen et al.
2021/0053973 A1 2/2021 Ali et al.
2021/0094943 A1 4/2021 Benz et al.
2021/0094971 A1 4/2021 Grether et al.
2021/0094972 A1 4/2021 Benz et al.
2021/0094973 A1 4/2021 Gobbi et al.
2021/0107920 A1 4/2021 Bell et al.
2021/0107921 A1 4/2021 Benz et al.
2021/0277020 A1 9/2021 Anselm et al.
2021/0387999 A1 12/2021 Kuhn et al.
2022/0098176 A1 3/2022 Benz et al.
2022/0106328 A1 4/2022 Benz et al.
2022/0135591 A1 5/2022 Benz et al.
2022/0202963 A1 6/2022 Collin et al.
2022/0213093 A1 7/2022 Benz et al.

(Continued)

FOREIGN PATENT DOCUMENTS

EP 3279191 A1 2/2018
EP 3312177 A2 4/2018

(Continued)

OTHER PUBLICATIONS

Alpar, A., et al., "Endocannabinoids modulate cortical development by configuring Slit2/Robo 1 signaling" Nat Commun 5(4421):1-13 (Jul. 17, 2014).
Ashton, K., et al., "Design and synthesis of novel amide AKTI inhibitors with selectivity over CDK2" Bioorg Med Chem Lett 21(18):5191-5196 (Sep. 15, 2011).
Aurora Fine Chemicals, Other Database, 1907579-56-9, (C26 H25 N3 O3), p. 1Creation Date May 10, 2016.
Barney, C., et al., "A convenient synthesis of hindered amines and α-trifluoromethylamines from ketones" Tetrahedron Lett 31(39):5547-5550 ( 1990).

(Continued)

*Primary Examiner* — Adam C Milligan
*Assistant Examiner* — William Y Lee
(74) *Attorney, Agent, or Firm* — Zong-Qiang Bill Tian

(57) ABSTRACT

The invention provides new heterocyclic compounds having the general formula (I)

(I)

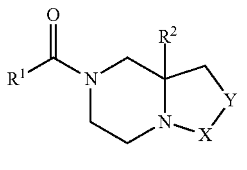

wherein $R^1$, $R^2$, X, and Y are as defined herein, compositions including the compounds, processes of manufacturing the compounds and methods of using the compounds.

28 Claims, No Drawings

(56) References Cited

U.S. PATENT DOCUMENTS

| | | | |
|---|---|---|---|
| 2022/0220373 | A1 | 7/2022 | Benz et al. |
| 2022/0267349 | A1 | 8/2022 | Benz et al. |
| 2022/0275005 | A1 | 9/2022 | Grether et al. |
| 2023/0117324 | A1 | 4/2023 | Bell et al. |
| 2023/0183224 | A1 | 6/2023 | Bell et al. |
| 2023/0203056 | A1 | 6/2023 | Benz et al. |
| 2024/0150373 | A1 | 5/2024 | Bell et al. |
| 2024/0199587 | A1 | 6/2024 | Amoussa et al. |

FOREIGN PATENT DOCUMENTS

| | | | |
|---|---|---|---|
| JP | 2010-520217 | A | 6/2010 |
| JP | 7269943 | B2 | 4/2023 |
| WO | 01/07043 | A1 | 2/2001 |
| WO | 2004/000832 | A1 | 12/2003 |
| WO | 2004/096763 | A1 | 11/2004 |
| WO | 2005/066187 | A1 | 7/2005 |
| WO | 2006/000914 | A1 | 1/2006 |
| WO | 2006/001894 | A1 | 1/2006 |
| WO | 2006/051410 | A1 | 5/2006 |
| WO | 2007/002057 | A1 | 1/2007 |
| WO | 2007/098418 | A1 | 8/2007 |
| WO | 2007/117557 | A2 | 10/2007 |
| WO | 2008/109336 | A1 | 9/2008 |
| WO | 2009/058347 | A1 | 5/2009 |
| WO | 2009/074789 | A1 | 6/2009 |
| WO | 2009/112845 | A1 | 9/2009 |
| WO | 2010/106333 | A1 | 9/2010 |
| WO | 2011/059118 | A1 | 5/2011 |
| WO | 2012/155199 | A1 | 11/2012 |
| WO | 2013/028474 | A1 | 2/2013 |
| WO | 2013/059118 | A1 | 4/2013 |
| WO | 2013/103973 | A1 | 7/2013 |
| WO | 2013/179024 | A1 | 12/2013 |
| WO | 2014/099633 | A2 | 6/2014 |
| WO | 2015/179559 | A2 | 11/2015 |
| WO | 2016/014975 | A2 | 1/2016 |
| WO | 2016/109501 | A1 | 7/2016 |
| WO | 2016/180536 | A1 | 11/2016 |
| WO | 2016/185279 | A1 | 11/2016 |
| WO | 2016/205590 | A1 | 12/2016 |
| WO | 2017/087854 | A1 | 5/2017 |
| WO | 2017/087858 | A1 | 5/2017 |
| WO | 2017/087863 | A1 | 5/2017 |
| WO | 2017/171100 | A1 | 10/2017 |
| WO | 2018/134698 | A1 | 7/2018 |
| WO | 2018/217809 | A1 | 11/2018 |
| WO | 2019/065791 | A1 | 4/2019 |
| WO | 2019/072785 | A1 | 4/2019 |
| WO | 2019/105915 | A1 | 6/2019 |
| WO | 2019/115660 | A1 | 6/2019 |
| WO | 2019/134985 | A1 | 7/2019 |
| WO | 2019/180185 | | 9/2019 |
| WO | 2020/035424 | A1 | 2/2020 |
| WO | 2020/035425 | A1 | 2/2020 |
| WO | 2020/104494 | A1 | 5/2020 |
| WO | 2020/207941 | A1 | 10/2020 |
| WO | 2021/005034 | A1 | 1/2021 |
| WO | 2021/048036 | A1 | 3/2021 |
| WO | 2021/048242 | A1 | 3/2021 |
| WO | 2021/058416 | A1 | 4/2021 |
| WO | 2021/058444 | A1 | 4/2021 |
| WO | 2021/058445 | A1 | 4/2021 |
| WO | 2022/043284 | A1 | 3/2022 |
| WO | 2022/049134 | A1 | 3/2022 |

OTHER PUBLICATIONS

Bernal-Chico, A., et al., "Blockade of Monoacylglycerol Lipase Inhibits Oligodendrocyte Excitotoxicity and Prevents Demyelination In Vivo" GLIA 63(1):163-176 (Jan. 1, 2015).

Chanda, P.K., et al., "Monoacylglycerol Lipase Activity Is a Critical Modulator of the Tone and Integrity of the Endocannabinoid System" Mol Pharmacol 78(6):996-1003 (Dec. 1, 2010).

Chang, J. et al., "Highly Selective Inhibitors of Monoacylglycerol Lipase Bearing a Reactive Group that is Bio-isosteric with Endocannabinoid Substrates" Chem Biol 19(5):579-588 (May 1, 2012).

Dugar, S. et al., "A Concise and Efficient Synthesis of Substituted Morpholines" Synthesis 47(5):712-720 (Mar. 1, 2015).

Duncan, M., et al., "Review article: endocannabinoids and their receptors in the enteric nervous system" Aliment Pharmacol Ther 22(8):667-683 (Oct. 15, 2005).

Enamine, CAS Registry Database, 931085-56-2, (Registry No. 931085-56-2), p. 1; Submission Date Apr. 20, 2007.

Evano, G., et al., "Copper-Mediated Coupling Reactions and Their Applications in Natural Products and Designed Biomolecules Synthesis" Chem Rev 108(8):3054-3131 (Aug. 13, 2008).

Feliu, A., et al., "2-Arachidonoylglycerol Reduces Proteoglycans and Enhances Remyelination in a Progressive Model of Demyelination" J Neurosci 37(35):8385-8398 (Aug. 30, 2017).

Fray, M., et al., "Second generation N-(1,2-diphenylethyl)piperazines as dual serotonin and noradrenaline reuptake inhibitors: improving metabolic stability and reducing ion channel activity" Bioorg Med Chem Lett 20(12):3788-3792 (Jun. 15, 2010).

Fray, M., et al., "Structure-activity relationships of N-substituted piperazine amine reuptake inhibitors" Bioorg Med Chem Lett 16(16):4349-4353 (Aug. 15, 2006).

Gavryushin, A., et al., "Efficient Cross-Coupling of Functionalized Arylzinc Halides Catalyzed by a Nickel Chloride-Diethyl Phosphite System" Org Lett 7(22):4871-4874 (Oct. 7, 2005).

Granchi, C., et al., "A patent review of monoacylglycerol lipase (MAGL) inhibitors" Expert Opin Ther Pat 27(12):1341-1351 (Dec. 1, 2017).

Grill, M., et al., "Members of the endocannabinoid system are distinctly regulated in inflammatory bowel disease and colorectal cancer" Sci Rep 9(2358):1-13 (Feb. 20, 2019).

Haas, D., et al., "Recent Developments in Negishi Cross-Coupling Reactions" ACS Catal 6(3):1540-1552 (Feb. 3, 2016).

He, S., et al., "High-Affinity Small-Molecule Inhibitors of the Menin-Mixed Lineage Leukemia (MLL) Interaction Closely Mimic a Natural Protein-Protein Interaction" J Med Chem 57(4):1543-1556 (Feb. 27, 2014).

Heravi, M., et al., "Buchwald-Hartwig reaction: An overview" J Organometallic Chem 861:17-104 (Apr. 15, 2018).

Hutchings, K., et al., "Synthesis and antibacterial activity of the C-7 side chain of 3-aminoquinazolinediones" Bioorg Med Chem Lett 18(18):5087-5090 (Sep. 15, 2008).

Iannotti, F. A., et al., "Endocannabinoids and endocannabinoid-related mediators: Targets, metabolism and role in neurological disorders" Prog Lipid Res 62:107-128 (Apr. 1, 2016).

Ignatowska-Jankowska, B., et al., "Selective Monoacylglycerol Lipase Inhibitors: Antinociceptive versus Cannabimimetic Effects in Mice" J Pharmacol Exp Ther 353(2):424-432 (May 1, 2015).

"International Preliminary Report on Patentability—PCT/EP2019/071520" (Report Issuance Date: Feb. 16, 2021, Chapter I),:pp. 1-8 (Feb. 25, 2021).

"International Preliminary Report on Patentability—PCT/EP2019/081870" (Report Issuance Date: May 25, 2021; Chapter I),:pp. 1-8 (Jun. 3, 2021).

"International Preliminary Report on Patentability—PCT/EP2019/057174" (Report Issuance Date: Sep. 22, 2020—Chapter I),:pp. 1-9 (Oct. 1, 2020).

"International Preliminary Report on Patentability—PCT/EP2019/071522" (Report Issuance Date: Feb. 16, 2021, Chapter I),:pp. 1-9 (Feb. 25, 2021).

"International Preliminary Report on Patentability—PCT/EP2019/050198" (Report Issuance Date: Jul. 14, 2020; Chapter I),:pp. 1-10 (Jul. 23, 2020).

"International Preliminary Report on Patentability—PCT/EP2020/068320" (Report Issuance Date: Aug. 4, 2021; Chapter II),:pp. 1-34 (Aug. 4, 2021).

"International Preliminary Report on Patentability—PCT/EP2020/069074" (Report Issuance Date: Jan. 11, 2022; Chapter I),:pp. 1-8 (Jan. 20, 2022).

(56) References Cited

OTHER PUBLICATIONS

"International Preliminary Report on Patentability—PCT/EP2020/059709" (Report Issuance Date: Sep. 28, 2021; Chapter I),:pp. 1-10 (Oct. 21, 2021).
"International Search Report—PCT/EP2019/057174" (w/Written Opinion),:pp. 1-14 (Jul. 3, 2019).
"International Search Report—PCT/EP2019/050198" (w/Written Opinion),:pp. 1-18 (Mar. 1, 2019).
"International Search Report—PCT/EP2019/071520" (w/Written Opinion),:pp. 1-14 (Sep. 17, 2019).
"International Search Report—PCT/EP2019/071522" (w/Written Opinion),:pp. 1-15 (Sep. 17, 2019).
"International Search Report—PCT/EP2019/081870" (w/Written Opinion),:pp. 1-12 (Jan. 14, 2020).
"International Search Report—PCT/EP2020/059709" (w/Written Opinion),:pp. 1-17 (Jun. 8, 2020).
"International Search Report—PCT/EP2020/068320" (w/Written Opinion),:pp. 1-16 (Aug. 13, 2020).
"International Search Report—PCT/EP2020/069074" (w/Written Opinion),:pp. 1-12 (Sep. 16, 2020).
"International Search Report—PCT/EP2020/074897" (w/Written Opinion),:pp. 1-15 (Nov. 18, 2020).
"International Search Report—PCT/EP2020/075260" (w/Written Opinion),:pp. 1-14 (Nov. 18, 2020).
"International Search Report—PCT/EP2020/076228" (w/Written Opinion),:pp. 1-14 (Nov. 12, 2020).
"International Search Report—PCT/EP2020/076346" (w/Written Opinion),:pp. 1-16 (Nov. 13, 2020).
"International Search Report—PCT/EP2020/076347" (w/Written Opinion),:pp. 1-16 (Nov. 30, 2020).
"International Search Report—PCT/EP2021/074150" (w/Written Opinion),:pp. 1-13 (Dec. 8, 2021).
Ishichi, Y., et al., "Novel triple reuptake inhibitors with low risk of CAD associated liabilities: design, synthesis and biological activities of 4-[(1S)-1-(3,4-dichlorophenyl)-2-methoxyethyl]piperidine and related compounds" Bioorg Med Chem 21(15):4600-4613 (Aug. 1, 2013).
Keenan, M., et al., "Design, structure-activity relationship and in vivo efficacy of piperazine analogues of fenarimol as inhibitors of Trypanosoma cruzi" Bioorg Med Chem 21(7):1756-1763 (Apr. 1, 2013).
Kitbunnadaj, R., et al., "Synthesis and structure-activity relationships of conformationally constrained histamine H(3) receptor agonists" J Med Chem 46(25):5445-5457 (Dec. 4, 2003).
Korhonen, J., et al., "Piperazine and piperidine carboxamides and carbamates as inhibitors of fatty acid amide hydrolase (FAAH) and monoacylglycerol lipase (MAGL)" Bioorg Med Chem 22(23):6694-6705 (Dec. 1, 2014).
Liu, F., et al., "Structure-Based Optimization of Pyridoxal 5'-Phosphate-Dependent Transaminase Enzyme (BioA) Inhibitors that Target Biotin Biosynthesis in *Mycobacterium tuberculosis*" J Med Chem 60(13):5507-5520 (Jul. 13, 2017).
Liu, Y. et al., "Discovery of 4-benzoylpiperidine and 3-(piperidin-4-yl)benzo[d]isoxazole derivatives as potential and selective GlyT1 inhibitors" RSC Adv 5(51):40964-40977 (Apr. 30, 2015).
Lleo, A., et al., "Molecular targets of non-steroidal anti-inflammatory drugs in neurodegenerative diseases" Cell Mol Life Sci 64(11):1403-1418 (Apr. 20, 2007).
Long, J.Z., et al., "Selective blockade of 2-arachidonoylglycerol hydrolysis produces cannabinoid behavioral effects" Nat Chem Biol 5(1):37-44 (Jan. 1, 2009).
Marquez, L., et al., "Ulcerative Colitis Induces Changes on the Expression of the Endocannabinoid System in the Human Colonic Tissue" Plos One 4(9):e6893 (1-13) (Sep. 4, 2009).
Mcallister, L., et al., "Discovery of Trifluoromethyl Glycol Carbamates as Potent and Selective Covalent Monoacylglycerol Lipase (MAGL) Inhibitors for Treatment of Neuroinflammation" J Med Chem 61(7):3008-3026 (Apr. 12, 2018).
Moir, E., et al., "Design, synthesis, and structure-activity relationship study of bicyclic piperazine analogs of indole-3-carboxamides as novel cannabinoid CB1 receptor agonists" Bioorg Med Chem Lett 20(24):7327-7330 (Dec. 15, 2010).
Muccioli, G., et al., "CAY10499, a Novel Monoglyceride Lipase Inhibitor Evidenced by an Expeditious MGL Assay" Chem Bio Chem 9(16):2704-2710 (Nov. 3, 2008).
Mul Vihill, M., et al., "Therapeutic Potential of Monoacylglycerol Lipase Inhibitors" Life Sci 92(8-9):492-497 (Nov. 8, 2013).
Negishi, E., "Palladium- or Nickel-Catalyzed Cross Coupling. A New Selective Method for Carbon-Carbon Bond Formation" ACC Chem Res 15(11):340-348 (Nov. 1, 1982).
Nomura, D.K., et al., "Endocannabinoid Hydrolysis Generates Brain Prostaglandins That Promote Neuroinflammation" Science 334(6057):809-813 (Nov. 11, 2011).
Nomura, D.K., et al., "Monoacylglycerol Lipase Exerts Dual Control over Endocannabinoid and Fatty Acid Pathways to Support Prostate Cancer" Chem Biol 18(7):846-856 (Jul. 29, 2011).
Nomura, D.K., et al., "Monoacylglycerol Lipase Regulates a Fatty Acid Network that Promotes Cancer Pathogenesis" Cell 140(1):49-61 (Jan. 8, 2010).
Patel, J. et al., "Loratadine analogues as MAGL inhibitors" Bioorg Med Chem Lett 25(7):1436-1442 (Feb. 24, 2015).
Perisetti, A., et al., "Role of cannabis in inflammatory bowel diseases" Ann Gastroenterol 33(2):134-144 (Feb. 12, 2020).
Qin, H., et al., "The role of monoacylglycerol lipase (MAGL) in the cancer progress" Cell Biochem Biophys 70:33-36 (Mar. 16, 2014).
Rafinski, Z. et al., "Enantioselective Synthesis of Chromanones Bearing Quaternary Substituted Stereocenters Catalyzed by (1R)-Camphor-Derived N-Heterocyclic Carbenes" J Org Chem 80(15):7468-7476 (Aug. 7, 2015).
Saleh, M.A., et al., "The Synthesis of 2,7 substituted Octahydro-2H-Pyrido[1,2-a] Pyrazines, Analogues of Quinolizidine and Piperazine Drugs" Tetrahedron 50(6):1811-1820 (Jan. 1, 1994).
Scalvini, L., et al., "Monoglyceride lipase: Structure and inhibitors" Chem Phys Lipids 197:13-24 (Jul. 26, 2015).
Senter, T., et al., "Progress towards small molecule menin-mixed lineage leukemia (MLL) interaction inhibitors with in vivo utility" Bioorg Med Chem Lett 25(13):2720-2725 (Jul. 1, 2015).
Surry, D., et al., "Biaryl Phosphane Ligands in Palladium-Catalyzed Amination" Angew Chem Int Ed Engl 47(34):6338-6361 (Aug. 11, 2008).
Ukrorgsyntez, Ltd., CAS Registry Database, 1941372-36-6, (Stereosearch-C20 H27 N3 O3), p. 1; Creation Date Jun. 29, 2016.
USPTO, et al., "U.S. Appl. No. 17/692,632, filed Mar. 11, 2022".
USPTO, U.S. Appl. No. 16/899,928, filed Jun. 12, 2020.
USPTO, "U.S. Appl. No. 17/497,633, filed Oct. 8, 2021".
USPTO, "U.S. Appl. No. 17/552,792, filed Dec. 16, 2021".
USPTO, "U.S. Appl. No. 17/700,987, filed Mar. 22, 2022".
Venkatesh, R., et al., "Novel benzothiazine-piperazine derivatives by peptide-coupling as potential anti-proliferative agents" Bioorg Med Chem Lett 27(2):354-359 (Jan. 15, 2017).
Viader, A., et al., "Metabolic Interplay between Astrocytes and Neurons Regulates Endocannabinoid Action" Cell Rep 12(5):798-808 (Aug. 4, 2015).
Walsh, D., et al., "Synthesis and antiallergy activity of 4-(diarylhydroxymethyl)-1-[3-(aryloxy)propyl]piperidines and structurally related compounds" J Med Chem 32(1):105-118 (Jan. 1, 1989).
Wang, J., et al., "Effect of monoacylglycerol lipase inhibition on intestinal permeability in chronic stress model" Biochem Biophys Res Commun 525(4):962-967 (May 14, 2020).
Wright, K., et al., "Differential expression of cannabinoid receptors in the human colon: cannabinoids promote epithelial wound healing" Gastroenterology 129(2):437-453 (Aug. 1, 2005).
Wu, W., et al., "Synthesis and structure-activity relationships of piperidine-based melanin-concentrating hormone receptor 1 antagonists" Bioorg Med Chem Lett 16(14):3668-3673 (Jul. 15, 2006).
Yin, J., et al., "ARS2/MAGL signaling in glioblastoma stem cells promotes self-renewal and M2-like polarization of tumor-associated macrophages" Nat Commun 11(1):2978(1-15) (Jun. 12, 2020).
Zhang, P., et al., "Silyl Radical Activation of Alkyl Halides in Metallaphotoredox Catalysis: A Unique Pathway for Cross-Electrophile Coupling" J Am Chem Soc 138(26):8084-8087 (Jul. 6, 2016).

(56) References Cited

OTHER PUBLICATIONS

Zhang, X., et al., "Direct Aldehyde C—H Arylation and Alkylation via the Combination of Nickel, Hydrogen Atom Transfer, and Photoredox Catalysis" J Am Chem Soc 139(33):11353-11356 (Aug. 23, 2017).
Zhong, P., et al., "Monoacylglycerol Lipase Inhibition Blocks Chronic Stress-Induced Depressive-Like Behaviors via Activation of mTOR Signaling" Neuropsychopharmacology 39(7):1763-1776 (Feb. 19, 2014).
Arata, Y., et al., "Studies on 1-Azabicyclo Compounds. XIV. Synthesis of 1-Methyldecahydro-1, 4-diazecin-5-one from Octahydropyrido [1, 2-a] pyrazine Derivatives" Chem & Pharma Bull—JP 21(6):1248-1253 (Jun. 25, 1973).
Belikov, V.G. Pharmaceutical Chemistry—Tutorial "Part I: General Pharmaceutical Chemistry" (Eng. Transl.), Fourth, Revised edition, Moscow-RU:MEDPress-Inform,:27-29 ( 2007).
Brethous, L., et al., "Synthesis and nicotinic receptor activity of chemical space analogues of N-(3R)-1-azabicyclo[2.2.2]oct-3-yl-4-chlorobenzamide (PNU-282,987) and 1,4-diazabicyclo[3.2.2]nonane-4-carboxylic acid 4-bromophenyl ester (SSR180711)" ACS J Med Chem 55(10):4605-4618 (May 24, 2012).
Dyson, G., et al. Chemistry of Synthetic Medicinal Substances (Russian w/ English Translation), Moscow::12-19 (Jan. 1, 1964).
Kummerer, K., "Pharmaceuticals in the Environment" Ann Rev Environ Res 35:57-75 (Nov. 1, 2010).
Likhosherstov, A.M., et al., "Synthesis and antiarrhythmic activity of 1, 4-diazabicyclo [4. m. o] alkanyl amides of P-nitro-and P-aminobenzoic acids" Khimiko-Farmatsevticheskii Zhurnal [Russ Pharma Chem J] (English translation), 15(8):55-57 (Jan. 26, 1981).
Likhosherstov, A.M., et al., "Synthesis and antiarrhythmic activity of 1, 4-diazabicyclo [4. m. o] alkanyl amides of P-nitro-and P-aminobenzoic acids" Khimiko-Farmatsevticheskii Zhurnal [Russ Pharma Chem J] (RU language version), 15(8):55-57 (Jan. 26, 1981).
Mikhlina, E.E., et al., "The properties and some reactions of 4-oxo-1, 5-diazabicyclo [4, 4, 0] decane and 5-oxo-1, 4-diazabicyclo [4, 4, 0] decane" Kimiya Geterotsiklicheskikh Soedinenii ((English translation)), 5(3):547-549 (May 1, 1969).
Mikhlina, E.E., et al., "The properties and some reactions of 4-oxo-1, 5-diazabicyclo [4, 4, 0] decane and 5-oxo-1, 4-diazabicyclo [4, 4, 0] decane" Kimiya Geterotsiklicheskikh Soedinenii ((RU language version)), 5(3):547-549 (May 1, 1969)

HETEROCYCLIC COMPOUNDS

CROSS-REFERENCE TO RELATED APPLICATIONS

This application is a continuation of International Application No. PCT/EP2020/069074, filed Jul. 7, 2020, which claims priority to EP Application No. 19185088.2, filed Jul. 9, 2019, the disclosures of which are incorporated herein by reference in their entireties

FIELD OF THE INVENTION

The present invention relates to organic compounds useful for therapy or prophylaxis in a mammal, and in particular to monoacylglycerol lipase (MAGL) inhibitors for the treatment or prophylaxis of neuroinflammation, neurodegenerative diseases, pain, cancer, mental disorders, multiple sclerosis, Alzheimer's disease, Parkinson's disease, amyotrophic lateral sclerosis, traumatic brain injury, neurotoxicity, stroke, epilepsy, anxiety, migraine and/or depression in a mammal.

BACKGROUND OF THE INVENTION

Endocannabinoids (ECs) are signaling lipids that exert their biological actions by interacting with cannabinoid receptors (CBRs), CB1 and CB2. They modulate multiple physiological processes including neuroinflammation, neurodegeneration and tissue regeneration (Iannotti, F. A., et al., *Progress in lipid research* 2016, 62, 107-28). In the brain, the main endocannabinoid, 2-arachidonoylglycerol (2-AG), is produced by diacyglycerol lipases (DAGL) and hydrolyzed by the monoacylglycerol lipase, MAGL. MAGL hydrolyses 85% of 2-AG; the remaining 15% being hydrolysed by ABHD6 and ABDH12 (Nomura, D. K., et al., *Science* 2011, 334, 809). MAGL is expressed throughout the brain and in most brain cell types, including neurons, astrocytes, oligodendrocytes and microglia cells (Chanda, P. K., et al., *Molecular pharmacology* 2010, 78, 996; Viader, A., et al., *Cell reports* 2015, 12, 798). 2-AG hydrolysis results in the formation of arachidonic acid (AA), the precursor of prostaglandins (PGs) and leukotrienes (LTs). Oxidative metabolism of AA is increased in inflamed tissues. There are two principal enzyme pathways of arachidonic acid oxygenation involved in inflammatory processes, the cyclo-oxygenase which produces PGs and the 5-lipoxygenase which produces LTs. Of the various cyclooxygenase products formed during inflammation, PGE2 is one of the most important. These products have been detected at sites of inflammation, e.g. in the cerebrospinal fluid of patients suffering from neurodegenerative disorders and are believed to contribute to inflammatory response and disease progression. Mice lacking MAGL (Mgll−/−) exhibit dramatically reduced 2-AG hydrolase activity and elevated 2-AG levels in the nervous system while other arachidonoyl-containing phospho- and neutral lipid species including anandamide (AEA), as well as other free fatty acids, are unaltered. Conversely, levels of AA and AA-derived prostaglandins and other eicosanoids, including prostaglandin E2 (PGE2), D2 (PGD2), F2 (PGF2), and thromboxane B2 (TXB2), are strongly decreased. Phospholipase $A_2$ ($PLA_2$) enzymes have been viewed as the principal source of AA, but $cPLA_2$-deficient mice have unaltered AA levels in their brain, reinforcing the key role of MAGL in the brain for AA production and regulation of the brain inflammatory process.

Neuroinflammation is a common pathological change characteristic of diseases of the brain including, but not restricted to, neurodegenerative diseases (e.g. multiple sclerosis, Alzheimer's disease, Parkinson disease, amyotrophic lateral sclerosis, traumatic brain injury, neurotoxicity, stroke, epilepsy and mental disorders such as anxiety and migraine). In the brain, production of eicosanoids and prostaglandins controls the neuroinflammation process. The pro-inflammatory agent lipopolysaccharide (LPS) produces a robust, time-dependent increase in brain eicosanoids that is markedly blunted in Mgll−/− mice. LPS treatment also induces a widespread elevation in pro-inflammatory cytokines including interleukin-1-a (IL-1-a), IL-lb, IL-6, and tumor necrosis factor-a (TNF-a) that is prevented in Mgll−/− mice.

Neuroinflammation is characterized by the activation of the innate immune cells of the central nervous system, the microglia and the astrocytes. It has been reported that anti-inflammatory drugs can suppress in preclinical models the activation of glia cells and the progression of disease including Alzheimer's disease and mutiple sclerosis (Lleo A., *Cell Mol Life Sci.* 2007, 64, 1403). Importantly, genetic and/or pharmacological disruption of MAGL activity also blocks LPS-induced activation of microglial cells in the brain (Nomura, D. K., et al., *Science* 2011, 334, 809).

In addition, genetic and/or pharmacological disruption of MAGL activity was shown to be protective in several animal models of neurodegeneration including, but not restricted to, Alzheimer's disease, Parkinson's disease and multiple sclerosis. For example, an irreversible MAGL inhibitor has been widely used in preclinical models of neuroinflammation and neurodegeneration (Long, J. Z., et al., *Nature chemical biology* 2009, 5, 37). Systemic injection of such inhibitor recapitulates the Mgll−/− mice phenotype in the brain, including an increase in 2-AG levels, a reduction in AA levels and related eicosanoids production, as well as the prevention of cytokines production and microglia activation following LPS-induced neuroinflammation (Nomura, D. K., et al., *Science* 2011, 334, 809), altogether confirming that MAGL is a druggable target.

Consecutive to the genetic and/or pharmacological disruption of MAGL activity, the endogenous levels of the MAGL natural substrate in the brain, 2-AG, are increased. 2-AG has been reported to show beneficial effects on pain with, for example, anti-nociceptive effects in mice (Ignatowska-Jankowska B. et al., *J. Pharmacol. Exp. Ther.* 2015, 353, 424) and on mental disorders, such as depression in chronic stress models (Zhong P. et al., *Neuropsychopharmacology* 2014, 39, 1763).

Furthermore, oligodendrocytes (OLs), the myelinating cells of the central nervous system, and their precursors (OPCs) express the cannabinoid receptor 2 (CB2) on their membrane. 2-AG is the endogenous ligand of CB1 and CB2 receptors. It has been reported that both cannabinoids and pharmacological inhibition of MAGL attenuate OLs's and OPCs's vulnerability to excitotoxic insults and therefore may be neuroprotective (Bernal-Chico, A., et al., *Glia* 2015, 63, 163). Additionally, pharmacological inhibition of MAGL increases the number of myelinating OLs in the brain of mice, suggesting that MAGL inhibition may promote differentiation of OPCs in myelinating OLs in vivo (Alpar, A., et al., *Nature communications* 2014, 5, 4421). Inhibition of MAGL was also shown to promote remyelination and functional recovery in a mouse model of progressive multiple sclerosis (Feliu A. et al., *Journal of Neuroscience* 2017, 37 (35), 8385).

Finally, in recent years, metabolism is talked highly important in cancer research, especially the lipid metabolism. Researchers believe that the de novo fatty acid synthesis plays an important role in tumor development. Many studies illustrated that endocannabinoids have anti-tumorigenic actions, including anti-proliferation, apoptosis induction and anti-metastatic effects.

MAGL as an important decomposing enzyme for both lipid metabolism and the endocannabinoids system, additionally as a part of a gene expression signature, contributes to different aspects of tumourigenesis (Qin, H., et al., *Cell Biochem. Biophys.* 2014, 70, 33; Nomura D K et al., *Cell* 2009, 140(1), 49-61; Nomura D K et al., *Chem. Biol.* 2011, 18(7), 846-856).

In conclusion, suppressing the action and/or the activation of MAGL is a promising new therapeutic strategy for the treatment or prevention of neuroinflammation, neurodegenerative diseases, pain, cancer and mental disorders. Furthermore, suppressing the action and/or the activation of MAGL is a promising new therapeutic strategy for providing neuroprotection and myelin regeneration. Accordingly, there is a high unmet medical need for new MAGL inhibitors.

SUMMARY OF THE INVENTION

In a first aspect, the present invention provides compounds of Formula (I), or pharmaceutically acceptable salts thereof, (I)

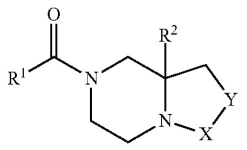

wherein $R^1$, $R^2$, X, and Y are as defined herein.

In a further aspect, the present invention provides a process of manufacturing the compounds of formula (I) as described in any one of the synthetic schemes disclosed herein.

In a further aspect, the present invention provides a compound of formula (I) as described herein, when manufactured according to the processes described herein.

In a further aspect, the present invention provides a compound of formula (I) as described herein, for use as therapeutically active substance.

In a further aspect, the present invention provides a pharmaceutical composition comprising a compound of formula (I) as described herein and a therapeutically inert carrier.

In a further aspect, the present invention provides a compound of formula (I) as described herein for use in a method of inhibiting monoacylglycerol lipase in a mammal.

In a further aspect, the present invention provides a compound of formula (I) as described herein for use in the treatment or prophylaxis of neuroinflammation, neurodegenerative diseases, pain, cancer and/or mental disorders in a mammal.

In a further aspect, the present invention provides a compound of formula (I) as described herein, for use in the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal.

DETAILED DESCRIPTION OF THE INVENTION

Definitions

Features, integers, characteristics, compounds, chemical moieties or groups described in conjunction with a particular aspect, embodiment or example of the invention are to be understood to be applicable to any other aspect, embodiment or example described herein, unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The term "alkyl" refers to a mono- or multivalent, e.g., a mono- or bivalent, linear or branched saturated hydrocarbon group of 1 to 6 carbon atoms ("$C_1$-$C_6$-alkyl"), e.g., 1, 2, 3, 4, 5, or 6 carbon atoms. In some embodiments, the alkyl group contains 1 to 3 carbon atoms, e.g., 1, 2 or 3 carbon atoms. Some non-limiting examples of alkyl include methyl, ethyl, propyl, 2-propyl (isopropyl), n-butyl, iso-butyl, sec-butyl, tert-butyl, and 2,2-dimethylpropyl. A particularly preferred, yet non-limiting example of alkyl is methyl.

The term "alkoxy" refers to an alkyl group, as previously defined, attached to the parent molecular moiety via an oxygen atom. In some preferred embodiments, the alkoxy group contains 1 to 6 carbon atoms ("$C_1$-$C_6$-alkoxy"), e.g. 1, 2, 3, 4, 5, or 6 carbon atoms. In other embodiments, the alkoxy group contains 1 to 4 carbon atoms. In still other embodiments, the alkoxy group contains 1 to 3 carbon atoms. Some non-limiting examples of alkoxy groups include methoxy, ethoxy, n-propoxy, isopropoxy, n-butoxy, isobutoxy, 1,1-dimethylpropoxy, 2,2-dimethylpropoxy, and tert-butoxy. A particularly preferred, yet non-limiting example of alkoxy is methoxy.

The term "halogen" or "halo" refers to fluoro (F), chloro (Cl), bromo (Br), or iodo (I). Preferably, the term "halogen" or "halo" refers to fluoro (F), chloro (Cl) or bromo (Br). Particularly preferred, yet non-limiting examples of "halogen" or "halo" are fluoro (F) and chloro (Cl).

The term "cycloalkyl" as used herein refers to a saturated or partly unsaturated monocyclic or bicyclic hydrocarbon group of 3 to 14 ring carbon atoms ("$C_{3-14}$-cycloalkyl"). In some preferred embodiments, the cycloalkyl group is a saturated monocyclic hydrocarbon group of 3 to 8 ring carbon atoms. "Bicyclic cycloalkyl" refers to cycloalkyl moieties consisting of two saturated carbocycles having two carbon atoms in common, i.e., the bridge separating the two rings is either a single bond or a chain of one or two ring atoms, and to spirocyclic moieties, i.e., the two rings are connected via one common ring atom. In one embodiment, the cycloalkyl group is a saturated monocyclic hydrocarbon group of 3 to 6 ring carbon atoms, e.g., of 3, 4, 5 or 6 carbon atoms. Some non-limiting examples of cycloalkyl include cyclopropyl, cyclobutyl, cyclopentyl, cyclohexyl, cycloheptyl, and 1-bicyclo[1.1.1]pentanyl.

The term "aryl" refers to a monocyclic, bicyclic, or tricyclic carbocyclic ring system having a total of 6 to 14 ring members ("$C_{6-14}$-aryl"), preferably, 6 to 12 ring members, and more preferably 6 to 10 ring members, and wherein at least one ring in the system is aromatic. Preferred, yet non-limiting examples of aryl includes phenyl and 3-bicyclo [4.2.0]octa-1(6),2,4-trienyl.

The term "heteroaryl" refers to a mono- or multivalent, monocyclic, bicyclic or tricyclic, preferably bicyclic ring system having a total of 5 to 14 ring members ("$C_{1-13}$-heteroaryl"), preferably, 5 to 12 ring members, and more preferably 5 to 10 ring members, wherein at least one ring in the system is aromatic, and at least one ring in the system contains one or more heteroatoms. Preferably, "heteroaryl" refers to a 5-10 membered heteroaryl comprising 1, 2, 3 or 4 heteroatoms independently selected from O, S and N. Most preferably, "heteroaryl" refers to a 5-10 membered heteroaryl comprising 1 to 2 heteroatoms independently selected from O and N. Some non-limiting examples of heteroaryl include 1H-pyrazol-4-yl, pyridazine, pyridyl, pyrimidinyl, oxazol-5-yl, isoxazol-4-yl, 1H-triazol-5-yl, 1H-imidazol-5-yl, 1H-benzimidazol-2-yl, and thiazolyl.

The term "hydroxy" refers to an —OH group.

The term "cyano" refers to a —CN (nitrile) group.

The term "oxo" refers to a double bonded oxygen (=O).

The term "haloalkyl" refers to an alkyl group, wherein at least one of the hydrogen atoms of the alkyl group has been replaced by a halogen atom, preferably fluoro. Preferably, "haloalkyl" refers to an alkyl group wherein 1, 2 or 3 hydrogen atoms of the alkyl group have been replaced by a halogen atom, most preferably fluoro. Particularly preferred, yet non-limiting examples of haloalkyl are fluoromethyl, difluoromethyl, trifluoromethyl, 3,3,3-trifluoropropyl, 2,2-difluoropropyl, 1-fluoro-1-methyl-ethyl, 2-fluoro-1,1-dimethyl-ethyl, 2-fluoro-2-methyl-propyl, trifluoromethyl and 2,2,2-trifluoroethyl.

The term "haloalkoxy" refers to an alkoxy group, wherein at least one of the hydrogen atoms of the alkoxy group has been replaced by a halogen atom, preferably fluoro. Preferably, "haloalkoxy" refers to an alkoxy group wherein 1, 2 or 3 hydrogen atoms of the alkoxy group have been replaced by a halogen atom, most preferably fluoro. Particularly preferred, yet non-limiting examples of haloalkoxy are trifluoromethoxy, 3,3,3-trifluoropropoxy, 2,2,2-trifluoro-1-methyl-ethoxy, and 3-fluoro-2-fluoro-propoxy.

The term "alkenyl" denotes a mono- or bivalent linear or branched hydrocarbon group of 2 to 6 carbon atoms with at least one double bond ("$C_2$-$C_6$-alkenyl"), e.g. 1 or 2 double bonds. In particular embodiments, alkenyl has 2 to 4 carbon atoms with at least one double bond, e.g. 1 or 2 double bonds. Examples of alkenyl include ethenyl, propenyl, prop-2-enyl, isopropenyl, n-butenyl (e.g. (Z)-but-1-enyl), iso-butenyl, allyl, 2-methylallyl, 2-methylprop-1-enyl, and propa-1,2-dienyl.

The term "alkynyl" denotes a mono- or bivalent linear or branched hydrocarbon group of 2 to 6 carbon atoms with at least one triple bond ("$C_2$-$C_6$-alkynyl"), e.g. 1 or 2 triple bonds. In particular embodiments, alkynyl has 2 to 4 carbon atoms with at least one triple bond. Examples of alkynyl include ethynyl, ethyndiyl, propynyl, n-butynyl or isobutynyl.

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are hydrochloride salts.

The term "protective group" (PG) denotes the group which selectively blocks a reactive site in a multifunctional compound such that a chemical reaction can be carried out selectively at another unprotected reactive site in the meaning conventionally associated with it in synthetic chemistry. Protective groups can be removed at the appropriate point. Exemplary protective groups are amino-protective groups, carboxy-protective groups or hydroxy-protective groups. Particular protective groups are the tert-butoxycarbonyl (Boc), benzyloxycarbonyl (Cbz), fluorenylmethoxycarbonyl (Fmoc) and benzyl (Bn). Further particular protective groups are the tert-butoxycarbonyl (Boc) and the fluorenylmethoxycarbonyl (Fmoc). More particular protective group is the tert-butoxycarbonyl (Boc). Exemplary protective groups and their application in organic synthesis are described, for example, in "Protective Groups in Organic Chemistry" by T. W. Greene and P. G. M. Wutts, 5th Ed., 2014, John Wiley & Sons, N.Y.

The compounds of formula (I) can contain several asymmetric centers and can be present in the form of optically pure enantiomers, mixtures of enantiomers such as, for example, racemates, optically pure diastereioisomers, mixtures of diastereoisomers, diastereoisomeric racemates or mixtures of diastereoisomeric racemates.

According to the Cahn-Ingold-Prelog Convention, the asymmetric carbon atom can be of the "R" or "S" configuration.

The abbreviation "MAGL" refers to the enzyme monoacylglycerol lipase. The terms "MAGL" and "monoacylglycerol lipase" are used herein interchangeably.

The term "treatment" as used herein includes: (1) inhibiting the state, disorder or condition (e.g. arresting, reducing or delaying the development of the disease, or a relapse thereof in case of maintenance treatment, of at least one clinical or subclinical symptom thereof); and/or (2) relieving the condition (i.e., causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

The term "prophylaxis" as used herein includes: preventing or delaying the appearance of clinical symptoms of the state, disorder or condition developing in a mammal and especially a human that may be afflicted with or predisposed to the state, disorder or condition but does not yet experience or display clinical or subclinical symptoms of the state, disorder or condition.

The term "neuroinflammation" as used herein relates to acute and chronic inflammation of the nervous tissue, which is the main tissue component of the two parts of the nervous system; the brain and spinal cord of the central nervous system (CNS), and the branching peripheral nerves of the peripheral nervous system (PNS). Chronic neuroinflammation is associated with neurodegenerative diseases such as Alzheimer's disease, Parkinson's disease and multiple sclerosis. Acute neuroinflammation usually follows injury to the central nervous system immediately, e.g., as a result of traumatic brain injury (TBI).

The term "traumatic brain injury" ("TBI", also known as "intracranial injury"), relates to damage to the brain resulting from external mechanical force, such as rapid acceleration or deceleration, impact, blast waves, or penetration by a projectile.

The term "neurodegenerative diseases" relates to diseases that are related to the progressive loss of structure or function of neurons, including death of neurons. Examples of neurodegenerative diseases include, but are not limited to, multiple sclerosis, Alzheimer's disease, Parkinson's disease and amyotrophic lateral sclerosis.

The term "mental disorders" (also called mental illnesses or psychiatric disorders) relates to behavioral or mental patterns that may cause suffering or a poor ability to function in life. Such features may be persistent, relapsing and remitting, or occur as a single episode. Examples of mental disorders include, but are not limited to, anxiety and depression.

The term "pain" relates to an unpleasant sensory and emotional experience associated with actual or potential tissue damage. Examples of pain include, but are not limited to, nociceptive pain, chronic pain (including idiopathic pain), neuropathic pain including chemotherapy induced neuropathy, phantom pain and phsychogenic pain. A particular example of pain is neuropathic pain, which is caused by damage or disease affecting any part of the nervous system involved in bodily feelings (i.e., the somatosensory system). In one embodiment, "pain" is neuropathic pain resulting from amputation or thoracotomy. In one embodiment, "pain" is chemotherapy induced neuropathy.

The term "neurotoxicity" relates to toxicity in the nervous system. It occurs when exposure to natural or artificial toxic substances (neurotoxins) alter the normal activity of the nervous system in such a way as to cause damage to nervous tissue. Examples of neurotoxicity include, but are not limited to, neurotoxicity resulting from exposure to substances used in chemotherapy, radiation treatment, drug therapies, drug abuse, and organ transplants, as well as exposure to heavy metals, certain foods and food additives, pesticides, industrial and/or cleaning solvents, cosmetics, and some naturally occurring substances.

The term "cancer" refers to a disease characterized by the presence of a neoplasm or tumor resulting from abnormal uncontrolled growth of cells (such cells being "cancer cells"). As used herein, the term cancer explicitly includes, but is not limited to, hepatocellular carcinoma, colon carcinogenesis and ovarian cancer.

The term "mammal" as used herein includes both humans and non-humans and includes but is not limited to humans, non-human primates, canines, felines, murines, bovines, equines, and porcines. In a particularly preferred embodiment, the term "mammal" refers to humans.

Compounds of the Invention

In a first aspect (A1), the present invention provides compounds of Formula (I)

(I)

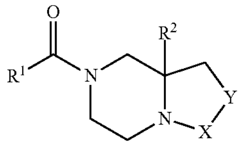

or a pharmaceutically acceptable salts thereof, wherein:

X is $—CH_2CR^3R^4—$ or $—CH{=}CR^3—$;

Y is —O—, —S—, —SO—, or $—SO_2—$;

$R^1$ is $C_6$-$C_{14}$-aryl or 5- to 14-membered heteroaryl, wherein said $C_6$-$C_{14}$-aryl or 5- to 14-membered heteroaryl are optionally substituted with 1-5 substituents independently selected from $C_1$-$C_6$-alkyl, $C_1$-$C_6$-alkoxy, halo-$C_1$-$C_6$-alkyl, halo-$C_1$-$C_6$-alkoxy, halogen, cyano, hydroxy, and a group

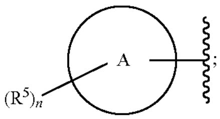

;

$R^2$ is hydrogen or $C_1$-$C_6$-alkyl;

$R^3$ is a group;

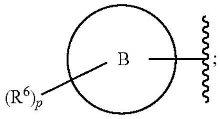

;

$R^4$ is hydrogen, halogen or hydroxy;

$R^5$ is hydrogen, halogen, hydroxy, amino, halo-$C_1$-$C_6$-alkyl, $C_1$-$C_6$-alkoxy, $C_1$-$C_6$-alkyl, halo-$C_1$-$C_6$-alkoxy, cyano or oxo;

$R^6$ is hydrogen, halogen, $C_6$-$C_{14}$-aryl, 5- to 14-membered heteroaryl, halo-$C_1$-$C_6$-alkoxy, halo-$C_1$-$C_6$-alkyl, oxo, $C_1$-$C_6$-alkyl, $C_1$-$C_6$-alkoxy, $C_2$-$C_6$-alkenyl, $C_2$-$C_6$-alkynyl, $C_3$-$C_{14}$-cycloalkyl or cyano; wherein said 5- to 14-membered heteroaryl or $C_6$-$C_{14}$-aryl is optionally substituted with 1-2 substituents selected from halogen, cyano, amino, hydroxy, $C_1$-$C_6$-alkyl and $C_1$-$C_6$-alkoxy;

A and B are each independently 5- to 14-membered heteroaryl, $C_6$-$C_{14}$-aryl, 3- to 14-membered heterocyclyl or $C_3$-$C_{14}$-cycloalkyl; and n and p are each independently 1, 2, 3, 4 or 5.

In a second aspect (A2), the present invention provides compounds of Formula (I)

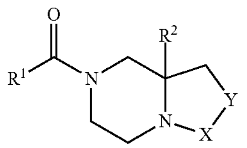

(I)

or a pharmaceutically acceptable salts thereof, wherein:

X is $-CH_2CR^3R^4-$ or $-CH=CR^3-$;

Y is —O—, —S—, —SO—, or $-SO_2-$;

$R^1$ is $C_6$-$C_{14}$-aryl or 5- to 14-membered heteroaryl, wherein said $C_6$-$C_{14}$-aryl or 5- to 14-membered heteroaryl are optionally substituted with 1-5 substituents independently selected from $C_1$-$C_6$-alkyl, $C_1$-$C_6$-alkoxy, halo-$C_1$-$C_6$-alkyl, halo-$C_1$-$C_6$-alkoxy, halogen, cyano, hydroxy, and a group

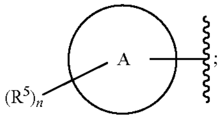

$R^2$ is hydrogen or $C_1$-$C_6$-alkyl;

$R^3$ is a group

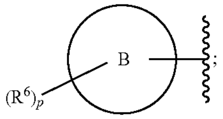

$R^4$ is hydrogen, halogen or hydroxy;

$R^5$ is hydrogen, halogen, hydroxy, halo-$C_1$-$C_6$-alkyl, $C_1$-$C_6$-alkoxy, $C_1$-$C_6$-alkyl, halo-$C_1$-$C_6$-alkoxy, cyano or oxo;

$R^6$ is hydrogen, halogen, $C_6$-$C_{14}$-aryl, 5- to 14-membered heteroaryl, halo-$C_1$-$C_6$-alkoxy, halo-$C_1$-$C_6$-alkyl, oxo, $C_1$-$C_6$-alkyl, $C_2$-$C_6$-alkenyl, $C_2$-$C_6$-alkynyl, $C_3$-$C_{14}$-cycloalkyl or cyano;

A and B are each independently 5- to 14-membered heteroaryl, $C_6$-$C_{14}$-aryl, 3- to 14-membered heterocyclyl or $C_3$-$C_{14}$-cycloalkyl; and n and p are each independently 1, 2, 3, 4 or 5.

The invention further provides the following enumerated embodiments (E) of the first and second Aspect A1 and A2:

E1 The compound of formula (I) according to A1 or A2, or a pharmaceutically acceptable salt thereof, wherein X is $-CH_2CR^3R^4-$.

E2 The compound of formula (I) according to any one of A1, A2 and E1, or a pharmaceutically acceptable salt thereof, wherein Y is —O— or —S—.

E3 The compound of formula (I) according to any one of A1, A2 and E1, or a pharmaceutically acceptable salt thereof, wherein Y is —O—.

E4 The compound of formula (I) according to any one of A1, A2, and E1 to E3, or a pharmaceutically acceptable salt thereof, wherein $R^1$ is $C_6$-$C_{14}$-aryl or 5- to 14-membered heteroaryl, wherein said $C_6$-$C_{14}$-aryl or 5- to 14-membered heteroaryl are substituted with 1-3 substituents independently selected from $C_1$-$C_6$-alkyl, $C_1$-$C_6$-alkoxy, halo-$C_1$-$C_6$-alkoxy, halogen, cyano and a group

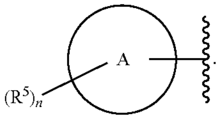

E5 The compound of formula (I) according to any one of A1, A2, and E1 to E3, or a pharmaceutically acceptable salt thereof, wherein $R^1$ is $C_6$-$C_{14}$-aryl substituted with 1-2 substituents independently selected from $C_1$-$C_6$-alkoxy, halogen, and a group

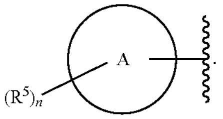

E6 The compound of formula (I) according to any one of A1, A2, and E1 to E3, or a pharmaceutically acceptable salt thereof, wherein $R^1$ is $C_6$-$C_{14}$-aryl substituted with 2-3 substituents independently selected from $C_1$-$C_6$-alkoxy, halogen, and a group

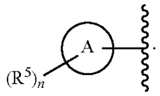

E7 The compound of formula (I) according to any one of A1, A2, and E1 to E3, or a pharmaceutically acceptable salt thereof, wherein $R^1$ is phenyl substituted with 2 substituents independently selected from chloro, methoxy and a group

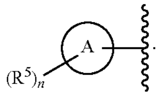

E8 The compound of formula (I) according to any one of A1, A2, and E1 to E3, or a pharmaceutically acceptable salt thereof, wherein $R^1$ is phenyl substituted with 2-3 substituents independently selected from chloro, fluoro, methoxy and a group

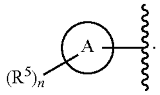

E9 The compound of formula (I) according to any one of A1, A2, and E1 to E8, or a pharmaceutically acceptable salt thereof, wherein $R^2$ is hydrogen.

E10 The compound of formula (I) according to any one of A1, A2, and E1 to E9, or a pharmaceutically acceptable salt thereof, wherein $R^4$ is hydrogen or hydroxy.

E11 The compound of formula (I) according to any one of A1, A2, and E1 to E10, or a pharmaceutically acceptable salt thereof, wherein $R^5$ is hydrogen, halogen, hydroxy, halo-$C_1$-$C_6$-alkyl, $C_1$-$C_6$-alkoxy, $C_1$-$C_6$-alkyl, cyano or oxo.

E12 The compound of formula (I) according to any one of A1, A2, and E1 to E10, or a pharmaceutically acceptable salt thereof, wherein $R^5$ is hydrogen, halogen, hydroxy or oxo.

E13 The compound of formula (I) according to any one of A1, A2, and E1 to E10, or a pharmaceutically acceptable salt thereof, wherein $R^5$ is hydrogen, halogen, cyano, hydroxy or oxo.

E14 The compound of formula (I) according to any one of A1, A2, and E1 to E10, or a pharmaceutically acceptable salt thereof, wherein $R^5$ is hydrogen, fluoro, hydroxy or oxo.

E15 The compound of formula (I) according to any one of A1, A2, and E1 to E10, or a pharmaceutically acceptable salt thereof, wherein $R^5$ is hydrogen, fluoro, cyano, hydroxy or oxo.

E16 The compound of formula (I) according to any one of A1, A2, and E1 to E15, or a pharmaceutically acceptable salt thereof, wherein $R^6$ is hydrogen, halogen, $C_6$-$C_{14}$-aryl, halo-$C_1$-$C_6$-alkoxy, halo-$C_1$-$C_6$-alkyl, oxo, $C_1$-$C_6$-alkyl, $C_2$-$C_6$-alkenyl, $C_2$-$C_6$-alkynyl, $C_3$-$C_{14}$-cycloalkyl or cyano.

E17 The compound of formula (I) according to any one of A1, A2, and E1 to E15, or a pharmaceutically acceptable salt thereof, wherein $R^6$ is hydrogen, halogen, $C_6$-$C_{14}$-aryl, 5- to 14-membered heteroaryl, halo-$C_1$-$C_6$-alkoxy, halo-$C_1$-$C_6$-alkyl, oxo, $C_1$-$C_6$-alkyl, $C_1$-$C_6$-alkoxy, $C_2$-$C_6$-alkenyl, $C_2$-$C_6$-alkynyl, $C_3$-$C_{14}$-cycloalkyl or cyano, wherein said 5- to 14-membered heteroaryl or $C_6$-$C_{14}$-aryl is optionally substituted with a substituent selected from halogen, $C_1$-$C_6$-alkyl and $C_1$-$C_6$-alkoxy.

E18 The compound of formula (I) according to any one of A1, A2, and E1 to E15, or a pharmaceutically acceptable salt thereof, wherein $R^6$ is halogen, halo-$C_1$-$C_6$-alkyl or halo-$C_1$-$C_6$-alkoxy.

E19 The compound of formula (I) according to any one of A1, A2, and E1 to E15, or a pharmaceutically acceptable salt thereof, wherein $R^6$ is halogen, oxo, halo-$C_1$-$C_6$-alkyl or halo-$C_1$-$C_6$-alkoxy.

E20 The compound of formula (I) according to any one of A1, A2, and E1 to E15, or a pharmaceutically acceptable salt thereof, wherein $R^6$ is chloro, fluoro, trifluoromethyl or difluoromethoxy.

E21 The compound of formula (I) according to any one of A1, A2, and E1 to E15, or a pharmaceutically acceptable salt thereof, wherein $R^6$ is chloro, fluoro, oxo, trifluoromethyl or difluoromethoxy.

E22 The compound of formula (I) according to any one of A1, A2, and E1 to E21, or a pharmaceutically acceptable salt thereof, wherein n is 1 or 2.

E23 The compound of formula (I) according to any one of A1, A2, and E1 to E21, or a pharmaceutically acceptable salt thereof, wherein n is 2.

E24 The compound of formula (I) according to any one of A1, A2, and E1 to E23, or a pharmaceutically acceptable salt thereof, wherein p is 1 or 2.

E25 The compound of formula (I) according to any one of A1, A2, and E1 to E23, or a pharmaceutically acceptable salt thereof, wherein p is 1, 2 or 3.

E26 The compound of formula (I) according to any one of A1, A2, and E1 to E25, or a pharmaceutically acceptable salt thereof, wherein A is 5- to 14-membered heteroaryl, $C_6$-$C_{14}$-aryl or 3- to 14-membered heterocyclyl.

E27 The compound of formula (I) according to any one of A1, A2, and E1 to E25, or a pharmaceutically acceptable salt thereof, wherein A is 5- to 14-membered heteroaryl or 3- to 14-membered heterocyclyl.

E28 The compound of formula (I) according to any one of A1, A2, and E1 to E25, or a pharmaceutically acceptable salt thereof, wherein A is imidazolyl, pyrazolyl, oxo-pyridinyl or 1,2-dihydropyridinyl.

E29 The compound of formula (I) according to any one of A1, A2, and E1 to E25, or a pharmaceutically acceptable salt thereof, wherein A is imidazolyl, pyrazolyl, pyrrolyl, or 1,2-dihydropyridinyl.

E30 The compound of formula (I) according to any one of A1, A2, and E1 to E29, or a pharmaceutically acceptable salt thereof, wherein B is $C_6$-$C_{14}$-aryl, 5- to 14-membered heteroaryl or 3- to 14-membered heterocyclyl.

E31 The compound of formula (I) according to any one of A1, A2, and E1 to E29, or a pharmaceutically acceptable salt thereof, wherein B is $C_6$-$C_{14}$-aryl or 5- to 14-membered heteroaryl.

E32 The compound of formula (I) according to any one of A1, A2, and E1 to E29, or a pharmaceutically acceptable salt thereof, wherein B is phenyl or pyridinyl.

E33 The compound of formula (I) according to any one of A1, A2, and E1 to E29, or a pharmaceutically acceptable salt thereof, wherein B is phenyl, 1,2-dihydropyridinyl or pyridyl.

E34 The compound of formula (I) according to A1 or A2, or a pharmaceutically acceptable salt thereof, wherein:

X is $-CH_2CR^3R^4-$ or $-CH{=}CR^3-$;

Y is $-O-$;

$R^1$ is $C_6$-$C_{14}$-aryl or 5- to 14-membered heteroaryl, wherein said $C_6$-$C_{14}$-aryl or 5- to 14-membered heteroaryl are substituted with 1-3 substituents independently selected from $C_1$-$C_6$-alkyl, $C_1$-$C_6$-alkoxy, halo-$C_1$-$C_6$-alkoxy, halogen, cyano and a group

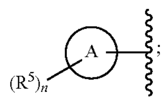

$R^2$ is hydrogen or $C_1$-$C_6$-alkyl;

$R^3$ is a group

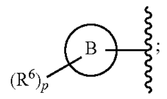

$R^4$ is hydrogen, halogen or hydroxy;

$R^5$ is hydrogen, halogen, hydroxy, halo-$C_1$-$C_6$-alkyl, $C_1$-$C_6$-alkoxy, $C_1$-$C_6$-alkyl, cyano or oxo;

$R^6$ is hydrogen, halogen, $C_6$-$C_{14}$-aryl, halo-$C_1$-$C_6$-alkoxy, halo-$C_1$-$C_6$-alkyl, oxo, $C_1$-$C_6$-alkyl, $C_2$-$C_6$-alkenyl, $C_2$-$C_6$-alkynyl, $C_3$-$C_{14}$-cycloalkyl or cyano;

A and B are each independently 5- to 14-membered heteroaryl, $C_6$-$C_{14}$-aryl or 3- to 14-membered heterocyclyl; and n and p are each independently 1 or 2.

E35 The compound of formula (I) according to A1 or A2, or a pharmaceutically acceptable salt thereof, wherein:

X is $-CH_2CR^3R^4-$;

Y is $-O-$;

$R^1$ is $C_6$-$C_{14}$-aryl substituted with 1-2 substituents independently selected from $C_1$-$C_6$-alkoxy, halogen, and a group

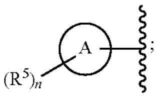

$R^2$ is hydrogen;

$R^3$ is a group

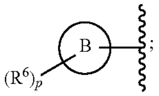

$R^4$ is hydrogen or hydroxy;

$R^5$ is hydrogen, halogen, hydroxy or oxo;

$R^6$ is halogen, halo-$C_1$-$C_6$-alkyl or halo-$C_1$-$C_6$-alkoxy;

A is 5- to 14-membered heteroaryl or 3- to 14-membered heterocyclyl;

B is $C_6$-$C_{14}$-aryl or 5- to 14-membered heteroaryl;

n is 2; and p is 1 or 2.

E36 The compound of formula (I) according to A1 or A2, or a pharmaceutically acceptable salt thereof, wherein:

X is —$CH_2CR^3R^4$—;

Y is —O—;

$R^1$ is phenyl substituted with 2 substituents independently selected from chloro, methoxy and a group

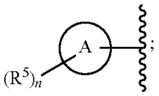

$R^2$ is hydrogen;

$R^3$ is a group

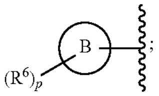

$R^4$ is hydrogen or hydroxy;

$R^5$ is hydrogen, fluoro, hydroxy or oxo;

$R^6$ is chloro, fluoro, trifluoromethyl or difluoromethoxy;

A is imidazolyl, pyrazolyl, oxo-pyridinyl or 1,2-dihydropyridinyl;

B is phenyl or pyridinyl;

n is 2; and p is 1 or 2.

E37 The compound of formula (I) according to A1 or A2, or a pharmaceutically acceptable salt thereof, wherein:

X is —$CH_2CR^3R^4$— or —CH═$CR^3$—;

Y is —O— or —S—;

$R^1$ is $C_6$-$C_{14}$-aryl or 5- to 14-membered heteroaryl, wherein said $C_6$-$C_{14}$-aryl or 5- to 14-membered heteroaryl are substituted with 1-3 substituents independently selected from $C_1$-$C_6$-alkyl, $C_1$-$C_6$-alkoxy, halo-$C_1$-$C_6$-alkoxy, halogen, cyano and a group

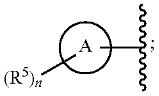

$R^2$ is hydrogen or $C_1$-$C_6$-alkyl;

$R^3$ is a group

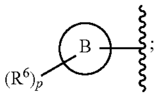

$R^4$ is hydrogen, halogen or hydroxy;

$R^5$ is hydrogen, halogen, hydroxy, halo-$C_1$-$C_6$-alkyl, $C_1$-$C_6$-alkoxy, $C_1$-$C_6$-alkyl, cyano or oxo;

$R^6$ is hydrogen, halogen, $C_6$-$C_{14}$-aryl, 5- to 14-membered heteroaryl, halo-$C_1$-$C_6$-alkoxy, halo-$C_1$-$C_6$-alkyl, oxo, $C_1$-$C_6$-alkyl, $C_1$-$C_6$-alkoxy, $C_2$-$C_6$-alkenyl, $C_2$-$C_6$-alkynyl, $C_3$-$C_{14}$-cycloalkyl or cyano, wherein said 5- to 14-membered heteroaryl or $C_6$-$C_{14}$-aryl is optionally substituted with a substituent selected from halogen, $C_1$-$C_6$-alkyl and $C_1$-$C_6$-alkoxy;

A and B are each independently 5- to 14-membered heteroaryl, $C_6$-$C_{14}$-aryl or 3- to 14-membered heterocyclyl;

n is 1 or 2; and p is 1, 2 or 3.

E38 The compound of formula (I) according to A1 or A2, or a pharmaceutically acceptable salt thereof, wherein:

X is —$CH_2CR^3R^4$—;

Y is —O—;

$R^1$ is $C_6$-$C_{14}$-aryl substituted with 1-2 substituents independently selected from $C_1$-$C_6$-alkoxy, halogen, and a group

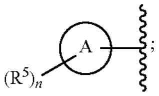

$R^2$ is hydrogen;

$R^3$ is a group

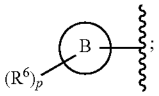

$R^4$ is hydrogen or hydroxy;

$R^5$ is hydrogen, halogen, cyano, hydroxy or oxo;

$R^6$ is halogen, oxo, halo-$C_1$-$C_6$-alkyl or halo-$C_1$-$C_6$-alkoxy;

A is 5- to 14-membered heteroaryl or 3- to 14-membered heterocyclyl;

B is $C_6$-$C_{14}$-aryl or 5- to 14-membered heteroaryl; and n and p are each independently 1 or 2.

E39 The compound of formula (I) according to A1 or A2, or a pharmaceutically acceptable salt thereof, wherein:

X is —$CH_2CR^3R^4$—;

Y is —O—;

$R^1$ is phenyl substituted with 2-3 substituents independently selected from chloro, fluro, methoxy and a group

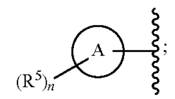

$R^2$ is hydrogen;

$R^3$ is a group

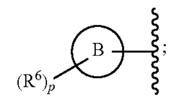

$R^4$ is hydrogen or hydroxy;

$R^5$ is hydrogen, fluoro, cyano, hydroxy or oxo;

$R^6$ is chloro, fluoro, oxo, trifluoromethyl or difluoromethoxy;

A is imidazolyl, pyrazolyl, pyrrolyl, or 1,2-dihydropyridinyl;

B is phenyl, 1,2-dihydropyridinyl or pyridyl; and n and p are each independently 1 or 2.

E40 The compound of formula (I) according to A1 or A2, or a pharmaceutically acceptable salt thereof, wherein the compound of formula (I) is selected from:

[(3R,9aS)-3-(3,4-difluorophenyl)-3-hydroxy-1,4,6,7,9,9a-hexahydropyrazino[2,1-c][1,4]oxazin-8-yl]-[3-(3-fluoro-1H-pyrazol-4-yl)phenyl]methanone;

[(3S,9aR)-3-(3-chloro-4-fluoro-phenyl)-3-hydroxy-1,4,6,7,9,9a-hexahydropyrazino[2,1-c][1,4]oxazin-8-yl]-(2-chloro-3-methoxy-phenyl)methanone;

[(3R,9aS)-3-(5-chloro-4-methyl-2-pyridyl)-3,4,6,7,9,9a-hexahydro-1H-pyrazino[2,1-c][1,4]oxazin-8-yl]-(2-chloro-3-methoxy-phenyl)methanone;

[(3S,9aS)-3-(3-chloro-4-fluoro-phenyl)-3,4,6,7,9,9a-hexahydro-1H-pyrazino[2,1-c][1,4]oxazin-8-yl]-[2-chloro-3-(3-fluoro-1H-pyrazol-4-yl)phenyl]methanone;

[(3R,9aR)-3-(4,5-dichloro-2-pyridyl)-3,4,6,7,9,9a-hexahydro-1H-pyrazino[2,1-c][1,4]oxazin-8-yl]-(2-chloro-3-methoxy-phenyl)methanone;

[(9aS)-3-(4-fluoro-3-phenyl-phenyl)-3,4,6,7,9,9a-hexahydro-1H-pyrazino[2,1-c][1,4]oxazin-8-yl]-(2-chloro-3-methoxy-phenyl)methanone;

[(3S,9aS)-3-(1H-benzimidazol-2-yl)-3-hydroxy-1,4,6,7,9,9a-hexahydropyrazino[2,1-c][1,4]oxazin-8-yl]-(2-chloro-3-methoxy-phenyl)methanone;

(2-chloro-3-methoxy-phenyl)-[rac-(3S,9aR)-3-(5-bromo-2-pyridyl)-3,4,6,7,9,9a-hexahydro-1H-pyrazino[2,1-c][1,4]oxazin-8-yl]methanone;

[(3S,9aS)-3-(3,4-difluorophenyl)-3,4,6,7,9,9a-hexahydro-1H-pyrazino[2,1-c][1,4]oxazin-8-yl]-[2-chloro-3-(3-fluoro-1H-pyrazol-4-yl)phenyl]methanone;

[(3S,9aR)-3-(3-chloro-4-fluoro-phenyl)-9a-methyl-1,3,4,6,7,9-hexahydropyrazino[2,1-c][1,4]oxazin-8-yl]-(2-chloro-3-methoxy-phenyl)methanone;

(2-chloro-3-methoxy-phenyl)-[rac-(3S,9aS)-3-(5-chloro-3-pyridyl)-3,4,6,7,9,9a-hexahydro-1H-pyrazino[2,1-c][1,4]oxazin-8-yl]methanone;

[(3R,9aS)-3-(4-chloro-2-pyridyl)-3,4,6,7,9,9a-hexahydro-1H-pyrazino[2,1-c][1,4]oxazin-8-yl]-(2-chloro-3-methoxy-phenyl)methanone;

[(3S,9aR)-3-(2,4-dimethylthiazol-5-yl)-3,4,6,7,9,9a-hexahydro-1H-pyrazino[2,1-c][1,4]oxazin-8-yl]-(2-chloro-3-methoxy-phenyl)methanone;

[2-chloro-3-(3-fluoro-1H-pyrazol-4-yl)phenyl]-[rac-(3R,9aS)-3-(3-chloro-4-fluoro-phenyl)-3,4,6,7,9,9a-hexahydro-1H-pyrazino[2,1-c][1,4]oxazin-8-yl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(1H-pyrazol-4-yl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(1H-imidazol-5-yl)phenyl]methanone;

[(3R,9aS)-3-(3,4-difluorophenyl)-3,4,6,7,9,9a-hexahydro-1H-pyrazino[2,1-c][1,4]oxazin-8-yl]-[2-chloro-3-(3-fluoro-1H-pyrazol-4-yl)phenyl]methanone;

[(3S,9aS)-3-(4,5-dichloro-2-pyridyl)-3,4,6,7,9,9a-hexahydro-1H-pyrazino[2,1-c][1,4]oxazin-8-yl]-(2-chloro-3-methoxy-phenyl)methanone;

4-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]-1H-pyridin-2-one;

[(3R,9aS)-3-(3,4-difluorophenyl)-3-hydroxy-1,4,6,7,9,9a-hexahydropyrazino[2,1-c][1,4]oxazin-8-yl]-[2-chloro-3-(3-fluoro-1H-pyrazol-4-yl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(3-hydroxyazetidin-1-yl)phenyl]methanone;

[(3R,9aS)-3-hydroxy-3-[6-(trifluoromethyl)-3-pyridyl]-1,4,6,7,9,9a-hexahydropyrazino[2,1-c][1,4]oxazin-8-yl]-[2-chloro-3-(3-fluoro-1H-pyrazol-4-yl)phenyl]methanone;

[2-chloro-3-(3-fluoro-1H-pyrazol-4-yl)phenyl]-[rac-(9aS)-3-[6-(trifluoromethyl)-3-pyridyl]-3,4,6,7,9,9a-hexahydro-1H-pyrazino[2,1-c][1,4]oxazin-8-yl]methanone;

[(3R,9aS)-3-(3-chloro-4-fluoro-phenyl)-3,4,6,7,9,9a-hexahydro-1H-pyrazino[2,1-c][1,4]oxazin-8-yl]-(2-chloro-3-methoxy-phenyl)methanone;

[(3R,9aS)-3-(3-chloro-4-fluoro-phenyl)-3-hydroxy-1,4,6,7,9,9a-hexahydropyrazino[2,1-c][1,4]oxazin-8-yl]-(2-chloro-3-methoxy-phenyl)methanone;

[2-chloro-3-(3-fluoro-1H-pyrazol-4-yl)phenyl]-[rac-(9aS)-3-[4-(difluoromethoxy)phenyl]-3,4,6,7,9,9a-hexahydro-1H-pyrazino[2,1-c][1,4]oxazin-8-yl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(5-methyl-1H-pyrazol-4-yl)phenyl]methanone;

[(3S,9aS)-3-fluoro-3-[6-(trifluoromethyl)-3-pyridyl]-1,4,6,7,9,9a-hexahydropyrazino[2,1-c][1,4]oxazin-8-yl]-[2-chloro-3-(3-fluoro-1H-pyrazol-4-yl)phenyl]methanone;

[(9aS)-3-(3-bromo-4-fluoro-phenyl)-3,4,6,7,9,9a-hexahydro-1H-pyrazino[2,1-c][1,4]oxazin-8-yl]-(2-chloro-3-methoxy-phenyl)methanone;

[(3S,9aS)-3-(4-bromo-5-chloro-2-pyridyl)-3,4,6,7,9,9a-hexahydro-1H-pyrazino[2,1-c][1,4]oxazin-8-yl]-(2-chloro-3-methoxy-phenyl)methanone;

5-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]-1H-pyridin-2-one;

[(9aS)-3-(3-chloro-4-fluoro-phenyl)-3,4,6,7,9,9a-hexahydro-1H-pyrazino[2,1-c][1,4]oxazin-8-yl]-(2-bromo-3-methoxy-phenyl)methanone;

[(3R,9aS)-3-(3-chloro-4-fluoro-phenyl)-3-hydroxy-1,4,6,7,9,9a-hexahydropyrazino[2,1-c][1,4]oxazin-8-yl]-(2-chloro-3-oxazol-5-yl-phenyl)methanone;

[(3R,9aS)-3-hydroxy-3-[6-(trifluoromethyl)-3-pyridyl]-1,4,6,7,9,9a-hexahydropyrazino[2,1-c][1,4]oxazin-8-yl]-[2-chloro-3-(1H-pyrazol-4-yl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-(2-chloro-3-phenyl-phenyl)methanone;

[(3R,9aS)-3-(3-chloro-4-fluoro-phenyl)-3,4,6,7,9,9a-hexahydro-TH-pyrazino[2,1-c][1,4]oxazin-8-yl]-[2-fluoro-3-[5-(trifluoromethyl)-1H-pyrazol-4-yl]phenyl]methanone;

4-[3-[(3R,9aS)-3-hydroxy-3-[6-(trifluoromethyl)-3-pyridyl]-1,4,6,7,9,9a-hexahydropyrazino[2,1-c][1,4]oxazine-8-carbonyl]-2-chloro-phenyl]-1H-pyrazole-3-carbonitrile;

[(3R,9aS)-3-(3-chloro-4-fluoro-phenyl)-3,4,6,7,9,9a-hexahydro-TH-pyrazino[2,1-c][1,4]oxazin-8-yl]-[2-chloro-3-(2-methoxyphenyl)phenyl]methanone;

[(9aS)-3-(3-chloro-4-fluoro-phenyl)-3,4,6,7,9,9a-hexahydro-TH-pyrazino[2,1-c][1,4]oxazin-8-yl]-(4-chlorothieno[2,3-b]pyridin-5-yl)methanone;

[(3R,9aS)-3-(3-chloro-4-fluoro-phenyl)-3,4,6,7,9,9a-hexahydro-TH-pyrazino[2,1-c][1,4]oxazin-8-yl]-[3-[5-(trifluoromethyl)-1H-pyrazol-4-yl]phenyl]methanone;

[(3S,9aS)-3-[5-chloro-4-(trifluoromethyl)-2-pyridyl]-3,4,6,7,9,9a-hexahydro-1H-pyrazino[2,1-c][1,4]oxazin-8-yl]-(2-chloro-3-methoxy-phenyl)methanone;

[(3R,9aS)-3-(3-chloro-4-fluoro-phenyl)-3,4,6,7,9,9a-hexahydro-TH-pyrazino[2,1-c][1,4]oxazin-8-yl]-[2-chloro-3-(3-methyl-4-pyridyl)phenyl]methanone;

[(3S,9aS)-3-hydroxy-3-[5-(trifluoromethyl)-2-pyridyl]-1,4,6,7,9,9a-hexahydropyrazino[2,1-c][1,4]oxazin-8-yl]-[2-chloro-3-(3-fluoro-1H-pyrazol-4-yl)phenyl]methanone;

[2-chloro-3-(3-fluoro-1H-pyrazol-4-yl)phenyl]-[rac-(9aS)-3-(5-bromo-2-pyridyl)-3,4,6,7,9,9a-hexahydro-1H-pyrazino[2,1-c][1,4]oxazin-8-yl]methanone;

3-[(3R,9aS)-8-[2-chloro-3-(3-fluoro-TH-pyrazol-4-yl)benzoyl]-3,4,6,7,9,9a-hexahydro-H-pyrazino[2,1-c][1,4]oxazin-3-yl]-5-chloro-TH-pyridin-2-one;

[(3R,9aS)-3-(3-chloro-4-fluoro-phenyl)-3,4,6,7,9,9a-hexahydro-TH-pyrazino[2,1-c][1,4]oxazin-8-yl]-[2-chloro-3-(2-oxa-6-azaspiro[3.3]heptan-6-yl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(2-pyridyl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(1,5-dimethylpyrazol-4-yl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(1H-triazol-5-yl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-(2-chloro-3,5-dimethoxy-phenyl)methanone;

[(3R,9aS)-3-[4-(difluoromethoxy)phenyl]-3-hydroxy-1,4,6,7,9,9a-hexahydropyrazino[2,1-c][1,4]oxazin-8-yl]-[2-chloro-3-(3-fluoro-1H-pyrazol-4-yl)phenyl]methanone;

3-[(3R,9aS)-8-[2-chloro-3-(3-fluoro-1H-pyrazol-4-yl)benzoyl]-3-hydroxy-1,4,6,7,9,9a-hexahydropyrazino[2,1-c][1,4]oxazin-3-yl]-6-(trifluoromethyl)-1H-pyridin-2-one;

5-[(9aS)-8-[2-chloro-3-(3-fluoro-1H-pyrazol-4-yl)benzoyl]-3,4,6,7,9,9a-hexahydro-1H-pyrazino[2,1-c][1,4]oxazin-3-yl]-2-fluoro-benzonitrile;

[(3R,9aS)-3-(3-chloro-4-fluoro-phenyl)-3,4,6,7,9,9a-hexahydro-1H-pyrazino[2,1-c][1,4]oxazin-8-yl]-(4-chloro-3-methyl-1H-indazol-5-yl)methanone;

(2-chloro-3-methoxy-phenyl)-[rac-(3R,9aR)-3-(5-bromo-2-pyridyl)-3,4,6,7,9,9a-hexahydro-1H-pyrazino[2,1-c][1,4]oxazin-8-yl]methanone;

[(3R,9aS)-3-hydroxy-3-[6-(trifluoromethyl)-3-pyridyl]-1,4,6,7,9,9a-hexahydropyrazino[2,1-c][1,4]oxazin-8-yl]-[3-(3-fluoro-1H-pyrazol-4-yl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-(2-fluoro-3-methoxy-phenyl)methanone;

[(3S,9aS)-3-[5-chloro-4-(difluoromethyl)-2-pyridyl]-3,4,6,7,9,9a-hexahydro-1H-pyrazino[2,1-c][1,4]oxazin-8-yl]-(2-chloro-3-methoxy-phenyl)methanone;

[(3S,9aS)-3-(5-chloro-4-methyl-2-pyridyl)-3,4,6,7,9,9a-hexahydro-1H-pyrazino[2,1-c][1,4]oxazin-8-yl]-(2-chloro-3-methoxy-phenyl)methanone;

[(9aS)-3-(3-cyclopropyl-4-fluoro-phenyl)-3,4,6,7,9,9a-hexahydro-1H-pyrazino[2,1-c][1,4]oxazin-8-yl]-(2-chloro-3-methoxy-phenyl)methanone;

[(3R,9aS)-3-(3-chloro-4-fluoro-phenyl)-3,4,6,7,9,9a-hexahydro-1H-pyrazino[2,1-c][1,4]oxazin-8-yl]-(2-chloro-3-morpholino-phenyl)methanone;

2-[(3R,9aS)-3-(3-chloro-4-fluoro-phenyl)-3,4,6,7,9,9a-hexahydro-1H-pyrazino[2,1-c][1,4]oxazine-8-carbonyl]-6-methyl-benzonitrile;

[(3R,9aS)-3-hydroxy-3-[6-(trifluoromethyl)-3-pyridyl]-1,4,6,7,9,9a-hexahydropyrazino[2,1-c][1,4]oxazin-8-yl]-[2-fluoro-3-(3-fluoro-1H-pyrazol-4-yl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(difluoromethoxy)phenyl]methanone;

[(9aS)-3-(3-chloro-4-fluoro-phenyl)-3,4,6,7,9,9a-hexahydro-1H-pyrazino[2,1-c][1,4]oxazin-8-yl]-(4-chloro-3-quinolyl)methanone;

[(3S,9aS)-3-[5-fluoro-4-(trifluoromethyl)-2-pyridyl]-3,4,6,7,9,9a-hexahydro-1H-pyrazino[2,1-c][1,4]oxazin-8-yl]-(2-chloro-3-methoxy-phenyl)methanone;

[3-(3-bicyclo[4.2.0]octa-1,3,5-trienyl)-3,4,6,7,9,9a-hexahydro-1H-pyrazino[2,1-c][1,4]oxazin-8-yl]-(2-chloro-3-methoxy-phenyl)methanone;

(2-chloro-3-methoxy-phenyl)-[3-[4-(difluoromethyl)phenyl]-3,4,6,7,9,9a-hexahydro-1H-pyrazino[2,1-c][1,4]oxazin-8-yl]methanone;

(2-chloro-3-methoxy-phenyl)-[rac-(3S,9aS)-3-(4-chloro-2-pyridyl)-3,4,6,7,9,9a-hexahydro-TH-pyrazino[2,1-c][1,4]oxazin-8-yl]methanone;

5-[(9aS)-8-(2-chloro-3-methoxy-benzoyl)-3,4,6,7,9,9a-hexahydro-TH-pyrazino[2,1-c][1,4]oxazin-3-yl]-2-fluoro-benzonitrile;

[(3R,9aS)-3-(3-chloro-4-fluoro-phenyl)-3,4,6,7,9,9a-hexahydro-TH-pyrazino[2,1-c][1,4]oxazin-8-yl]-[2-chloro-3-(3-methylisoxazol-4-yl)phenyl]methanone;

[(3R,9aS)-3-(3-chloro-4-fluoro-phenyl)-3,4,6,7,9,9a-hexahydro-TH-pyrazino[2,1-c][1,4]oxazin-8-yl]-(2-chloro-3-pyridazin-3-yl-phenyl)methanone;

(2-chloro-3-methoxy-phenyl)-[rac-(9aS)-3-[4-fluoro-3-[rac-(E)-prop-1-enyl]phenyl]-3,4,6,7,9,9a-hexahydro-1H-pyrazino[2,1-c][1,4]oxazin-8-yl]methanone;

[(3R,9aS)-3-(3-chloro-4-fluoro-phenyl)-3,4,6,7,9,9a-hexahydro-TH-pyrazino[2,1-c][1,4]oxazin-8-yl]-(2-chloro-3-pyridazin-4-yl-phenyl)methanone;

[(3R,9aS)-3-(3-chloro-4-fluoro-phenyl)-3,4,6,7,9,9a-hexahydro-TH-pyrazino[2,1-c][1,4]oxazin-8-yl]-[2-chloro-3-(4-methyl-3-pyridyl)phenyl]methanone;

[(9aS)-3-[5-(trifluoromethyl)-2-pyridyl]-6,7,9,9a-tetrahydro-TH-pyrazino[2,1-c][1,4]oxazin-8-yl]-[2-chloro-3-(3-fluoro-TH-pyrazol-4-yl)phenyl]methanone;

[(3S,9aS)-3-(4-chloro-2-pyridyl)-3,4,6,7,9,9a-hexahydro-1H-pyrazino[2,1-c][1,4]oxazin-8-yl]-(2-chloro-3-methoxy-phenyl)methanone;

[(3S,9aS)-3-hydroxy-3-[5-(trifluoromethyl)-2-pyridyl]-1,4,6,7,9,9a-hexahydropyrazino[2,1-c][1,4]oxazin-8-yl]-(2-chloro-3-oxazol-5-yl-phenyl)methanone;

[(9aS)-3-(4-fluoro-3-prop-1-ynyl-phenyl)-3,4,6,7,9,9a-hexahydro-1H-pyrazino[2,1-c][1,4]oxazin-8-yl]-(2-chloro-3-methoxy-phenyl)methanone;

[(9aS)-3-(4-fluoro-3-phenyl-phenyl)-3,4,6,7,9,9a-hexahydro-1H-pyrazino[2,1-c][1,4]oxazin-8-yl]-(2-chloro-3-methoxy-phenyl)methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(3-methyl-2-pyridyl)phenyl]methanone;

[(3S,9aS)-3-[4-(trifluoromethoxy)-2-pyridyl]-3,4,6,7,9,9a-hexahydro-1H-pyrazino[2,1-c][1,4]oxazin-8-yl]-(2-chloro-3-methoxy-phenyl)methanone;

[(3R,9aR)-3-(1H-benzimidazol-2-yl)-3-hydroxy-1,4,6,7,9,9a-hexahydropyrazino[2,1-c][1,4]oxazin-8-yl]-(2-chloro-3-methoxy-phenyl)methanone;

[(3R,9aS)-3-(3-chloro-4-fluoro-phenyl)-3,4,6,7,9,9a-hexahydro-1H-pyrazino[2,1-c][1,4]oxazin-8-yl]-(2-chloro-3,4-dimethoxy-phenyl)methanone;

4-(2-chloro-3-((3R,9aS)-3-(3,4-difluorophenyl)-3-hydroxyoctahydropyrazino[2,1-c][1,4]oxazine-8-carbonyl)phenyl)-1H-pyrrole-2-carbonitrile;

(2-chloro-3-methoxyphenyl)((3R,9aS)-3-hydroxy-3-(2,4,5-trifluorophenyl)hexahydropyrazino[2,1-c][1,4]oxazin-8(1H)-yl)methanone;

(2-chloro-3-methoxyphenyl)((3R,9aS)-3-(2,4,5-trifluorophenyl)hexahydropyrazino[2,1-c][1,4]oxazin-8(1H)-yl)methanone;

(2-chloro-3-(isothiazol-4-yl)phenyl)((3R,9aS)-3-(3-chloro-4-fluorophenyl)-3-hydroxyhexahydropyrazino[2,1-c][1,4]oxazin-8(1H)-yl)methanone;

4-(2-chloro-3-((3R,9aS)-3-(5-chloro-2-oxo-1,2-dihydropyridin-3-yl)octahydropyrazino[2,1-c][1,4]oxazine-8-carbonyl)phenyl)-1H-pyrrole-2-carbonitrile;

5-(2-chloro-3-((3R,9aS)-3-(3,4-dichlorophenyl)octahydropyrazino[2,1-c][1,4]oxazine-8-carbonyl)phenyl)oxazol-2(3H)-one;

5-(2-chloro-3-((3R,9aS)-3-(3-chloro-4-fluorophenyl)octahydropyrazino[2,1-c][1,4]oxazine-8-carbonyl)phenyl)oxazol-2(3H)-one;

4-(2-chloro-3-((3R,9aS)-3-(3-chloro-4-fluorophenyl)-3-hydroxyoctahydropyrazino[2,1-c][1,4]oxazine-8-carbonyl)phenyl)-1H-pyrrole-2-carbonitrile;

4-(2-chloro-3-((3R,9aS)-3-(3-chloro-4-fluorophenyl)octahydropyrazino[2,1-c][1,4]oxazine-8-carbonyl)-5-fluorophenyl)pyridin-2(1H)-one;

(2-chloro-3-methoxyphenyl)((9aS)-3-(4-fluoro-3-(oxazol-5-yl)phenyl)hexahydropyrazino[2,1-c][1,4]oxazin-8(1H)-yl)methanone;

5-(2-chloro-3-((3R,9aS)-3-(3,4-dichlorophenyl)-3-hydroxyoctahydropyrazino[2,1-c][1,4]oxazine-8-carbonyl)phenyl)oxazol-2(3H)-one;

(2-chloro-3-methoxyphenyl)((9aS)-3-(4-fluoro-3-(1-methyl-1H-pyrrol-3-yl)phenyl)hexahydropyrazino[2,1-c][1,4]oxazin-8(1H)-yl)methanone;

((3R,9aS)-3-(4-bromo-3-chlorophenyl)hexahydropyrazino[2,1-c][1,4]oxazin-8(1H)-yl)(2-chloro-3-methoxyphenyl)methanone;

4-(2-chloro-3-((3R,9aS)-3-(3-chloro-4-fluorophenyl)octahydropyrazino[2,1-c][1,4]oxazine-8-carbonyl)phenyl)-6-methylpyridin-2(1H)-one;

5-(2-chloro-3-((3R,9aS)-3-(3-chloro-4-fluorophenyl)octahydropyrazino[2,1-c][1,4]oxazine-8-carbonyl)phenyl)-6-methylpyridin-2(1H)-one;

(2-chloro-3-methoxyphenyl)((3R,9aS)-3-(2-chlorophenyl)-3-hydroxyhexahydropyrazino[2,1-c][1,4]oxazin-8(1H)-yl)methanone;

(2-chloro-3-methoxyphenyl)((3R,9aS)-3-(2,4-dichlorophenyl)-3-hydroxyhexahydropyrazino[2,1-c][1,4]oxazin-8(1H)-yl)methanone;

(2-chloro-3-methoxyphenyl)((3R,9aS)-3-hydroxy-3-(4-(trifluoromethyl)phenyl)hexahydropyrazino[2,1-c][1,4]oxazin-8(1H)-yl)methanone;

(2-chloro-3-methoxyphenyl)((3R,9aS)-3-hydroxy-3-(2,3,4-trifluorophenyl)hexahydropyrazino[2,1-c][1,4]oxazin-8(1H)-yl)methanone;

(2-chloro-3-methoxyphenyl)((3R,9aS)-3-(3-chloro-4-(oxazol-5-yl)phenyl)hexahydropyrazino[2,1-c][1,4]oxazin-8(1H)-yl)methanone;

4-(2-chloro-3-((3R,9aS)-3-(3-chloro-4-fluorophenyl)octahydropyrazino[2,1-c][1,4]oxazine-8-carbonyl)phenyl)piperazin-2-one;

5-(2-chloro-3-((3R,9aS)-3-(3-chloro-4-fluorophenyl)octahydropyrazino[2,1-c][1,4]oxazine-8-carbonyl)phenyl)-1,3,4-oxadiazol-2(3H)-one;

((3R,9aS)-3-(3-bromo-5-chlorophenyl)-3-hydroxyhexahydropyrazino[2,1-c][1,4]oxazin-8(1H)-yl)(2-chloro-3-methoxyphenyl)methanone;

(2-chloro-3-methoxyphenyl)((3R,9aS)-3-hydroxy-3-(3-(trifluoromethyl)phenyl)hexahydropyrazino[2,1-c][1,4]oxazin-8(1H)-yl)methanone;

(2-chloro-3-methoxyphenyl)((3R,9aS)-3-(3-chloro-5-(oxazol-5-yl)phenyl)-3-hydroxyhexahydropyrazino[2,1-c][1,4]oxazin-8(1H)-yl)methanone;

((3R,9aS)-3-(4-chloro-3-fluorophenyl)-3-hydroxyhexahydropyrazino[2,1-c][1,4]oxazin-8(1H)-yl)(2-chloro-3-methoxyphenyl)methanone;

(2-chloro-3-methoxyphenyl)((3R,9aS)-3-(2,3-difluorophenyl)-3-hydroxyhexahydropyrazino[2,1-c][1,4]oxazin-8(1H)-yl)methanone;

(2-chloro-3-methoxyphenyl)((3R,9aS)-3-(2,3-difluorophenyl)hexahydropyrazino[2,1-c][1,4]oxazin-8(1H)-yl)methanone;

3-(2-chloro-3-((3R,9aS)-3-(3-chloro-4-fluorophenyl)octahydropyrazino[2,1-c][1,4]oxazine-8-carbonyl)phenyl)-1H-pyrazole-5-carbonitrile;

((3S,9aS)-3-(benzo[d]thiazol-2-yl)-3-hydroxyhexahydropyrazino[2,1-c][1,4]oxazin-8(1H)-yl)(2-chloro-3-methoxyphenyl)methanone;

(2-chloro-3-methoxyphenyl)((3S,9aS)-3-hydroxy-3-(3-phenylisoxazol-5-yl)hexahydropyrazino[2,1-c][1,4]oxazin-8(1H)-yl)methanone;

(2-chloro-3-methoxyphenyl)((3S,9aS)-3-(2-(4-fluorophenyl)thiazol-4-yl)-3-hydroxyhexahydropyrazino[2,1-c][1,4]oxazin-8(1H)-yl)methanone;

(2-chloro-3-methoxyphenyl)((3S,9aS)-3-hydroxy-3-(2-(6-methoxypyridin-3-yl)thiazol-4-yl)hexahydropyrazino[2,1-c][1,4]oxazin-8(1H)-yl)methanone;

(2-chloro-3-methoxyphenyl)((3S,9aS)-3-(5-chloro-6-(trifluoromethyl)pyridin-2-yl)hexahydropyrazino[2,1-c][1,4]oxazin-8(1H)-yl)methanone;

((3S,9aS)-3-(4-bromo-5-methoxythiophen-2-yl)-3-hydroxyhexahydropyrazino[2,1-c][1,4]oxazin-8(1H)-yl)(2-chloro-3-methoxyphenyl)methanone;

((3S,9aS)-3-(3-bromoisoxazol-5-yl)-3-hydroxyhexahydropyrazino[2,1-c][1,4]oxazin-8(1H)-yl)(2-chloro-3-methoxyphenyl)methanone;

3-((3R,9aS)-8-(2-chloro-3-methoxybenzoyl)-3-hydroxyoctahydropyrazino[2,1-c][1,4]oxazin-3-yl)-6-(trifluoromethyl)pyridin-2(1H)-one;

5-[(3#R!,9#a!#S!)-8-(2-chloro-3-methoxybenzoyl)-3,4,6,7,9,9#a!-hexahydro-1#H!-pyrazino[2,1-c][1,4]oxazin-3-yl]-3-chloro-2-fluorobenzonitrile;

5-(2-chloro-3-((3R,9aS)-3-(3,4-difluorophenyl)-3-hydroxyoctahydropyrazino[2,1-c][1,4]oxazine-8-carbonyl)phenyl)-1H-imidazole-2-carbonitrile;

(2-chloro-3-methoxyphenyl)((3R,9aS)-3-hydroxy-3-(2-methyl-6-(trifluoromethyl)pyridin-3-yl)hexahydropyrazino[2,1-c][1,4]oxazin-8(1H)-yl)methanone;

5-(2-chloro-3-((3R,9aS)-3-(3-chloro-4-fluorophenyl)octahydropyrazino[2,1-c][1,4]oxazine-8-carbonyl)phenyl)pyridazin-4(1H)-one;

5-chloro-3-((3R,9aS)-8-(2-chloro-5-fluoro-3-(3-fluoro-1H-pyrazol-4-yl)benzoyl)octahydropyrazino[2,1-c][1,4]oxazin-3-yl)pyridin-2(1H)-one;

4-(2-chloro-3-((3R,9aS)-3-(5-chloro-2-oxo-1,2-dihydropyridin-3-yl)octahydropyrazino[2,1-c][1,4]oxazine-8-carbonyl)-5-fluorophenyl)-1H-pyrrole-2-carbonitrile;

5-chloro-3-((3R,9aS)-8-(2-chloro-3-(4-fluoro-1H-pyrazol-3-yl)benzoyl)octahydropyrazino[2,1-c][1,4]oxazin-3-yl)pyridin-2(1H)-one;

4-(2-chloro-5-fluoro-3-((3R,9aS)-3-(4-oxo-6-(trifluoromethyl)-1,4-dihydropyridin-3-yl)octahydropyrazino[2,1-c][1,4]oxazine-8-carbonyl)phenyl)-1H-pyrrole-2-carbonitrile;

4-(2-chloro-5-fluoro-3-((3R,9aS)-3-(2-oxo-6-(trifluoromethyl)-1,2-dihydropyridin-3-yl)octahydropyrazino[2,1-c][1,4]oxazine-8-carbonyl)phenyl)-1H-pyrrole-2-carbonitrile;

4-(2-chloro-5-fluoro-3-((3S,9aS)-3-(4-oxo-6-(trifluoromethyl)-1,4-dihydropyridin-3-yl)octahydropyrazino[2,1-c][1,4]oxazine-8-carbonyl)phenyl)-1H-pyrrole-2-carbonitrile;

3-((3R,9aS)-8-(2-chloro-3-methoxybenzoyl)octahydropyrazino[2,1-c][1,4]oxazin-3-yl)-6-(trifluoromethyl)pyridin-2(1H)-one;

((3R,9aS)-3-(3-chloro-4-fluorophenyl)-3-hydroxyhexahydropyrazino[2,1-c][1,4]oxazin-8(1H)-yl)(2-chloro-6-fluoro-3-methoxyphenyl)methanone;

((3R,9aS)-3-(3-chloro-4-fluorophenyl)hexahydropyrazino[2,1-c][1,4]oxazin-8(1H)-yl)(2-chloro-6-fluoro-3-methoxyphenyl)methanone;

((3S,9aS)-3-(3-chloro-4-fluorophenyl)hexahydropyrazino[2,1-c][1,4]oxazin-8(1H)-yl)(2-chloro-6-fluoro-3-methoxyphenyl)methanone;

5-chloro-3-((3R,9aS)-8-(2-chloro-6-fluoro-3-methoxybenzoyl)octahydropyrazino[2,1-c][1,4]oxazin-3-yl)pyridin-2(1H)-one; and

[(9aS)-3-(3-chloro-4-fluoro-phenyl)-3,4,6,7,9,9a-hexahydro-1H-pyrazino[2,1-c][1,4]thiazin-8-yl]-(2-chloro-3-methoxy-phenyl)methanone.

E41 The compound of formula (I) according to A1 or A2, or a pharmaceutically acceptable salt thereof, wherein the compound of formula (I) is selected from:

4-(2-chloro-3-((3R,9aS)-3-(5-chloro-2-oxo-1,2-dihydropyridin-3-yl)octahydropyrazino[2,1-c][1,4]oxazine-8-carbonyl)phenyl)-1H-pyrrole-2-carbonitrile;

4-(2-chloro-3-((3R,9aS)-3-(3-chloro-4-fluorophenyl)-3-hydroxyoctahydropyrazino[2,1-c][1,4]oxazine-8-carbonyl)phenyl)-1H-pyrrole-2-carbonitrile;

4-(2-chloro-3-((3R,9aS)-3-(3-chloro-4-fluorophenyl)octahydropyrazino[2,1-c][1,4]oxazine-8-carbonyl)-5-fluorophenyl)pyridin-2(1H)-one;

4-(2-chloro-3-((3R,9aS)-3-(5-chloro-2-oxo-1,2-dihydropyridin-3-yl)octahydropyrazino[2,1-c][1,4]oxazine-8-carbonyl)-5-fluorophenyl)-1H-pyrrole-2-carbonitrile;

4-(2-chloro-5-fluoro-3-((3R,9aS)-3-(2-oxo-6-(trifluoromethyl)-1,2-dihydropyridin-3-yl)octahydropyrazino[2,1-c][1,4]oxazine-8-carbonyl)phenyl)-1H-pyrrole-2-carbonitrile;

((3R,9aS)-3-(3-chloro-4-fluorophenyl)hexahydropyrazino[2,1-c][1,4]oxazin-8(1H)-yl)(2-chloro-6-fluoro-3-methoxyphenyl)methanone;

[2-chloro-3-(3-fluoro-1H-pyrazol-4-yl)phenyl]-[rac-(3R,9aS)-3-(3-chloro-4-fluoro-phenyl)-3,4,6,7,9,9a-hexahydro-1H-pyrazino[2,1-c][1,4]oxazin-8-yl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(1H-pyrazol-4-yl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(1H-imidazol-5-yl)phenyl]methanone;

[(3R,9aS)-3-(3,4-difluorophenyl)-3,4,6,7,9,9a-hexahydro-1H-pyrazino[2,1-c][1,4]oxazin-8-yl]-[2-chloro-3-(3-fluoro-1H-pyrazol-4-yl)phenyl]methanone;

[(3S,9aS)-3-(4,5-dichloro-2-pyridyl)-3,4,6,7,9,9a-hexahydro-1H-pyrazino[2,1-c][1,4]oxazin-8-yl]-(2-chloro-3-methoxy-phenyl)methanone;

4-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]-1H-pyridin-2-one;

[(3R,9aS)-3-(3,4-difluorophenyl)-3-hydroxy-1,4,6,7,9,9a-hexahydropyrazino[2,1-c][1,4]oxazin-8-yl]-[2-chloro-3-(3-fluoro-1H-pyrazol-4-yl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(3-hydroxyazetidin-1-yl)phenyl]methanone;

[(3R,9aS)-3-hydroxy-3-[6-(trifluoromethyl)-3-pyridyl]-1,4,6,7,9,9a-hexahydropyrazino[2,1-c][1,4]oxazin-8-yl]-[2-chloro-3-(3-fluoro-1H-pyrazol-4-yl)phenyl]methanone;

[2-chloro-3-(3-fluoro-1H-pyrazol-4-yl)phenyl]-[rac-(9aS)-3-[6-(trifluoromethyl)-3-pyridyl]-3,4,6,7,9,9a-hexahydro-1H-pyrazino[2,1-c][1,4]oxazin-8-yl]methanone;

[(3R,9aS)-3-(3-chloro-4-fluoro-phenyl)-3,4,6,7,9,9a-hexahydro-TH-pyrazino[2,1-c][1,4]oxazin-8-yl]-(2-chloro-3-methoxy-phenyl)methanone;

[(3R,9aS)-3-(3-chloro-4-fluoro-phenyl)-3-hydroxy-1,4,6,7,9,9a-hexahydropyrazino[2,1-c][1,4]oxazin-8-yl]-(2-chloro-3-methoxy-phenyl)methanone; and

[2-chloro-3-(3-fluoro-1H-pyrazol-4-yl)phenyl]-[rac-(9aS)-3-[4-(difluoromethoxy)phenyl]-3,4,6,7,9,9a-hexahydro-1H-pyrazino[2,1-c][1,4]oxazin-8-yl]methanone.

In one embodiment, the present invention provides a compound of formula (I) as described herein, or a pharmaceutically acceptable salt thereof, wherein X is $—CH_2CR^3R^4—$ or $—CH═CR^3—$;

$R^3$ is a group

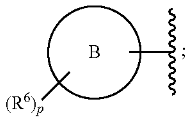

;

$R^4$ is hydrogen, halogen or hydroxy;

$R^6$ is hydrogen, halogen, $C_6$-$C_{14}$-aryl, 5- to 14-membered heteroaryl, halo-$C_1$-$C_6$-alkoxy, halo-$C_1$-$C_6$-alkyl, oxo, $C_1$-$C_6$-alkyl, $C_1$-$C_6$-alkoxy, $C_2$-$C_6$-alkenyl, $C_2$-$C_6$-alkynyl, $C_3$-$C_{14}$-cycloalkyl or cyano, wherein said 5- to 14-membered heteroaryl or $C_6$-$C_{14}$-aryl is optionally substituted with a substituent selected from halogen, $C_1$-$C_6$-alkyl and $C_1$-$C_6$-alkoxy;

B is 5- to 14-membered heteroaryl, $C_6$-$C_{14}$-aryl or 3- to 14-membered heterocyclyl; and p is 1, 2 or 3.

In a preferred embodiment, the present invention provides a compound of formula (I) as described herein, or a pharmaceutically acceptable salt thereof, wherein X is —$CH_2CR^3R^4$—;

$R^3$ is a group

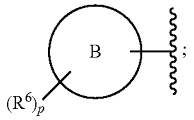

$R^4$ is hydrogen or hydroxy;

$R^6$ is halogen, oxo, halo-$C_1$-$C_6$-alkyl or halo-$C_1$-$C_6$-alkoxy;

B is $C_6$-$C_{14}$-aryl or 5- to 14-membered heteroaryl; and p is 1 or 2.

In a particularly preferred embodiment, the present invention provides a compound of formula (I) as described herein, or a pharmaceutically acceptable salt thereof, wherein X is —$CH_2CR^3R^4$—;

$R^3$ is a group

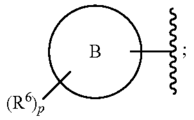

$R^4$ is hydrogen or hydroxy;

$R^6$ is chloro, fluoro, oxo, trifluoromethyl or difluoromethoxy;

B is phenyl, 1,2-dihydropyridinyl or pyridyl; and p is 1 or 2.

In one embodiment, the present invention provides a compound of formula (I) as described herein, or a pharmaceutically acceptable salt thereof, wherein $R^3$ is a group

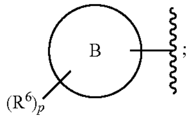

wherein $R^6$ is hydrogen, halogen, $C_6$-$C_{14}$-aryl, 5- to 14-membered heteroaryl, halo-$C_1$-$C_6$-alkoxy, halo-$C_1$-$C_6$-alkyl, oxo, $C_1$-$C_6$-alkyl, $C_1$-$C_6$-alkoxy, $C_2$-$C_6$-alkenyl, $C_2$-$C_6$-alkynyl, $C_3$-$C_{14}$-cycloalkyl or cyano, wherein said 5- to 14-membered heteroaryl or $C_6$-$C_{14}$-aryl is optionally substituted with a substituent selected from halogen, $C_1$-$C_6$-alkyl and $C_1$-$C_6$-alkoxy;

B is 5- to 14-membered heteroaryl, $C_6$-$C_{14}$-aryl or 3- to 14-membered heterocyclyl; and p is 1, 2 or 3.

In a preferred embodiment, the present invention provides a compound of formula (I) as described herein, or a pharmaceutically acceptable salt thereof, wherein $R^3$ is a group

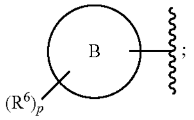

wherein $R^6$ is halogen, oxo, halo-$C_1$-$C_6$-alkyl or halo-$C_1$-$C_6$-alkoxy;

B is $C_6$-$C_{14}$-aryl or 5- to 14-membered heteroaryl; and p is 1 or 2.

In a particularly preferred embodiment, the present invention provides a compound of formula (I) as described herein, or a pharmaceutically acceptable salt thereof, wherein $R^3$ is a group

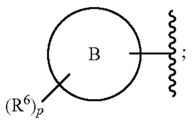

wherein $R^6$ is chloro, fluoro, oxo, trifluoromethyl or difluoromethoxy;

B is phenyl, 1,2-dihydropyridinyl or pyridyl; and p is 1 or 2.

In one embodiment, the present invention provides a compound of formula (I) as described herein, or a pharmaceutically acceptable salt thereof, wherein $R^1$ is $C_6$-$C_{14}$-aryl or 5- to 14-membered heteroaryl, wherein said $C_6$-$C_{14}$-aryl or 5- to 14-membered heteroaryl are substituted with 1-3 substituents independently selected from $C_1$-$C_6$-alkyl, $C_1$-$C_6$-alkoxy, halo-$C_1$-$C_6$-alkoxy, halogen, cyano and a group

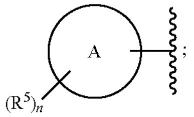

$R^5$ is hydrogen, halogen, hydroxy, halo-$C_1$-$C_6$-alkyl, $C_1$-$C_6$-alkoxy, $C_1$-$C_6$-alkyl, cyano or oxo;

A is 5- to 14-membered heteroaryl, $C_6$-$C_{14}$-aryl or 3- to 14-membered heterocyclyl; and n is 1 or 2.

In a preferred embodiment, the present invention provides a compound of formula (I) as described herein, or a pharmaceutically acceptable salt thereof, wherein $R^1$ is $C_6$-$C_{14}$-aryl substituted with 1-2 substituents independently selected from $C_1$-$C_6$-alkoxy, halogen, and a group

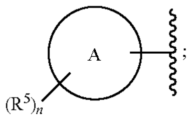

$R^5$ is hydrogen, halogen, cyano, hydroxy or oxo;

A is 5- to 14-membered heteroaryl or 3- to 14-membered heterocyclyl; and n is 1 or 2.

In a particularly preferred embodiment, the present invention provides a compound of formula (I) as described herein, or a pharmaceutically acceptable salt thereof, wherein $R^1$ is phenyl substituted with 2 substituents independently selected from chloro, methoxy and a group

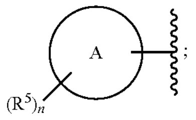

$R^5$ is hydrogen, fluoro, cyano, hydroxy or oxo;

A is imidazolyl, pyrazolyl, pyrrolyl or 1,2-dihydropyridinyl; and n is 1 or 2.

In one embodiment, the present invention provides a compound of formula (I) as described herein, or a pharmaceutically acceptable salt thereof, wherein $R^5$ is hydrogen, halogen, hydroxy, halo-$C_1$-$C_6$-alkyl, $C_1$-$C_6$-alkoxy, $C_1$-$C_6$-alkyl, cyano or oxo;

A is 5- to 14-membered heteroaryl, $C_6$-$C_{14}$-aryl or 3- to 14-membered heterocyclyl; and n is 1 or 2.

In a preferred embodiment, the present invention provides a compound of formula (I) as described herein, or a pharmaceutically acceptable salt thereof, wherein $R^5$ is hydrogen, halogen, cyano, hydroxy or oxo;

A is 5- to 14-membered heteroaryl or 3- to 14-membered heterocyclyl; and n is 1 or 2.

In a particularly preferred embodiment, the present invention provides a compound of formula (I) as described herein, or a pharmaceutically acceptable salt thereof, wherein $R^5$ is hydrogen, fluoro, cyano, hydroxy or oxo;

A is imidazolyl, pyrazolyl, pyrrolyl or 1,2-dihydropyridinyl; and n is 1 or 2.

In one embodiment, the present invention provides a compound of formula (I) as described herein, or a pharmaceutically acceptable salt thereof, wherein $R^1$ is (a) 5- to 14-membered heteroaryl substituted with 1 substituent selected from halogen; or (b) a group

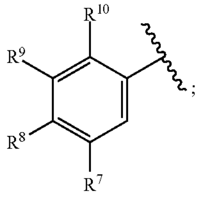

wherein $R^7$ is hydrogen or $C_1$-$C_6$-alkoxy;

$R^8$ is hydrogen or $C_1$-$C_6$-alkoxy;

$R^9$ is hydrogen, $C_1$-$C_6$-alkyl, $C_1$-$C_6$-alkoxy, halo-$C_1$-$C_6$-alkoxy or a group

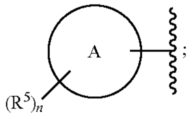

wherein $R^5$, A and n are as defined herein; and $R^{10}$ is hydrogen, halogen, or cyano.

In one embodiment, the present invention provides a compound of formula (I) as described herein, or a pharmaceutically acceptable salt thereof, wherein X is $—CH_2CR^3R^4—$ or $—CH{=}CR^3—$;

Y is —O—;

$R^1$ is (a) 5- to 14-membered heteroaryl substituted with 1 substituent selected from halogen; or (b) a group

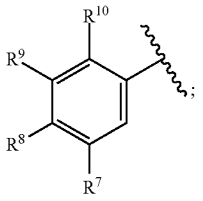

$R^2$ is hydrogen or $C_1$-$C_6$-alkyl;

$R^3$ is a group

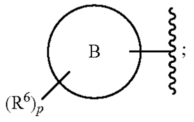

$R^4$ is hydrogen, halogen or hydroxy;

$R^5$ is hydrogen, halogen, hydroxy, halo-$C_1$-$C_6$-alkyl, $C_1$-$C_6$-alkoxy, $C_1$-$C_6$-alkyl, cyano or oxo;

$R^6$ is hydrogen, halogen, $C_6$-$C_{14}$-aryl, halo-$C_1$-$C_6$-alkoxy, halo-$C_1$-$C_6$-alkyl, oxo, $C_1$-$C_6$-alkyl, $C_2$-$C_6$-alkenyl, $C_2$-$C_6$-alkynyl, cycloalkyl or cyano;

$R^7$ is hydrogen or $C_1$-$C_6$-alkoxy;

$R^8$ is hydrogen or $C_1$-$C_6$-alkoxy;

$R^9$ is hydrogen, $C_1$-$C_6$-alkyl, $C_1$-$C_6$-alkoxy, halo-$C_1$-$C_6$-alkoxy or a group

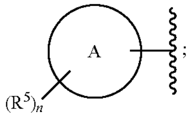

$R^{10}$ is hydrogen, halogen, or cyano;

A and B are each independently 5- to 14-membered heteroaryl, $C_6$-$C_{14}$-aryl or 3- to 14-membered heterocyclyl; and n and p are each independently 1 or 2.

In a preferred embodiment, the present invention provides a compound of formula (I) as described herein, or a pharmaceutically acceptable salt thereof, wherein the compound of formula (I) is a compound of formula (II)

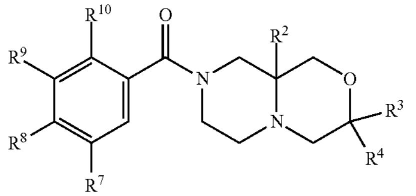

(II)

wherein $R^2$, $R^3$ and $R^4$ are as defined herein and wherein:

$R^7$ is hydrogen or $C_1$-$C_6$-alkoxy;

$R^8$ is hydrogen or $C_1$-$C_6$-alkoxy;

$R^9$ is hydrogen, $C_1$-$C_6$-alkyl, $C_1$-$C_6$-alkoxy, halo-$C_1$-$C_6$-alkoxy or a group

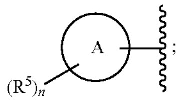

wherein $R^5$, A and n are as defined herein; and $R^{10}$ is hydrogen, halogen, or cyano.

In one embodiment, the present invention provides a compound of formula (I) as described herein, or a pharmaceutically acceptable salt thereof, wherein A is (i) heteroaryl selected from the group consisting of 1H-pyrazol-4-yl, pyridazine, pyridyl, pyrimidinyl, oxazol-5-yl, isoxazol-4-yl, 1H-triazol-5-yl, and 1H-imidazol-5-yl; or (ii) phenyl; or (iii) heterocyclyl selected from the group consisting of 1,2-dihydropyridine, 2-oxa-6-azaspiro[3.3]heptan-6-yl, morpholinyl, and azetidinyl.

In one embodiment, the present invention provides a compound of formula (I) as described herein, or a pharmaceutically acceptable salt thereof, wherein B is (i) heteroaryl selected from the group consisting of pyridyl, 1H-benzimidazol-2-yl, pyridazine, and thiazolyl; or (ii) aryl selected from the group consisting of phenyl and 3-bicyclo[4.2.0]octa-1(6),2,4-trienyl; or (iii) 1,2-dihydropyridine.

In one embodiment, the present invention provides a compound of formula (I) as described herein, or a pharmaceutically acceptable salt thereof, wherein the compound of formula (I) is a compound of formula (III)

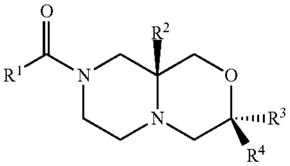

(III)

In one embodiment, the present invention provides a compound of formula (I) as described wherein, or a pharmaceutically acceptable salt thereof, wherein the compound of formula (I) is a compound of formula (IV)

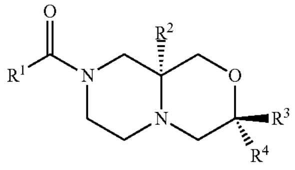

(IV)

In one embodiment, the present invention provides a compound of formula (I) as described herein, or a pharmaceutically acceptable salt thereof, wherein the compound of formula (I) is a compound of formula (V)

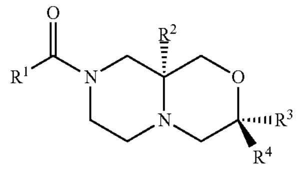

(V)

In one embodiment, the present invention provides a compound of formula (I) as described herein, or a pharmaceutically acceptable salt thereof, wherein the compound of formula (I) is a compound of formula (VI)

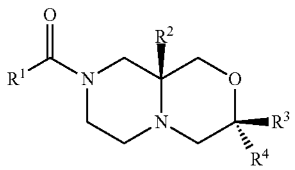

(VI)

In a particular embodiment, the present invention provides pharmaceutically acceptable salts of the compounds of formula (I) as described herein, especially hydrochloride salts. In a further particular embodiment, the present invention provides compounds according to formula (I) as described herein.

In some embodiments, the compounds of formula (I) are isotopically-labeled by having one or more atoms therein replaced by an atom having a different atomic mass or mass number. Such isotopically-labeled (i.e., radiolabeled) compounds of formula (I) are considered to be within the scope of this disclosure. Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Certain isotopically-labeled compounds of formula (I), for example, those incorporating a radioactive isotope, are useful in drug and/or substrate tissue distribution studies. The radioactive isotopes tritium, i.e. $^3H$, and carbon-14, i.e., $^{14}C$, are particularly useful for this purpose in view of their ease of incorporation and ready means of detection. For example, a compound of formula (I) can be enriched with 1, 2, 5, 10, 25, 50, 75, 90, 95, or 99 percent of a given isotope.

Substitution with heavier isotopes such as deuterium, i.e. $^2H$, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

Processes of Manufacturing

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. The substituents and indices used in the following description of the processes have the significance given herein, unless indicated to the contrary.

If one of the starting materials, intermediates or compounds of formula (I) contain one or more functional groups which are not stable or are reactive under the reaction conditions of one or more reaction steps, appropriate protective groups (as described e.g., in "Protective Groups in Organic Chemistry" by T. W. Greene and P. G. M. Wutts, 5th Ed., 2014, John Wiley & Sons, N.Y.) can be introduced before the critical step applying methods well known in the art. Such protective groups can be removed at a later stage of the synthesis using standard methods described in the literature.

If starting materials or intermediates contain stereogenic centers, compounds of formula (I) can be obtained as mixtures of diastereomers or enantiomers, which can be separated by methods well known in the art e.g., chiral HPLC, chiral SFC or chiral crystallization. Racemic compounds can e.g., be separated into their antipodes via diastereomeric salts by crystallization with optically pure acids or by separation of the antipodes by specific chromatographic methods using either a chiral adsorbent or a chiral eluent. It is equally possible to separate starting materials and intermediates containing stereogenic centers to afford diastereomerically/enantiomerically enriched starting materials and intermediates. Using such diastereomerically/enantiomerically enriched starting materials and intermediates in the synthesis of compounds of formula (I) will typically lead to the respective diastereomerically/enantiomerically enriched compounds of formula (I).

A person skilled in the art will acknowledge that in the synthesis of compounds of formula (I)—insofar not desired otherwise—an "orthogonal protection group strategy" will be applied, allowing the cleavage of several protective groups one at a time each without affecting other protective groups in the molecule. The principle of orthogonal protection is well known in the art and has also been described in literature (e.g. Barany and R. B. Merrifield, *J Am. Chem. Soc.* 1977, 99, 7363; H. Waldmann et al., *Angew. Chem. Int. Ed. Engl.* 1996, 35, 2056).

A person skilled in the art will acknowledge that the sequence of reactions may be varied depending on reactivity and nature of the intermediates.

In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations,* 2nd Edition, Richard C. Larock. John Wiley & Sons, New York, NY. 1999). It was found convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 hours to several days will usually suffice to yield the described intermediates and compounds. The reaction sequence is not limited to the one displayed in the schemes, however, depending on the starting materials and their respective reactivity, the sequence of reaction steps can be freely altered.

If starting materials or intermediates are not commercially available or their synthesis not described in literature, they can be prepared in analogy to existing procedures for close analogues or as outlined in the experimental section.

Compounds of formula (I) wherein $R^1$ and $R^3$ are as defined herein and wherein $R^2$ and $R^4$ are hydrogen may be synthesized according to the general procedure outlined in Scheme 1.

Scheme 1

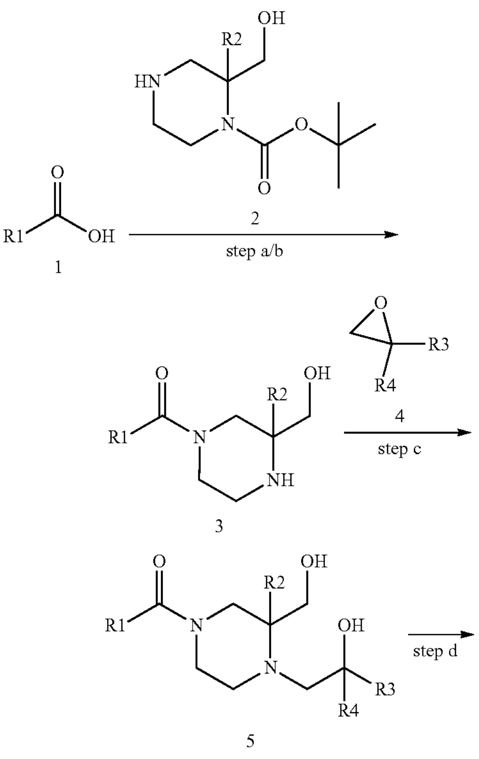

-continued

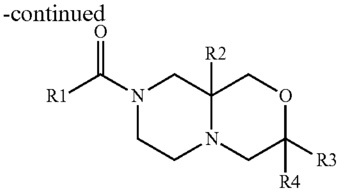

I

Accordingly, the secondary amine 2 can be acylated with a carboxylic acid 1, which are either commercially available or may be prepared by methods known to the man skilled in the art, using suitable conditions, for example coupling reagents such as HATU, T3P, EDC, in combination with a base such as TEA or DIPEA. Deprotection of the Boc group using an acid such as TFA or HCl leads to the corresponding intermediate 3 (Scheme 1, step a and b). Treatment of piperazine 3 with an epoxide 4, which is either commercially available or may be prepared by methods known to the man skilled in the art, in a solvent like methanol or ethanol, and in a temperature range between 100° C. and 140° C. affords the corresponding diol 5 (Scheme 1, step c). The two hydroxy groups of 5 are being cyclized, using a etherification reagent such as (cyanomethylene)tributylphosphorane (CMBP, Tsunoda reagent) to yield compound of formula (I) (Scheme 1, step d).

If $R^3$ is carrying a protecting group, for example a benzyl-group as a protecting group for a pyridone, a final deprotection step is required, using suitable conditions such as TFA in DCM, to eventually afford a compound of formula (I).

Compounds of formula (I) wherein $R^1$, $R^2$ and $R^3$ are as defined herein and wherein and $R^4$ is hydrogen may also be synthesized according to the general procedure outlined in Scheme 2.

Scheme 2

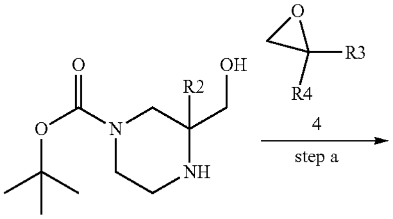

6

-continued

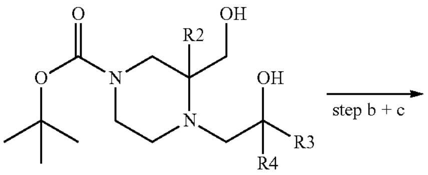

7

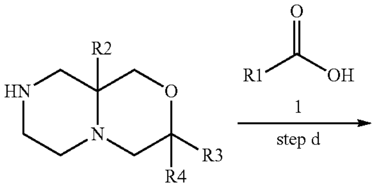

8

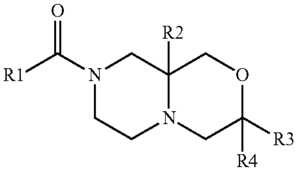

I

Treatment of secondary amine 6 with an epoxide 4 in a solvent like methanol or ethanol, and in a temperature range between 100° C. and 140° C. affords the corresponding intermediate 7 (Scheme 2, step a). The two hydroxy groups of 7 are being cyclized, using a etherification reagent such as (cyanomethylene)tributylphosphorane (CMBP, Tsunoda reagent, scheme 2, step b). Subsequent deprotection of the Boc group using an acid such as TFA or HCl leads to the corresponding morpholine analogue 8 (Scheme 2, step c). If $R^3$ is carrying a protecting group, for example a benzyl as a protecting group for a pyridone, this is deprotected as well during acid treatment (scheme 2, step c). The secondary amine 8 can then be acylated with a suitable carboxylic acid 1, using conditions known in the art, for example coupling reagents such as HATU, T3P or EDC, in combination with a base such as TEA or DIPEA (scheme 2, step d), to afford a compound of formula (I).

Compounds of formula (I) wherein $R^1$, $R^2$, $R^3$ and $R^4$ are as defined herein, may also be synthesized according to the general procedure outlined in Scheme 3a.

Scheme 3a

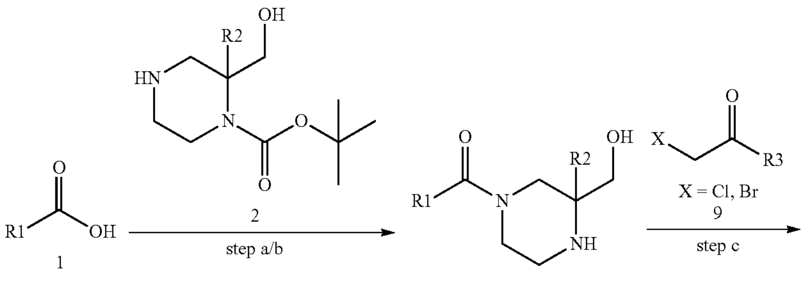

1

3

-continued

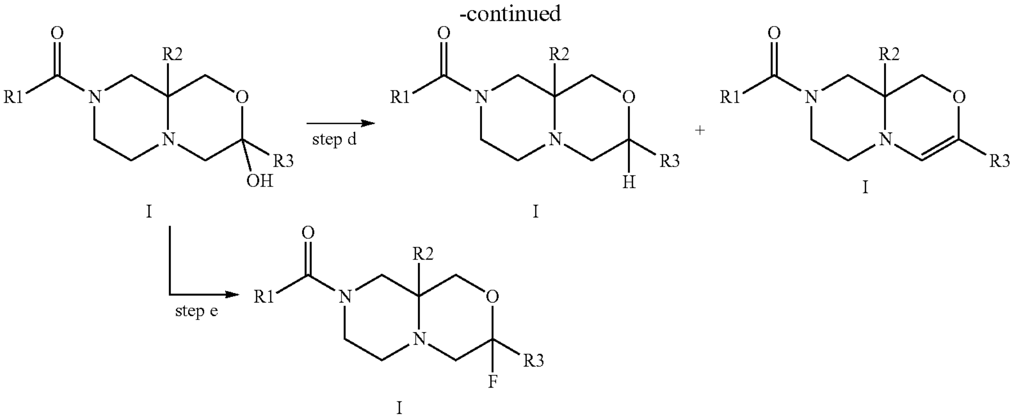

The secondary amine 2 can be acylated with a suitable carboxylic acid 1, using conditions known in the art, for example coupling reagents such as HATU, T3P, EDC, in combination with a base such as TEA or DIPEA. Deprotection of the Boc group using an acid such as TFA or HCl leads to the corresponding intermediate 3 (Scheme 3a, step a and b). Treatment of piperazine 3 with a haloketone 9 (obtainable e.g. by the general procedure outlined in Scheme 4) in a solvent like THF and a base such as DIPEA, and in a temperature range between 0° C. and 25° C. affords the corresponding acetale I, corresponding to compounds of formula (I) wherein $R^4$ is hydroxy (Scheme 3a, step c). Further reaction of compounds of formula (I) wherein $R^4$ is hydroxy under dehydrating conditions, for example using TES and TFA in DCM at elevated temperatures between 50° C. and 80° C. leads to compounds of formula (I) wherein $R^4$ is hydrogen (Scheme 3a, step d). The alkene (X=—CH=$CR^3$—) can be isolated in some cases, if elimination is an additional reaction path, depending on the chosen conditions.

Treatment of compounds of formula (I) wherein $R^4$ is hydroxy with a nucleophilic fluorinating agent such as DAST, using a solvent such a DCM, at temperatures between −78° C. and 25° C., yields compounds of formula (I) wherein $R^4$ is fluoride (scheme 3a, step e).

Compounds of formula (I) wherein $R^1$, $R^2$, $R^3$ and $R^4$ are as defined herein, may also be synthesized according to the general procedure outlined in Scheme 3b.

Scheme 3b

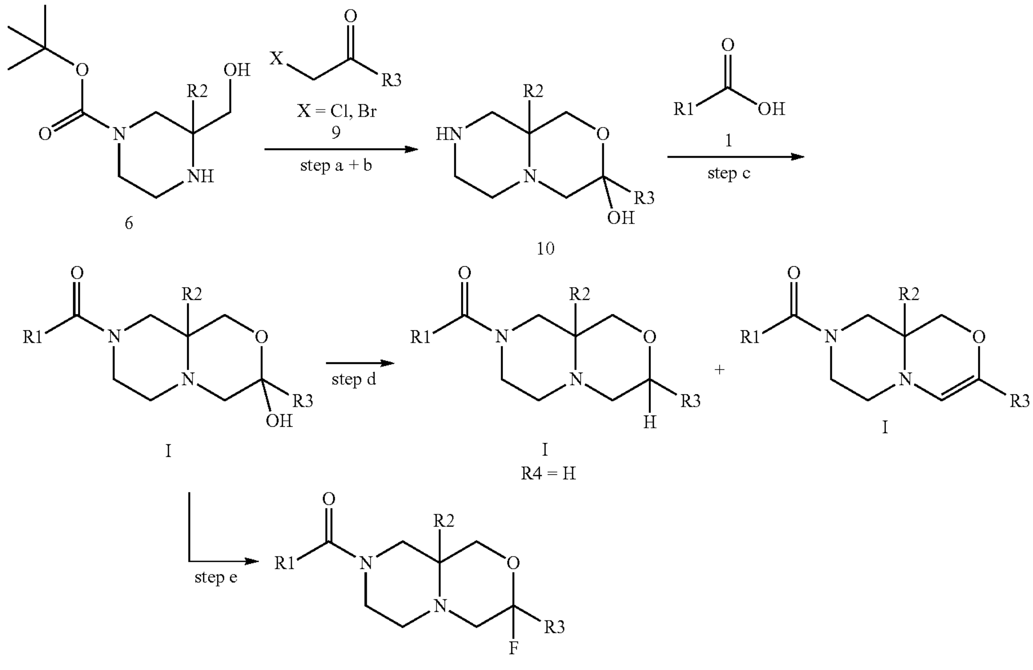

I
R4 = F

Treatment of the secondary amine 6 with an haloketone 9 in a solvent like THF and a base such as DIPEA, and in a temperature range between 0° C. and 25° C. affords the corresponding acetale. Deprotection of the Boc group using an acid such as TFA or HCl leads to compounds of formula 10 wherein $R^4$ is hydroxy (Scheme 3b, step a and b). The secondary amine of 10 can be acylated with a suitable carboxylic acid 1, using conditions known in the art, for example coupling reagents such as HATU, T3P, EDC, in combination with a base such as TEA or DIPEA, leading to compounds of formula I with $R^4$=OH (scheme 3b, step c). Further reaction of compounds of formula (I) wherein $R^4$ is hydroxy under dehydrating conditions, for example using TES and TFA in DCM at elevated temperatures between 50° C. and 80° C. leads to compounds of formula (I) wherein $R^4$ is hydrogen (Scheme 3, step d). The alkene (X=—CH=$CR^3$—) can be isolated in some cases, if elimination is an additional reaction path, depending on the chosen conditions.

Treatment of compounds of formula (I) wherein $R^4$ is hydroxy with a nucleophilic fluorinating agent such as DAST, using a solvent such a DCM, at temperatures between −78° C. and 25° C., yields compounds of formula (I) wherein $R^4$ is fluoride (scheme 3b, step e).

Bromoketone intermediates 9 can be obtained by reacting a ketone 11, which is either commercially available or may be prepared by methods known to the man skilled in the art, with bromine in acetic acid, at elevated temperatures between 60 and 90° C. (Scheme 4).

Scheme 4

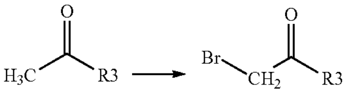

11 9

Compounds of formula (I) wherein $R^1$, $R^2$ and $R^4$ are as defined herein and wherein $R^3$ is B substituted with bromo, can be further modified according to the general procedure outlined in Scheme 5.

Scheme 5

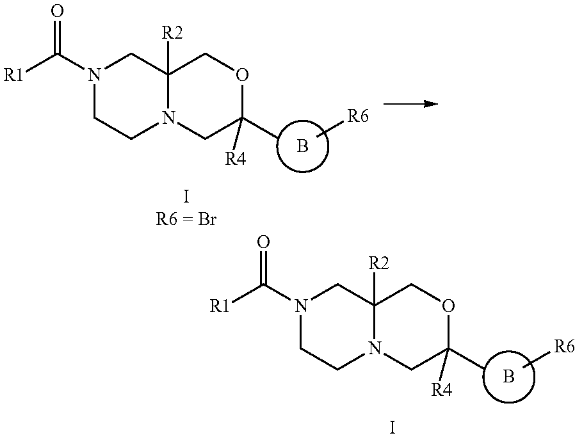

I
R6 = Br

I
R6 = aryl, alkenyl, alkynyl, alkyl, cyano, cycloalkyl, heteroaryl

Treatment of compounds of formula I, containing a bromoaryl as $R^3$ under typical conditions of a Suzuki-Miyaura reaction, a Sonogashira reaction, or other organometallic cross couplings known in the art lead to substituted compounds of formula I where the bromine has been replaced with an aryl, alkenyl, alkynyl, alkyl, cycloalkyl, heteroaryl or cyano moiety. This typically requires a suitable reaction partner such as a boronic acid, a potassium trifluoroborate, a pinacol boronate, a terminal alkyne or an organozinc compound, a suitable catalyst for example tetrakis(triphenylphosphine)palladium (0), $PdCl_2$(dppf)-$CH_2Cl_2$, $Pd_2(dba)_3$+Xantphos, cataCXium A Pd G2, an organic or inorganic base such as sodium carbonate, TEA, TMEDA or cesium carbonate in a solvent system such as Dioxane/Water, DMF or toluene/water.

Reactions are typically carried out at elevated temperatures between 100 and 120° C. under inert atmosphere (argon). In the case of the Sonogashira coupling, the addition of copper(I)iodide is required to get to I where $R^6$=alkynyl.

Compounds of formula (I) wherein $R^2$, $R^3$, $R^4$, $R^5$, and n are as defined herein and wherein $R^1$ is aryl or heteroaryl substituted with aryl, heteroaryl or heterocyclyl, can be obtained according to the procedure outlined in Scheme 6.

Scheme 6

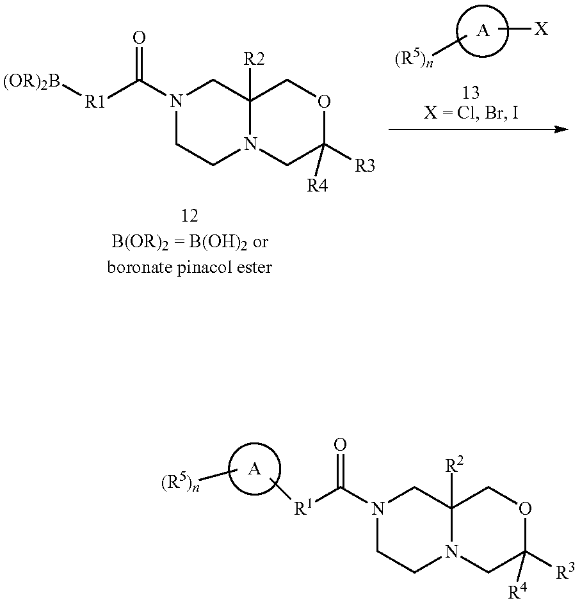

12
$B(OR)_2$ = $B(OH)_2$ or boronate pinacol ester

I
A = aryl, heteroaryl or heterocyclyl

Treatment of compounds of formula 12, containing a boronic acid or boronate ester under typical conditions of a Suzuki-Miyaura reaction lead to substituted compounds of formula I where the boronate has been replaced with an aryl, heteroaryl or heterocyclyl moiety. This typically requires a suitable reaction partner 13 that can be for example a haloaryl, haloheteroaryl or haloheterocyclyl, and a suitable catalyst for example PdCl2(DPPF)-CH2Cl2, Pd2(dba)3+Xantphos, (A-$^{ta}$Phos)$_2$PdCl$_2$, cataCXium A Pd G2, an organic or inorganic base such as sodium carbonate, TEA, TMEDA or cesium carbonate in a solvent system such as dioxane/water, DMF, toluene/water. Reactions are typically carried out at elevated temperatures between 100 and 120° C. under inert atmosphere (argon).

Compounds of formula (I) wherein $R^1$, $R^2$, and $R^3$ are as defined herein, $R^4$ is hydrogen and wherein Y is —S— can also be obtained according to the general procedure outlined in Scheme 7.

Scheme 7

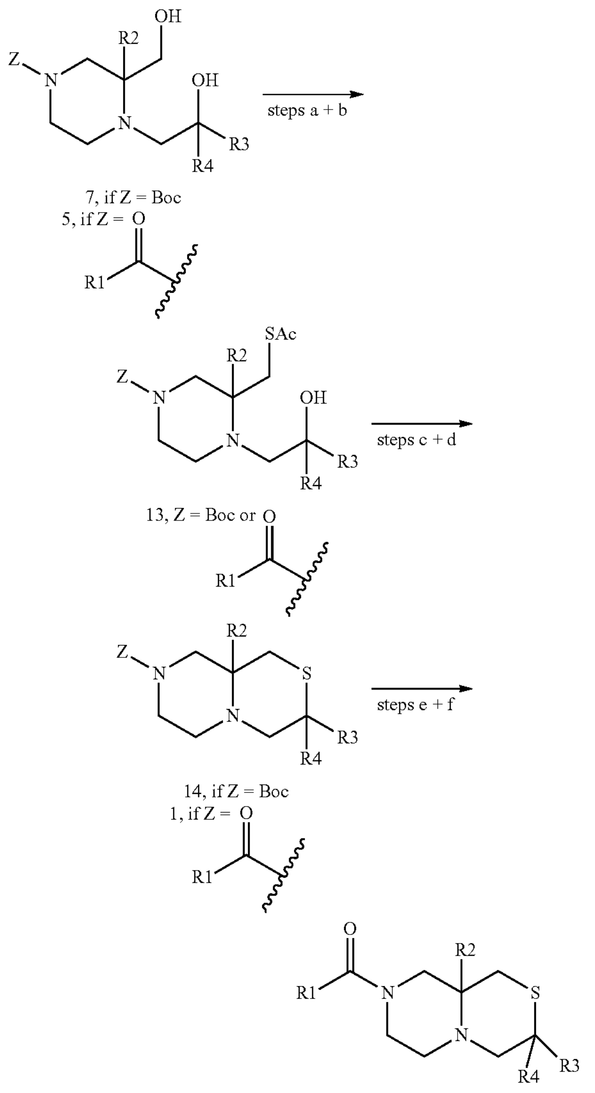

Diols 5 or 7 are converted to their corresponding mono-mesylates by treatment with methanesulfonyl chloride, a base such as triethylamine, and a catalyst such as 4-dimethylaminopyridine. Subsequent reaction with potassium thioacetate in a solvent such as DMSO provides intermediate 13 (Scheme 7, steps a and b). The remaining hydroxy group of 13 is then converted to the corresponding chloro intermediate by treatment with, for example, thionyl chloride, followed by addition of a base such as pyridine. The resulting chloro intermediate is then treated with sodium methoxide to afford the cyclized sulfides I (if Z═—CO—$R^1$) or 14 (if Z=Boc) (scheme 7, steps c+d). In case of compounds of type 14, deprotection of the Boc group using an acid such as TFA or HCl, and subsequent acylation with a suitable carboxylic acid 1, using for example coupling reagents such as HATU, T3P, EDC, in combination with a base such as TEA or DIPEA, leads to compounds of formula I (scheme 7, steps e+f). According to *Bioorg. Med. Chem. Lett.* 2016, 26 (23), p. 5695-5702. and U.S. Pat. No. 9,573,961 B2

Compounds of formula (I) wherein $R^1$, $R^2$, and $R^3$ are as defined herein, $R^4$ is hydrogen and wherein Y is sulfur, can be further modified according to the general procedure outlined in Scheme 8. Oxidizing the thioether I by employing a method known to man skilled in the art, for example by treating with mCPBA, hydrogen peroxide or sodium periodate, will lead to compounds of formula I, depending on the chosen conditions, as mixtures or pure compounds of type I with Y being a sulfoxide and or a sulfone. Mixtures of sulfones and sulfoxides of type I can then be separated be preparative HPLC or SFC to obtain pure products.

Scheme 8

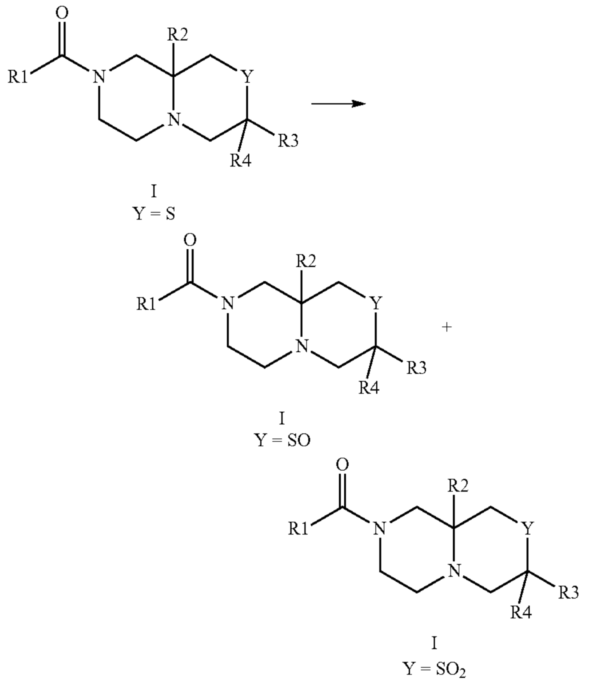

Carboxylic acids 1, wherein $R^5$ is as defined herein which are not commercially available can be prepared by methods known to the man skilled in the art, for example by the methods described below in schemes 9a-9e.

Scheme 9a

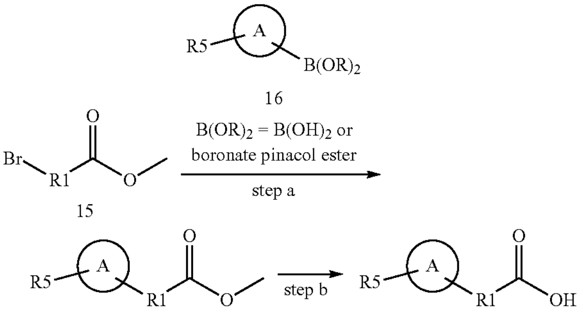

Scheme 9a

Starting from a bromo benzoate 15, intermediate 17 can be obtained by using typical conditions for a Suzuki-Miyaura reaction. That requires a suitable boronic acid or boronate ester 16, a palladium catalyst such as XPhos-Pd- G2, (A-[ta]Phos)$_2$PdCl$_2$, (APhos)$_2$PdCl$_2$, a base such as $K_3PO_4$, $K_2CO_3$ or $Cs_2CO_3$ in a solvent system such as THF/$H_2O$ or dioxane/$H_2O$. Reactions are typically carried out at elevated temperatures between 100 and 120° C. under inert atmosphere (argon). Reactions of 2-heterocyclic boronates are ideally facilitated by additionally adding copper(I) chloride (Scheme 9a, step a). Saponification using a base such as lithium hydroxide in an aqueous solution leads to carboxylic acids of type 1 (Scheme 9a, step b).

Scheme 9b

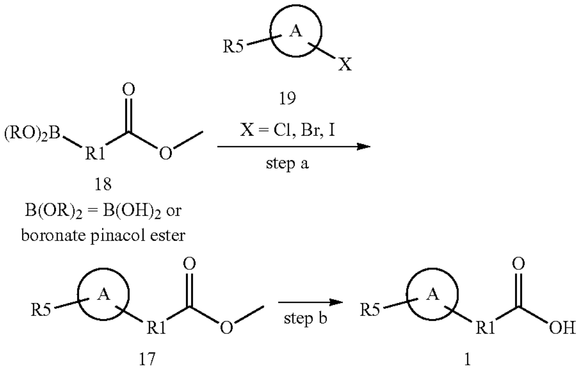

Starting from a boronic acid or boronate ester benzoate 18, intermediate 17 can be also obtained by using typical conditions for a Suzuki-Miyaura reaction. That requires a suitable haloaryl, haloheteroaryl or haloheterocyclyl 19, a palladium catalyst such as XPhos-Pd-G2, (A-[ta]Phos)$_2$PdCl$_2$, (APhos)$_2$PdCl$_2$, a base such as $K_3PO_4$, $K_2CO_3$ or $Cs_2CO_3$ in a solvent system such as THF/$H_2O$ or Dioxane/$H_2O$. Reactions are typically carried out at elevated temperatures between 100 and 120° C. under inert atmosphere (argon). Reactions of 2-heteroaryl boronates are ideally facilitated by additionally adding copper(I) chloride (Scheme 9b, step a). Saponification using a base such as lithium hydroxide in an aqueous solution leads to carboxylic acids of type 1 (Scheme 9b, step b).

Scheme 9c

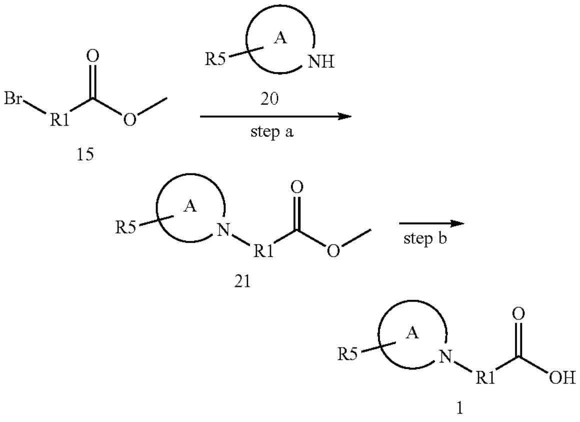

Starting from a bromo benzoate 15, intermediate 21 can be obtained by using typical conditions for a Buchwald-Hartwig reaction. That requires a suitable amine 20, a palladium catalyst such as $Pd_2(dba)_3$ with phosphin ligand such as DavePhos or Xantphos, a base such as $K_3PO_4$, $K_2CO_3$ or $Cs_2CO_3$ in a solvent such as toluene or dioxane. Reactions are typically carried out at elevated temperatures between 100 and 120° C. under inert atmosphere using argon (Scheme 9c, step a). Saponification of 21 using a base such as lithium hydroxide in an aqueous solution leads to carboxylic acids of type 1 (Scheme 9c, step b).

Scheme 9d

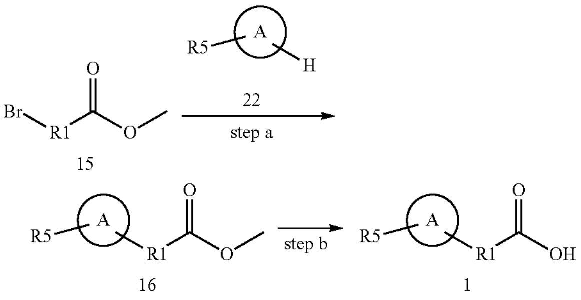

In some cases, especially with A being an oxazole, the coupling to the bromo benzoate can be achieved directly by using the unsubstituted oxazole 22 (scheme 9d), as described in *Org. Lett.* 2010, 12 (16), p. 3578-3581.

Saponification of 16 using a base such as lithium hydroxide in an aqueous solution leads to carboxylic acids of type 1 (Scheme 9d, step b).

Scheme 9e

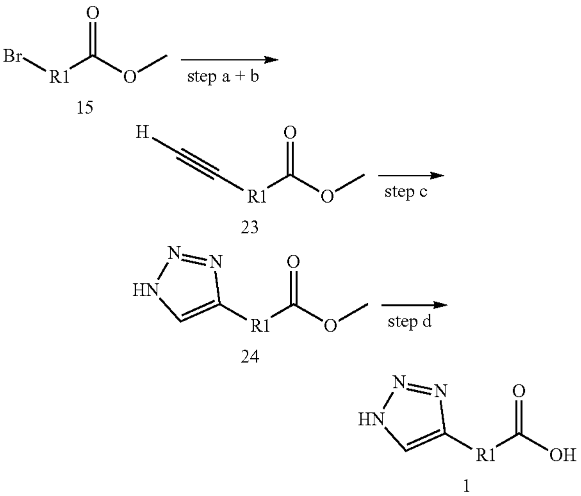

Aryl/heteroaryl halide 15 can be cross coupled with ethynyltrimethylsilane using typical conditions for a Sonogashira reaction (Pd(dppf)$Cl_2$, copper (I) iodide, diethylamine, DMF, 120° C.). Deprotection with potassium carbonate in THF/MeOH at room temperature leads to alkyne intermediate 23 (Scheme 9e, steps a+b). Treatment of 23 with azidotrimethylsilane using a suitable copper catalyst such as copper (I) iodide in a solvent system such as DMF/MeOH at elevated temperatures between 100 and 130° C. leads to triazole 24 (Scheme 9e, step c).

Saponification of 24 using a base such as lithium hydroxide in an aqueous solution leads to carboxylic acids of type 1 (Scheme 9e, step d).

Oxiranes 4, wherein B, $R^6$ and p are as defined herein, which are not commercially available can be prepared by methods known to the man skilled in the art, for example by the methods described below.

Scheme 10

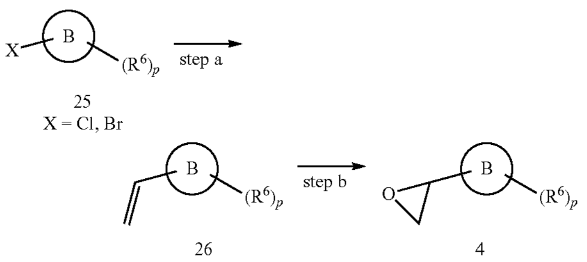

Treating arylhalides or heteroarylhalides 25 with potassium trifluoro(vinyl)borate under typical Suzuki-Miyaura conditions (1,1'-bis(diphenylphosphino)ferrocene-palladium(II)dichloride dichloromethane complex, triethylamine, in ethanol under argon at 100°-130° C.) leads to vinylarenes or vinylheteroarens 26 (scheme 10, step a). These can be oxidized toward oxiranes 4 by using for example methyltrioxorhenium plus 1H-pyrazole and hydrogen peroxide, in DCM, at 0° C.; NBS in water and dioxane, at room temperature, then treatment with aq. NaOH at 0° C.; mCPBA in DCM at room temperature (Scheme 10, step b).

In one aspect, the present invention provides a process of manufacturing the compounds of formula (I) as described in any one of the schemes disclosed herein.

In a further aspect, the present invention provides processes of manufacturing the compounds of formula (I) as described herein, comprising:

(a) reacting a diol 5, wherein $R^1$ and $R^3$ are as defined herein,

5

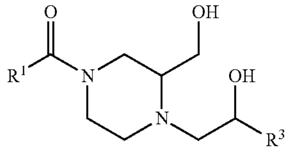

with an etherification reagent, such as (cyanomethylene)tributylphosphorane (CMBP, Tsunoda reagent) to yield said compound of formula (I), wherein X is —$CH_2CHR^3$—, Y is —O—, $R^1$ and $R^3$ are as defined herein, and $R^2$ is hydrogen; or (b) reacting an amine 8a, wherein Y, $R^2$ and $R^3$ are as defined herein, 8a

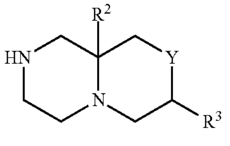

with a carboxylic acid 1, wherein $R^1$ is as defined herein,

1

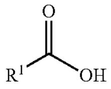

in the presence of a base, such as trimethylamine or diisopropylamine, and a coupling reagent, such as HATU, T3P or EDC*HCl, to yield said compound of formula (I), wherein X is —$CH_2CHR^3$—, Y, $R^1$ and $R^3$ are as defined herein, and $R^2$ is hydrogen; or (c) submitting a compound of formula (I), wherein Y is as defined herein, X is —$CH_2CR_3R^4$—, $R^1$ to $R^3$ are as defined herein and $R^4$ is hydroxy to dehydrating conditions, for example using TES and TFA at elevated temperatures, to yield a compound of formula (I) wherein Y is as defined herein, X is —$CH_2CHR^3$— and $R^1$ to $R^3$ are as defined herein and/or a compound of formula (I) wherein Y is as defined herein, X is —CH═$CR^3$— and $R^1$ to $R^3$ are as defined herein; or (d) reacting a compound of formula (I), wherein Y is as defined herein, X is —$CH_2CR_3R^4$—, $R^1$ to $R^3$ are as defined herein and $R^4$ is hydroxy, with a nucleophilic fluorinating agent, such as DAST, to yield a compound of formula (I) wherein X is —$CH_2CFR^3$— and $R^1$ to $R^3$ are as defined herein; or (e) submitting a compound of formula (I),

I

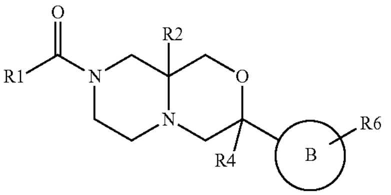

wherein $R^1$, $R^2$, $R^4$, and B are as defined herein, and $R^6$ is bromo, to a transition metal catalyzed cross-coupling reaction, such as a Suzuki-Miyaura reaction or a Sonogashira reaction, to afford compound of formula (I)

I

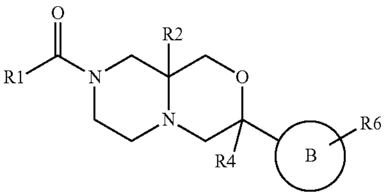

wherein $R^1$, $R^2$, $R^4$, and B are as defined herein, and $R^6$ is selected from aryl, alkenyl, alkynyl, alkyl, cyano, cycloalkyl, and heteroaryl; or (f) submitting a compound 12, wherein $R^1$ is aryl or heteroaryl optionally substituted with 1-4 substituents independently selected from $C_1$-$C_6$-alkyl, $C_1$-$C_6$-alkoxy, halo-$C_1$-$C_6$-alkyl, halo-$C_1$-$C_6$-alkoxy, halogen, and cyano; and $R^2$ to $R^4$ are as defined herein,

12

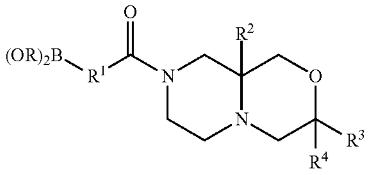

B(OR)2 = B(OH)2 or boronate pinacol ester to a Suzuki-Miyaura cross coupling reaction with a compound 13, wherein A, $R^5$, and n are as defined herein

13

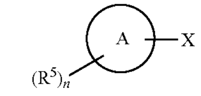

X = Cl, Br, I, OTf in the presence of a transition metal catalyst, e.g. $PdCl_2(dppf)$-$CH_2Cl_2$, $Pd_2(dba)_3$+Xantphos, $(A\text{-}^{t}Phos)_2PdCl_2$, or cataCXium A Pd G2, and an organic or inorganic base such as sodium carbonate, triethylamine, TMEDA or cesium carbonate; to afford said compound of formula (I), wherein $R^1$ is aryl or heteroaryl optionally substituted with 1-4 substituents independently selected from $C_1$-$C_6$-alkyl, $C_1$-$C_6$-alkoxy, halo-$C_1$-$C_6$-alkyl, halo-$C_1$-$C_6$-alkoxy, halogen, and cyano; and $R^2$ to $R^5$ and n are as defined herein

I

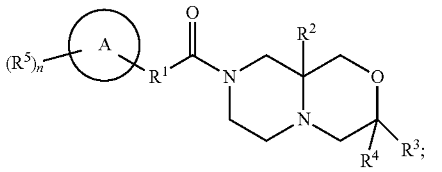

(g) reacting a compound of formula (I), wherein Y is sulfur and $R^1$, $R^2$, and $R^3$ are as defined herein,

I

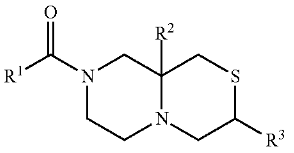

with an oxidizing agent, such as mCPBA, hydrogen peroxide or sodium periodate, to afford a compound of formula (I), wherein Y is a sulfoxide or a sulfone and $R^1$, $R^2$, and $R^3$ are as defined herein.

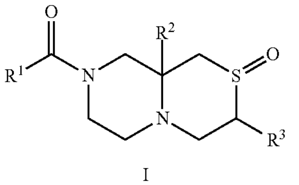

+

I

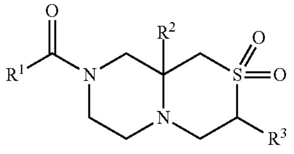

I

In one aspect, the present invention provides a compound of formula (I) as described herein, when manufactured according to any one of the processes described herein.

MAGL Inhibitory Activity

Compounds of the present invention are MAGL inhibitors. Thus, in one aspect, the present invention provides the use of compounds of formula (I) as described herein for inhibiting MAGL in a mammal.

In a further aspect, the present invention provides compounds of formula (I) as described herein for use in a method of inhibiting MAGL in a mammal.

In a further aspect, the present invention provides the use of compounds of formula (I) as described herein for the preparation of a medicament for inhibiting MAGL in a mammal.

In a further aspect, the present invention provides a method for inhibiting MAGL in a mammal, which method comprises administering an effective amount of a compound of formula (I) as described herein to the mammal.

Compounds were profiled for MAGL inhibitory activity by determining the enzymatic activity by following the hydrolysis of the natural substrate 2-arachidonoylglycerol (2-AG) resulting in arachidonic acid, which can be followed by mass spectrometry. This assay is hereinafter abbreviated “2-AG assay”.

The 2-AG assay was carried out in 384 well assay plates (PP, Greiner Cat #784201) in a total volume of 20 μL. Compound dilutions were made in 10000 DMSO (VWR Chemicals 23500.297) in a polypropylene plate in 3-fold dilution steps to give a final concentration range in the assay from 12.5 μM to 0.8 μM. 0.25 μL compound dilutions (100% DMSO) were added to 9 μL MAGL in assay buffer (50 mM TRIS (GIBCO, 15567-027), 1 mM EDTA (Fluka, 03690-100 mL), 0.010 (v/v) Tween. After shaking, the plate was incubated for 15 min at RT. To start the reaction, 10 μL 2-arachidonoylglycerol in assay buffer was added. The final concentrations in the assay was 50 μM MAGL and 8 μM 2-arachidonoylglyerol. After shaking and 30 min incubation at RT, the reaction was quenched by the addition of 40 μL of ACN containing 4 μM of d8-arachidonic acid. The amount of arachidonic acid was traced by an online SPE system (Agilent Rapidfire) coupled to a triple quadrupole mass spectrometer (Agilent 6460). A C18 SPE cartridge (G9205A) was used in an ACN/water liquid setup. The mass spectrometer was operated in negative electrospray mode following the mass transitions 303.1→259.1 for arachidonic acid and 311.1→267.0 for d8-arachidonic acid. The activity of the compounds was calculated based on the ratio of intensities [arachidonic acid/d8-arachidonic acid].

TABLE 1

| Ex. | Structure | IUPAC Name | MAGL IC50 (nM) |
|---|---|---|---|
| 1 | 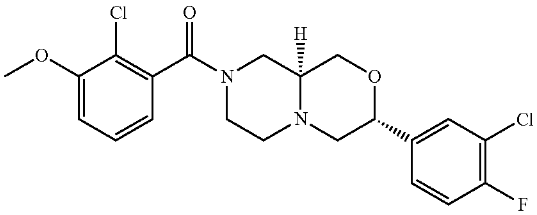 | [(3R,9aS)-3-(3-chloro-4-fluoro-phenyl)-3,4,6,7,9,9a-hexahydro-1H-pyrazino[2,1-c][1,4]oxazin-8-yl]-(2-chloro-3-methoxy-phenyl)methanone | 18.3 |
| 2 | 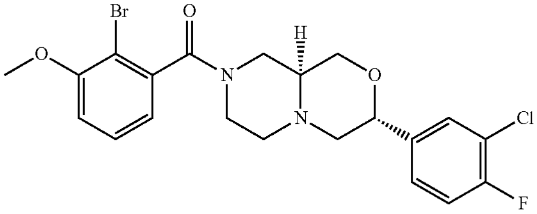 [SMILES: COc1cccc(C(=O)N2CCN3C[C@@H](c4ccc(F)c(Cl)c4)OC[C@@H]3C2)c1Cl] | (2-bromo-3-methoxy-phenyl)-[rac-(3R,9aS)-3-(3-chloro-4-fluoro-phenyl)-3,4,6,7,9,9a-hexahydro-1H-pyrazino[2,1-c][1,4]oxazin-8-yl]methanone | 14.6 |
| 5 | Chiral 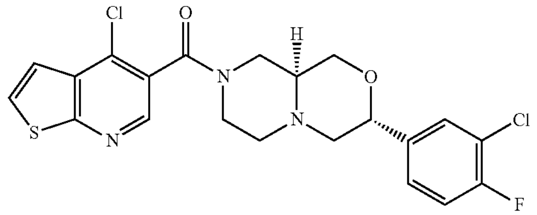 | (4-chlorothieno[2,3-b]pyridin-5-yl)-[(3R,9aS)-3-(3-chloro-4-fluoro-phenyl)-3,4,6,7,9,9a-hexahydro-1H-pyrazino[2,1-c][1,4]oxazin-8-yl]methanone | 28.2 |
| 6 | Chiral 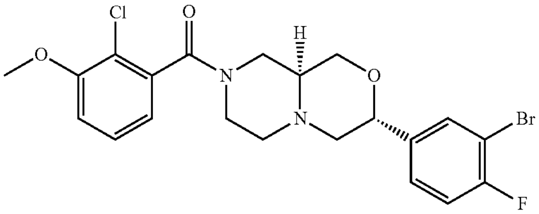 | [(3R,9aS)-3-(3-bromo-4-fluoro-phenyl)-3,4,6,7,9,9a-hexahydro-1H-pyrazino[2,1-c][1,4]oxazin-8-yl]-(2-chloro-3-methoxy-phenyl)methanone | 10.9 |
| 8 | Chiral 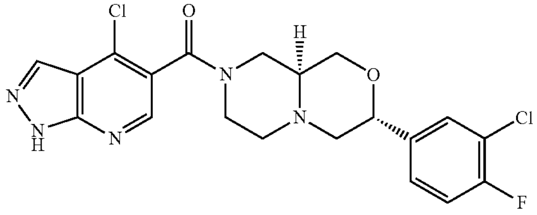 | [(3R,9aS)-3-(3-chloro-4-fluoro-phenyl)-3,4,6,7,9,9a-hexahydro-1H-pyrazino[2,1-c][1,4]oxazin-8-yl]-(4-chloro-1H-pyrazolo[3,4-b]pyridin-5-yl)methanone | 705.2 |
| 9 | Chiral 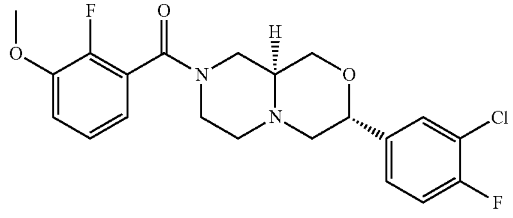 | [(3R,9aS)-3-(3-chloro-4-fluoro-phenyl)-3,4,6,7,9,9a-hexahydro-1H-pyrazino[2,1-c][1,4]oxazin-8-yl]-(2-fluoro-3-methoxy-phenyl)methanone | 85.6 |

TABLE 1-continued

| Ex. | Structure | IUPAC Name | MAGL IC50 (nM) |
|---|---|---|---|
| 10 | 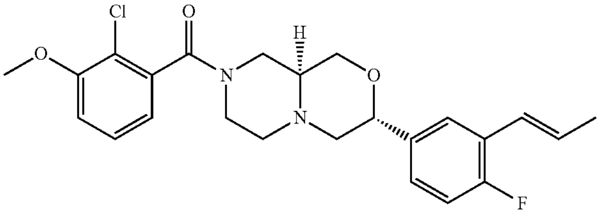 [SMILES: C/C=C/c1cc([C@@H]2CN3CCN(C(=O)c4cccc(OC)c4Cl)C[C@H]3CO2)ccc1F] | (2-chloro-3-methoxy-phenyl)-[(3R,9aS)-3-[4-fluoro-3-[rac-(E)-prop-1-enyl]phenyl]-3,4,6,7,9,9a-hexahydro-1H-pyrazino[2,1-c][1,4]oxazin-8-yl]methanone | 178.6 |
| 11 | Chiral 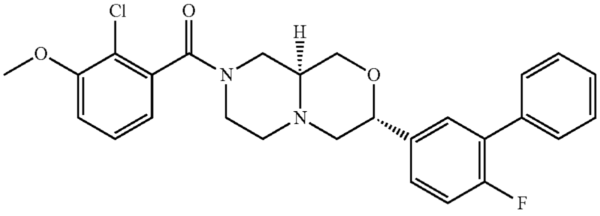 | [(3R,9aS)-3-(4-fluoro-3-phenyl-phenyl)-3,4,6,7,9,9a-hexahydro-1H-pyrazino[2,1-c][1,4]oxazin-8-yl]-(2-chloro-3-methoxy-phenyl)methanone | 259 |
| 12 | Chiral 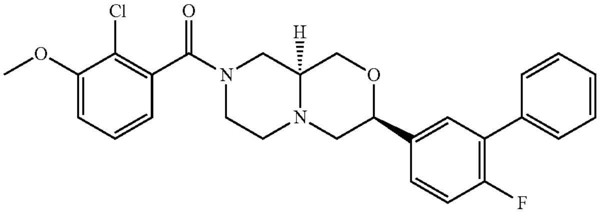 | [(3S,9aS)-3-(4-fluoro-3-phenyl-phenyl)-3,4,6,7,9,9a-hexahydro-1H-pyrazino[2,1-c][1,4]oxazin-8-yl]-(2-chloro-3-methoxy-phenyl)methanone | 575.3 |
| 13 | 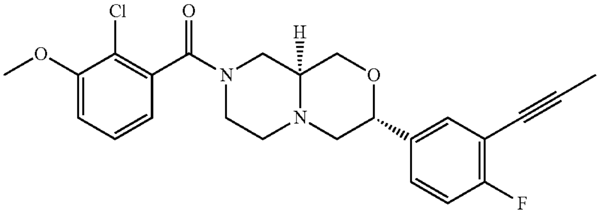 [SMILES: CC#Cc1cc([C@@H]2CN3CCN(C(=O)c4cccc(OC)c4Cl)C[C@H]3CO2)ccc1F] | [(3R,9aS)-3-(4-fluoro-3-prop-1-ynyl-phenyl)-3,4,6,7,9,9a-hexahydro-1H-pyrazino[2,1-c][1,4]oxazin-8-yl]-(2-chloro-3-methoxy-phenyl)methanone | 237.9 |
| 14 | Chiral 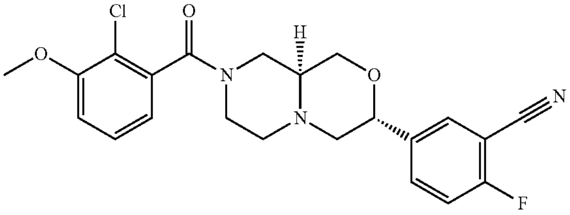 | [(3,9aS)-3-(3-cyano-4-fluoro-phenyl)-3,4,6,7,9,9a-hexahydro-1H-pyrazino[2,1-c][1,4]oxazin-8-yl]-(2-chloro-3-methoxy-phenyl)methanone | 153.5 |
| 16 | Chiral 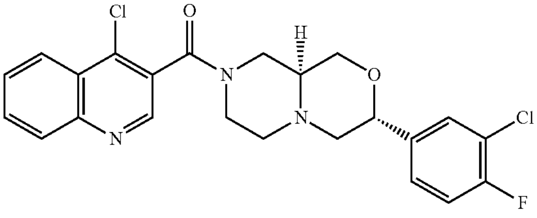 | [(3R,9aS)-3-(3-chloro-4-fluoro-phenyl)-3,4,6,7,9,9a-hexahydro-1H-pyrazino[2,1-c][1,4]oxazin-8-yl]-(4-chloro-3-quinolyl)methanone | 131.5 |

TABLE 1-continued

| Ex. | Structure | IUPAC Name | MAGL IC50 (nM) |
|---|---|---|---|
| 17 | Chiral 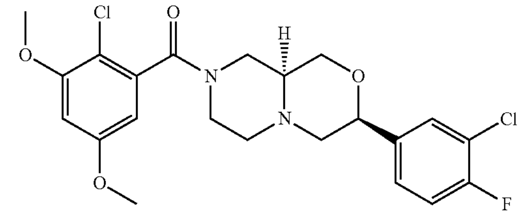 | [(3S,9aS)-3-(3-chloro-4-fluoro-phenyl)-3,4,6,7,9,9a-hexahydro-1H-pyrazino[2,1-c][1,4]oxazin-8-yl]-(2-chloro-3,5-dimethoxy-phenyl)methanone | 4567.8 |
| 18 | Chiral 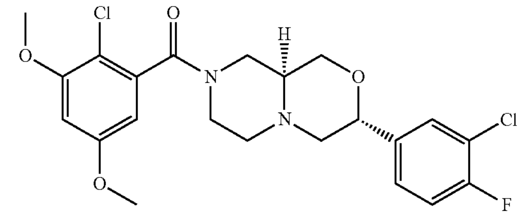 | [(3R,9aS)-3-(3-chloro-4-fluoro-phenyl)-3,4,6,7,9,9a-hexahydro-1H-pyrazino[2,1-c][1,4]oxazin-8-yl]-(2-chloro-3,5-dimethoxy-phenyl)methanone | 51.2 |
| 19 | Chiral 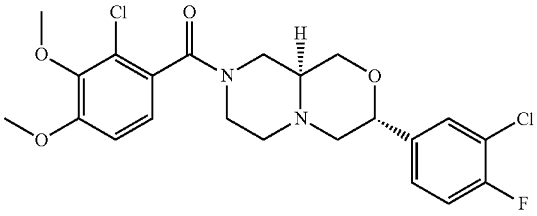 | [(3R,9aS)-3-(3-chloro-4-fluoro-phenyl)-3,4,6,7,9,9a-hexahydro-1H-pyrazino[2,1-c][1,4]oxazin-8-yl]-(2-chloro-3,4-dimethoxy-phenyl)methanone | 304.7 |
| 20 | Chiral 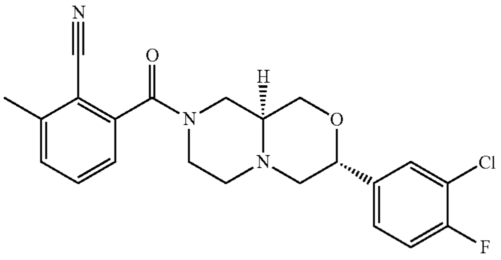 | 2-[(3R,9aS)-3-(3-chloro-4-fluoro-phenyl)-3,4,6,7,9,9a-xahydro-1H-pyrazino[2,1-c][1,4]oxazine-8-carbonyl]-6-methyl-benzonitrile | 120.6 |
| 21 | Chiral 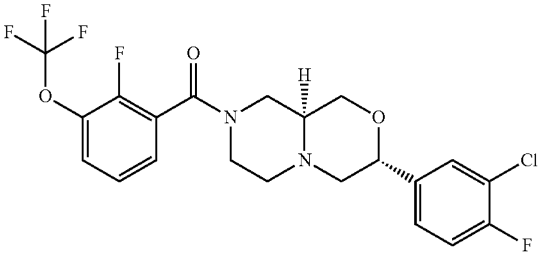 | [(3R,9aS)-3-(3-chloro-4-fluoro-phenyl)-3,4,6,7,9,9a-hexahydro-1H-pyrazino[2,1-c][1,4]oxazin-8-yl]-[2-fluoro-3-(trifluoromethoxy)phenyl] methanone | 746.3 |

TABLE 1-continued

| Ex. | Structure | IUPAC Name | MAGL IC50 (nM) |
| --- | --- | --- | --- |
| 22 | Chiral 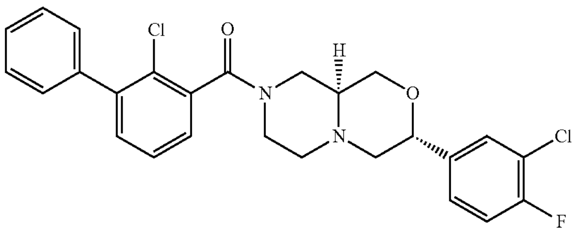 | [(3R,9aS)-3-(3-chloro-4-fluoro-phenyl)-3,4,6,7,9,9a-hexahydro-1H-pyrazino[2,1-c][1,4]oxazin-8-yl]-(2-chloro-3-phenyl-phenyl)methanone | 16.1 |
| 23 | Chiral 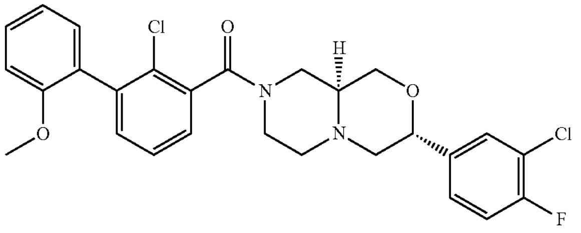 | [(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(2-methoxyphenyl)phenyl] methanone | 26.3 |
| 24 | Chiral 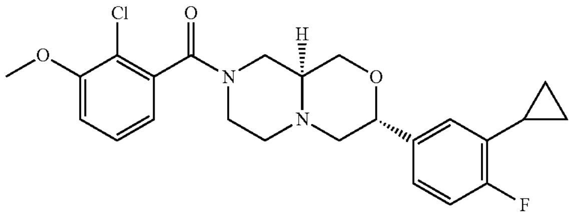 | [(3R,9aS)-3-(3-cyclopropyl-4-fluoro-phenyl)-3,4,6,7,9,9a-hexahydro-1H-pyrazino[2,1-c][1,4]oxazin-8-yl]-(2-chloro-3-methoxy-phenyl)methanone | 94.8 |
| 25 | Chiral 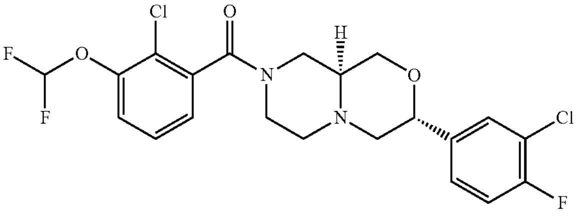 | [(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(difluoromethoxy)phenyl] methanone | 131.1 |
| 26 | Chiral 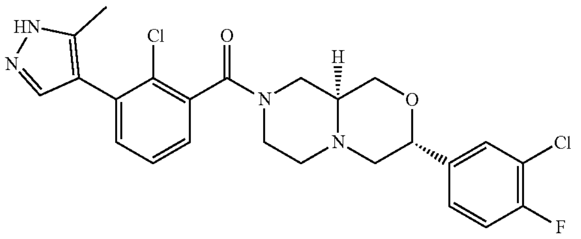 | [(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(5-methyl-1H-pyrazol-4-yl)phenyl]methanone | 10.6 |

TABLE 1-continued

| Ex. | Structure | IUPAC Name | MAGL IC50 (nM) |
|---|---|---|---|
| 27 | Chiral 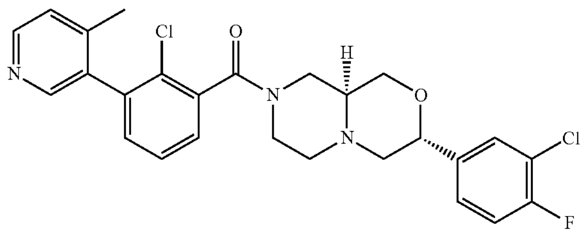 | [(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(4-methyl-3-pyridyl)phenyl]methanone | 210 |
| 28 | Chiral 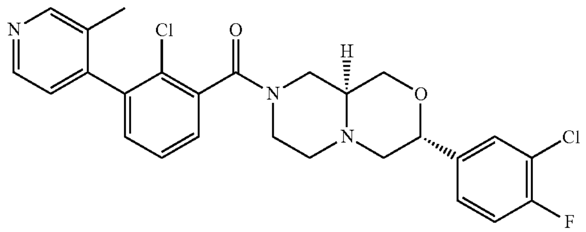 | [(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(3-methyl-4-pyridyl)phenyl]methanone | 32.6 |
| 29 | Chiral 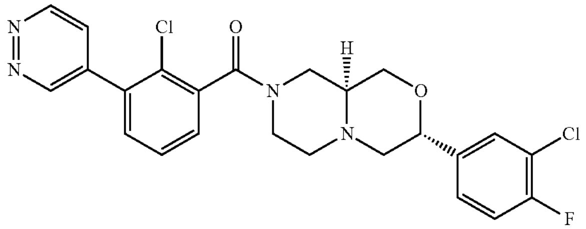 | [(3R,9aS)-3-(3-chloro-4-fluoro-phenyl)-3,4,6,7,9,9a-hexahydro-1H-pyrazino[2,1-c][1,4]oxazin-8-yl]-(2-chloro-3-pyridazin-4-yl-phenyl)methanone | 202 |
| 30 | Chiral 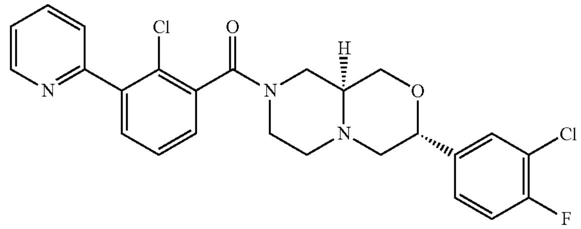 | [(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(2-pyridyl)phenyl] methanone | 49.2 |
| 31 | Chiral 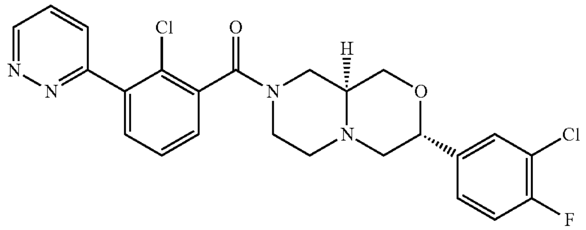 | [(3R,9aS)-3-(3-chloro-4-fluoro-phenyl)-3,4,6,7,9,9a-hexahydro-1H-pyrazino[2,1-c][1,4]oxazin-8-yl]-(2-chloro-3-pyridazin-3-yl-phenyl)methanone | 173.2 |
| 32 | 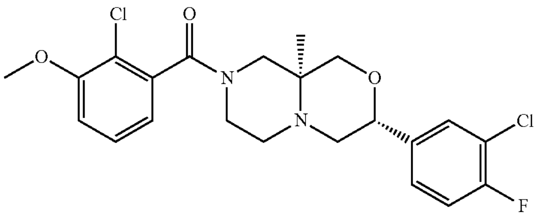 [SMILES: COc1cccc(C(=O)N2CCN3C[C@@H](c4ccc(F)c(Cl)c4)OC[C@]3(C)C2)c1Cl] | (2-chloro-3-methoxy-phenyl)-[(rel-3R,9aS)-3-(3-chloro-4-fluoro-phenyl)-9a-methyl-1,3,4,6,7,9-hexahydropyrazino[2,1-c][1,4]oxazin-8-yl]methanone | 334.5 |

TABLE 1-continued

| Ex. | Structure | IUPAC Name | MAGL IC50 (nM) |
|---|---|---|---|
| 33 | Chiral 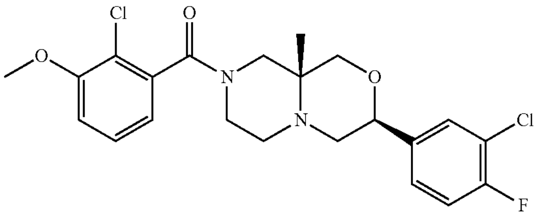 | (2-chloro-3-methoxy-phenyl)-[(rel-3S,9aR)-3-(3-chloro-4-fluoro-phenyl)-9a-methyl-1,3,4,6,7,9-hexahydropyrazino[2,1-c][1,4]oxazin-8-yl]methanone | 1912 |
| 34 | Chiral 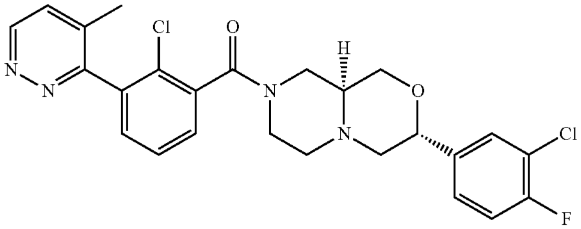 | [(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(4-methylpyridazin-3-yl)phenyl]methanone | 1444.2 |
| 35 | Chiral 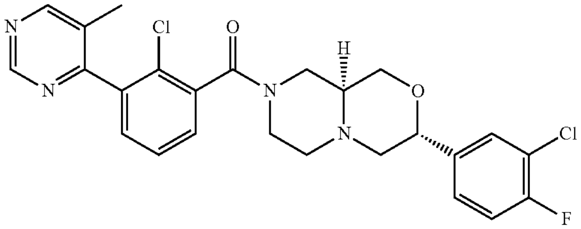 | [(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(5-methylpyrimidin-4-yl)phenyl]methanone | 1084.9 |
| 36 | Chiral 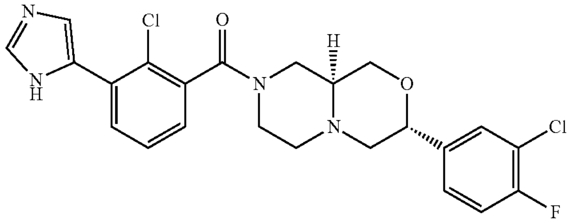 | [(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(1H-imidazol-5-yl)phenyl]methanone | 7.4 |
| 37 | Chiral 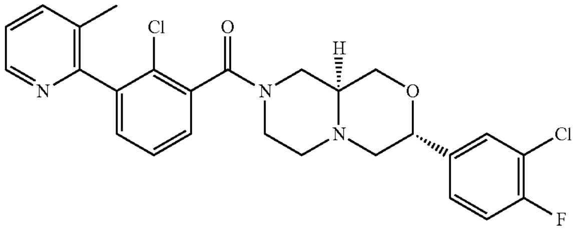 | [(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(3-methyl-2-pyridyl)phenyl]methanone | 277.4 |
| 38 | Chiral 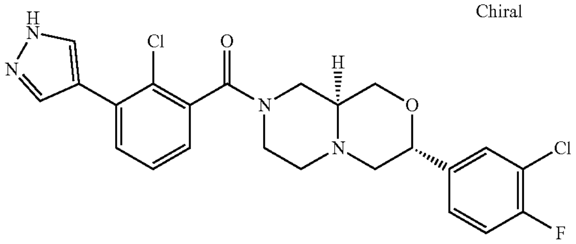 [SMILES: O=C(c1cccc(-c2cn[nH]c2)c1Cl)N1CCN2C[C@@H](c3ccc(F)c(Cl)c3)OC[C@@H]2C1] | [(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(1H-pyrazol-4-yl)phenyl]methanone | 1.9 |

TABLE 1-continued

| Ex. | Structure | IUPAC Name | MAGL IC50 (nM) |
|---|---|---|---|
| 39 | 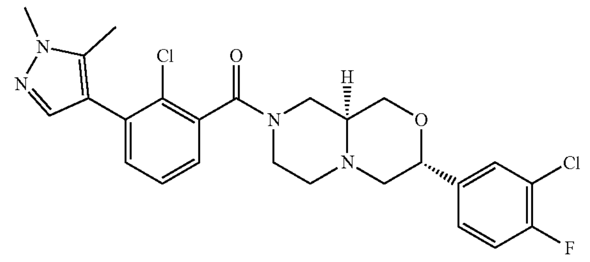 Chiral | [(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(1,5-dimethylpyrazol-4-yl)phenyl]methanone | 49.7 |
| 40 | 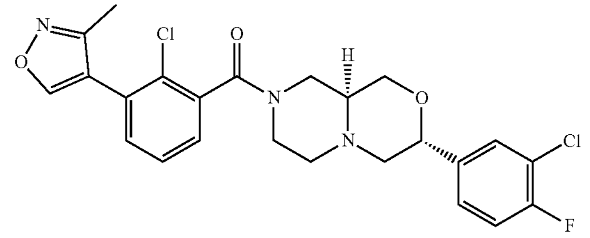 Chiral | [(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(3-methylisoxazol-4-yl)phenyl]methanone | 160.3 |
| 41 | 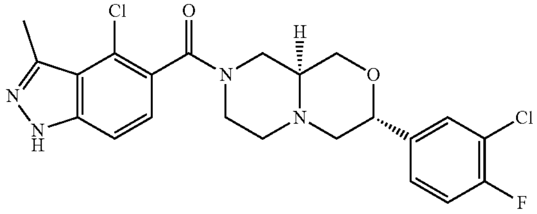 Chiral | [(3R,9aS)-3-(3-chloro-4-fluoro-phenyl)-3,4,6,7,9,9a-hexahydro-1H-pyrazino[2,1-c][1,4]oxazin-8-yl]-(4-chloro-3-methyl-1H-indazol-5-yl)methanone | 63.8 |
| 42 | 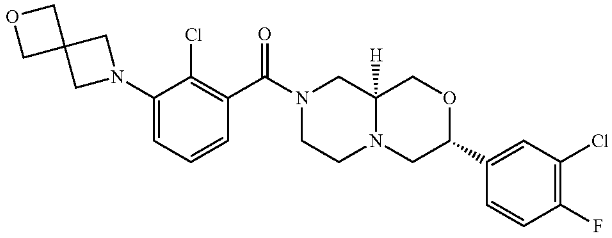 Chiral | [(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(2-oxa-6-azaspiro[3.3]heptan-6-yl)phenyl]methanone | 48.6 |
| 43 | 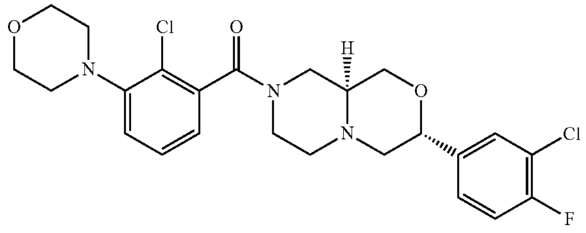 Chiral | [(3R,9aS)-3-(3-chloro-4-fluoro-phenyl)-3,4,6,7,9,9a-hexahydro-1H-pyrazino[2,1-c][1,4]oxazin-8-yl]-(2-chloro-3-morpholino-phenyl)methanone | 119.7 |

TABLE 1-continued

| Ex. | Structure | IUPAC Name | MAGL IC50 (nM) |
|---|---|---|---|
| 44 | 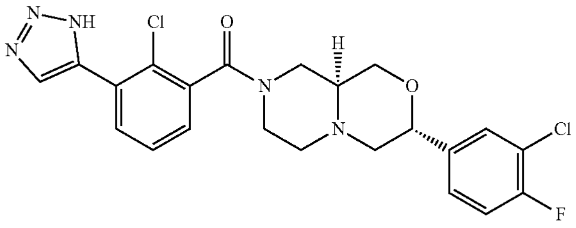 Chiral | [(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(1H-triazol-5-yl)phenyl]methanone | 50 |
| 45 | 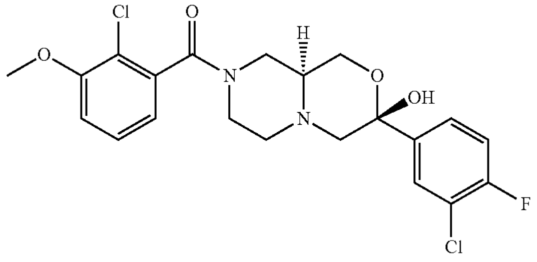 Chiral | [(3R,9aS)-3-(3-chloro-4-fluoro-phenyl)-3-hydroxy-1,4,6,7,9,9a-hexahydropyrazino[2,1-c][1,4]oxazin-8-yl]-(2-chloro-3-methoxy-phenyl)methanone | 19.4 |
| 46 | 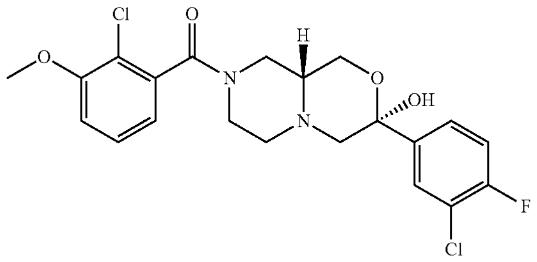 Chiral | [(3S,9aR)-3-(3-chloro-4-fluoro-phenyl)-3-hydroxy-1,4,6,7,9,9a-hexahydropyrazino[2,1-c][1,4]oxazin-8-yl]-(2-chloro-3-methoxy-phenyl)methanone | 177.5 |
| 47 | 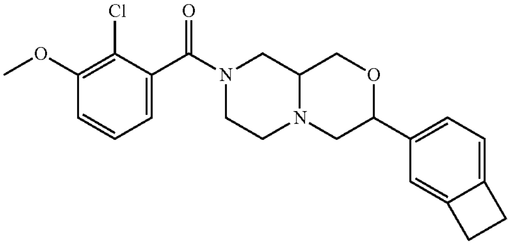 [SMILES: COc1cccc(C(=O)N2CCN3CC(c4ccc5c(c4)CC5)OCC3C2)c1Cl] | [3-(3-bicyclo[4.2.0]octa-1,3,5-trienyl)-3,4,6,7,9,9a-hexahydro-1H-pyrazino[2,1-c][1,4]oxazin-8-yl]-(2-chloro-3-methoxy-phenyl)methanone | 133.7 |
| 48 | 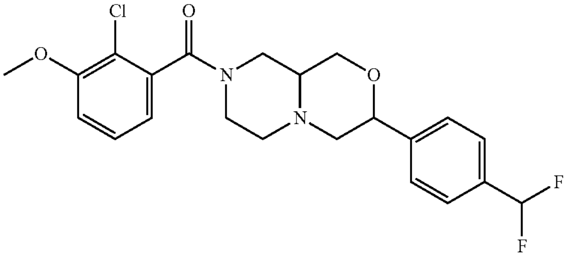 [SMILES: COc1cccc(C(=O)N2CCN3CC(c4ccc(C(F)F)cc4)OCC3C2)c1Cl] | (2-chloro-3-methoxy-phenyl)-[3-[4-(difluoromethyl)phenyl]-3,4,6,7,9,9a-hexahydro-1H-pyrazino[2,1-c][1,4]oxazin-8-yl]methanone | 146.2 |

TABLE 1-continued

| Ex. | Structure | IUPAC Name | MAGL IC50 (nM) |
|---|---|---|---|
| 49 | Chiral 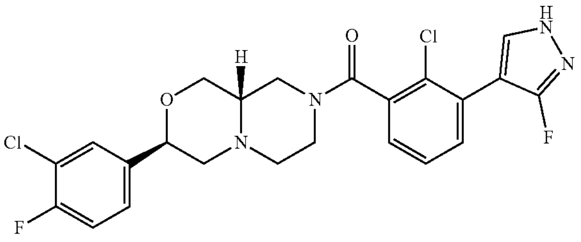 | [(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(3-fluoro-1H-pyrazol-4-yl)phenyl]methanone | 1 |
| 50 | Chiral 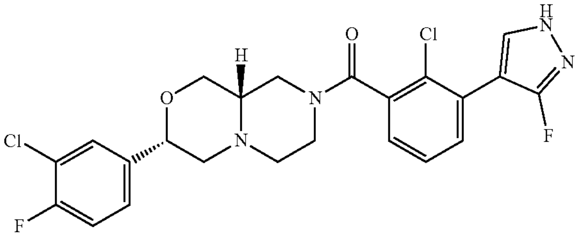 | [(3S,9aS)-3-(3-chloro-4-fluoro-phenyl)-3,4,6,7,9,9a-hexahydro-1H-pyrazino[2,1-c][1,4]oxazin-8-yl]-[2-chloro-3-(3-fluoro-1H-pyrazol-4-yl)phenyl]methanone | 417.6 |
| 51 | 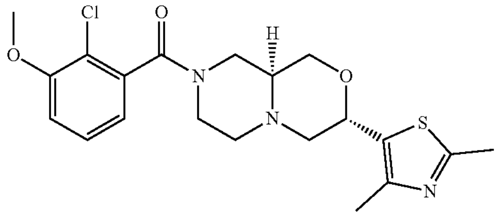 [SMILES: COc1cccc(C(=O)N2CCN3C[C@@H](c4sc(C)nc4C)OC[C@@H]3C2)c1Cl] | (2-chloro-3-methoxy-phenyl)-[rel-(3S,9aS)-3-(2,4-dimethylthiazol-5-yl)-3,4,6,7,9,9a-hexahydro-1H-pyrazino[2,1-c][1,4]oxazin-8-yl]methanone | 4984.9 |
| 52 | 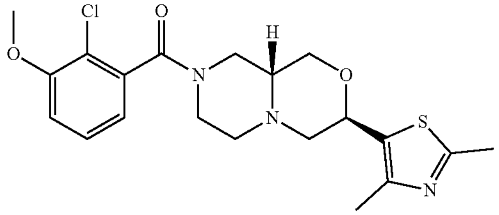 [SMILES: COc1cccc(C(=O)N2CCN3C[C@H](c4sc(C)nc4C)OC[C@H]3C2)c1Cl] | (2-chloro-3-methoxy-phenyl)-[rel-(3R,9aR)-3-(2,4-dimethylthiazol-5-yl)-3,4,6,7,9,9a-hexahydro-1H-pyrazino[2,1-c][1,4]oxazin-8-yl]methanone | 1383.2 |
| 53 | 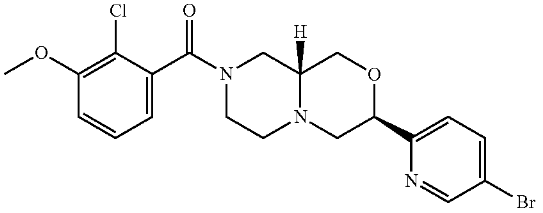 [SMILES: COc1cccc(C(=O)N2CCN3C[C@H](c4ccc(Br)cn4)OC[C@H]3C2)c1Cl] | (2-chloro-3-methoxy-phenyl)-[rac-(3R,9aR)-3-(5-bromo-2-pyridyl)-3,4,6,7,9,9a-hexahydro-1H-pyrazino[2,1-c][1,4]oxazin-8-yl]methanone | 76 |
| 54 | 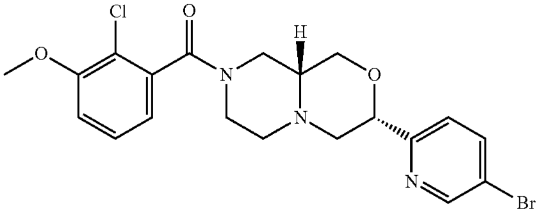 [SMILES: COc1cccc(C(=O)N2CCN3C[C@@H](c4ccc(Br)cn4)OC[C@H]3C2)c1Cl] | (2-chloro-3-methoxy-phenyl)-[rac-(3S,9aR)-3-(5-bromo-2-pyridyl)-3,4,6,7,9,9a-hexahydro-1H-pyrazino[2,1-c][1,4]oxazin-8-yl]methanone | 975.4 |

TABLE 1-continued

| Ex. | Structure | IUPAC Name | MAGL IC50 (nM) |
|---|---|---|---|
| 58 | 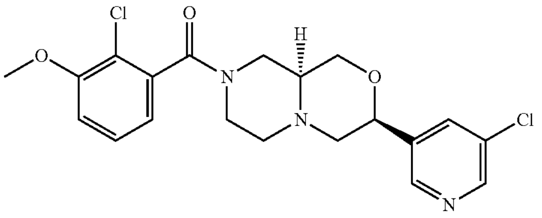 [SMILES: COc1cccc(C(=O)N2CCN3C[C@H](c4cncc(Cl)c4)OC[C@@H]3C2)c1Cl] | (2-chloro-3-methoxy-phenyl)-[rac-(3S,9aS)-3-(5-chloro-3-pyridyl)-3,4,6,7,9,9a-hexahydro-1H-pyrazino[2,1-c][1,4]oxazin-8-yl]methanone | 2221.6 |
| 59 | 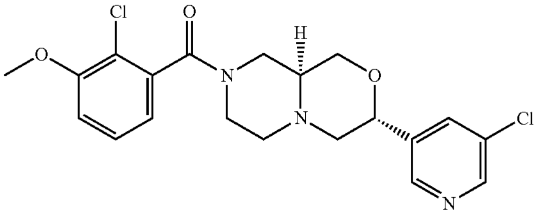 [SMILES: COc1cccc(C(=O)N2CCN3C[C@@H](c4cncc(Cl)c4)OC[C@@H]3C2)c1Cl] | (2-chloro-3-methoxy-phenyl)-[rac-(3R,9aS)-3-(5-chloro-3-pyridyl)-3,4,6,7,9,9a-hexahydro-1H-pyrazino[2,1-c][1,4]oxazin-8-yl]methanone | 543.6 |
| 60 | 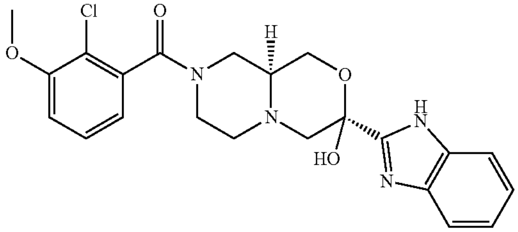 [SMILES: COc1cccc(C(=O)N2CCN3C[C@@](O)(c4nc5ccccc5[nH]4)OC[C@@H]3C2)c1Cl] | (2-chloro-3-methoxy-phenyl)-[rel-(3S,9aS)-3-(1H-benzimidazol-2-yl)-3-hydroxy-1,4,6,7,9,9a-hexahydropyrazino[2,1-c][1,4]oxazin-8-yl]methanone | 951.1 |
| 61 | 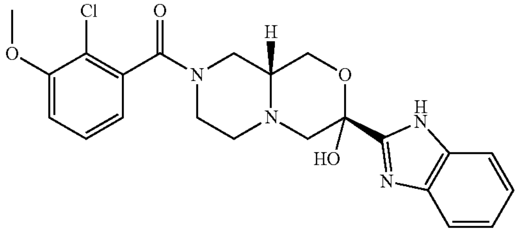 [SMILES: COc1cccc(C(=O)N2CCN3C[C@](O)(c4nc5ccccc5[nH]4)OC[C@H]3C2)c1Cl] | (2-chloro-3-methoxy-phenyl)-[rel-(3R,9aR)-3-(1H-benzimidazol-2-yl)-3-hydroxy-1,4,6,7,9,9a-hexahydropyrazino[2,1-c][1,4]oxazin-8-yl]methanone | 294.4 |
| 63 | 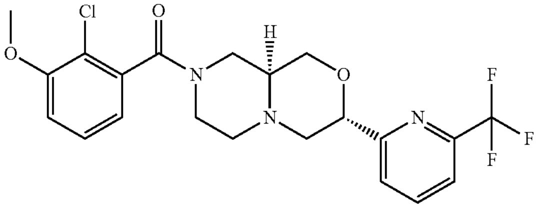 [SMILES: COc1cccc(C(=O)N2CCN3C[C@@H](c4cccc(C(F)(F)F)n4)OC[C@@H]3C2)c1Cl] | (2-chloro-3-methoxy-phenyl)-[rel-(3S,9aS)-3-[6-(trifluoromethyl)-2-pyridyl]-3,4,6,7,9,9a-hexahydro-1H-pyrazino[2,1-c][1,4]oxazin-8-yl]methanone | 1309.0 |
| 65 | 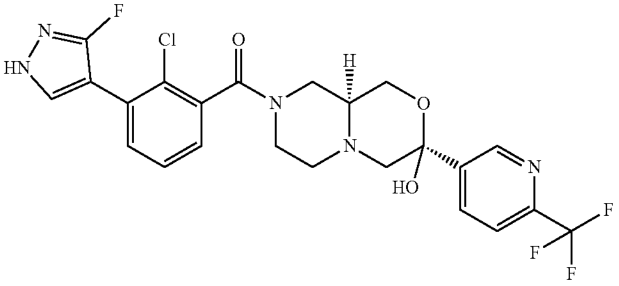 [SMILES: O=C(c1cccc(-c2c[nH]nc2F)c1Cl)N1CCN2C[C@@](O)(c3ccc(C(F)(F)F)nc3)OC[C@@H]2C1] | [(3R,9aS)-3-hydroxy-3-[6-(trifluoromethyl)pyridin-3-yl]-1,4,6,7,9,9a-hexahydropyrazino[2,1-c][1,4]oxazin-8-yl]-[2-chloro-3-(3-fluoro-1H-pyrazol-4-yl)phenyl]methanone | 13.8 |

TABLE 1-continued

| Ex. | Structure | IUPAC Name | MAGL IC50 (nM) |
|---|---|---|---|
| 66 | 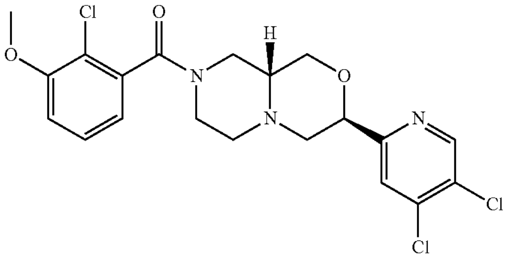 [SMILES: COc1cccc(C(=O)N2CCN3C[C@H](c4cc(Cl)c(Cl)cn4)OC[C@H]3C2)c1Cl] | (2-chloro-3-methoxy-phenyl)-[rel-(3R,9aR)-3-(4,5-dichloro-2-pyridyl)-3,4,6,7,9,9a-hexahydro-1H-pyrazino[2,1-c][1,4]oxazin-8-yl]methanone | 531.1 |
| 67 | 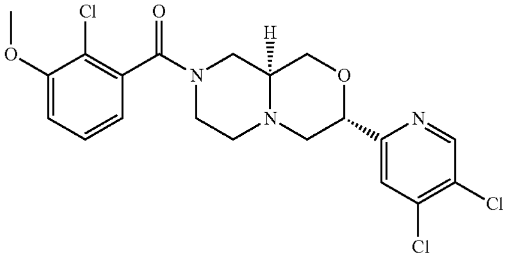 | (2-chloro-3-methoxy-phenyl)-[rel-(3S,9aS)-3-(4,5-dichloro-2-pyridyl)-3,4,6,7,9,9a-hexahydro-1H-pyrazino[2,1-c][1,4]oxazin-8-yl]methanone | 8.4 |
| 68 | 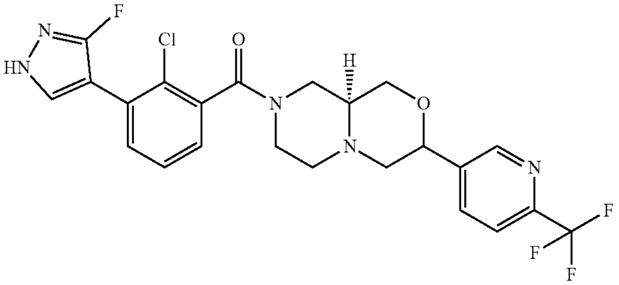 [SMILES: O=C(c1cccc(-c2c[nH]nc2F)c1Cl)N1CCN2CC(c3ccc(C(F)(F)F)nc3)OC[C@@H]2C1] | [(9aS)-3-[6-(trifluoromethyl)-3-pyridyl]-3,4,6,7,9,9a-hexahydro-1H-pyrazino[2,1-c][1,4]oxazin-8-yl]-[2-chloro-3-(3-fluoro-1H-pyrazol-4-yl)phenyl]methanone | 15.8 |
| 69 | 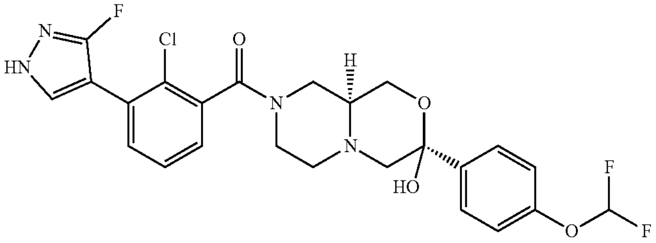 [SMILES: O=C(c1cccc(-c2c[nH]nc2F)c1Cl)N1CCN2C[C@@](O)(c3ccc(OC(F)F)cc3)OC[C@@H]2C1] | [2-chloro-3-(3-fluoro-1H-pyrazol-4-yl)phenyl]-[(3R,9aS)-3-[4-(difluoromethoxy)phenyl]-3-hydroxy-1,4,6,7,9,9a-hexahydropyrazino[2,1-c][1,4]oxazin-8-yl]methanone | 51.8 |
| 70 | 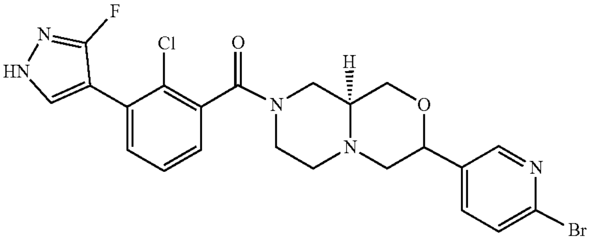 [SMILES: O=C(c1cccc(-c2c[nH]nc2F)c1Cl)N1CCN2CC(c3ccc(Br)nc3)OC[C@@H]2C1] | [2-chloro-3-(3-fluoro-1H-pyrazol-4-yl)phenyl]-[(9aS)-3-(6-bromo-3-pyridyl)-3,4,6,7,9,9a-hexahydro-1H-pyrazino[2,1-c][1,4]oxazin-8-yl]methanone | 44.6 |
| 71 | Chiral 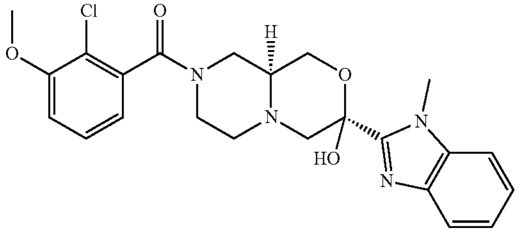 | [(3S,9aS)-3-hydroxy-3-(1-methylbenzimidazol-2-yl)-1,4,6,7,9,9a-hexahydropyrazino[2,1-c][1,4]oxazin-8-yl]-(2-chloro-3-methoxy-phenyl)methanone | 4026.0 |

TABLE 1-continued

| Ex. | Structure | IUPAC Name | MAGL IC50 (nM) |
|---|---|---|---|
| 72 | 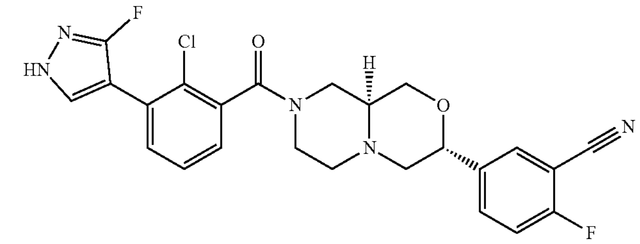 Chiral | 5-[(3R,9aS)-8-[2-chloro-3-(3-fluoro-1H-pyrazol-4-yl)benzoyl]-3,4,6,7,9,9a-hexahydro-1H-pyrazino[2,1-c][1,4]oxazin-3-yl]-2-fluoro-benzonitrile | 61.4 |
| 73 | 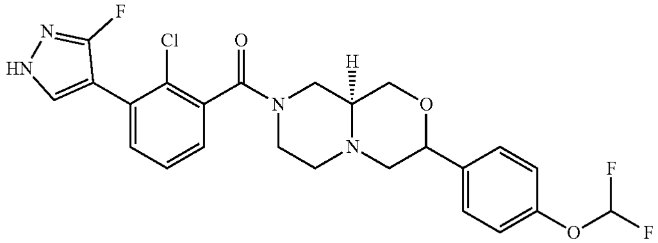 [SMILES: O=C(c1cccc(-c2c[nH]nc2F)c1Cl)N1CCN2CC(c3ccc(OC(F)F)cc3)OC[C@@H]2C1] | (2-chloro-3-(3-fluoro-1H-pyrazol-4-yl)phenyl)((9aS)-3-(4-(difluoromethoxy)phenyl)hexahydropyrazino[2,1-c][1,4]oxazin-8(1H)-yl)methanone | 53.3 |
| 74 | 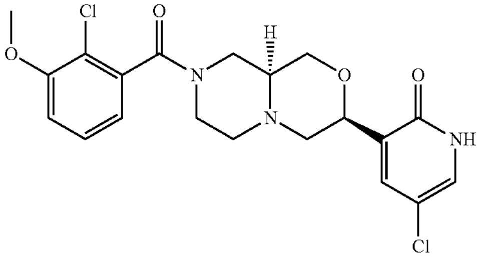 Chiral | 3-[(3S,9aS)-8-(2-chloro-3-methoxy-benzoyl)-3,4,6,7,9,9a-hexahydro-1H-pyrazino[2,1-c][1,4]oxazin-3-yl]-5-chloro-1H-pyridin-2-one | 2211.9 |
| 75 | 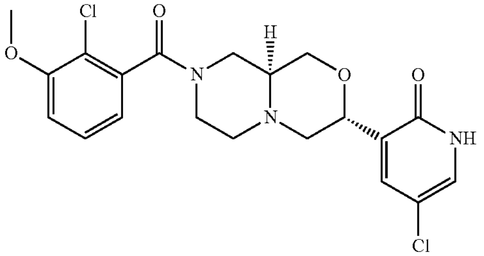 Chiral | 3-[(3R,9aS)-8-(2-chloro-3-methoxy-benzoyl)-3,4,6,7,9,9a-hexahydro-1H-pyrazino[2,1-c][1,4]oxazin-3-yl]-5-chloro-1H-pyridin-2-one | 850.4 |
| 76 | 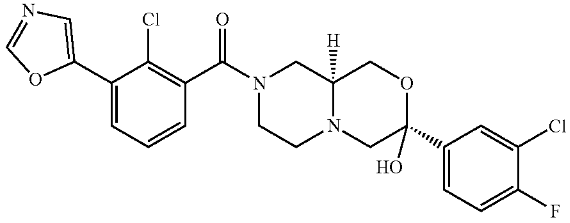 Chiral | [(3R,9aS)-3-(3-chloro-4-fluoro-phenyl)-3-hydroxy-1,4,6,7,9,9a-hexahydropyrazino[2,1-c][1,4]oxazin-8-yl]-(2-chloro-3-oxazol-5-yl-phenyl)methanone | 15.5 |

TABLE 1-continued

| Ex. | Structure | IUPAC Name | MAGL IC50 (nM) |
|---|---|---|---|
| 77 | Chiral 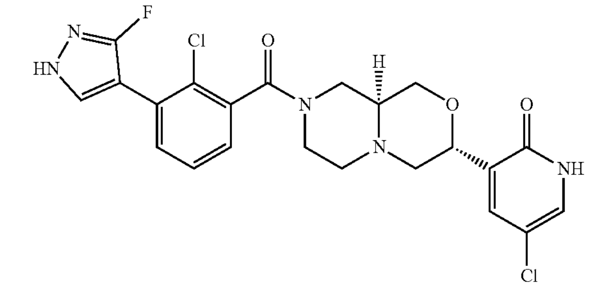 | 3-[(3R,9aS)-8-[2-chloro-3-(3-fluoro-1H-pyrazol-4-yl)benzoyl]-3,4,6,7,9,9a-hexahydro-1H-pyrazino[2,1-c][1,4]oxazin-3-yl]-5-chloro-1H-pyridin-2-one | 46.3 |
| 78 | Chiral 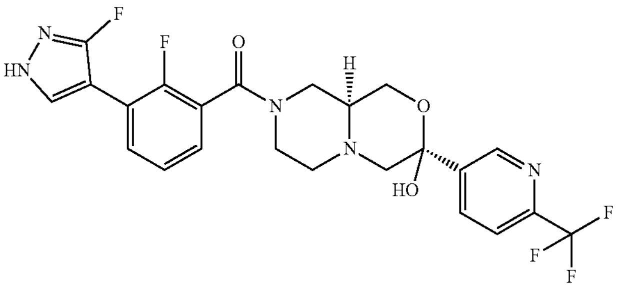 | [(3R,9aS)-3-hydroxy-3-[6-(trifluoromethyl)-3-pyridyl]-1,4,6,7,9,9a-hexahydropyrazino[2,1-c][1,4]oxazin-8-yl]-[2-fluoro-3-(3-fluoro-1H-pyrazol-4-yl)phenyl]methanone | 129.7 |
| 80 | Chiral 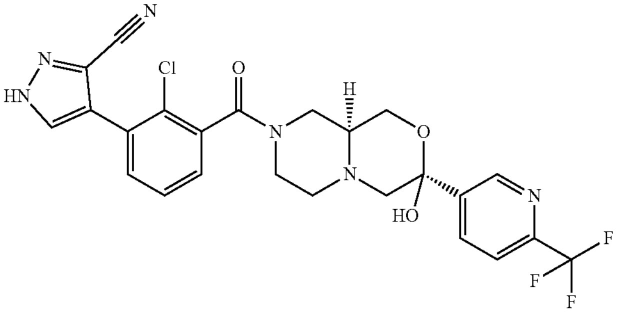 | 4-[3-[(3R,9aS)-3-hydroxy-3-[6-(trifluoromethyl)-3-pyridyl]-1,4,6,7,9,9a-hexahydropyrazino[2,1-c][1,4]oxazine-8-carbonyl]-2-chloro-phenyl]-1H-pyrazole-3-carbonitrile | 26.2 |
| 81 | Chiral 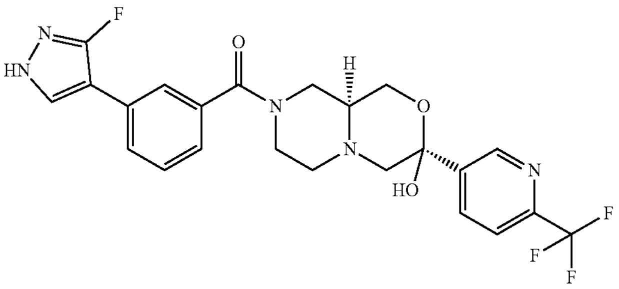 | [(3R,9aS)-3-hydroxy-3-[6-(trifluoromethyl)-3-pyridyl]-1,4,6,7,9,9a-hexahydropyrazino[2,1-c][1,4]oxazin-8-yl]-[3-(3-fluoro-1H-pyrazol-4-yl)phenyl]methanone | 80.4 |

TABLE 1-continued

| Ex. | Structure | IUPAC Name | MAGL IC50 (nM) |
|---|---|---|---|
| 82 | Chiral 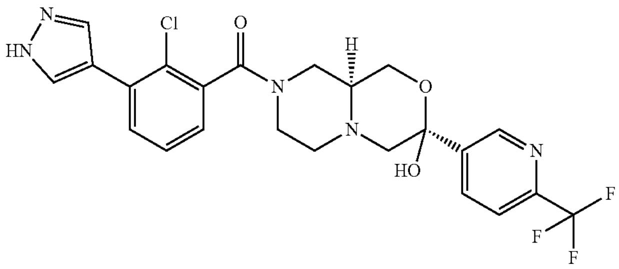 | [(3R,9aS)-3-hydroxy-3-[6-(trifluoromethyl)-3-pyridyl]-1,4,6,7,9,9a-hexahydropyrazino[2,1-c][1,4]oxazin-8-yl]-[2-chloro-3-(1H-pyrazol-4-yl)phenyl]methanone | 15.9 |
| 83 | 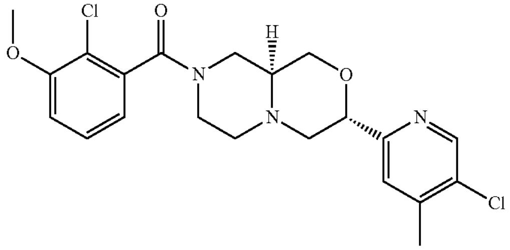 [SMILES: COc1cccc(C(=O)N2CCN3C[C@@H](c4cc(C)c(Cl)cn4)OC[C@@H]3C2)c1Cl] | (2-chloro-3-methoxyphenyl)((3S,9aS)-3-(5-chloro-4-methylpyridin-2-yl)hexahydropyrazino[2,1-c][1,4]oxazin-8(1H)-yl)methanone | 94.4 |
| 84 | 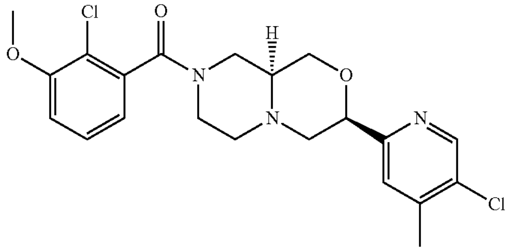 [SMILES: COc1cccc(C(=O)N2CCN3C[C@H](c4cc(C)c(Cl)cn4)OC[C@@H]3C2)c1Cl] | (2-chloro-3-methoxyphenyl)((3R,9aS)-3-(5-chloro-4-methylpyridin-2-yl)hexahydropyrazino[2,1-c][1,4]oxazin-8(1H)-yl)methanone | 332.7 |
| 85 | Chiral 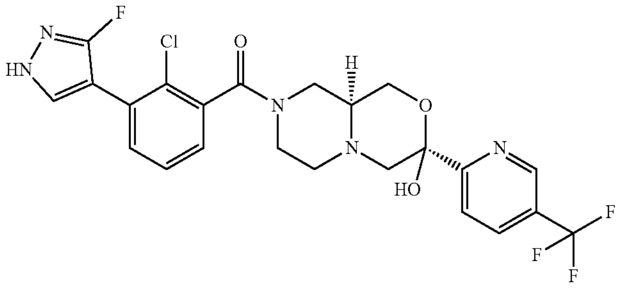 | [(3S,9aS)-3-hydroxy-3-[5-(trifluoromethyl)-2-pyridyl]-1,4,6,7,9,9a-hexahydropyrazino[2,1-c][1,4]oxazin-8-yl]-[2-chloro-3-(3-fluoro-1H-pyrazol-4-yl)phenyl]methanone | 38.2 |
| 86 | Chiral 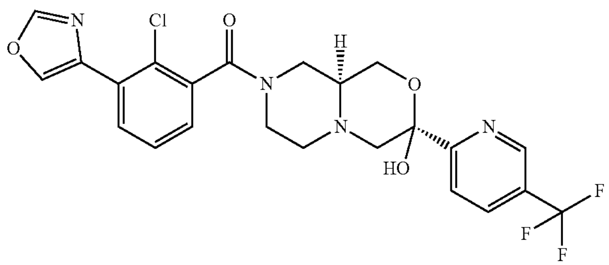 | [(3S,9aS)-3-hydroxy-3-[5-(trifluoromethyl)-2-pyridyl]-1,4,6,7,9,9a-hexahydropyrazino[2,1-c][1,4]oxazin-8-yl]-(2-chloro-3-oxazol-4-yl-phenyl)methanone | 237.3 |

TABLE 1-continued

| Ex. | Structure | IUPAC Name | MAGL IC50 (nM) |
|---|---|---|---|
| 87 | 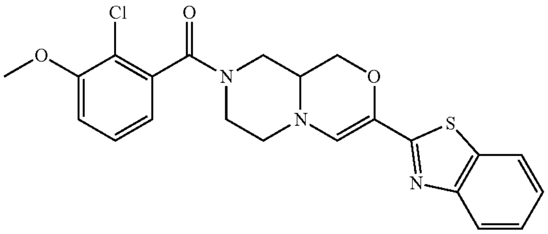 [SMILES: COc1cccc(C(=O)N2CCN3C=C(c4nc5ccccc5s4)OCC3C2)c1Cl] | [3-(1,3-benzothiazol-2-yl)-6,7,9,9a-tetrahydro-1H-pyrazino[2,1-c][1,4]oxazin-8-yl]-(2-chloro-3-methoxy-phenyl)methanone | 983.2 |
| 88 | 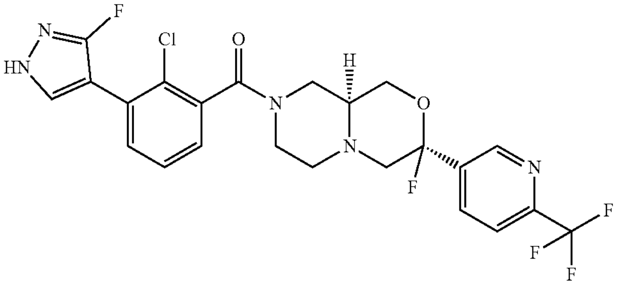 [SMILES: O=C(c1cccc(-c2c[nH]nc2F)c1Cl)N1CCN2C[C@@](F)(c3ccc(C(F)(F)F)nc3)OC[C@@H]2C1] | [2-chloro-3-(3-fluoro-1H-pyrazol-4-yl)phenyl]-[(3S,9aS)-3-fluoro-3-[6-(trifluoromethyl)-3-pyridyl]-1,4,6,7,9,9a-hexahydropyrazino[2,1-c][1,4]oxazin-8-yl]methanone | 10.7 |
| 89 | 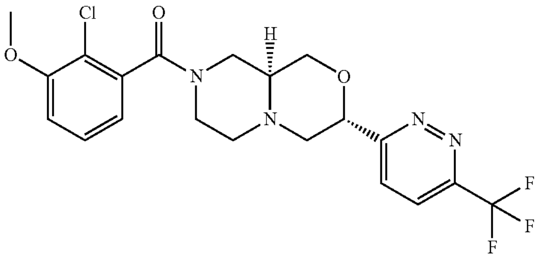 [SMILES: COc1cccc(C(=O)N2CCN3C[C@@H](c4ccc(C(F)(F)F)nn4)OC[C@@H]3C2)c1Cl] | (2-chloro-3-methoxy-phenyl)-[(3S,9aS)-3-[6-(trifluoromethyl) pyridazin-3-yl]-3,4,6,7,9,9a-hexahydro-1H-pyrazino[2,1-c] [1,4]oxazin-8-yl]methanone | 2030.6 |
| 90 | 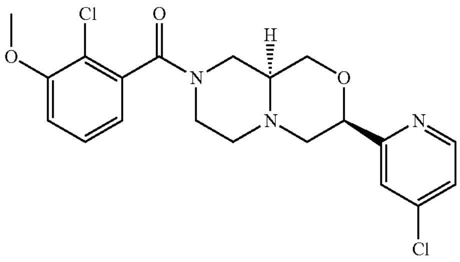 Chiral | [(3R,9aS)-3-(4-chloro-2-pyridyl)-3,4,6,7,9,9a-hexahydro-1H-pyrazino[2,1-c][1,4]oxazin-8-yl]-(2-chloro-3-methoxy-phenyl)methanone | 2311.4 |
| 91 | 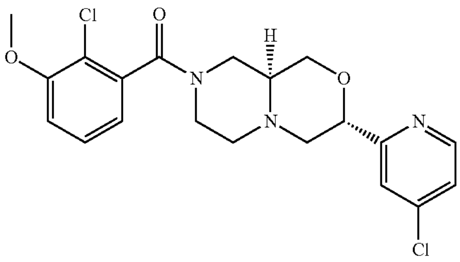 Chiral | [(3S,9aS)-3-(4-chloro-2-pyridyl)-3,4,6,7,9,9a-hexahydro-1H-pyrazino[2,1-c][1,4]oxazin-8-yl]-(2-chloro-3-methoxy-phenyl)methanone | 232.5 |

TABLE 1-continued

| Ex. | Structure | IUPAC Name | MAGL IC50 (nM) |
|---|---|---|---|
| 92 | Chiral 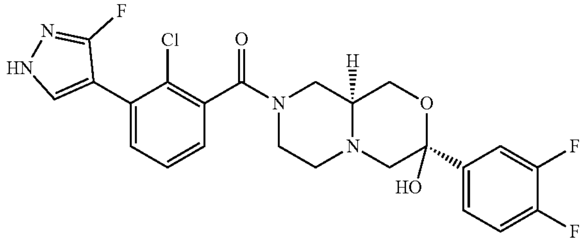 | [(3R,9aS)-3-(3,4-difluorophenyl)-3-hydroxy-1,4,6,7,9,9a-hexahydropyrazino[2,1-c][1,4]oxazin-8-yl]-[2-chloro-3-(3-fluoro-1H-pyrazol-4-yl)phenyl]methanone | 9.1 |
| 93 | Chiral 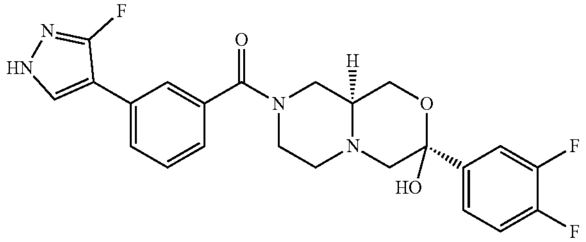 | [(3R,9aS)-3-(3,4-difluorophenyl)-3-hydroxy-1,4,6,7,9,9a-hexahydropyrazino[2,1-c][1,4]oxazin-8-yl]-[3-(3-fluoro-1H-pyrazol-4-yl)phenyl]methanone | 81.9 |
| 94 | Chiral 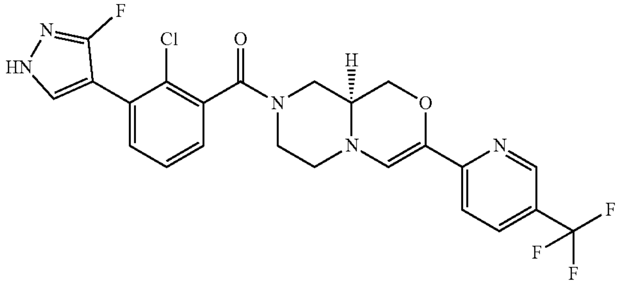 | [(9aS)-3-[5-(trifluoromethyl)-2-pyridyl]-6,7,9,9a-tetrahydro-1H-pyrazino[2,1-c][1,4]oxazin-8-yl]-[2-chloro-3-(3-fluoro-1H-pyrazol-4-yl)phenyl]methanone | 219.7 |
| 95 | Chiral 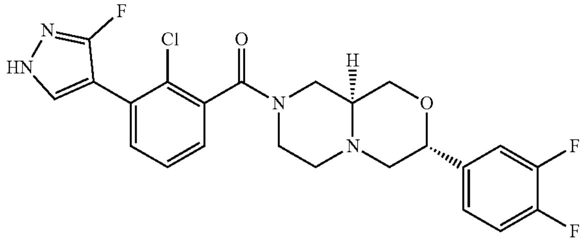 | [(3R,9aS)-3-(3,4-difluorophenyl)-3,4,6,7,9,9a-hexahydro-1H-pyrazino[2,1-c][1,4]oxazin-8-yl]-[2-chloro-3-(3-fluoro-1H-pyrazol-4-yl)phenyl]methanone | 7.6 |
| 96 | Chiral 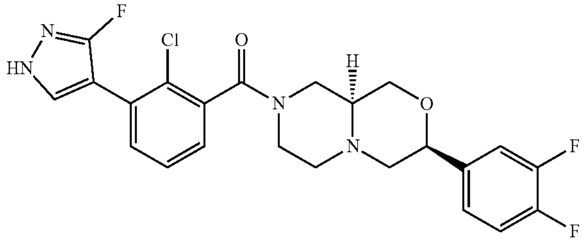 | [(3S,9aS)-3-(3,4-difluorophenyl)-3,4,6,7,9,9a-hexahydro-1H-pyrazino[2,1-c][1,4]oxazin-8-yl]-[2-chloro-3-(3-fluoro-1H-pyrazol-4-yl)phenyl]methanone | 1242.7 |

TABLE 1-continued

| Ex. | Structure | IUPAC Name | MAGL IC50 (nM) |
|---|---|---|---|
| 97 | Chiral 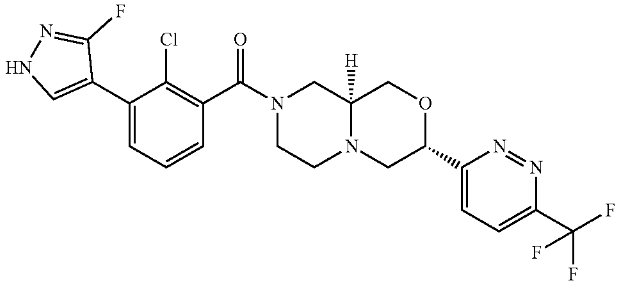 | [(3S,9aS)-3-[6-(trifluoromethyl) pyridazin-3-yl]-3,4,6,7,9,9a-hexahydro-1H-pyrazino[2,1-c][1,4]oxazin-8-yl]-[2-chloro-3-(3-fluoro-1H-pyrazol-4-yl)phenyl]methanone | 439.4 |
| 98 | 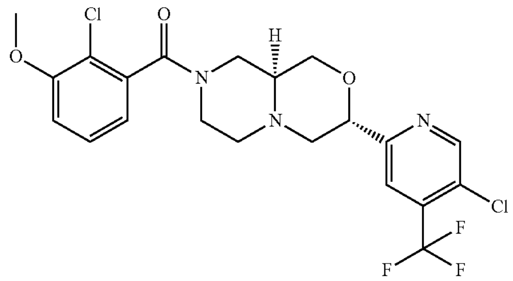 [SMILES: COc1cccc(C(=O)N2CCN3C[C@@H](c4cc(C(F)(F)F)c(Cl)cn4)OC[C@@H]3C2)c1Cl] | (2-chloro-3-methoxy-phenyl)-[(3S,9aS)-3-[5-chloro-4-(trifluoromethyl)-2-pyridyl]-3,4,6,7,9,9a-hexahydro-1H-pyrazino[2,1-c][1,4]oxazin-8-yl]methanone | 30.7 |
| 99 | 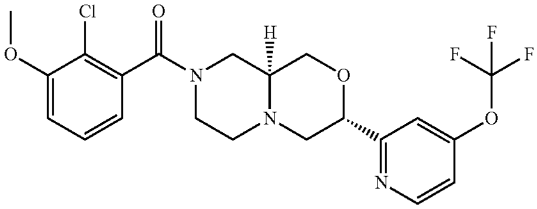 [SMILES: COc1cccc(C(=O)N2CCN3C[C@@H](c4cc(OC(F)(F)F)ccn4)OC[C@@H]3C2)c1Cl] | (2-chloro-3-methoxy-phenyl)-[(3S,9aS)-3-[4-(trifluoromethoxy)-2-pyridyl]-3,4,6,7,9,9a-hexahydro-1H-pyrazino[2,1-c][1,4]oxazin-8-yl]methanone | 284.1 |
| 100 | Chiral 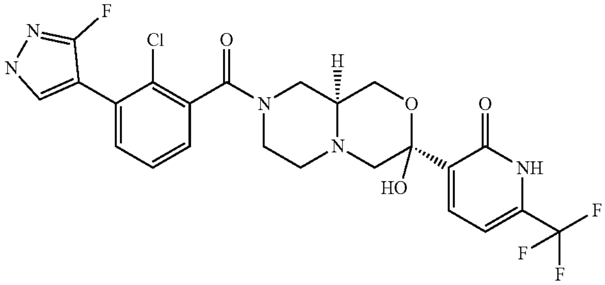 | 3-[(3R,9aS)-8-[2-chloro-3-(3-fluoro-1H-pyrazol-4-yl)benzoyl]-3-hydroxy-1,4,6,7,9,9a-hexahydropyrazino[2,1-c][1,4]oxazin-3-yl]-6-(trifluoromethyl)-1H-pyridin-2-one | 55.3 |
| 101 | 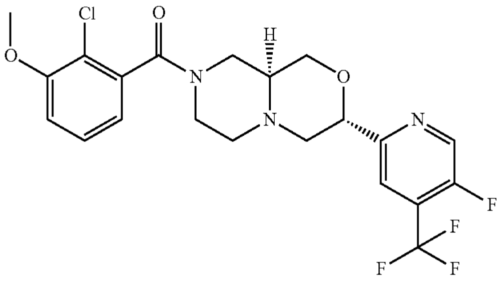 [SMILES: COc1cccc(C(=O)N2CCN3C[C@@H](c4cc(C(F)(F)F)c(F)cn4)OC[C@@H]3C2)c1Cl] | (2-chloro-3-methoxy-phenyl)-[(3S,9aS)-3-[5-fluoro-4-(trifluoromethyl)-2-pyridyl]-3,4,6,7,9,9a-hexahydro-1H-pyrazino[2,1-c][1,4]oxazin-8-yl]methanone | 133.2 |

TABLE 1-continued

| Ex. | Structure | IUPAC Name | MAGL IC50 (nM) |
|---|---|---|---|
| 102 | Chiral 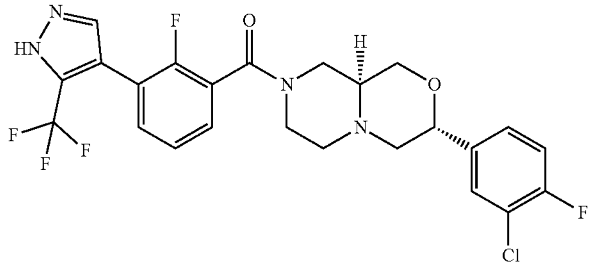 | [(3R,9aS)-3-(3-chloro-4-fluoro-phenyl)-3,4,6,7,9,9a-hexahydro-1H-pyrazino[2,1-c][1,4]oxazin-8-yl]-[2-fluoro-3-[5-(trifluoromethyl)-1H-pyrazol-4-yl]phenyl]methanone | 20.7 |
| 103 | Chiral 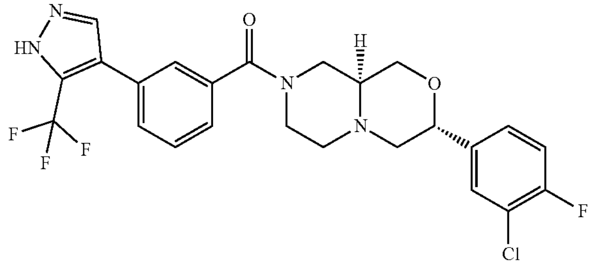 | [(3R,9aS)-3-(3-chloro-4-fluoro-phenyl)-3,4,6,7,9,9a-hexahydro-1H-pyrazino[2,1-c][1,4]oxazin-8-yl]-[3-[5-(trifluoromethyl)-1H-pyrazol-4-yl]phenyl]methanone | 28.2 |
| 104 | 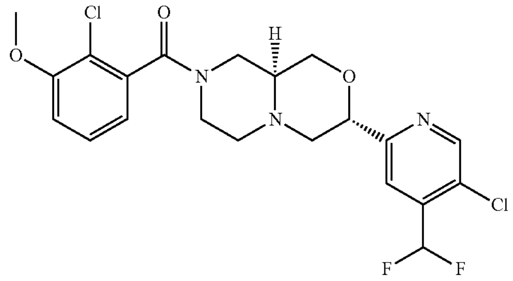 [SMILES: COc1cccc(C(=O)N2CCN3C[C@@H](c4cc(C(F)F)c(Cl)cn4)OC[C@@H]3C2)c1Cl] | (2-chloro-3-methoxy-phenyl)-[(3S,9aS)-3-[4-(difluoromethyl)-5-fluoro-2-pyridyl]-3,4,6,7,9,9a-hexahydro-1H-pyrazino[2,1-c][1,4]oxazin-8-yl]methanone | 89.5 |
| 105 | Chiral 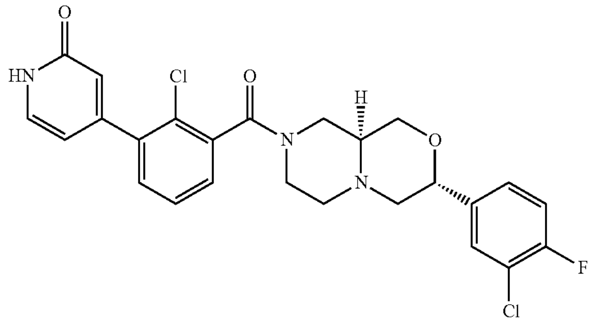 | 4-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]-1H-pyridin-2-one | 8.9 |
| 106 | Chiral 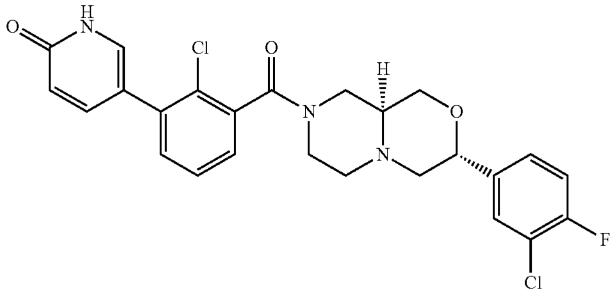 | 5-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]-1H-pyridin-2-one | 14.3 |

TABLE 1-continued

| Ex. | Structure | IUPAC Name | MAGL IC50 (nM) |
|---|---|---|---|
| 107 | 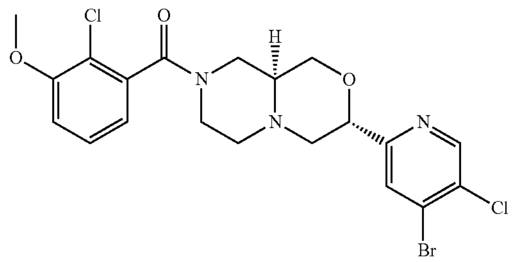 [SMILES: COc1cccc(C(=O)N2CCN3C[C@@H](c4cc(Br)c(Cl)cn4)OC[C@@H]3C2)c1Cl] | (2-chloro-3-methoxy-phenyl)-[(3S,9aS)-3-[5-chloro-4-bromo-2-pyridyl]-3,4,6,7,9,9a-hexahydro-1H-pyrazino[2,1-c][1,4]oxazin-8-yl]methanone | 12.6 |
| 108 | Chiral 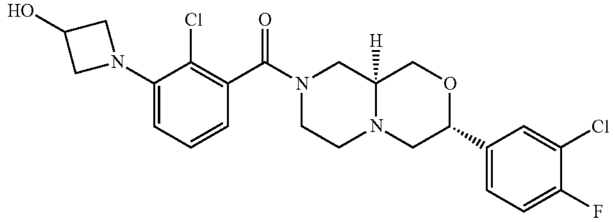 | [(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(3-hydroxyazetidin-1-yl)phenyl]methanone | 10.5 |
| 109 | Chiral 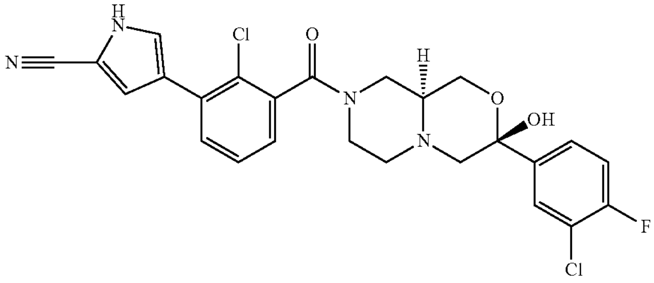 | 4-[3-[(3R,9aS)-3-(3-chloro-4-fluoro-phenyl)-3-hydroxy-1,4,6,7,9,9a-hexahydropyrazino[2,1-c][1,4]oxazine-8-carbonyl]-2-chloro-phenyl]-1H-pyrrole-2-carbonitrile | 1.6 |
| 110 | Chiral 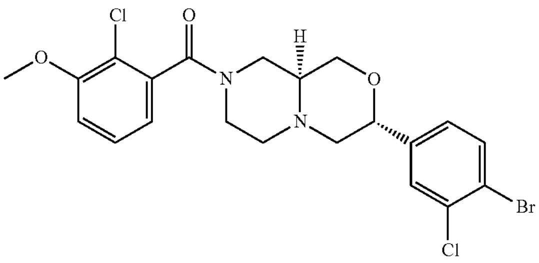 | [(3R,9aS)-3-(4-bromo-3-chloro-phenyl)-3,4,6,7,9,9a-hexahydro-1H-pyrazino[2,1-c][1,4]oxazin-8-yl]-(2-chloro-3-methoxy-phenyl)methanone | 5.0 |
| 111 | Chiral 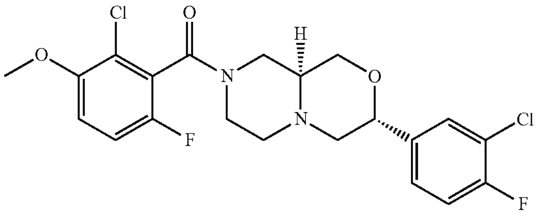 | [(3R,9aS)-3-(3-chloro-4-fluoro-phenyl)-3,4,6,7,9,9a-hexahydro-1H-pyrazino[2,1-c][1,4]oxazin-8-yl]-(2-chloro-6-fluoro-3-methoxy-phenyl)methanone | 5.8 |

TABLE 1-continued

| Ex. | Structure | IUPAC Name | MAGL IC50 (nM) |
|---|---|---|---|
| 112 | Chiral 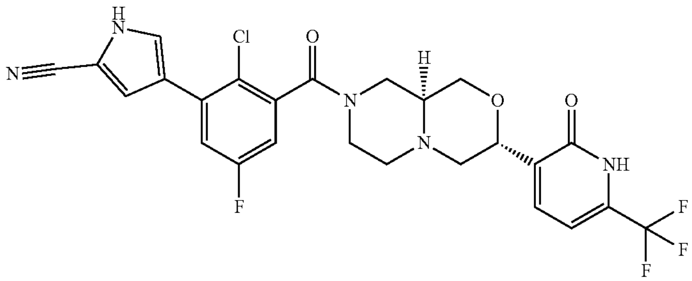 | 4-[3-[(3R,9aS)-3-[2-oxo-6-(trifluoromethyl)-1H-pyridin-3-yl]-3,4,6,7,9,9a-hexahydro-1H-pyrazino[2,1-c][1,4]oxazine-8-carbonyl]-2-chloro-5-fluoro-phenyl]-1H-pyrrole-2-carbonitrile | 6.5 |
| 113 | Chiral 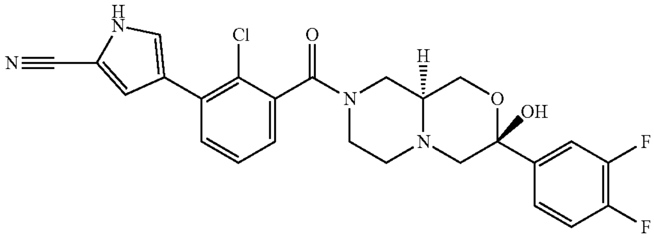 | 4-[3-[(3R,9aS)-3-(3,4-difluorophenyl)-3-hydroxy-1,4,6,7,9,9a-hexahydropyrazino[2,1-c][1,4]oxazine-8-carbonyl]-2-chloro-phenyl]-1H-pyrrole-2-carbonitrile | 7.6 |
| 114 | Chiral 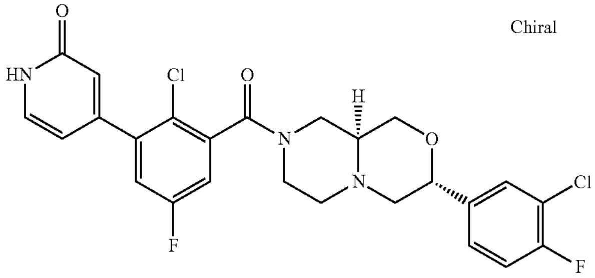 [SMILES: O=C(c1cc(F)cc(-c2cc[nH]c(=O)c2)c1Cl)N1CCN2C[C@@H](c3ccc(F)c(Cl)c3)OC[C@@H]2C1] | 4-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-5-fluoro-phenyl]-1H-pyridin-2-one | 10.8 |
| 115 | Chiral 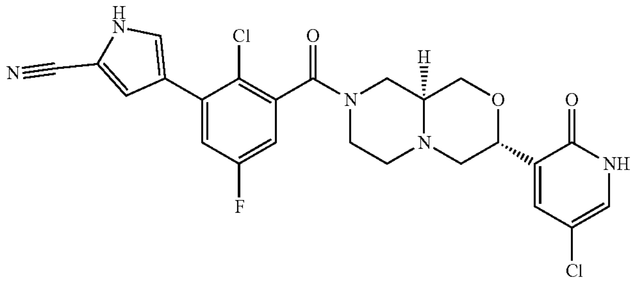 | 4-[3-[(3R,9aS)-3-(5-chloro-2-oxo-1H-pyridin-3-yl)-3,4,6,7,9,9a-hexahydro-1H-pyrazino[2,1-c][1,4]oxazine-8-carbonyl]-2-chloro-5-fluoro-phenyl]-1H-pyrrole-2-carbonitrile | 13.5 |
| 116 | Chiral 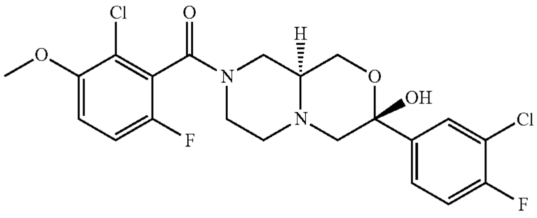 | [(3R,9aS)-3-(3-chloro-4-fluoro-phenyl)-3-hydroxy-1,4,6,7,9,9a-hexahydropyrazino[2,1-c][1,4]oxazin-8-yl]-(2-chloro-6-fluoro-3-methoxy-phenyl)methanone | 15.9 |

TABLE 1-continued

| Ex. | Structure | IUPAC Name | MAGL IC50 (nM) |
|---|---|---|---|
| 117 | 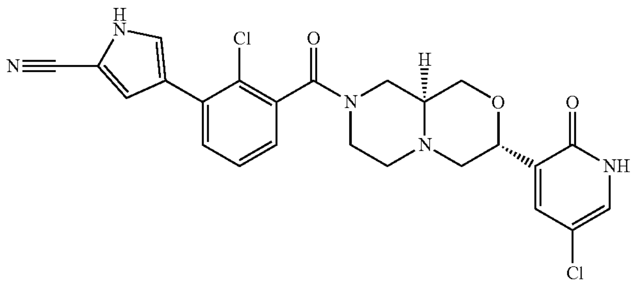 Chiral | 4-[3-[(3R,9aS)-3-(5-chloro-2-oxo-1H-pyridin-3-yl)-3,4,6,7,9,9a-hexahydro-1H-pyrazino[2,1-c][1,4]oxazine-8-carbonyl]-2-chloro-phenyl]-1H-pyrrole-2-carbonitrile | 17.4 |
| 118 | 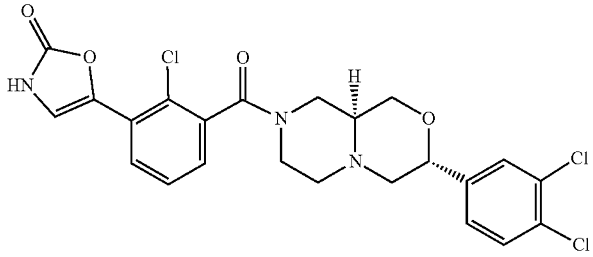 Chiral | 5-[3-[(3R,9aS)-3-(3,4-dichlorophenyl)-3,4,6,7,9,9a-hexahydro-1H-pyrazino[2,1-c][1,4]oxazine-8-carbonyl]-2-chloro-phenyl]-3H-oxazol-2-one | 33.1 |
| 119 | 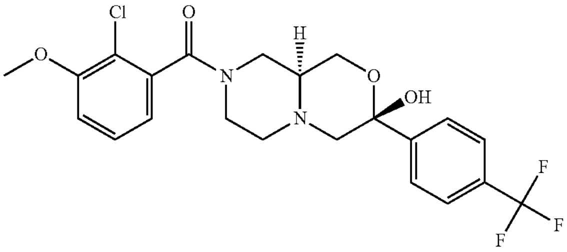 Chiral | [(3R,9aS)-3-hydroxy-3-[4-(trifluoromethyl)phenyl]-1,4,6,7,9,9a-hexahydropyrazino[2,1-c][1,4]oxazin-8-yl]-(2-chloro-3-methoxy-phenyl)methanone | 34.7 |
| 120 | 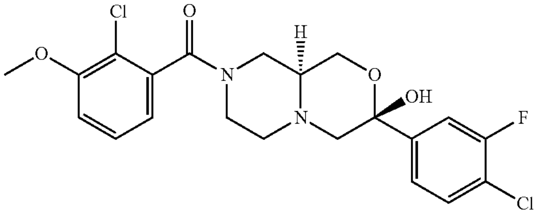 Chiral | [(3R,9aS)-3-(4-chloro-3-fluoro-phenyl)-3-hydroxy-1,4,6,7,9,9a-hexahydropyrazino[2,1-c][1,4]oxazin-8-yl]-(2-chloro-3-methoxy-phenyl)methanone | 42.4 |
| 121 | 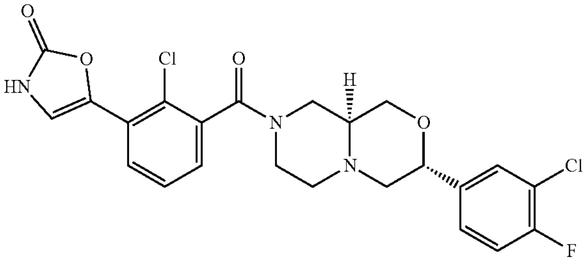 Chiral | 5-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]-3H-oxazol-2-one | 46.4 |

TABLE 1-continued

| Ex. | Structure | IUPAC Name | MAGL IC50 (nM) |
|---|---|---|---|
| 122 | Chiral 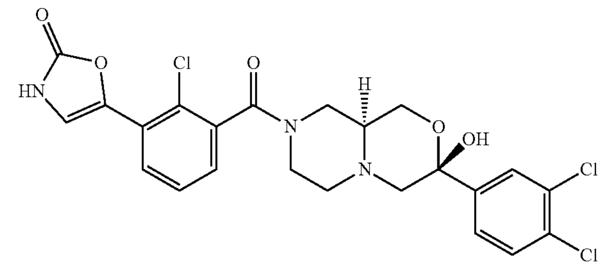 | 5-[3-[(3R,9aS)-3-(3,4-dichlorophenyl)-3-hydroxy-1,4,6,7,9,9a-hexahydropyrazino[2,1-c][1,4]oxazine-8-carbonyl]-2-chloro-phenyl]-3H-oxazol-2-one | 48.6 |
| 123 | Chiral 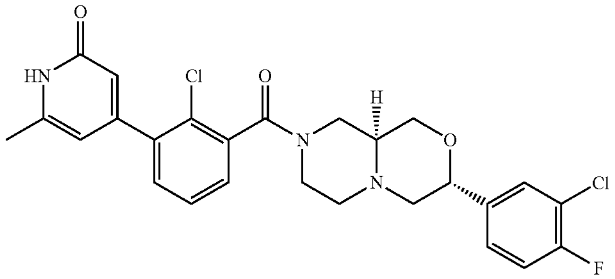 | 4-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]-6-methyl-1H-pyridin-2-one | 55.7 |
| 124 | Chiral 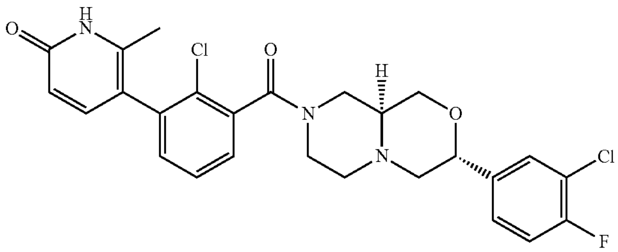 | 5-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]-6-methyl-1H-pyridin-2-one | 57.6 |
| 125 | Chiral 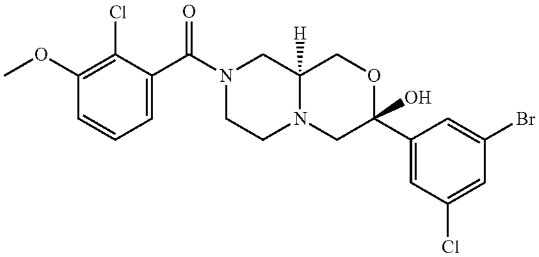 | [(3R,9aS)-3-(3-bromo-5-chloro-phenyl)-3-hydroxy-1,4,6,7,9,9a-hexahydropyrazino[2,1-c][1,4]oxazin-8-yl]-(2-chloro-3-methoxy-phenyl)methanone | 82.8 |
| 126 | Chiral 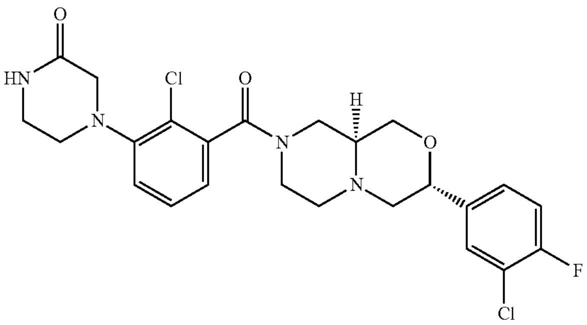 | 4-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]piperazin-2-one | 96.2 |

TABLE 1-continued

| Ex. | Structure | IUPAC Name | MAGL IC50 (nM) |
|---|---|---|---|
| 127 | Chiral 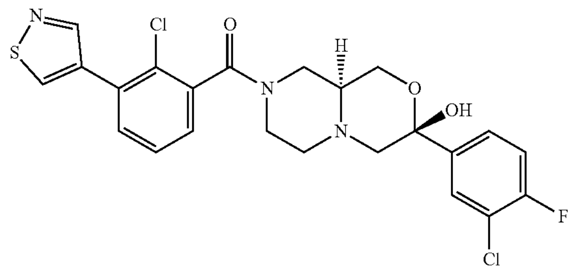 | [(3R,9aS)-3-(3-chloro-4-fluoro-phenyl)-3-hydroxy-1,4,6,7,9,9a-hexahydropyrazino[2,1-c][1,4]oxazin-8-yl]-(2-chloro-3-isothiazol-4-yl-phenyl)methanone | 97.7 |
| 128 | Chiral 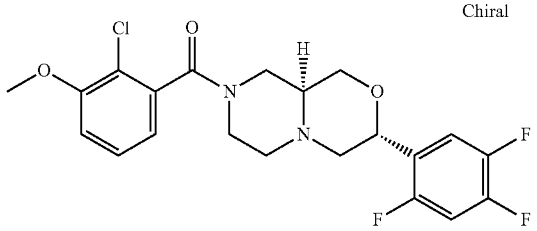 [SMILES: COc1cccc(C(=O)N2CCN3C[C@@H](c4cc(F)c(F)cc4F)OC[C@@H]3C2)c1Cl] | [(3R,9aS)-3-(2,4,5-trifluorophenyl)-3,4,6,7,9,9a-hexahydro-1H-pyrazino[2,1-c][1,4]oxazin-8-yl]-(2-chloro-3-methoxy-phenyl)methanone | 102.6 |
| 129 | Chiral 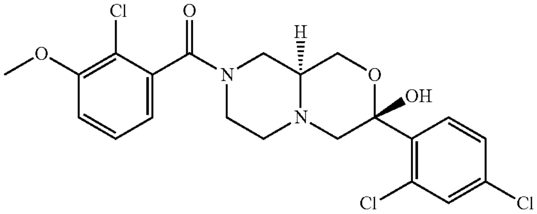 | [(3R,9aS)-3-(2,4-dichlorophenyl)-3-hydroxy-1,4,6,7,9,9a-hexahydropyrazino[2,1-c][1,4]oxazin-8-yl]-(2-chloro-3-methoxy-phenyl)methanone | 112.9 |
| 130 | Chiral 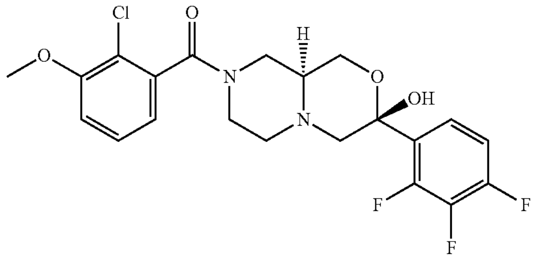 | [(3R,9aS)-3-hydroxy-3-(2,3,4-trifluorophenyl)-1,4,6,7,9,9a-hexahydropyrazino[2,1-c][1,4]oxazin-8-yl]-(2-chloro-3-methoxy-phenyl)methanone | 117.1 |
| 131 | Chiral 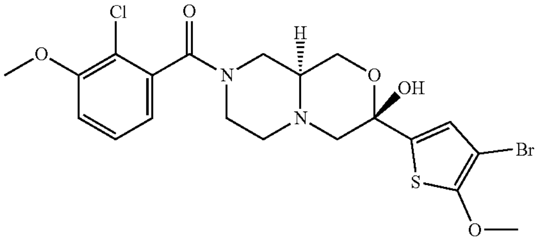 | [(3S,9aS)-3-(4-bromo-5-methoxy-2-thienyl)-3-hydroxy-1,4,6,7,9,9a-hexahydropyray.ino[2,1-c][1,4]oxazin-8-yl]-(2-chloro-3-methoxy-phenyl)methanone | 118.1 |

TABLE 1-continued

| Ex. | Structure | IUPAC Name | MAGL IC50 (nM) |
|---|---|---|---|
| 132 | Chiral 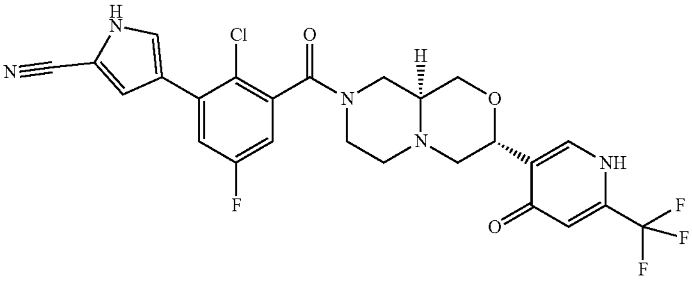 | 4-[3-[(3R,9aS)-3-[4-oxo-6-(trifluoromethyl)-1H-pyridin-3-yl]-3,4,6,7,9,9a-hexahydro-1H-pyrazino[2,1-c][1,4]oxazine-8-carbonyl]-2-chloro-5-fluoro-phenyl]-1H-pyrrole-2-carbonitrile | 131.1 |
| 133 | Chiral 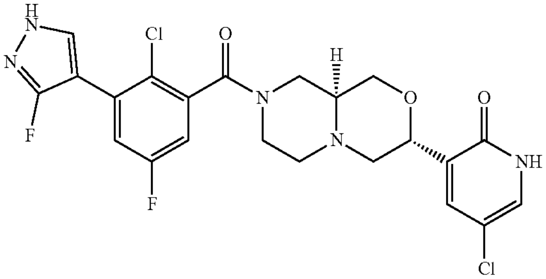 | 3-[(3R,9aS)-8-[2-chloro-5-fluoro-3-(3-fluoro-1H-pyrazol-4-yl)benzoyl]-3,4,6,7,9,9a-hexahydro-1H-pyrazino[2,1-c][1,4]oxazin-3-yl]-5-chloro-1H-pyridin-2-one | 141.8 |
| 134 | Chiral 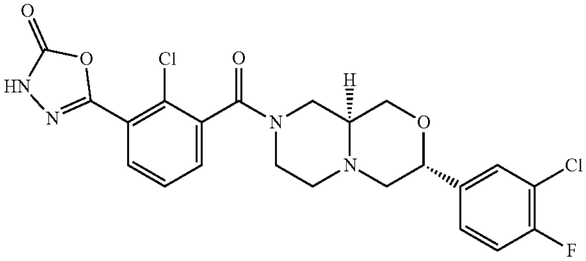 | 5-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]-3H-1,3,4-oxadiazol-2-one | 144.1 |
| 135 | Chiral 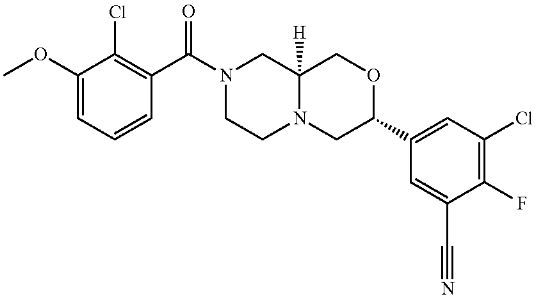 | 5-[(3R,9aS)-8-(2-chloro-3-methoxy-benzoyl)-3,4,6,7,9,9a-hexahydro-1H-pyrazino[2,1-c][1,4]oxazin-3-yl]-3-chloro-2-fluoro-benzonitrile | 145.5 |
| 136 | Chiral 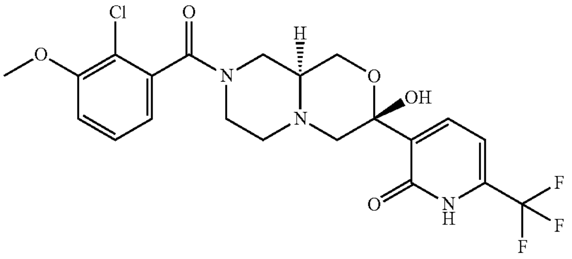 | 3-[(3R,9aS)-8-(2-chloro-3-methoxy-benzoyl)-3-hydroxy-1,4,6,7,9,9a-hexahydropyrazino[2,1-c][1,4]oxazin-3-yl]-6-(trifluoromethyl)-1H-pyridin-2-one | 152.1 |

TABLE 1-continued

| Ex. | Structure | IUPAC Name | MAGL IC50 (nM) |
|---|---|---|---|
| 137 | Chiral 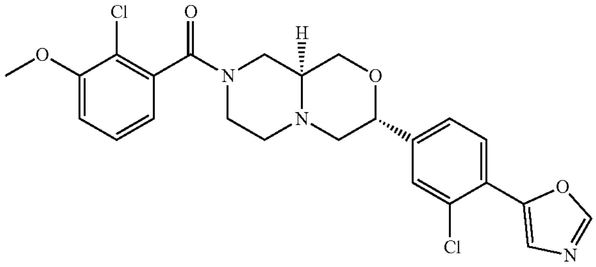 | [(3R,9aS)-3-(3-chloro-4-oxazol-5-yl-phenyl)-3,4,6,7,9,9a-hexahydro-1H-pyrazino[2,1-c][1,4]oxazin-8-yl]-(2-chloro-3-methoxy-phenyl)methanone | 182.4 |
| 138 | Chiral 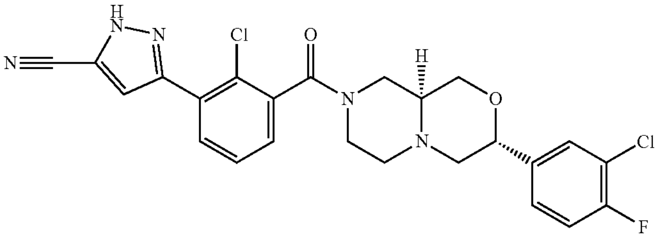 | 3-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]-1H-pyrazole-5-carbonitrile | 190.3 |
| 139 | Chiral 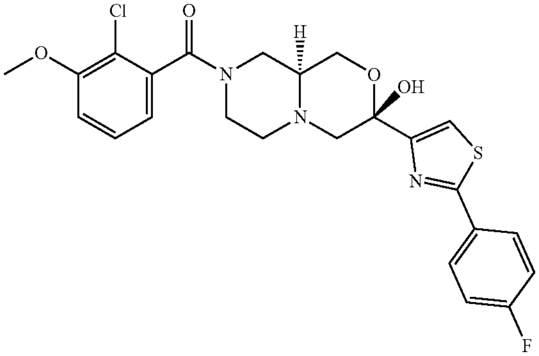 | [(3S,9aS)-3-[2-(4-fluorophenyl)thiazol-4-yl]-3-hydroxy-1,4,6,7,9,9a-hexahydropyrazino[2,1-c][1,4]oxazin-8-yl]-(2-chloro-3-methoxy-phenyl)methanone | 254.4 |
| 140 | Chiral 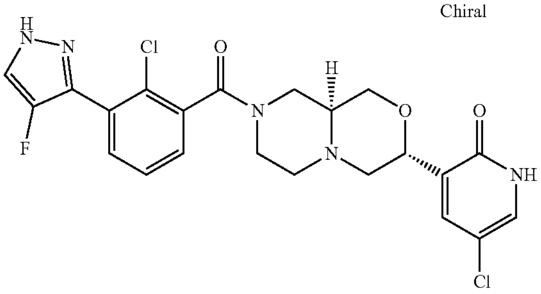 [SMILES: O=C(c1cccc(-c2n[nH]cc2F)c1Cl)N1CCN2C[C@@H](c3cc(Cl)c[nH]c3=O)OC[C@@H]2C1] | 3-[(3R,9aS)-8-[2-chloro-3-(4-fluoro-1H-pyrazol-3-yl)benzoyl]-3,4,6,7,9,9a-hexahydro-1H-pyrazino[2,1-c][1,4]oxazin-3-yl]-5-chloro-1H-pyridin-2-one | 277.0 |
| 141 | Chiral 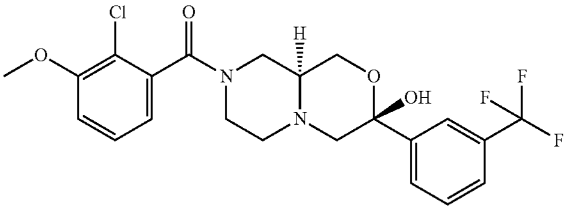 | [(3R,9aS)-3-hydroxy-3-[3-(trifluoromethyl)phenyl]-1,4,6,7,9,9a-hexahydropyrazino[2,1-c][1,4]oxazin-8-yl]-(2-chloro-3-methoxy-phenyl)methanone | 288.3 |

TABLE 1-continued

| Ex. | Structure | IUPAC Name | MAGL IC50 (nM) |
|---|---|---|---|
| 142 | Chiral 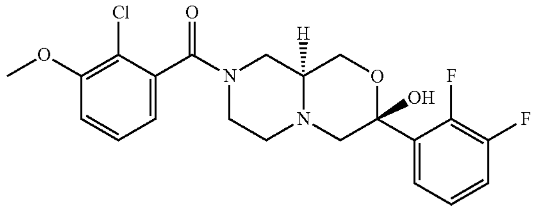 | [(3R,9aS)-3-(2,3-difluorophenyl)-3-hydroxy-1,4,6,7,9,9a-hexahydropyrazino[2,1-c][1,4]oxazin-8-yl]-(2-chloro-3-methoxy-phenyl)methanone | 332.0 |
| 143 | Chiral 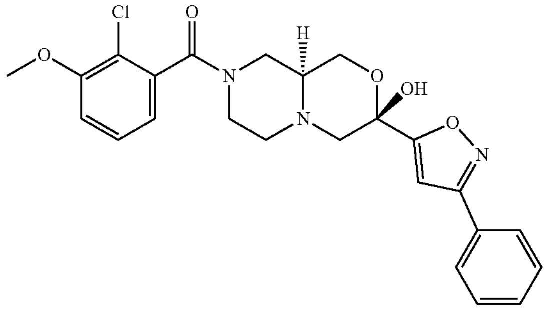 | [(3S,9aS)-3-hydroxy-3-(3-phenylisoxazol-5-yl)-1,4,6,7,9,9a-hexahydropyrazino[2,1-c][1,4]oxazin-8-yl]-(2-chloro-3-methoxy-phenyl)methanone | 348.3 |
| 144 | Chiral 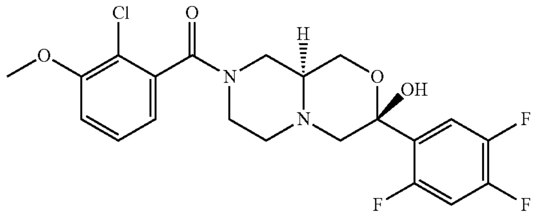 | [(3R,9aS)-3-hydroxy-3-(2,4,5-trifluorophenyl)-1,4,6,7,9,9a-hexahydropyrazino[2,1-c][1,4]oxazin-8-yl]-(2-chloro-3-methoxy-phenyl)methanone | 354.8 |
| 145 | Chiral 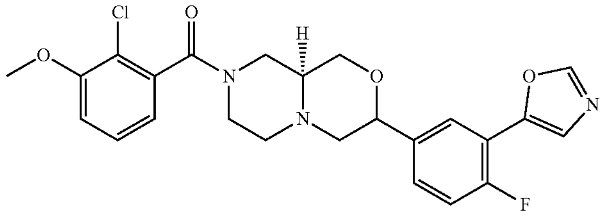 | [(9aS)-3-(4-fluoro-3-oxazol-5-yl-phenyl)-3,4,6,7,9,9a-hexahydro-1H-pyrazino[2,1-c][1,4]oxazin-8-yl]-(2-chloro-3-methoxy-phenyl)methanone | 363.0 |
| 146 | Chiral 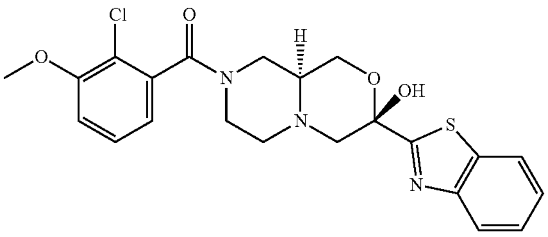 | [(3S,9aS)-3-(1,3-benzothiazol-2-yl)-3-hydroxy-1,4,6,7,9,9a-hexahydropyrazino[2,1-c][1,4]oxazin-8-yl]-(2-chloro-3-methoxy-phenyl)methanone | 378.0 |

TABLE 1-continued

| Ex. | Structure | IUPAC Name | MAGL IC50 (nM) |
|---|---|---|---|
| 147 | Chiral 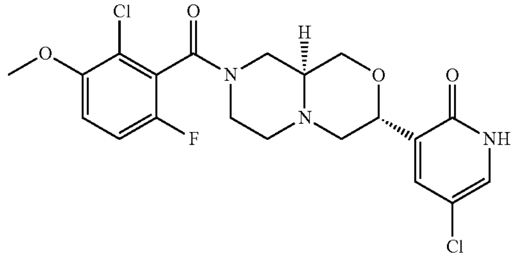 | 3-[(3R,9aS)-8-(2-chloro-6-fluoro-3-methoxy-benzoyl)-3,4,6,7,9,9a-hexahydro-1H-pyrazino[2,1-c][1,4]oxazin-3-yl]-5-chloro-1H-pyridin-2-one | 384.9 |
| 148 | Chiral 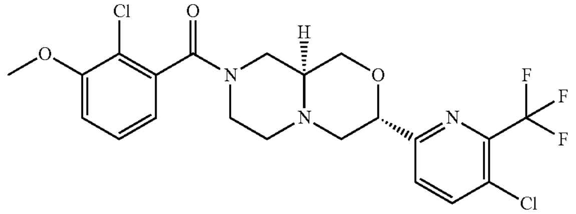 | [(3S,9aS)-3-[5-chloro-6-(trifluoromethyl)-2-pyridyl]-3,4,6,7,9,9a-hexahydro-1H-pyrazino[2,1-c][1,4]oxazin-8-yl]-(2-chloro-3-methoxy-phenyl)methanone | 426.1 |
| 149 | Chiral 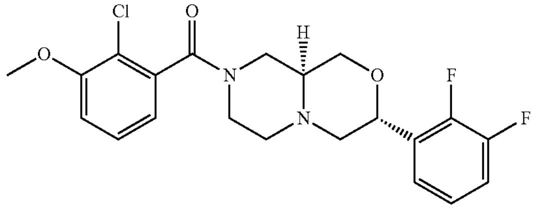 | [(3R,9aS)-3-(2,3-difluorophenyl)-3,4,6,7,9,9a-hexahydro-1H-pyrazino[2,1-c][1,4]oxazin-8-yl]-(2-chloro-3-methoxy-phenyl)methanone | 467.8 |
| 150 | Chiral 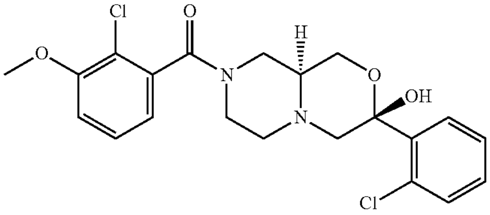 | [(3R,9aS)-3-(2-chlorophenyl)-3-hydroxy-1,4,6,7,9,9a-hexahydropyrazino[2,1-c][1,4]oxazin-8-yl]-(2-chloro-3-methoxy-phenyl)methanone | 546.3 |
| 151 | Chiral 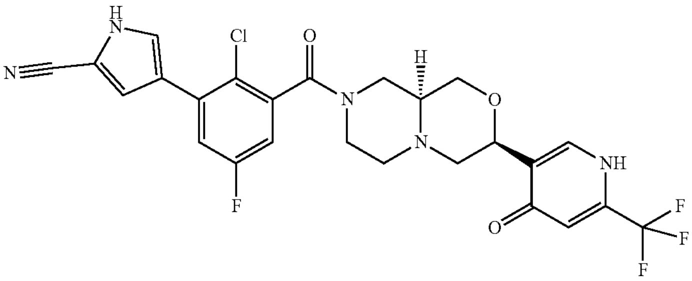 | 4-[3-[(3S,9aS)-3-[4-oxo-6-(trifluoromethyl)-1H-pyridin-3-yl]-3,4,6,7,9,9a-hexahydro-1H-pyrazino[2,1-c][1,4]oxazine-8-carbonyl]-2-chloro-5-fluoro-phenyl]-1H-pyrrole-2-carbonitrile | 575.4 |

TABLE 1-continued

| Ex. | Structure | IUPAC Name | MAGL IC50 (nM) |
|---|---|---|---|
| 152 | Chiral 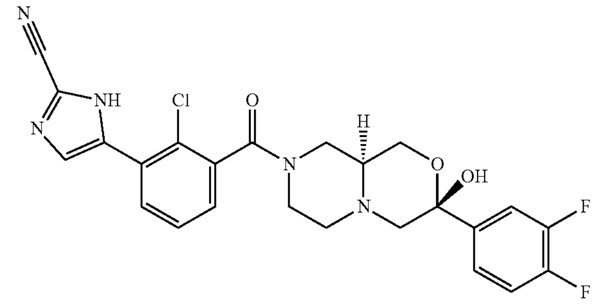 | 5-[3-[(3R,9aS)-3-(3,4-difluorophenyl)-3-hydroxy-1,4,6,7,9,9a-hexahydropyrazino[2,1-c][1,4]oxazine-8-carbonyl]-2-chloro-phenyl]-1H-imidazole-2-carbonitrile | 580.6 |
| 153 | Chiral 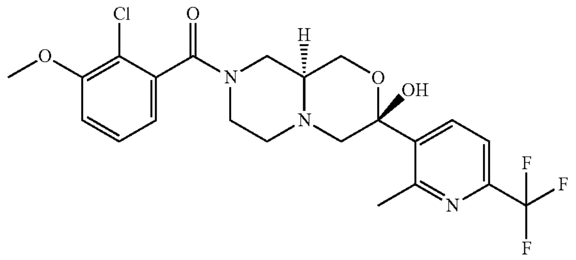 | [(3R,9aS)-3-hydroxy-3-[2-methyl-6-(trifluoromethyl)-3-pyridyl]-1,4,6,7,9,9a-hexahydropyrazino[2,1-c][1,4]oxazin-8-yl]-(2-chloro-3-methoxy-phenyl)methanone | 704.7 |
| 154 | Chiral 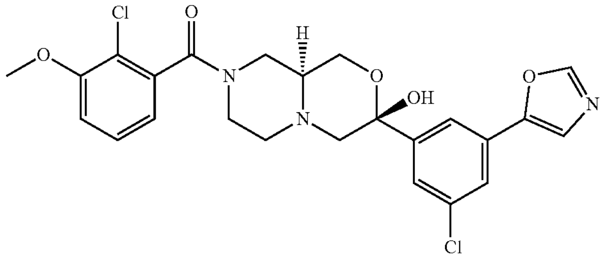 | [(3R,9aS)-3-(3-chloro-5-oxazol-5-yl-phenyl)-3-hydroxy-1,4,6,7,9,9a-hexahydropyrazino[2,1-c][1,4]oxazin-8-yl]-(2-chloro-3-methoxy-phenyl)methanone | 769.0 |
| 155 | Chiral 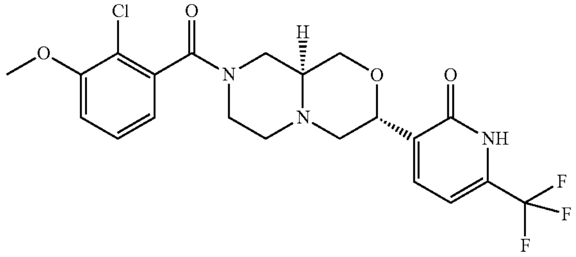 | 3-[(3R,9aS)-8-(2-chloro-3-methoxy-benzoyl)-3,4,6,7,9,9a-hexahydro-1H-pyrazino[2,1-c][1,4]oxazin-3-yl]-6-(trifluoromethyl)-1H-pyridin-2-one | 780.1 |
| 156 | Chiral 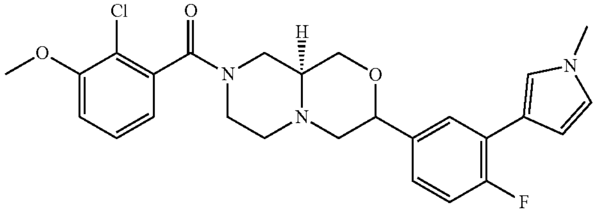 | [(9aS)-3-[4-fluoro-3-(1-methylpyrrol-3-yl)phenyl]-3,4,6,7,9,9a-hexahydro-1H-pyrazino[2,1-c][1,4]oxazin-8-yl]-(2-chloro-3-methoxy-phenyl)methanone | 814.7 |

TABLE 1-continued

| Ex. | Structure | IUPAC Name | MAGL IC50 (nM) |
|---|---|---|---|
| 157 | Chiral 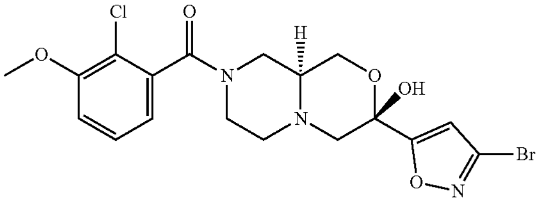 | [(3S,9aS)-3-(3-bromoisoxazol-5-yl)-3-hydroxy-1,4,6,7,9,9a-hexahydropyrazino[2,1-c][1,4]oxazin-8-yl]-(2-chloro-3-methoxy-phenyl)methanone | 849.3 |
| 158 | Chiral 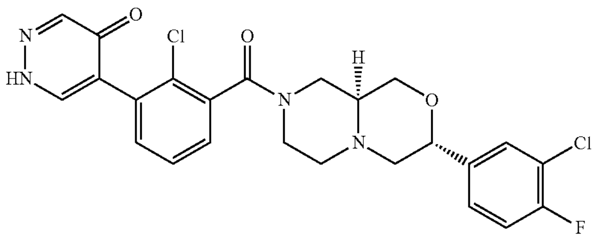 | 5-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]-1H-pyridazin-4-one | 1016.3 |
| 159 | Chiral 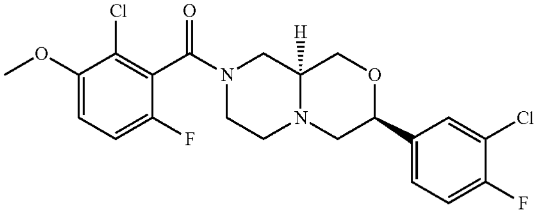 | [(3S,9aS)-3-(3-chloro-4-fluoro-phenyl)-3,4,6,7,9,9a-hexahydro-1H-pyrazino[2,1-c][1,4]oxazin-8-yl]-(2-chloro-6-fluoro-3-methoxy-phenyl)methanone | 1481.3 |
| 160 | Chiral 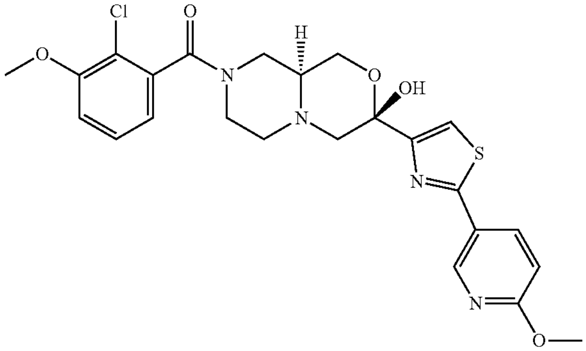 | [(3S,9aS)-3-hydroxy-3-[2-(6-methoxy-3-pyridyl)thiazol-4-yl]-1,4,6,7,9,9a-hexahydropyrazino[2,1-c][1,4]oxazin-8-yl]-(2-chloro-3-methoxy-phenyl)methanone | 1600.4 |
| 161 | Chiral 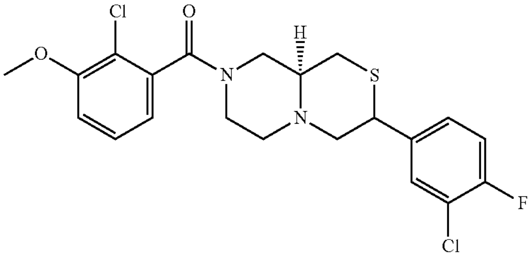 | [(9aS)-3-(3-chloro-4-fluoro-phenyl)-3,4,6,7,9,9a-hexahydro-1H-pyrazino[2,1-c][1,4]thiazin-8-yl]-(2-chloro-3-methoxy-phenyl)methanone | 3.1 |

TABLE 1-continued

| Ex. | Structure | IUPAC Name | MAGL IC50 (nM) |
|---|---|---|---|
| 162 | Chiral 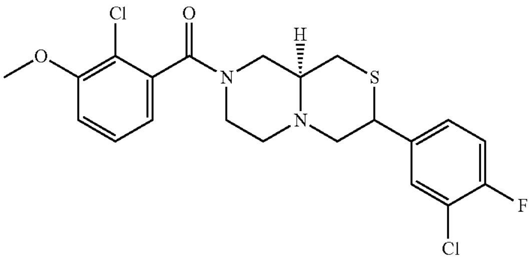 | [(9aS)-3-(3-chloro-4-fluoro-phenyl)-3,4,6,7,9,9a-hexahydro-1H-pyrazino[2,1-c][1,4]thiazin-8-yl]-(2-chloro-3-methoxy-phenyl)methanone | 21.6 |

In one aspect, the present invention provides compounds of formula (I) and their pharmaceutically acceptable salts or esters as described herein, wherein said compounds of formula (I) and their pharmaceutically acceptable salts or esters have $IC_{50}$'s for MAGL inhibition below 25 μM, preferably below 10 μM, more preferably below 5 μM as measured in the MAGL assay described herein.

In one embodiment, compounds of formula (I) and their pharmaceutically acceptable salts or esters as described herein have $IC_{50}$ (MAGL inhibition) values between 0.000001 μM and 25 μM, particular compounds have $IC_{50}$ values between 0.000005 μM and 10 μM, further particular compounds have $IC_{50}$ values between 0.00005 μM and 5 μM, as measured in the MAGL assay described herein.

Using the Compounds of the Invention

In one aspect, the present invention provides compounds of formula (I) as described herein for use as therapeutically active substance.

In a further aspect, the present invention provides the use of compounds of formula (I) as described herein for the treatment or prophylaxis of neuroinflammation, neurodegenerative diseases, pain, cancer and/or mental disorders in a mammal.

In one embodiment, the present invention provides the use of compounds of formula (I) as described herein for the treatment or prophylaxis of neuroinflammation and/or neurodegenerative diseases in a mammal.

In one embodiment, the present invention provides the use of compounds of formula (I) as described herein for the treatment or prophylaxis of neurodegenerative diseases in a mammal.

In one embodiment, the present invention provides the use of compounds of formula (I) as described herein for the treatment or prophylaxis of cancer in a mammal.

In one aspect, the present invention provides the use of compounds of formula (I) as described herein for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal.

In a preferred embodiment, the present invention provides the use of compounds of formula (I) as described herein for the treatment or prophylaxis of multiple sclerosis, Alzheimer's disease and/or Parkinson's disease in a mammal.

In a particularly preferred embodiment, the present invention provides the use of compounds of formula (I) as described herein for the treatment or prophylaxis of multiple sclerosis in a mammal.

In one aspect, the present invention provides compounds of formula (I) as described herein for use in the treatment or prophylaxis of neuroinflammation, neurodegenerative diseases, pain, cancer and/or mental disorders in a mammal.

In one embodiment, the present invention provides compounds of formula (I) as described herein for use in the treatment or prophylaxis of neuroinflammation and/or neurodegenerative diseases in a mammal.

In one embodiment, the present invention provides compounds of formula (I) as described herein for use in the treatment or prophylaxis of cancer in a mammal.

In one embodiment, the present invention provides compounds of formula (I) as described herein for use in the treatment or prophylaxis of neurodegenerative diseases in a mammal.

In one aspect, the present invention provides compounds of formula (I) as described herein for use in the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal.

In a preferred embodiment, the present invention provides compounds of formula (I) as described herein for use in the treatment or prophylaxis of multiple sclerosis, Alzheimer's disease and/or Parkinson's disease in a mammal.

In a particularly preferred embodiment, the present invention provides compounds of formula (I) as described herein for use in the treatment or prophylaxis of multiple sclerosis in a mammal.

In one aspect, the present invention provides the use of compounds of formula (I) as described herein for the preparation of a medicament for the treatment or prophylaxis of neuroinflammation, neurodegenerative diseases, pain, cancer and/or mental disorders in a mammal.

In one embodiment, the present invention provides the use of compounds of formula (I) as described herein for the preparation of a medicament for the treatment or prophylaxis of neuroinflammation and/or neurodegenerative diseases in a mammal.

In one embodiment, the present invention provides the use of compounds of formula (I) as described herein for the preparation of a medicament for the treatment or prophylaxis of neurodegenerative diseases in a mammal.

In one embodiment, the present invention provides the use of compounds of formula (I) as described herein for the preparation of a medicament for the treatment or prophylaxis of cancer in a mammal.

In a further aspect, the present invention provides the use of compounds of formula (I) as described herein for the preparation of a medicament for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal.

In a preferred embodiment, the present invention provides the use of compounds of formula (I) as described herein for the preparation of a medicament for the treatment or prophylaxis of multiple sclerosis, Alzheimer's disease and/or Parkinson's disease in a mammal.

In a particularly preferred embodiment, the present invention provides the use of compounds of formula (I) as described herein for the preparation of a medicament for the treatment or prophylaxis of multiple sclerosis in a mammal.

In one aspect, the present invention provides a method for the treatment or prophylaxis of neuroinflammation, neurodegenerative diseases, pain, cancer and/or mental disorders in a mammal, which method comprises administering an effective amount of a compound of formula (I) as described herein to the mammal.

In one embodiment, the present invention provides a method for the treatment or prophylaxis of neuroinflammation and/or neurodegenerative diseases in a mammal, which method comprises administering an effective amount of a compound of formula (I) as described herein to the mammal.

In one embodiment, the present invention provides a method for the treatment or prophylaxis of neurodegenerative diseases in a mammal, which method comprises administering an effective amount of a compound of formula (I) as described herein to the mammal.

In one aspect, the present invention provides a method for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression and/or pain in a mammal, which method comprises administering an effective amount of a compound of formula (I) as described herein to the mammal.

In a preferred embodiment, the present invention provides a method for the treatment or prophylaxis of multiple sclerosis, Alzheimer's disease and/or Parkinson's disease in a mammal, which method comprises administering an effective amount of a compound of formula (I) as described herein to the mammal.

In a particularly preferred embodiment, the present invention provides a method for the treatment or prophylaxis of multiple sclerosis in a mammal, which method comprises administering an effective amount of a compound of formula (I) as described herein to the mammal.

Pharmaceutical Compositions and Administration

In one aspect, the present invention provides a pharmaceutical composition comprising a compound of formula (I) as described herein and a therapeutically inert carrier.

The compounds of formula (I) and their pharmaceutically acceptable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

EXAMPLES

The invention will be more fully understood by reference to the following examples. The claims should not, however, be construed as limited to the scope of the examples.

In case the preparative examples are obtained as a mixture of enantiomers, the pure enantiomers can be separated by methods described herein or by methods known to the man skilled in the art, such as e.g., chiral chromatography (e.g., chiral SFC) or crystallization.

All reaction examples and intermediates were prepared under an argon atmosphere if not specified otherwise.

Abbreviations

AcOH=acetic acid, ACN=acetonitrile, Bn=benzyl, BINAP=(2,2'-bis(diphenylphosphino)-1,1'-binaphthyl), Boc=tert-butyloxycarbonyl, CAS RN=chemical abstracts registration number, Cbz=benzyloxycarbonyl, $Cs_2CO_3$=cesium carbonate, CO=carbon monoxide, CuCl=copper(I) chloride, CuCN=copper(I) cyanide, CuI=copper(I) iodide, DAST=(diethylamino)sulfur trifluoride, DBU=1,8-diazabicyclo[5,4,0]undec-7-ene, DEAD=diethyl azodicarboxylate, DIAD=diisopropyl azodicarboxylate, DMAP=4-dimethylaminopyridine, DME=dimethoxyethane, DMEDA=N,N'-dimethylethylenediamine, DMF=N,N-dimethylformamide, DIPEA=N,N-diisopropylethylamine, dppf=1,1 bis(diphenyl phosphino)ferrocene, EDC HCl=N-(3-dimethylaminopropyl)-N'-ethylcarbodiimide hydrochloride, EI=electron impact, ESI=electrospray ionization, EtOAc=ethyl acetate, EtOH=ethanol, h=hour(s), FA=formic acid, $H_2O$=water, $H_2SO_4$=sulfuric acid, HATU=1-[bis(dimethylamino)methylene]-1H-1,2,3-triazolo[4,5-b]pyridinium-3-oxide hexafluorophosphate, HBTU=O-benzotriazole-N,N,N',N'-tetramethyl-uronium-hexafluoro-phosphate, HCl=hydrogen chloride, HOBt=1-hydroxy-TH-benzotriazole, HPLC=high performance liquid chromatography, iPrMgCl=isopropylmagnesium chloride, $I_2$=iodine, IPA=2-propanol, ISP=ion spray positive (mode), ISN=ion spray negative (mode), $K_2CO_3$=potassium carbonate, $KHCO_3$=potassium bicarbonate, KI=potassium iodide, KOH=potassium hydroxide, $K_3PO_4$=potassium phosphate tribasic, $LiAlH_4$ or LAH=lithium aluminium hydride, LiHMDS=lithium bis(trimethylsilyl)amide, LiOH=lithium hydroxide, mCPBA=meta-chloroperoxybenzoic acid, $MgSO_4$=magnesium sulfate, min=minute(s), mL=milliliter, MPLC=medium pressure liquid chromatography, MS=mass spectrum, nBuLi=n-butyllithium, $NaBH_3CN$=sodium cyanoborohydride, NaH=sodium hydride, NBS=N-bromosuccinimide, $NaHCO_3$=sodium hydrogen carbonate, $NaNO_2$=sodium nitrite, $NaBH(OAc)_3$=sodium triacetoxyborohydride, NaOH=sodium hydroxide, $Na_2CO_3$=sodium carbonate, $Na_2SO_4$=sodium sulfate, $Na_2S_2O_3$=sodium thiosulfate, NBS=N-bromosuccinimide, nBuLi=n-butyllithium, $NEt_3$=triethylamine (TEA), $NH_4Cl$=ammonium chloride, NMP=N-methyl-2-pyrrolidone, OAc=Acetoxy, $T_3P$=propylphosphonic anhydride, PE=petroleum ether, PG=protective group, Pd-C=palladium on activated carbon, $PdCl_2(dppf)$-$CH_2Cl_2$=1,1'-bis(diphenylphosphino)ferrocene-palladium(II)dichloride dichloromethane complex, $Pd_2(dba)_3$=tris(dibenzylideneacetone)dipalladium(0), $Pd(OAc)_2$=palladium(II) acetate, $Pd(OH)_2$=palladium hydroxide, $Pd(PPh_3)_4$=tetrakis(triphenylphosphine)palladium(0), PTSA=p-toluenesulfonic acid, R=any group, RP=reverse phase, RT=room temperature, SFC=Supercritical Fluid Chromatography, S-PHOS=2-dicyclohexylphosphino-2',6'-dimethoxybiphenyl, TBAI=tetra butyl ammonium iodine, TEA=triethylamine, TES=triethylsilane, TFA=trifluoroacetic acid, THF=tetrahydrofuran, TMEDA=N,N,N',N'-tetramethylethylenediamine, T3P=1-propanephosphonic anhydride, $ZnCl_2$=zinc chloride, Hal=halogen.

Intermediate 1

(2-chloro-3-methoxy-phenyl)-[3-(hydroxymethyl) piperazin-1-yl]methanone tert-butyl 4-(2-chloro-3-methoxybenzoyl)-2-(hydroxymethyl)piperazine-1-carboxylate (2.5 g, 6.5 mmol) was dissolved in 25 ml 4M HCl in dioxane and stirred for 90 min at room temperature. The solvent was removed in vacuo, and the residue was dissolved in 0.1 M HCl(aq), extracted with ethylacetate, basified with 4M NaOH(aq) and extracted again with EtOAC to get the product. Due to the high polarity of the product, an excess of ethyl acetate was used and the extraction was done several times to get the product out of the basic aqueous phase. The organic fractions were combined, dried over Na2SO4 and concentrated in vacuo to yield 1.295 g Intermediate 1. No further purification. ESI (MS) m/z=285.3 $[M+H]^+$ a) tert-butyl 4-(2-chloro-3-methoxybenzoyl)-2-(hydroxymethyl)piperazine-1-carboxylate A mixture of 2-chloro-3-methoxybenzoic acid (1.29 g, 6.94 mmol), tert-butyl 2-(hydroxymethyl)piperazine-1-carboxylate (1500 mg, 6.94 mmol) and HATU (2.51 g, 6.59 mmol) was dissolved in 25 ml ethyl acetate. DIPEA (1.79 g, 2.42 ml, 13.9 mmol) was added to the solution and the reaction mixture was stirred at rt for 2 hr. The reaction mixture was washed twice with sat. $NaHCO_3$, dried over $Na_2SO_4$, filtered, evaporated and further dried on the high vacuum. The resultant crude residue was purified by flash column chromatography (silica 50 g, 40 ml/min EtOAc/Heptan 0-100%). The product fractions were combined and evaporated to yield 2.5 g of the desired product. ESI (MS) m/z=329.2 $[M-56]^+$ Intermediate 1S (2-chloro-3-methoxy-phenyl)-[(3S)-3-(hydroxymethyl)piperazin-1-yl]methanone Intermediate 1S was synthesized as described for Intermediate 1, starting from enantiopure tert-butyl (S)-2-(hydroxymethyl)piperazine-1-carboxylate.

Intermediate 2

(3R,9aS)-3-(3-chloro-4-fluoro-phenyl)-1,3,4,6,7,8,9,9a-octahydropyrazino[2,1-c][1,4]oxazine tert-butyl (3R,9aS)-3-(3-chloro-4-fluorophenyl)hexahydropyrazino[2,1-c][1,4]oxazine-8(1H)-carboxylate (2.52 g, 6.8 mmol) was dissolved in HCl 4M in dioxan (17 ml, 68 mmol) and the solution was stirred overnight at room temperature. The solvents were removed in vacuo, the residue was dissolved in 1M aq. HCl and washed with EtOAc. The aq. phase was basified with 4M NaOH, became turbid and extracted with EtOAc. The organic phases were combined, dried over Na2SO4 and the solvent was removed in vacuo. 1.52 g of Intermediate 2 were obtained as a waxy yellow solid and used directly for the next step. ESI (MS) m/z=271.2 $[M+H]^+$ a) 2-(3-chloro-4-fluoro-phenyl)oxirane 2-chloro-1-fluoro-4-vinylbenzene (2.97 g, 19 mmol) was dissolved in DCM (100 ml) at 0° C. then 3-chlorobenzoperoxoic acid (4.91 g, 28.5 mmol) was added and the mixture was slowly warmed up to room temperature overnight. The reaction mixture was then washed once each with saturated aq. Na2S2O3, $NaHCO_3$, and brine. The organic layer was dried over MgSO4, filtered, and evaporated to dryness. The crude material was purified by flash chromatography (silica gel, 100 g, 0% to 70% EtOAc in heptane) to yield in the product as a colorless liquid (2.57 g). The compound did not ionize on ESI (MS).

b) tert-butyl (3S)-4-(2-(3-chloro-4-fluorophenyl)-2-hydroxyethyl)-3-(hydroxymethyl)piperazine-1-carboxylate 2-(3-chloro-4-fluorophenyl)oxirane (1.285 g, 7.45 mmol) and tert-butyl (S)-3-(hydroxymethyl)piperazine-1-carboxylate (2.42 g, 11.2 mmol) were dissolved in ethanol (20 mL) then placed in a sealed tubes and heated in the microwave at 150° C. for 40 min. The solvent was evaporated, the crude material was purified by flash chromatography (silica gel, 100 g, 10% to 100% EtOAc (+10% EtOH) in Heptane) to yield 2.57 g of desired product as a light yellow oil. ESI (MS) m/z=389.2 $[M+H]^+$ c) tert-butyl (3R,9aS)-3-(3-chloro-4-fluorophenyl) hexahydropyrazino[2,1-c][1,4]oxazine-8(1H)-carboxylate tert-butyl (3S)-4-(2-(3-chloro-4-fluorophenyl)-2-hydroxyethyl)-3-(hydroxymethyl)piperazine-1-carboxylate (5.14 g, 13.2 mmol) was dissolved in toluene anhydrous (50 ml), the solution was transferred to a argon-purged, flame dried flask and the solution was further degassed with argon, subsequently 2-(tributyl-15-phosphaneylidene)acetonitrile (5.58 g, 6.07 ml, 23.1 mmol) was added in one portion. The reaction mixture was heated for 1.5 h at 100° C. The reaction mixture was extracted with EtOAc/sat. $NaHCO_3$, combined organic layers washed with brine, dried over Na2SO4 and concentrated in vacuo. The crude material was purified by flash chromatography (silica gel, 100 g, 0% to 100% EtOAc in heptane) 2 times. The product fractions were combined and evaporated to yield 2.53 g of the desired product as a light brown oil. ESI (MS) m/z=371.2 $[M+H]^+$. The desired trans isomer (3R,9aS) was the major product (ratio 4:1)

Intermediate 3

(9aS)-3-(3-bromo-4-fluoro-phenyl)-1,3,4,6,7,8,9,9a-octahydropyrazino[2,1-c][1,4]oxazine tert-butyl (S)-3-(3-bromo-4-fluorophenyl)hexahydropyrazino[2,1-c][1,4]oxazine-8(1H)-carboxylate (1.78 g, 4.29 mmol) was dissolved in 21.4 ml 4M HCl in dioxane and stirred for 120 min at room temperature. The solvent was removed in vacuo, and the residue was dissolved in 0.1 M HCl(aq), extracted with ethylacetate, basified with 4M NaOH(aq) and extracted again with EtOAC to get the product. The organic fractions were combined, dried over $Na_2SO_4$ and concentrated in vacuo to yield 1.3 g Intermediate 3. No further purification. ESI (MS) m/z=315.1 $[M+H]^+$ a) tert-butyl (S)-4-(2-(3-bromo-4-fluorophenyl)-2-hydroxyethyl)-3-(hydroxymethyl)piperazine-1-carboxylate 2-(3-bromo-4-fluorophenyl)oxirane (1.0 g, 4.6 mmol) and tert-butyl (S)-3-(hydroxymethyl)piperazine-1-carboxylate (1.49 g, 6.91 mmol) were dissolved in ethanol (17 mL) then placed in a sealed tubes and heated in the microwave at 130° C. for 80 min and for 25 min at 150° C. to complete the reaction. The solvent was evaporated, the crude material was purified by flash chromatography (silica gel, 120 g, 0% to 60% EtOAc (+10% EtOH) in Heptane) to yield 1.57 g of desired product as a colorless oil. ESI (MS) m/z=433.1 $[M+H]^+$ b) tert-butyl (S)-3-(3-bromo-4-fluorophenyl)hexahydropyrazino[2,1-c][1,4]oxazine-8(1H)-carboxylate tert-butyl (S)-4-(2-(3-bromo-4-fluorophenyl)-2-hydroxyethyl)-3-(hydroxymethyl)piperazine-1-carboxylate (3.2 g, 7.38 mmol) was dissolved in toluene anhydrous (50 ml), the solution was transferred to a argon-purged, flame dried flask and the solution was further degassed with argon, subsequently 2-(tributyl-15-phosphaneylidene)acetonitrile (3.12 g, 3.39 ml, 12.9 mmol) was added in one portion. The reaction mixture was heated for 1.5 h at 100° C. The reaction mixture was extracted with EtOAc/sat. $NaHCO_3$, combined organic layers washed with brine, dried over Na2SO4 and concentrated in vacuo. The crude material was purified by flash chromatography (silica gel, 100 g, 0% to 60% EtOAc in heptane). The product fractions were combined and evaporated to yield 1.8 g of the desired product as a waxy yellow solid. ESI (MS) m/z=415.2 $[M+H]^+$ Intermediate 4

(3R,9aS)-3-(3-chloro-4-fluoro-phenyl)-1,3,4,6,7,8,9,9a-octahydropyrazino[2,1-c][1,4]oxazine tert-butyl 3-(3-chloro-4-fluorophenyl)hexahydropyrazino[2,1-c][1,4]oxazine-8(1H)-carboxylate (350 mg, 944 μmol) was dissolved in 4.72 ml 4M HCl in dioxane and stirred for 120 min at room temperature. The solvent was removed in vacuo, and the residue was dissolved in 0.1 M HCl(aq), extracted with ethylacetate, basified with 4M NaOH(aq) and extracted again with EtOAC to get the product. The organic fractions were combined, dried over $Na_2SO_4$ and concentrated in vacuo to yield 243 mg Intermediate 4 as a waxy, orange solid. No further purification. ESI (MS) m/z=285.2 $[M+H]^+$ a) tert-butyl 4-(2-(3-chloro-4-fluorophenyl)-2-hydroxyethyl)-3-(hydroxymethyl)-3-methylpiperazine-1-carboxylate 2-(3-chloro-4-fluorophenyl)oxirane (843 mg, 3.91 mmol) and tert-butyl 3-(hydroxymethyl)-3-methylpiperazine-1-carboxylate (1 g, 3.91 mmol) were dissolved in Ethanol (17 ml) then placed in a sealed tubes and microwaved at 140° C. for 115 min and 150° C. for 20 min. Almost complete conversion. The solvent was evaporated and the residue was purified by flash chromatography (120 g $SiO_2$, 0%-80% ethyl acetate in heptane)). The product fractions were combined and evaporated to yield 950 mg of desired product as a colorless, waxy solid. ESI (MS) m/z=403.4 $[M+H]^+$ b) tert-butyl 3-(3-chloro-4-fluorophenyl)hexahydropyrazino[2,1-c][1,4]oxazine-8(1H)-carboxylate tert-butyl 4-(2-(3-chloro-4-fluorophenyl)-2-hydroxyethyl)-3-(hydroxymethyl)-3-methylpiperazine-1-carboxylate (950 mg, 2.36 mmol was dissolved in toluene anhydrous (14.3 ml), the solution was transferred to a argon-purged, flame dried flask and the solution was further degassed with argon, subsequently 2-(tributyl-15-phosphaneylidene)acetonitrile (1.14 g, 1.24 ml, 4.72 mmol) was added in one portion. The reaction mixture was heated for 5 h at 100° C. The reaction mixture was extracted with EtOAc/sat. $NaHCO_3$, combined organic layers washed with brine, dried over $Na_2SO_4$ and concentrated in vacuo. The crude material was purified by flash chromatography (silica gel, 20 g, 0% to 70% EtOAc in heptane). The product fractions were combined and evaporated to yield 340 mg of the desired product as a viscous, yellow oil. ESI (MS) m/z=385.3 $[M+H]^+$ Intermediate 5

[2-chloro-3-(3-fluoro-1H-pyrazol-4-yl)phenyl]-[(3S)-3-(hydroxymethyl)piperazin-1-yl]methanone tert-butyl (S)-4-(2-chloro-3-(3-fluoro-1H-pyrazol-4-yl)benzoyl)-2-(hydroxymethyl)piperazine-1-carboxylate (0.151 g, 344 μmol) was combined with 4 M HCl in dioxane (1.29 ml, 5.16 mmol) to give a colorless solution. The reaction mixture was stirred at room temperature for 2 hr. It was then concentrated, dissolved in 10 ml sat. $NaHCO_3$ and extracted with EtOAc (2×50 mL). The organic layers were combined, washed with brine, dried over $Na_2SO_4$ and concentrated in vacuo to yield in the target compound as a colorless oil (117 mg). ESI (MS) m/z=339.1 $[M+H]^+$ a) methyl 2-chloro-3-(3-fluoro-1H-pyrazol-4-yl) benzoate Methyl 2-chloro-3-(4,4,5,5-tetramethyl-1,3,2-dioxaborolan-2-yl)benzoate (849 mg, 2.86 mmol), 4-bromo-3-fluoro-1H-pyrazole (350 mg, 2.12 mmol), $(APhos)_2PdCl_2$ (150 mg, 212 μmol) and $K_2CO_3$ (880 mg, 6.36 mmol) were dispersed in 15 ml dioxane and 4 ml water and degassed with argon. It was then reacted in the microwave (90° C., 30 min) before it was poured into sat. $NaHCO_3$ and extracted into EtOAc twice, dried over Na2SO4 and concentrated in vacuo. The crude was then purified by flash chromatography (silica gel, 50 g, 0% to 50% EtOAc in heptane). The product fractions were combined and evaporated to yield 201 mg of the desired product as a yellow solid. ESI (MS) m/z=255.1 $[M+H]^+$ b) 2-chloro-3-(3-fluoro-1H-pyrazol-4-yl)benzoic acid To a solution of methyl 2-chloro-3-(3-fluoro-1H-pyrazol-4-yl)benzoate (326 mg, 1.28 mmol) in THF (10 ml) was added 1 M aq. LiOH (3.84 ml, 3.84 mmol) and the resulting mixture was stirred at room temperature overnight. The mixture was then acidified with 1 M aq. HCl and extracted with 2-MeTHF twice, dried over $Na_2SO_4$, filtered and concentrated in vacuo to result in 304 mg the desired product as a yellow solid. ESI (MS) m/z=241.1 $[M+H]^+$ c) tert-butyl (S)-4-(2-chloro-3-(3-fluoro-1H-pyrazol-4-yl)benzoyl)-2-(hydroxymethyl)piperazine-1-carboxylate 2-chloro-3-(3-fluoro-1H-pyrazol-4-yl)benzoic acid (300 mg, 1.25 mmol), tert-butyl (S)-2-(hydroxymethyl)piperazine-1-carboxylate (200 mg, 0.925 mmol) and HATU (527 mg, 1.39 mmol) were dissolved in DMF (5 ml). DIPEA (359 mg, 2.77 mmol) was added and the reaction stirred at room temperature for 2.5 hr. Then the reaction mixture was diluted with EtOAc, washed twice with sat. $NaHCO_3$ and the aq. phase was backexracted twice with EtOAc. The combined org. phases were dried over $Na_2SO_4$, filtered, mixed with silica gel and concentrated in vacuo. It was then purified by flash chromatography (silica gel, 20 g, 0% to 10% MeOH in DCM) and then reverse phase column chromatography (HPLC Prep Method F). The product was obtained as a white solid (151 mg). ESI (MS) m/z=437.3 $[M-H]^-$ Intermediate 6

(3R,9aS)-3-(3-chloro-4-fluoro-phenyl)-4,6,7,8,9,9a-hexahydro-1H-pyrazino[2,1-c][1,4]oxazin-3-ol tert-butyl (3R,9aS)-3-(3-chloro-4-fluorophenyl)-3-hydroxyhexahydropyrazino[2,1-c][1,4]oxazine-8(1H)-carboxylate (1 eq, 2.356 g) was mixed with 27 ml 4 M HCl in dioxane and 10 ml dioxane and the resulting greenish slurry stirred at room temperature. After 2.5 hr, the mixture was basified with 4 M aq. NaOH and extracted twice into EtOAc, dried over $Na_2SO_4$, filtered and concentrated in vacuo. The product was obtained as a yellow-white foam (1.75 g) and used without further purification for the next step. ESI (MS) m/z=287.1 $[M+H]^+$ a) tert-butyl (3R,9aS)-3-(3-chloro-4-fluorophenyl)-3-hydroxyhexahydropyrazino[2,1-c][1,4]oxazine-8(1H)-carboxylate tert-butyl (S)-3-(hydroxymethyl)piperazine-1-carboxylate (1 eq, 1.52 g) and DIPEA (1.3 eq, 1.6 ml) were dissolved in 25 ml THF. 2-bromo-1-(3-chloro-4-fluorophenyl)ethan-1-one (1 eq, 1.77 g) in 5 ml THF was added dropwise over 10 min at room temperature. After 20 hr, the crude was filtered and then adsorbed on silica, concentrated in vacuo and purified by silica column chromatograhy (two times 70 g, EtOAc in Hept 0% to 70%). The product was obtained as a white-yellow foam (2.356 g). ESI (MS) m/z=387.2 $[M+H]^+$ Intermediate 7

2-fluoro-5-[rac-(9aS)-1,3,4,6,7,8,9,9a-octahydropyrazino[2,1-c][1,4]oxazin-3-yl]benzonitrile tert-butyl (9aS)-3-(3-cyano-4-fluorophenyl)hexahydropyrazino[2,1-c][1,4]oxazine-8(1H)-carboxylate (0.294 g, 813 μmol, impure) was dissolved in 0.5 mL 4 M HCl in dioxane and stirred at room temperature for one hour. Subsequently, it was concentrated in vacuo and used directly in the next step without further purification. ESI (MS) m/z=262.2 $[M+H]^+$ a) 2-fluoro-5-vinylbenzonitrile 5-bromo-2-fluorobenzonitrile (500 mg, 2.5 mmol), potassium trifluoro(vinyl)borate (402 mg, 3 mmol), 1,1'-bis(diphenylphosphino)ferrocene-palladium(II)dichloride dichloromethane complex (102 mg, 125 μmol) and triethylamine (253 mg, 2.5 mmol) were dispersed in 12 ml ethanol, degassed with argon and reacted in the microwave (120° C., 20 min). The mixture was then concentrated in vacuo, diluted with EtOAc, washed with water, dried over Na2SO4, filtered and concentrated in vacuo before it was purified by silica column chromatography (50 g, EtOAc in Hept 0% to 50%). The product was obtained as a white solid (312 mg). Product confirmed by 1H-NMR.

b) 2-fluoro-5-(oxiran-2-yl)benzonitrile 2-fluoro-5-vinylbenzonitrile (0.15 g, 1.02 mmol) was dispersed in 2 ml water and 1 ml dioxane under heavy stirring. NBS (218 mg, 1.22 mmol) was dissolved in 2 ml water and 1 ml dioxane and added to the mixture dropwise over 15 min. The reaction mixture was stirred at room temperature overnight. Then, the mixture was cooled to 0° C. and 4 M aq. NaOH (765 μl, 3.06 mmol) was added dropwise. After one hour, the reaction mixture was poured into 15 ml sat. aq. $NaHCO_3$ and extracted with EtOAc (2×25 mL). The organic layers were combined, washed with water and then brine, dried over Na2SO4 and concentrated in vacuo. The target molecule was obtained as a yellow oil (153 mg) and used directly for the next step. Product confirmed by 1H-NMR.

c) tert-butyl (3R)-4-(2-(3-cyano-4-fluorophenyl)-2-hydroxyethyl)-3-(hydroxymethyl)piperazine-1-carboxylate 2-fluoro-5-(oxiran-2-yl)benzonitrile (153 mg, 938 μmol) and tert-butyl (S)-3-(hydroxymethyl)piperazine-1-carboxylate (223 mg, 1.03 mmol) were dissolved in MeOH (4 ml) and reacted in the microwave (60 min, 120° C.). It was then concentrated in vacuo and purified by silica column chromatography (20 g, MeOH in DCM 0% to 10%) to yield in 264 mg of the target compound as a yellow oil. ESI (MS) m/z=380.2 $[M+H]^+$ d) tert-butyl (9aR)-3-(3-cyano-4-fluorophenyl)hexahydropyrazino[2,1-c][1,4]oxazine-8(H)-carboxylate tert-butyl (3S)-4-(2-(3-cyano-4-fluorophenyl)-2-hydroxyethyl)-3-(hydroxymethyl)piperazine-1-carboxylate (0.260 g, 685 μmol) and (cyanomethylene)tributylphosphorane (331 mg, 1.37 mmol were dissolved in dry toluene (5 ml), degassed with argon and then reacted at 100° C. for 2 hr. The solution was then concentrated in vacuo and purified by silica column chromatography (20 g, MeOH in DCM 0% to 10%). The desired product was obtained as a light brown oil together with residual tributylphosphine oxide (301 mg). It was used in the next step without further purification ESI (MS) m/z=362.2 $[M+H]^+$ Intermediate 8

(3R,9aS)-3-[6-(trifluoromethyl)-3-pyridyl]-4,6,7,8,9,9a-hexahydro-1H-pyrazino[2,1-c][1,4]oxazin-3-ol tert-butyl (7R,9aR)-7-hydroxy-7-(6-(trifluoromethyl)pyridin-2-yl)octahydro-2H-pyrido[1,2-a]pyrazine-2-carboxylate (150 mg, 0.372 mmol) was mixed with 6 ml 4 M HCl in dioxane and 5 ml dioxane and stirred at room temperature. After 4 hr, the mixture was concentrated in vacuo, basified with 4 M aq. NaOH, diluted with brine and extracted into excess EtOAc and then 2-MeTHF. The combined organic phases were dried over $Na_2SO_4$, filtered and concentrated in vacuo. The product was obtained as an impure orange oil (165 mg). It was used in the next step without further purification. ESI (MS) m/z=304.2 $[M+H]^+$ a) 2-bromo-1-(6-(trifluoromethyl)pyridin-2-yl)ethan-1-one 1-(5-(trifluoromethyl)pyridin-2-yl)ethan-1-on (224 mg, 1.19 mmol), bromine (61 ul, 1.19 mmol) and acetic acid (1.2 ml) were mixed in a pressure tube and reacted at 75° C. for one hour upon which the red solution turned into a yellow suspension. It was concentrated in vacuo and purified by silica column chromatography (20 g, EtOAc in Heptane 0% to 40%). The target compound was isolated as a white solid (240 mg). ESI (MS) m/z=270.0 $[M+H]^+$ b) tert-butyl (7R,9aR)-7-hydroxy-7-(6-(trifluoromethyl)pyridin-2-yl)octahydro-2H-pyrido[1,2-a]pyrazine-2-carboxylate tert-butyl (S)-3-(hydroxymethyl)piperazine-1-carboxylate (97 mg, 0.45 mmol) and DIPEA (97 ul, 0.55 mmol) were dissolved in 2 ml THF and cooled to 0° C. 2-bromo-1-(6-(trifluoromethyl)pyridin-2-yl)ethan-1-one (114 mg, 0.425 mmol) in 1.5 mL THF was added dropwise over 10 min. After 30 min, the solution was warmed up to room temperature and after 4 hr, it was diluted with water and extracted into EtOAc. The aq. phase was dried over $Na_2SO_4$, filtered, concentrated in vacuo and purified by silica column chromatography (20 g, EtOAc in Hept 0% to 70%). The product was obtained as a white solid (150 mg). ESI (MS) m/z=404.2 $[M+H]^+$ Intermediate 9

(3S,9aS)-3-[5-(trifluoromethyl)-2-pyridyl]-4,6,7,8,9,9a-hexahydro-1H-pyrazino[2,1-c][1,4]oxazin-3-ol Synthesis according to intermediate 8. ESI (MS) m/z=304.2 $[M+H]^+$ a) tert-butyl (3S,9aS)-3-hydroxy-3-(5-(trifluoromethyl)pyridin-2-yl)hexahydropyrazino[2,1-c][1,4]oxazine-8(1H)-carboxylate 2-chloro-1-(5-(trifluoromethyl)pyridin-2-yl)ethan-1-one (473 mg, 2.12 mmol), tert-butyl (S)-3-(hydroxymethyl)piperazine-1-carboxylate (503 mg, 2.33 mmol) and DIPEA (480 ul, 2.75 mmol) were dissolved in 10 mL dry THF and stirred at 50° C. overnight and then at 60° C. for 24 hr. Subsequently, it was concentrated in vacuo, diluted with EtOAc, washed with water, dried over $Na_2SO_4$, filtered and concentrated in vacuo again. The crude was purified by silica column chromatography (50 g, EtOAc in Hept 0% to 80%). The target compound was obtained as an off-white solid (437 mg). ESI (MS) m/z=404.2 $[M+H]^+$ Intermediate 10

(3R,9aS)-3-(3,4-difluorophenyl)-4,6,7,8,9,9a-hexahydro-1H-pyrazino[2,1-c][1,4]oxazin-3-ol hydrochloride Synthesis according to Intermediate 8 starting from 2-bromo-1-(3,4-difluorophenyl)ethan-1-one (500 mg, 2.13 mmol) and tert-butyl (S)-3-(hydroxymethyl)piperazine-1-carboxylate (506 mg, 2.34 mmol). Intermediate 10 was obtained as alight blue solid (596 mg, 1.94 mmol). ESI (MS) m/z=271.2 $[M+H]^+$ Intermediate 11

(3S,9aS)-3-[6-(trifluoromethyl)pyridazin-3-yl]-1,3,4,6,7,8,9,9a-octahydropyrazino[2,1-c][1,4]oxazine tert-butyl (9aS)-3-(6-(trifluoromethyl)pyridazin-3-yl)hexahydropyrazino[2,1-c][1,4]oxazine-8(1H)-carboxylate (266 mg, ca. 50% purity, 0.34 mmol) was dissolved in 1.5 mL dioxane and 3 mL 4 M HCl in dioxane and stirred at room temperature. After 90 min, the red mixture was concentrated in vacuo and purified by reverse phase column chromatography (HPLC Prep Method E). The desired diastereomer was obtained as a white solid (50 mg). ESI (MS) m/z=289.2 $[M+H]^+$ a) 3-(trifluoromethyl)-6-vinylpyridazine Synthesis according to Intermediate 7 a), starting from 3-chloro-6-(trifluoromethyl)pyridazine (800 mg, 4.38 mmol). ESI (MS) m/z=175.0 $[M+H]^+$ b) 3-(oxiran-2-yl)-6-(trifluoromethyl)pyridazine 3-(trifluoromethyl)-6-vinylpyridazine (592 mg, 3.4 mmol) was dispersed in 6 ml dioxane and 6 ml water and cooled to 0° C. NBS (726 mg, 4.08 mmol) dissolved in 6 ml dioxane and 12 ml water was added dropwise over 15 min and the flask was warmed up to room temperature and 2 hr later, it was cooled down to 0° C. again and NaOH (2.55 mL of a 4 M aq. solution, 10.2 mmol) was added dropwise and after 30 min it was warmed up to room temperature. After another 30 min, the mixture was diluted with sat. aq. $NaHCO_3$ solution containing additional NaCl and was extracted three times into EtOAc before being dried over $Na_2SO_4$, filtered and concentrated in vacuo. The crude was purified by silica column chromatography (50 g, EtOAc in heptane, 0% to 50%) to yield in 272 mg of the product as a light brown solid. ESI (MS) m/z=191.0 $[M+H]^+$ c) tert-butyl (3S)-4-(2-hydroxy-2-(6-(trifluoromethyl)pyridazin-3-yl)ethyl)-3-(hydroxymethyl)piperazine-1-carboxylate Synthesis according to Intermediate 7 c). ESI (MS) m/z=407.2 $[M+H]^+$ d) tert-butyl (9aS)-3-(6-(trifluoromethyl)pyridazin-3-yl)hexahydropyrazino[2,1-c][1,4]oxazine-8(1H)-carboxylate Synthesis according to Intermediate 7 d). ESI (MS) m/z=389.2 $[M+H]^+$ Intermediate 12

3-[(3R,9aS)-3-hydroxy-4,6,7,8,9,9a-hexahydro-1H-pyrazino[2,1-c][1,4]oxazin-3-yl]-6-(trifluoromethyl)-1H-pyridin-2-one tert-butyl (3R,9aS)-3-hydroxy-3-(2-oxo-6-(trifluoromethyl)-1,2-dihydropyridin-3-yl)hexahydropyrazino[2,1-c][1,4]oxazine-8(1H)-carboxylate (527 mg, 70% purity, 0.88 mmol) was mixed with 1.6 ml dioxane and 4.4 ml 4 M HCl in dioxane and stirred at room temperature for two hours. The mixture was concentrated in vacuo, basified with 4 M aq. NaOH, diluted with brine and extracted into excess EtOAc, dried over sodium sulfate, filtered and concentrated in vacuo. It was then purified by reverse phase column chromatography (HPLC Prep Method E). The product was obtained as a light yellow solid (22.3 mg). ESI (MS) m/z=320.1 $[M+H]^+$ a) tert-butyl (3R,9aS)-3-hydroxy-3-(2-oxo-6-(trifluoromethyl)-1,2-dihydropyridin-3-yl)hexahydropyrazino[2,1-c][1,4]oxazine-8(H)-carboxylate Synthesis according to Intermediate 8 b), starting from 3-(2-bromoacetyl)-6-(trifluoromethyl)pyridin-2(1H)-one (400 mg, 1.41 mmol) and tert-butyl (S)-3-(hydroxymethyl) piperazine-1-carboxylate (335 mg, 1.55 mmol). ESI (MS) m/z=420.3 $[M+H]^+$ Intermediate 13

2-chloro-3-(5-methyl-1H-pyrazol-4-yl)benzoic acid i) In a microwave vial, methyl 3-bromo-2-chlorobenzoate (400 mg, 1.6 mmol), 5-methyl-4-(4,4,5,5-tetramethyl-1,3,2-dioxaborolan-2-yl)-1H-pyrazole (500 mg, 2.4 mmol) and $K_3PO_4$ (4.81 ml of an 1 M aqueous solution, 4.81 mmol) in THF (3.2 ml) was degassed with argon. XPhos-Pd-G2 (126 mg, 160 μmol) was added and the mixture was heated at 100° C. for 2 hr before it was concentrated in vacuo and purified via flash chromatography ($SiO_2$, Hep/EtOAc 35-90% in 40 min) to yield the desired product as an orange waxy solid (122 mg, 30%). ESI (MS) m/z=251.2 $[M+H]^+$ ii) To a solution of methyl 2-chloro-3-(5-methyl-1H-pyrazol-4-yl)benzoate (167 mg, 666 μmol) in THF (3.5 ml) was added a 1 M aqueous solution of LiOH (1.33 ml, 1.33 mmol), and the resulting mixture was stirred at 22° C. overnight. It was then acidified with 1 M HCl and the aqueous layer extracted with 2-MeTHF, washed with brine, dried over Na2SO4, filtered and concentrated in vacuo. The product was obtained as an orange viscouos oil (142 mg, 90%).

ESI (MS) m/z=237.2 $[M+H]^+$

Intermediate 14

2-chloro-3-(4-methyl-3-pyridyl)benzoic acid i) In a microwave vial, methyl 3-bromo-2-chlorobenzoate (200 mg, 802 μmol), (4-methylpyridin-3-yl)boronic acid (137 mg, 1 mmol) and $K_2CO_3$ (276 mg, 2.4 mmol) were mixed with dioxane (6 ml) and degassed with argon. (A-$^t$Phos)$_2$PdCl$_2$ (56.8 mg, 80.2 μmol) was added and the mixture heated at 80° C. for 15 hr. After concentration in vacuo, the residue was purified via flash chromatography ($SiO_2$, Hep/EtOAc 30-90% in 30 min) to yield the desired product as a yellow waxy solid (105 mg, 50%). ESI (MS) m/z=262.2 $[M+H]^+$ ii) To a solution of methyl 2-chloro-3-(4-methylpyridin-3-yl)benzoate (120 mg, 459 μmol) in THF (2.5 ml) was added a 1 M aqueous solution of LiOH (923 μl, 923 μmol) and the resulting mixture was stirred at 22° C. overnight. 3 mL toluene were added and the mixture concentrated in vacuo. No yield was calculated and it was used for the next step without further purification. ESI (MS) m/z=248.1 $[M+H]^+$ Intermediate 15

2-chloro-3-(3-methyl-4-pyridyl)benzoic acid

Synthesis according to intermediate 14. ESI (MS) m/z=248.1 $[M+H]^+$

Intermediate 16

2-chloro-3-(pyridazin-4-yl)benzoic acid

Synthesis according to intermediate 14. ESI (MS) m/z=235.2 $[M+H]^+$

Intermediate 17

2-chloro-3-(pyridin-2-yl)benzoic acid i) In a microwave vial, methyl 3-bromo-2-chlorobenzoate (200 mg, 802 μmol), 2-(4,4,5,5-tetramethyl-1,3,2-dioxaborolan-2-yl)pyridine (329 mg, 1.6 mmol), $Cs_2CO_3$ (522 mg, 1.6 mmol) and copper (I) chloride (79.4 mg, 802 μmol) were dissolved in DMF (8.02 ml) and degassed with argon. XPhos Pd G2 (44.2 mg, 56.1 μmol) was added and the mixture was reacted at 100° C. for 16 hr before it was concentrated in vacuo and purified via flash chromatography ($SiO_2$, Hep/EtOAc 30-90% in 30 min) to yield the desired product as a light yellow waxy solid (35 mg, 18%). ESI (MS) m/z=248.2 $[M+H]^+$ ii) According to intermediate 13, ii). ESI (MS) m/z=234.1 $[M+H]^+$ Intermediate 18

2-chloro-3-(pyridazin-3-yl)benzoic acid i) In a microwave vial, methyl 2-chloro-3-(4,4,5,5-tetramethyl-1,3,2-dioxaborolan-2-yl)benzoate (215 mg, 725 μmol), 3-chloropyridazine hydrochloride (230 mg, 1.52 mmol) and $K_2CO_3$ (411 mg, 2.97 mmol) were mixed with dioxane (4.5 ml) and degassed with argon. (A-taPhos)$_2PdCl_2$ (51.3 mg, 72.5 μmol) was added and the mixture reacted at 80° C. for 80 min before it was concentrated in vacuo and and purified via flash chromatography ($SiO_2$, Hep/EtOAc 30-100% in 30 min) to yield the desired product as a light yellow waxy solid (24 mg, 13%). ESI (MS) m/z=249.1 $[M+H]^+$ ii) According to intermediate 13, ii). ESI (MS) m/z=235.1 $[M+H]^+$ Intermediate 19

2-chloro-3-(4-methylpyridazin-3-yl)benzoic acid i) In a microwave vial, methyl 2-chloro-3-(4,4,5,5-tetramethyl-1,3,2-dioxaborolan-2-yl)benzoate (219 mg, 739 μmol), 3-chloro-4-methylpyridazine (95 mg, 739 μmol) and $K_2CO_3$ (204 mg, 1.48 mmol) was mixed with toluene (2.1 ml) and water (0.23 mL) and degassed with argon. (A-taPhos)$_2PdCl_2$ (52.3 mg, 73.9 μmol) was added and the mixture was reacted at 120° C. for 30 min before it was concentrated in vacuo and purified via flash chromatography ($SiO_2$, Hep/EtOAc 30-100% in 35 min) to yield the desired product as a yellow waxy solid (30 mg, 16%). ESI (MS) m/z=263.2 $[M+H]^+$ ii) According to intermediate 13, ii). ESI (MS) m/z=249.1 $[M+H]^+$ Intermediate 20

2-chloro-3-(5-methylpyrimidin-4-yl)benzoic acid i) A microwave vial was charged with methyl 2-chloro-3-(4,4,5,5-tetramethyl-1,3,2-dioxaborolan-2-yl)benzoate (200 mg, 674 μmol), 4-chloro-5-methylpyrimidine (104 mg, 809 μmol) and $K_2CO_3$ (186 mg, 1.35 mmol), toluene (2.25 ml) and was degassed with argon. (A-$^{ta}$Phos)$_2PdCl_2$ (47.8 mg, 67.4 μmol) was added and the mixture was heated at 120° C. for 30 min. The mixture was concentrated in vacuo. The residue was purified via flash chromatography ($SiO_2$, DCM, 0-10% MeOH) resulting in not completely pure product. Repurification with gradient of Hep/EtOAc 0-60% lead to the the desired product as a yellow oil (130 mg, 73%). ESI (MS) m/z=263.2 $[M+H]^+$ ii) According to intermediate 13. ESI (MS) m/z=249.1 $[M+H]^+$ Intermediate 21

2-chloro-3-(1H-imidazol-4-yl)benzoic acid i) In a microwave vial, methyl 2-chloro-3-(4,4,5,5-tetramethyl-1,3,2-dioxaborolan-2-yl)benzoate (300 mg, 1.01 mmol), 4-iodo-1H-imidazole (196 mg, 1.01 mmol) and $K_2CO_3$ (2.53 ml, 3.03 mmol) were mixed with dioxane (7.5 ml) and water (2.5 ml) and degassed with argon. (APhos)$_2$PdCl2 (71.6 mg, 101 μmol) was added and the mixture reacted at 115° C. for 30 min before it was concentrated in vacuo and purified via flash chromatography ($SiO_2$, DCM/MeOH 0-10% in 35 min) and then reverse phase column chromatography to yield the desired product as a white solid (60.1 mg, 25%). ESI (MS) m/z=237.2 $[M+H]^+$ ii) According to intermediate 13. ESI (MS) m/z=223.1 $[M+H]^+$ Intermediate 22

2-chloro-3-(3-methylpyridin-2-yl)benzoic acid i) According to intermediate 19 i). ESI (MS) m/z=262.2 $[M+H]^+$ ii) According to intermediate 13, ii). ESI (MS) m/z=248.2 $[M+H]^+$ Intermediate 23

2-chloro-3-(1H-pyrazol-4-yl)benzoic acid i) In a microwave vial, methyl 3-bromo-2-chlorobenzoate (300 mg, 1.2 mmol), 4-(4,4,5,5-tetramethyl-1,3,2-dioxaborolan-2-yl)-1H-pyrazole (350 mg, 1.8 mmol) and $K_2CO_3$ (3.01 ml, 3.61 mmol) were mixed with dioxane (9 ml) and water (3 ml) and degassed with argon. (APhos)$_2PdCl_2$ (85.1 mg, 120 μmol) was added and the mixture was reacted at 115° C. for 30 min before it was concentrated in vacuo and purified via flash chromatography ($SiO_2$, DCM/MeOH 0-8% in 35 min) and then reverse phase column chromatography to yield the desired product as a white solid (34 mg, 12%). ESI (MS) m/z=237.2 $[M+H]^+$ ii) According to intermediate 13, ii). ESI (MS) m/z=223.1 $[M+H]^+$ Intermediate 24

2-chloro-3-(1,5-dimethyl-1H-pyrazol-4-yl)benzoic acid i) In a microwave vial, methyl 2-chloro-3-(5-methyl-1H-pyrazol-4-yl)benzoate (as described in intermediate 13 i), 70 mg, 279 μmol) and $Cs_2CO_3$ (136 mg, 419 μmol) were dissolved in DMF (2 ml), treated with methyl iodide (198 mg, 1.4 mmol) and then reacted at 100° C. for 15 min. The reaction was subsequently diluted with saturated aqueous ammonium chloride solution and extracted into ethyl acetate. The organic phase was washed with brine, dried over $Na_2SO_4$, filtered, concentrated in vacuo and purified via flash chromatography ($SiO_2$, Hep/EtOAc 0-100%) to yield the desired product as a yellow oil (23 mg, 31%). ESI (MS) m/z=265.2 $[M+H]^+$ ii) According to intermediate 13, ii). ESI (MS) m/z=251.2 $[M+H]^+$ Intermediate 25

2-chloro-3-(3-methylisoxazol-4-yl)benzoic acid i) In a microwave vial, methyl 3-bromo-2-chlorobenzoate (200 mg, 802 μmol), 3-methyl-4-(4,4,5,5-tetramethyl-1,3,2-dioxaborolan-2-yl)isoxazole (251 mg, 1.2 mmol) and $K_3PO_4$ (1.6 ml of a 1 M aqueous solution, 1.6 mmol) were mixed with THF (1.6 ml) and degassed with argon. XPhos-Pd-G2 (44.2 mg, 56.1 μmol) was added and the mixture reacted at 60° C. for 1 hr before it was concentrated in vacuo and purified via flash chromatography ($SiO_2$, Hep/EtOAc 0-40% in 35 min) to yield the desired product as a yellow oil (171 mg, 85%). ESI (MS) m/z=252.1 $[M+H]^+$ ii) According to intermediate 13 ii). ESI (MS) m/z=238.1 $[M+H]^+$ Intermediate 26

2-chloro-3-(2-oxa-6-azaspiro[3.3]heptan-6-yl)benzoic acid i) In a pressure vial, methyl 3-bromo-2-chlorobenzoate (250 mg, 1 mmol), 2-oxa-6-azaspiro[3.3]heptane (199 mg, 2 mmol), $K_3PO_4$ (425 mg, 2 mmol), $Pd_2(dba)_3$ (91.8 mg, 100 μmol) and DavePhos (59.2 mg, 150 μmol) were mixed with toluene (4 ml) and then degassed with argon. It was then reacted at 100° C. for 16 hr before it was concentrated in vacuo and purified via flash chromatography ($SiO_2$, Hep/EtOAc 0-45%) to yield the desired product as a dark red oil (210 mg, 78%). ESI (MS) m/z=268.3 $[M+H]^+$ ii) To a solution of methyl 2-chloro-3-(2-oxa-6-azaspiro[3.3]heptan-6-yl)benzoate (210 mg, 784 μmol) in THF (5 ml) was added a 1 M aqueous solution of LiOH (1.57 ml, 1.57 mmol), and the resulting mixture was stirred at 22° C. overnight and then at 50° C. for 4 hr. The mixture was acidified with 1 M HCl and the aqueous layer extracted with 2-MeTHF, washed with brine, dried over $Na_2SO_4$, filtered and concentrated in vacuo. The product was obtained as light yellow solid, 233 mg (94%, 80% purity). Used directly in the next step. ESI (MS) m/z=254.2 $[M+H]^+$ Intermediate 27

2-chloro-3-morpholinobenzoic acid i) According to intermediate 26, i). ESI (MS) m/z=256.2 $[M+H]^+$ ii) According to intermediate 26, ii). ESI (MS) m/z=242.2 $[M+H]^+$ Intermediate 28

2-chloro-3-(1H-1,2,3-triazol-4-yl)benzoic acid

Ester cleavage was performed according to intermediate 13, ii). ESI (MS) m/z=224.1 $[M+H]^+$ a) methyl 2-chloro-3-((trimethylsilyl)ethynyl)benzoate Methyl 3-bromo-2-chlorobenzoate (800 mg, 3.21 mmol), $PdCl_2$(DPPF) (262 mg, 321 μmol) and copper (I) iodide (30.5 mg, 160 μmol) were dissolved in dry DMF (2 ml) upon which diethylamine (11.7 g, 160 mmol) was added. The reaction mixture was degassed with argon and after the addition of ethynyltrimethylsilane (472 mg, 4.81 mmol) it was reacted at 120° C. for 30 min under microwave irradiation. It was then concentrated in vacuo and purified via flash chromatography ($SiO_2$, Hep/EtOAc 0-20%) to yield the desired product as a yellow liquid (580 mg, 68%). Product confirmed by 1H-NMR.

b) methyl 2-chloro-3-ethynylbenzoate

Methyl 2-chloro-3-((trimethylsilyl)ethynyl)benzoate (270 mg, 1.01 mmol) was dissolved in THF (4 ml) and MeOH (4 ml) upon which potassium carbonate (559 mg, 4.05 mmol)

was added and the reaction was stirred at room temperature for 2 hr, then the residual potassium carbonate was removed by filtration and the solvent was removed under reduced pressure. The light red solid crude (200 mg, 100%) was used for the next step without further purification. ESI (MS) m/z=195.0 $[M+H]^+$ c) methyl 2-chloro-3-(1H-1,2,3-triazol-4-yl)benzoate In a microwave vial, copper (I) iodide (9.79 mg, 51.4 μmol), methyl 2-chloro-3-ethynylbenzoate (200 mg, 1.03 mmol) and azidotrimethylsilane (317 mg, 2.57 mmol) were suspended in DMF (3.6 ml) and MeOH (0.6 ml). The mixture was degassed with argon and then stirred at 100° C. for 7 hr before it was concentrated in vacuo and purified via flash chromatography ($SiO_2$, Hep/EtOAc 10-70%) to yield the desired product as a light yellow solid (185 mg, 76%). ESI (MS) m/z=238.2 $[M+H]^+$ Intermediate 29

2-chloro-3-(3-fluoro-1H-pyrazol-4-yl)benzoic acid i) According to intermediate 21, i). ESI (MS) m/z=255.2 $[M+H]^+$ ii) According to intermediate 13, ii). ESI (MS) m/z=241.1 $[M+H]^+$ Intermediate 30

2-chloro-2'-methoxy-[1,1'-biphenyl]-3-carboxylic acid i) In a microwave vial, methyl 3-bromo-2-chlorobenzoate (150 mg, 601 μmol), (2-methoxyphenyl)boronic acid (119 mg, 782 μmol) and $K_3PO_4$ (255 mg, 1.2 mmol) in THF (1.2 ml) was degassed with argon. XPhos-Pd-G2 (23.7 mg, 30.1 μmol) was added and the mixture reacted at 60° C. for 35 min before it was was diluted with water, extracted into EtOAc, dried and concentrated in vacuo and purified via flash chromatography ($SiO_2$, Hep/EtOAc 0-30%) to yield the desired product as a brown oil (131 mg, 79%). ESI (MS) m/z=277.1 $[M+H]^+$ ii) According to intermediate 13, ii). ESI (MS) m/z=263.1 $[M+H]^+$ Intermediate 31

Lithium 2-chloro-3-(3-hydroxyazetidin-1-yl)benzoate i) In a sealed tube, methyl 3-bromo-2-chlorobenzoate (CAS RN 871224-19-0, 0.1 g, 0.401 mmol), cesium carbonate (0.261 g, 0.802 mmol), $Pd_2(dba)_3$ (0.037 g, 0.040 mmol) and Xantphos (23.2 mg, 40.1 μmol) were mixed in dioxane (1 mL). The mixture was degassed with argon, then azetidin-3-ol (CAS RN 45347-82-8, 0.059 g, 0.802 mmol) was added and the reaction mixture was heated to 100° C. for 16 hours. The mixture was diluted with EtOAc and washed with water and brine. The organic phase was dried over $Na_2SO_4$, filtered and concentrated in vacuo. The residue was purified by silica gel flash chromatography (EtOAc in heptane, 0% to 50%) to give Methyl 2-chloro-3-(3-hydroxyazetidin-1-yl)benzoate (0.034 g, 35%) as an orange viscous oil; MS (ESI): m/z=242.1 $[M+H]^+$.

ii) To a solution of methyl 2-chloro-3-(3-hydroxyazetidin-1-yl)benzoate (0.035 g, 0.145 mmol) in THF (0.35 mL) was added a 1 M LiOH aq. solution (0.29 mL, 290 mmol) and the reaction mixture was stirred at room temperature for 5 hours. The mixture was concentrated in vacuo and the residue triturated in diisopropylether, filtered off and further dried on the high vacuum to give the crude title compound (0.032 g, 82%) as a light brown solid as lithium salt; MS (ESI): m/z=228.1 $[M+H]^+$.

Intermediate 32

2-chloro-3-(oxazol-5-yl)benzoic acid i) Methyl 3-bromo-2-chlorobenzoate (300 mg, 1.2 mmol), oxazole (166 mg, 2.4), palladium acetate (13.5 mg, 0.06 mmol), potassium carbonate (500 mg, 3.61 mmol), pivalic acid (49 mg, 0.48 mmol) and di-tert-butyl(2',4',6'-triisopropyl-3,4,5,6-tetramethyl-[1,1'-biphenyl]-2-yl)phosphane (58 mg, 0.12 mmol) were dispersed in 6.6 mL DMA, degassed with argon and reacted for 15 hours at 110° C. After reaction completion, the mixture was diluted with water and extracted into EtOAc twice. The combined organic phases were dried over Na2SO4, filtered and concentrated in vacuo. The residue was purified by silica gel flash chromatography (EtOAc/heptane 0% to 50%). The product was obtained as a light yellow solid (89 mg, ca. 75% purity, 23% yield). MS (ESI): m/z=238.1 $[M+H]^+$ ii) According to intermediate 14, ii). ESI (MS) m/z=224.0 $[M+H]^+$ Intermediate 33

2-fluoro-3-(3-fluoro-1H-pyrazol-4-yl)benzoic acid i) According to Intermediate 21 i), starting from 4-bromo-3-fluoro-1H-pyrazole and methyl 2-fluoro-3-(4,4,5,5-tetramethyl-1,3,2-dioxaborolan-2-yl)benzoate, yielding methyl 2-fluoro-3-(3-fluoro-1H-pyrazol-4-yl)benzoate as a yellow solid, 49%. MS (ESI): m/z=239.1 $[M+H]^+$ ii) According to Intermediate 14 ii). MS (ESI): m/z=225.1 $[M+H]^+$ Intermediate 34

2-chloro-3-(3-cyano-1H-pyrazol-4-yl)benzoic acid i) i) According to Intermediate 21 i), starting from 4-bromo-TH-pyrazole-3-carbonitrile and methyl 2-chloro-3-(4,4,5,5-tetramethyl-1,3,2-dioxaborolan-2-yl)benzoate, yielding methyl 2-chloro-3-(3-cyano-TH-pyrazol-4-yl)benzoate as a red solid. m/z=260.1 $[M-H]^-$ ii) According to Intermediate 14 ii). m/z=246.1 $[M-H]^-$ Intermediate 35A/35B

[(3R,9aS)-3-(2-benzyloxy-5-chloro-3-pyridyl)-3,4,6,7,9,9a-hexahydro-1H-pyrazino[2,1-c][1,4]oxazin-8-yl]-(2-chloro-3-methoxy-phenyl)methanone and [(3S,9aS)-3-(2-benzyloxy-5-chloro-3-pyridyl)-3,4,6,7,9,9a-hexahydro-1H-pyrazino[2,1-c][1,4]oxazin-8-yl]-(2-chloro-3-methoxy-phenyl)methanone ((3S)-4-(2-(2-(benzyloxy)-5-chloropyridin-3-yl)-2-hydroxyethyl)-3-(hydroxymethyl)piperazin-1-yl)(2-chloro-3-methoxyphenyl)methanone (197 mg, 361 umol) and 2-(tributyl-15-phosphaneylidene)acetonitrile (174 mg, 721 umol) were dissolved in 2.5 mL dry toluene, degassed and heated to 110° C. After 5 h, it was concentrated in vacuo and purified by silica column chromatography (EA in Heptane). Both diastereomers could be separated Intermediate 35A (first eluting diastereomer) was obtained as a brown oil (44.7 mg, 23.5%) ESI (MS) m/z=528.2 $[M+H]^+$ Intermediate 35B (second eluting diastereomer) was obtained as a brown oil (31.6 mg, 16.6%) ESI (MS) m/z=528.2 $[M+H]^+$ a) 2-(benzyloxy)-3-bromo-5-chloropyridine 3-bromo-5-chloropyridin-2(1H)-one (600 mg, 2.88 mmol), silver carbonate (1.06 g, 3.84 mmol) and benzyl bromide (591 mg, 3.45 mmol) were weighed in the dark into an aluminium-wrapped round bottom flask, mixed with 5 ml toluene and reacted at 50° C. After 28 h, the mixture was cooled down to room temperature, filtered and washed with aqueous sat. bicarbonate solution and then water twice. The organic phase was dried over Na2SO4, filtered and concentrated in vacuo. The crude residue was purified by silica column chromatography (EtOAc/heptane 0% to 50%) and the target compound was isolated as a white solid (895 mg, 95%). MS (ESI): m/z=300.0 $[M+H]^+$.

b) 2-(benzyloxy)-5-chloro-3-vinylpyridine 2-(benzyloxy)-3-bromo-5-chloropyridine (595 mg, 1.99 mmol), potassium trifluoro(vinyl)borate (320 mg, 2.39 mmol), 1,1'-bis(diphenylphosphino)ferrocene-palladium(II) dichloride dichloromethane complex (82 mg, 0.1 mmol) and triethylamine (202 mg, 1.99 mmol) were dispersed in 15 ml EtOH and degassed with argon. It was reacted in the microwave (120° C., 20 min) and then then concentrated in vacuo, diluted with EtOAc, washed with water, dried over Na2SO4, filtered, adsorbed on silica and concentrated in vacuo. It was purified by silica column chromatography (EtOAc/heptane 0% to 10%). The product was isolated as a colorless oil which turned into a white solid upon standing (443 mg, 91%). MS (ESI): m/z=246.1 $[M+H]^+$.

c) 2-(benzyloxy)-5-chloro-3-(oxiran-2-yl)pyridine

According to Intermediate 7, step b). MS (ESI): m/z=262.1 $[M+H]^+$.

d) ((3S)-4-(2-(2-(benzyloxy)-5-chloropyridin-3-yl)-2-hydroxyethyl)-3-(hydroxymethyl)piperazin-1-yl)(2-chloro-3-methoxyphenyl)methanone 2-(benzyloxy)-5-chloro-3-(oxiran-2-yl)pyridine (365 mg, 1.39 mmol) and (S)-(2-chloro-3-methoxyphenyl)(3-(hydroxymethyl)piperazin-1-yl)methanone (intermediate 1S, 437 mg, 1.53 mmol) were dissolved in 2.5 mL THF and 2.5 mL EtOH and reacted in the microwave (120° C., 70 min) and then again (130° C., 30 min). It was then concentrated in vacuo and purified by silica column chromatography (MeOH in DCM 0% to 10%). ((3S)-4-(2-(2-(benzyloxy)-5-chloropyridin-3-yl)-2-hydroxyethyl)-3-(hydroxymethyl)piperazin-1-yl)(2-chloro-3-methoxyphenyl)methanone was isolated as a yellow oil (197 mg, 26%). ESI (MS) m/z=546.2 $[M+H]^+$ Intermediate 36

2-(3-bicyclo[4.2.0]octa-1(6),2,4-trienyl)oxirane 3-vinylbicyclo[4.2.0]octa-1,3,5-triene (170 mg, 1.31 mmol) was dissolved in 2.4 ml DCM. Methyltrioxorhenium (3.2 mg, 0.013 mmol) and 1H-pyrazole (10.7 mg, 0.157 mmol) were added. The purple solution was cooled to 0° C. and upon addition of hydrogen peroxide (225 ul of a 35% aq. solution, 2.61 mmol) the solution turned yellow. It was stirred vigorously for 60 min. A few grains of manganese dioxide were added and after no bubbling was observed anymore the reaction mixture was diluted with sat. aqueous bicarbonate solution and extracted into DCM twice. It was then dried over $Na_2SO_4$, filtered, concentrated in vacuo and purified by silica column chromatography (EtOAc/heptane 0% to 10%). The product was isolated as a colorless oil (132 mg, 69%). Structure confirmed by 1H-NMR.

Intermediate 37

4,5-dichloro-2-(oxiran-2-yl)pyridine

According to Intermediate 7, step b), starting from 4,5-dichloro-2-vinylpyridine ESI (MS): m/z=190.0 $[M+H]^+$ a) 4,5-dichloro-2-vinylpyridine 2-Bromo-4,5-dichloropyridine (500 mg, 2.2 mmol), potassium vinyl trifluoroborate (1.2 eq, 354 mg), [1,1'-Bis (diphenylphosphino)ferrocene]dichloropalladium(II), complex with dichloromethane (0.05 eq, 90 mg) and TEA (307 uL, 2.2 mol) were dispersed in 12 mL ethanol in a large microwave vial. The mixture was degassed with argon and heated in the microwave (120° C., 20 min). It was then concentrated in vacuo, diluted with EtOAc, washed with water, dried over sodium sulfate, filtered and concentrated in vacuo. It was purified by silica column chromatography (EA in Heptane 0% to 50%). The product was obtained as a light yellow oil (278 mg, 73%). Structure confirmed by $^1$H-NMR.

Intermediate 38

(9aS)-3-(5-bromopyridin-2-yl)octahydropyrazino[2,1-c][1,4]oxazine hydrochloride

Boc-deprotection of tert-butyl (9aS)-3-(5-bromo-2-pyridyl)-3,4,6,7,9,9a-hexahydro-1H-pyrazino[2,1-c][1,4] oxazine-8-carboxylate performed according to Intermediate 7. ESI (MS): m/z=300.0 $[M+H]^+$.

a) tert-butyl (3S)-4-(2-(5-bromopyridin-2-yl)-2-hydroxyethyl)-3-(hydroxymethyl)piperazine-1-carboxylate 5-bromo-2-(oxiran-2-yl)pyridine (44 mg, 0.22 mmol) and tert-butyl (S)-3-(hydroxymethyl)piperazine-1-carboxylate (52 mg, 0.242 mmol) were dissolved in 1.5 ml MeOH and reacted in the microwave (60 min, 120° C.). It was then concentrated in vacuo and purified by silica column chromatography (MeOH/DCM 0% to 10%). The product was isolated as a slightly yellow oil (60 mg, 66%). ESI (MS): m/z=418.2 $[M+H]^+$ b) tert-butyl (9aS)-3-(5-bromo-2-pyridyl)-3,4,6,7,9,9a-hexahydro-1H-pyrazino[2,1-c][1,4]oxazine-8-carboxylate tert-butyl (3S)-4-(2-(5-bromopyridin-2-yl)-2-hydroxyethyl)-3-(hydroxymethyl)piperazine-1-carboxylate (60 mg, 0.144 mmol) and (cyanomethylene)tributylphosphorane (69 mg, 0.288 mmol) were dissolved in 1 ml dry toluene, the solution was degassed with argon and then heated to 100° C.

After 2 hours, it was concentrated in vacuo and purified by silica column chromatography (MeOH/DCM 0% to 10%). The product was obtained as a brown oil (39 mg, ca. 30% purity, 20% yield) and used without further purification for the next step. MS (ESI): m/z=398.2 $[M+H]^+$ Intermediate 39

5-chloro-4-methyl-2-(oxiran-2-yl)pyridine

According to Intermediate 7, step b, starting from 5-chloro-4-methyl-2-vinyl-pyridine. MS (ESI): m/z=170.0 $[M+H]^+$ a) 5-chloro-4-methyl-2-vinyl-pyridine According to Intermediate 7, step a, starting from 2,5-dichloro-4-methylpyridine. MS (ESI): m/z=154.0 $[M+H]^+$.

Intermediate 40

5-chloro-2-(oxiran-2-yl)-4-(trifluoromethyl)pyridine

According to Intermediate 7, step b, starting from 5-chloro-4-(trifluoromethyl)-2-vinylpyridine. Structure confirmed by 1H-NMR.

a) 5-chloro-4-(trifluoromethyl)-2-vinylpyridine

According to Intermediate 7, step a, starting from 2,5-dichloro-4-(trifluoromethyl)pyridine. Structure confirmed by 1H-NMR.

Intermediate 41

2-(oxiran-2-yl)-4-(trifluoromethoxy)pyridine

According to Intermediate 7, step b, starting from 4-trifluoromethoxy-2-vinylpyridine. MS (ESI): m/z=206.0 $[M+H]^+$ a) 4-trifluoromethoxy-2-vinylpyridine According to Intermediate 7, step a, starting from 2-chloro-4-(trifluoromethoxy)pyridine. MS (ESI): m/z=190.0 $[M+H]^+$.

Intermediate 42

5-fluoro-2-(oxiran-2-yl)-4-(trifluoromethyl)pyridine

According to Intermediate 7, step b, starting from 5-fluoro-4-(trifluoromethyl)-2-vinylpyridine. Structure confirmed by 1H-NMR.

a) 5-fluoro-4-(trifluoromethyl)-2-vinylpyridine

According to Intermediate 7, step a, starting from 2-chloro-5-fluoro-4-(trifluoromethyl)pyridine.

Structure confirmed by 1H-NMR.

Intermediate 43

5-chloro-4-(difluoromethyl)-2-(oxiran-2-yl)pyridine

According to Intermediate 7, step b, starting from 5-chloro-4-(difluoromethyl)-2-vinylpyridine MS (ESI): m/z=206.0 $[M+H]^+$ a) 5-chloro-4-(difluoromethyl)-2-vinylpyridine According to Intermediate 7, step a, starting from 2,5-dichloro-4-(difluoromethyl)pyridine. After the silica column chromatography, the solvent was not removed completely due to suspected volatility of the compound. MS (ESI): m/z=189.9 $[M+H]^+$ Intermediate 44

4-bromo-5-chloro-2-(oxiran-2-yl)pyridine

According to Intermediate 7, step b, starting from 4-bromo-5-chloro-2-vinylpyridine MS (ESI): m/z=236.0 $[M+H]^+$ a) -bromo-5-chloro-2-vinylpyridine According to Intermediate 7, step a, starting from 2,4-dibromo-5-chloropyridine. After the silica column chromatography, the solvent was not removed completely due to suspected volatility of the compound. MS (ESI): m/z=219.9 $[M+H]^+$ Intermediate 45

2-fluoro-3-(5-(trifluoromethyl)-1H-pyrazol-4-yl) benzoic acid

According to Intermediate 13, step ii), starting from Methyl 2-fluoro-3-(5-(trifluoromethyl)-1H-pyrazol-4-yl) benzoate. MS (ESI): m/z=275.1 $[M+H]^+$.

a) Methyl 2-fluoro-3-(5-(trifluoromethyl)-1H-pyrazol-4-yl)benzoate

Methyl 2-fluoro-3-(4,4,5,5-tetramethyl-1,3,2-dioxaborolan-2-yl)benzoate (CAS 1638847-77-4, 292 mg with 75% purity, 0.7 mmol), 4-bromo-5-(trifluoromethyl)-1H-pyrazole (168 mg, 0.78 mmol), bis(di-tert-butyl(4-dimethylaminophenyl)phosphine)dichloropalladium(II) (55 mg, 0.078 mmol) and $K_2CO_3$ (324 mg, 2.35 mmol) were mixed with 4.5 ml dioxane and 1.5 ml water, degassed with argon and reacted in the microwave (115° C., 30 min). It was diluted with water and extracted into EtOAc twice, dried over Na2SO4, filtered, adsorbed on silica, concentrated in vacuo and purified by silica column chromatography (20 g, EtOAc/heptane 0% to 40%). The desired product was isolated as a yellow oil (123 mg, 55%). MS (ESI): m/z=289.1 $[M+H]^+$.

Intermediate 46

3-(5-(trifluoromethyl)-1H-pyrazol-4-yl)benzoic acid

According to Intermediate 13, step ii), starting from Ethyl 3-(5-(trifluoromethyl)-1H-pyrazol-4-yl)benzoate. MS (ESI): m/z=257.1 $[M+H]^+$ a) Ethyl 3-(5-(trifluoromethyl)-1H-pyrazol-4-yl) benzoate According to Intermediate 45, step b, starting from with ethyl 3-(4,4,5,5-tetramethyl-1,3,2-dioxaborolan-2-yl)benzoate. MS (ESI): m/z=285.1 $[M+H]^+$ Intermediate 47

Lithium 2-chloro-3-(2-oxo-1,2-dihydropyridin-4-yl)benzoate

According to Intermediate 13, step ii), starting from Methyl 2-chloro-3-(2-oxo-1,2-dihydropyridin-4-yl)benzoate. The target compound was not extracted into organic solvent but the reaction mixture was lyophilized and used in the next step without further purification. MS (ESI): m/z=250.1 $[M+H]^+$ a) Methyl 2-chloro-3-(2-oxo-1,2-dihydropyridin-4-yl)benzoate Synthesis according to Intermediate 21, step i), starting from 4-bromopyridin-2(1H)-one. MS (ESI): m/z=264.1 $[M+H]^+$ Intermediate 48

2-chloro-3-(6-oxo-1H-pyridin-3-yl)benzoic acid

Methyl 2-chloro-3-(6-oxo-1,6-dihydropyridin-3-yl)benzoate (120 mg, 0.455 mmol) and LiOH monohydrate (57 mg, 1.37 mmol) were dispersed in 1.4 ml water, 0.5 ml MeOH and 3.9 ml THF and stirred at 22° C. 19 hours later, it was acidified with 1 M aqueous HCl and diluted with brine. It was concentrated in vacuo, suspended in EtOH, stirred heavily for a few minutes and filtered. The process was repeated twice and the combined filtered solutions concentrated in vacuo. The target compound was obtained as a white solid together with residual NaCl and LiCl.

a) Methyl 2-chloro-3-(6-oxo-1,6-dihydropyridin-3-yl)benzoate

According to Intermediate 21, step i), starting from 5-bromopyridin-2(1H)-one. MS (ESI): m/z=264.1 $[M+H]^+$ Intermediate 49

5-chloro-3-((3R,9aS)-octahydropyrazino[2,1-c][1,4] oxazin-3-yl)pyridin-2-ol 2,2,2-trifluoroacetate tert-butyl (3R,9aS)-3-(2-(benzyloxy)-5-chloropyridin-3-yl)hexahydropyrazino[2,1-c][1,4]oxazine-8(1H)-carboxylate (29.2 mg, 63.5 umol) was dissolved in 1.5 mL DCM. TFA (50 uL) was added and the yellow solution stirred at RT. After 4 h, another portion of TFA (1 ml) was added slowly. 3 h later, the mixture was concentrated in vacuo, redissolved in toluene and concentrated in vacuo again to obtain a brown solid. The crude was used in the next step without further purification. MS (ESI): m/z=270.2 $[M+H]^+$.

a) tert-butyl (3S)-4-(2-(2-(benzyloxy)-5-chloropyridin-3-yl)-2-hydroxyethyl)-3-(hydroxymethyl)piperazine-1-carboxylate Synthesis according to Intermediate 35A/35B, step d, starting from 2-(benzyloxy)-5-chloro-3-(oxiran-2-yl)pyridine (see Intermediate 35A/35B for the synthesis, 208 mg, 795 umol) and tert-butyl (S)-3-(hydroxymethyl)piperazine-1-carboxylate (189 mg, 874 umol). Product obtained as a yellow oil, 181 mg (47.6%). MS (ESI): m/z=478.3 $[M+H]^+$ b) tert-butyl (3R,9aS)-3-(2-(benzyloxy)-5-chloropyridin-3-yl)hexahydropyrazino[2,1-c][1,4]oxazine-8(H)-carboxylate tert-butyl (3S)-4-(2-(2-(benzyloxy)-5-chloropyridin-3-yl)-2-hydroxyethyl)-3-(hydroxymethyl)piperazine-1-carboxylate (132 mg, 276 umol) was dissolved in 1.7 mL dry toluene. 2-(tributyl-15-phosphaneylidene)acetonitrile (133 mg, 552 umol) in 0.3 mL dry toluene was added and the mixture heated up to 100° C. After 5 h another (100 mg, 414 umol) of 2-(tributyl-15-phosphaneylidene)acetonitrile in 0.2 mL dry toluene was added. The solution was warmed up to 110° C. After 5 h the reaction mixture was concentrated and purified by column chromatography (EA in Heptane 0% to 90%). The first eluting diastereomer was carried forward to the next step. Product obtained as a yellow oil, 29.2 mg (23%). MS (ESI): m/z=460.3 $[M+H]^+$ Intermediate 50

(3-bromo-2-chloro-5-fluorophenyl)((3R,9aS)-3-(3-chloro-4-fluorophenyl)hexahydropyrazino[2,1-c][1,4]oxazin-8(1H)-yl)methanone (3R,9aS)-3-(3-chloro-4-fluoro-phenyl)-1,3,4,6,7,8,9,9a-octahydropyrazino[2,1-c][1,4]oxazine (Intermediate 2, 1 eq, 74.6 mg), 3-bromo-2-chloro-5-fluorobenzoic acid (1.35 eq, 105 mg) and HATU (1.35 eq, 141 mg) were mixed with 2 mL dry DMF and cooled to 0° C. DIPEA (3 eq, 144 uL) was added upon which a yellow solution formed. After 10 min, it was warmed up to RT. 3 h later, it was diluted with EtOAc and washed with cold water and then sat. bicarbonate solution and finally brine, dried over sodium sulfate, filtered and concentrated in vacuo. The crude was puriied by silica column chromatography (10 g, EtOAc in Hept 30% to 80%). The product was obtained as a white solid (102 mg, ca. 80% purity, yield ca. 59%).

Also a fraction recuperated form the waste was obtained: 19 mg, ca 80% pure, yield ca. 11%

Intermediate 51a (3R,9aS)-3-(3,4-dichlorophenyl)-4,6,7,8,9,9a-hexahydro-1H-pyrazino[2,1-c][1,4]oxazin-3-ol According to Intermediate 52, step b, starting from tert-butyl (3R,9aS)-3-(3,4-dichlorophenyl)-3-hydroxy-1,4,6,7,9,9a-hexahydropyrazino[2,1-c][1,4]oxazine-8-carboxylate. MS (ESI): m/z=303.2 $[M+H]^+$.

a) tert-butyl (3R,9aS)-3-(3,4-dichlorophenyl)-3-hydroxy-1,4,6,7,9,9a-hexahydropyrazino[2,1-c][1,4]oxazine-8-carboxylate Synthesis according to Intermediate 52, step a, starting from 2-bromo-1-(3,4-dichlorophenyl)ethan-1-one and tert-butyl (S)-3-(hydroxymethyl)piperazine-1-carboxylate. MS (ESI): m/z=403.3 $[M+H]^+$.

Intermediate 51b (3R,9aS)-3-(3,4-dichlorophenyl)-1,3,4,6,7,8,9,9a-octahydropyrazino[2,1-c][1,4]oxazine Synthesis according to Intermediate 53, starting from tert-butyl (3R,9aS)-3-(3,4-dichlorophenyl)-3-hydroxy-1,4,6,7,9,9a-hexahydropyrazino[2,1-c][1,4]oxazine-8-carboxylate (product of step a, Intermediate 51a). MS (ESI): m/z=287.2 $[M+H]^+$.

Intermediate 52

(2-chloro-3-(4,4,5,5-tetramethyl-1,3,2-dioxaborolan-2-yl)phenyl)((3R,9aS)-3-(3-chloro-4-fluorophenyl)-3-hydroxyhexahydropyrazino[2,1-c][1,4]oxazin-8(1H)-yl)methanone Bis(pinacolato)diboron (327 mg, 1.29 mmol), [(3R,9aS)-3-(3-chloro-4-fluoro-phenyl)-3-hydroxy-1,4,6,7,9,9a-hexahydropyrazino[2,1-c][1,4]oxazin-8-yl]-(3-bromo-2-chloro-phenyl)methanone (0.500 g, 992 μmol) and potassium acetate (292 mg, 2.98 mmol) were dispersed in Dioxane (4 ml) and degassed. 1,1'-bis(diphenylphosphino)ferrocene-palladium(II)dichloride complex (121 mg, 149 μmol) was then added. It was reacted in the microwave (30 min, 100° C.). It was then extracted with EtOAc and water. The combined organic layers were combined, washed with brine, dried over sodium sulfate and concentrated in vacuo. The crude material was purified by silica column chromatography (EtOAc/Hept 0% to 80%). The product was obtained as a brown oil (234 mg, ca. 72% purity, 42% yield) and used without further purification for the next step. MS (ESI): m/z=551.3 $[M-H]^-$.

a) tert-butyl (3R,9aS)-3-(3-chloro-4-fluoro-phenyl)-3-hydroxy-1,4,6,7,9,9a-hexahydropyrazino[2,1-c][1,4]oxazine-8-carboxylate tert-butyl (S)-3-(hydroxymethyl)piperazine-1-carboxylate (1 eq, 1.52 g) and Hunig's base (1.3 eq, 1.6 mL) were dissolved in 25 mL THF. 2-bromo-1-(3-chloro-4-fluorophenyl)ethan-1-one (1 eq, 1.77 g) in 5 mL THF was added dropwise at 0° C. over 10 min. The reaction mixture was stirred at room temperature for 20 hours. The crude was then filtered, and the yellow mother liquor solution was concentrated in vacuo and purified by silica column chromatography (EtOAc/Hept 0% to 70%). The product was isolated as a light yellow foam (2.3 g, 85%). ESI (MS): m/z=387.1 $[M+H]^+$ b) (3R,9aS)-3-(3-chloro-4-fluoro-phenyl)-4,6,7,8,9,9a-hexahydro-1H-pyrazino[2,1-c][1,4]oxazin-3-ol tert-butyl (3R,9aS)-3-(3-chloro-4-fluoro-phenyl)-3-hydroxy-1,4,6,7,9,9a-hexahydropyrazino[2,1-c][1,4]oxazine-8-carboxylate (2.3 g, 5.95 mmol) was mixed with HCl 4M in dioxane (29.7 ml, 119 mmol) and Dioxane (10 ml) and stirred at room temperature for 2.5 hours. The mixture was then diluted in EtOAc, basified with 4 M NaOH and extracted twice with EtOAc. The organic layers were combined, dried over sodium sulfate, filtered and concentrated in vacuo. The product was obtained as light yellow foam (1.7 g, ca. 80% purity, 99% yield) and used without further purification for the next step. MS (ESI): m/z=287.1 $[M+H]^+$ c) [(3R,9aS)-3-(3-chloro-4-fluoro-phenyl)-3-hydroxy-1,4,6,7,9,9a-hexahydropyrazino[2,1-c][1,4]oxazin-8-yl]-(3-bromo-2-chloro-phenyl)methanone (3R,9aS)-3-(3-chloro-4-fluoro-phenyl)-4,6,7,8,9,9a-hexahydro-1H-pyrazino[2,1-c][1,4]oxazin-3-ol (1 g, 3.49 mmol), 3-bromo-2-chlorobenzoic acid (985 mg, 4.19 mmol) and HATU (1.59 g, 4.19 mmol) were combined with DMF (20 ml). Hunig's base (1.35 g, 1.83 ml, 10.5 mmol) was added and the reaction mixture was stirred at RT for 1 hour. It was then extracted with water and EtOAc. The organic layers were combined, washed with brine, dried over sodium sulfate and concentrated in vacuo. The crude material was purified by silica column chromatography (EtOAc/Hept 0% to 100%). The product was isolated as a yellow oil (1.48 g, 84%). ESI (MS): m/z=505.1 $[M+H]^+$ Intermediate 53

(3R,9aS)-3-(4-bromo-3-chlorophenyl)octahydropyrazino[2,1-c][1,4]oxazine tert-butyl (3R,9aS)-3-(4-bromo-3-chloro-phenyl)-3-hydroxy-1,4,6,7,9,9a-hexahydropyrazino[2,1-c][1,4]oxazine-8-carboxylate (0.959 g, 2.14 mmol) was mixed with triethylsilane (747 mg, 1.03 ml, 6.43 mmol) and DCM (11 ml). Trifluoroacetic acid (7.33 g, 4.92 ml, 64.3 mmol) was added and the solution heated to 45° C. for 2 hours. The crude yellow solution was concentrated in vacuo, mixed with water/1 M HCl and washed with diethyl ether. The organic phase was backextracted with 0.5 M HCl twice. The combined aqueous phases were then basified with 4 M NaOH, supplemented with NaCl and extracted into EtOAc twice. The organic phase was dried over sodium sulfate, filtered and concentrated in vacuo to result in an yellow oil (0.643 g, 91%). The diastereomeric ratio is ca. eq/ax 8:1 as estimated by NMR. ESI (MS): m/z=333.2 $[M+H]^+$ a) tert-butyl (3R,9aS)-3-(4-bromo-3-chloro-phenyl)-3-hydroxy-1,4,6,7,9,9a-hexahydropyrazino[2,1-c][1,4]oxazine-8-carboxylate Synthesis according to Intermediate 52, step a, starting from 2-bromo-1-(4-bromo-3-chlorophenyl)ethan-1-one and tert-butyl (S)-3-(hydroxymethyl)piperazine-1-carboxylate. MS (ESI): m/z=449.2 $[M+H]^+$ Intermediate 54

2-chloro-3-(3-oxopiperazin-1-yl)benzoic acid

To a solution of methyl 2-chloro-3-(3-oxopiperazin-1-yl) benzoate (0.175 g, 651 μmol) in THF (2 ml) was added LiOH 1M in H2O (1.95 ml, 1.95 mmol) and the resulting mixture was stirred at RT for 3 hours. The reaction mixture was poured into 1M HCl and extracted twice with EtOAc. The organic layers were combined, washed with brine, dried over sodium sulfate and concentrated in vacuo. The product was obtained as a light yellow oil (100 mg, ca. 72% purity, 60% yield) and used without further purification for the next step. MS (ESI): m/z=255.05 $[M+H]^+$ a) methyl 2-chloro-3-(3-oxopiperazin-1-yl)benzoate A solution of methyl 3-bromo-2-chlorobenzoate (0.600 g, 2.4 mmol), piperazin-2-one (265 mg, 2.65 mmol), cesium carbonate (1.57 g, 4.81 mmol) in Dioxane (15 ml) was degassed with argon. $Pd(OAc)_2$ (54 mg, 240 μmol) and xantphos (139 mg, 240 μmol) were added, reaction degassed once more and the reaction was stirred at 90° C. overnight. The reaction was filtered on decalite and concenrated in vacuo. The yellow oil was then dissolved in EtOAc and extracted with water. Organic layer was washed with brine, dried over sodium sulfate and concentrated in vacuo. The crude material was purified by Si-Amine column chromatography (MeOH/DCM 0% to 10%). The product was isolated as a yellow oil (175 mg, 27%). ESI (MS): m/z=269.2 $[M+H]^+$ Intermediate 55

2-chloro-3-(5-cyano-1H-pyrrol-3-yl)benzoic acid

Saponification according to Intermediate 54, starting from methyl 2-chloro-3-(5-cyano-1H-pyrrol-3-yl)benzoate. MS (ESI): m/z=245.1 $[M-H]^-$ a) methyl 2-chloro-3-(4,4,5,5-tetramethyl-1,3,2-dioxaborolan-2-yl)benzoate Borylation according to Intermediate 52, starting from methyl 3-bromo-2-chlorobenzoate. MS (ESI): m/z=297.2 $[M+H]^+$ b) methyl 2-chloro-3-(5-cyano-1H-pyrrol-3-yl)benzoate methyl 2-chloro-3-(4,4,5,5-tetramethyl-1,3,2-dioxaborolan-2-yl)benzoate (0.203 g, 685 μmol), 4-bromo-1H-pyrrole-2-carbonitrile (129 mg, 753 μmol), potassium carbonate (284 mg, 2.05 mmol) were combined with Dioxane (5 ml) and Water (850 μl). The reaction mixture was degassed and Bis(di-tert-butyl(4-dimethylaminophenyl)phosphine) dichloropalladium(II) (48.5 mg, 68.5 μmol) was added. The reaction mixture was heated at 80° C. for 2 hours, and then extracted with saturated $NaHCO_3$ solution/EtOAc. The organic layer was washed with brine, dried over sodium sulfate and concentrated in vacuo. The crude material was purified by silica column chromatography (MeOH/DCM 0% to 10%). The product was isolated as a yellow oil (177 mg, 99%). ESI (MS): m/z=259.1 $[M-H]^-$ Intermediate 56

2-chloro-3-(2-cyano-1H-imidazol-5-yl)benzoic acid

Saponification according to Intermediate 54, starting from methyl 2-chloro-3-(2-cyano-1H-imidazol-5-yl)benzoate. MS (ESI): m/z=248.1 $[M+H]^+$ a) methyl 2-chloro-3-(4,4,5,5-tetramethyl-1,3,2-dioxaborolan-2-yl)benzoate Borylation according to Intermediate 52, starting from methyl 3-bromo-2-chlorobenzoate. MS (ESI): m/z=297.2 $[M+H]^+$ b) methyl 2-chloro-3-(2-cyano-1H-imidazol-5-yl) benzoate Cross coupling according to Intermediate 55, step b, starting from methyl 2-chloro-3-(4,4,5,5-tetramethyl-1,3,2- dioxaborolan-2-yl)benzoate and 5-bromo-1H-imidazole-2-carbonitrile. MS (ESI): m/z=262.1 $[M+H]^+$ Intermediate 57

2-chloro-3-(2-oxo-3H-1,3,4-oxadiazol-5-yl)benzoic acid 5-(3-bromo-2-chloro-phenyl)-3H-1,3,4-oxadiazol-2-one (1 eq, 138 mg) was dissolved in 3 mL dry THF at 0° C. upon which isopropyl magnesium chloride LiCl complex (1.1 eq, 425 uL of a 1.3 M solution in THF) was added dropwise upon which the solution turned orange and then dark red. After the addition, the mixture was allowed to warm up to RT. The transmetallation was monitored by LCMS. After 20 min, ca. 30% transmetallation was observed which did not change 40 min later, so another 400 uL isopropyl magnesium chloride LiCl complex was added upon which precipitation formed. 20 min later, LCMS confirmed complete transmetallation.

Through the suspension, gaseous $CO_2$ was bubbled via a balloon, and after 5 min 5 mL more dry THF was added to the flask to ensure good bubbling and stirring. It was diluted with 1 N NaOH and washed with EtOAc twice. The aq. phase was acidified with 1 M HCl, a bit of NaCl was added and then extracted into EtOAc twice. The organic phase was dried over sodium sulfate, filtered and concentrated in vacuo. The product was obtained as an off-white solid (68 mg). MS (ESI): m/z=241.1 $[M+H]^+$ a) 3-bromo-2-chloro-benzohydrazide methyl 3-bromo-2-chlorobenzoate (1 eq, 500 mg) and hydrazine hydrate (5 eq, 490 uL) were dissolved in 15 mL EtOH and heated to 80° C. for 2.5 days. It was then concentrated in vacuo and purified by silica column chromatography (50 g, EtOAc in n-heptane 40% to 100%). The product was isolated as a white solid (315 mg, 63%). MS (ESI): m/z=251.0 $[M+H]^+$ 5-(3-bromo-2-chloro-phenyl)-3H-1,3,4-oxadiazol-2-one 3-bromo-2-chlorobenzohydrazide (1 eq, 271 mg) and TEA (1.4 eq, 212 uL) were dispersed in 4 mL dry THF at 0° C. and then Carbonyldiimidazole (1.1 eq, 194 mg) in 2 mL dry THF was added dropwise and the mixture slowly warmed to RT upon which a clear yellow solution formed. Even though the reaction had not gone to full completion, it was diluted with EtOAc and washed with 1 M HCl, sat. bicarbonate solution and then brine before it was dried over sodium sulfate, filtered and concentrated in vacuo to result in a shiny crystalline white solid (236 mg, 79%). MS (ESI): m/z=274.9 $[M-H]^-$ Intermediate 58

2-chloro-3-(2-oxo-2,3-dihydrooxazol-5-yl)benzoic acid 5-(3-bromo-2-chloro-phenyl)-3H-oxazol-2-one (1 eq, 71 mg) was dissolved in 1.2 mL dry THF with the aid of sonication and cooled to 0° C. Isopropyl magnesium chloride LiCl complex (1.3 eq, 233 uL of a 1.3 M solution in THF) was slowly added upon which the mixture turned dark. 15 min later, it was slowly warmed to RT. An orange-red mixture had formed. 30 min after the addition, 8% transmetallation was observed and another 120 uL isopropyl magnesium chloride LiCl complex was added at 0° C. and the mixture then warmed up to RT. 30 min later, ca. 50% transmetallation was observed. Even though the transmetallation was not complete gaseous $CO_2$ (1 balloon) was bubbled trough at ca. 10° C. Another 2 mL dry THF were added and another balloon $CO_2$ was bubbled through at RT in the sonicator. A yellowish suspension formed, it was diluted with ca. 0.5 M NaOH and washed with diethyl ether twice. The aqueous phase was acidified with 1 M HCl and treated with NaCl and then extracted into EtOAc twice. The combined organic phases were dried over sodium sulfate, filtered and concentrated in vacuo. The impure product was obtained as an orange solid (61 mg). MS (ESI): m/z=238.1 $[M-H]^-$ a) 2-bromo-1-(3-bromo-2-chloro-phenyl)ethanone 1-(3-bromo-2-chlorophenyl)ethan-1-one (1 eq, 340 mg), NBS (1.05 eq, 272 mg) and pTsOH monohydrate (0.11 eq, 30 mg) were mixed with 12 mL dry DCM and reacted in the microwave (90° C., 80 min) and then again (90° C., 40 min). The mixture was diluted with DCM and washed with sat. bicarbonate solution, water and then brine. The combined aq. phases were backextrated into DCM, the combined organic layers dried over sodium sulfate, filtered and concentrated in vacuo to result in a crude yellow oil (460 mg). It was purified by silica column chromatography (50 g, EtOAc in Hept 0-30%). The target was obtained as a yellow oil (429 mg, ca. 80% pure, 75% yield). Confirmed by $^1$H-NMR.

b) 3-(2-(3-bromo-2-chloro-phenyl)-2-oxo-ethyl)thiazolidine-2,4-dione 2-bromo-1-(3-bromo-2-chloro-phenyl)ethanone (1 eq, 226 mg), thiazolidine-2,4-dione (1 eq, 68 mg), postassium carbonate (1.05 eq, 84 mg) and TBAI (0.1 eq, 21 mg) were mixed with 3 mL DMF and the yellow solution stirred at RT. After 20 min, the mixture had turned slightly orange and after 1 h, an orange suspension had formed. After 70 min, the mixture was diluted with EtOAc and washed with ice water (2×) and then brine, dried over sodium sulfate, filtered and concentrated in vacuo to give the desired compound as a red solid (249 mg, ca. 100%). MS (ESI): m/z=346.1 $[M-H]^-$ c) 5-(3-bromo-2-chloro-phenyl)-3H-oxazol-2-one 3-(2-(3-bromo-2-chloro-phenyl)-2-oxo-ethyl)thiazolidine-2,4-dione (1 eq, 248 mg of ca. 80% purity) and triethylamine (2.5 eq, 200 uL) were mixed with 2.8 mL EtOH in a pressure vial and heated to 80° C. in a sandbath. After a reaction time of 15 h, 70% conversion was observed (UV). The reaction mixture was diluted with EtOAc and washed with half-saturated ammonium chloride solution and then brine, dried over sodium sulfate, filtered and concentrated in vacuo to a red/white solid (241 mg). The residuewas adsorbed on silica and purified by silica column chromatography (20 g, EtOAc in n-heptane 20% to 60%). The product was isolated as an white solid with also some red parts (123 mg, ca. 90% purity, 71% yield). MS (ESI): m/z=274.0 $[M+H]^+$ Intermediate 59

2-chloro-3-(6-methyl-2-oxo-1,2-dihydropyridin-4-yl)benzoic acid

Saponification according to Intermediate 54, starting from methyl 2-chloro-3-(2-methyl-6-oxo-1H-pyridin-4-yl)benzoate. MS (ESI): m/z=264.2 $[M+H]^+$ a) methyl 2-chloro-3-(4,4,5,5-tetramethyl-1,3,2-dioxaborolan-2-yl)benzoate In a microwave vial, 4,4,4',4',5,5,5',5'-octamethyl-2,2'-bi(1,3,2-dioxaborolane) (1.3 eq, 1.32 g), methyl 3-bromo-2-chlorobenzoate (1 eq, 1 g), $PdCl_2$(DPPF) (0.1 eq, 327 mg) and potassium acetate (3 eq, 1.18 g) were dispersed in 17 mL dioxane and degassed. It was reacted in the microwave (80° C., 25 min. The mixture was filtered into an extraction funnel, washed with water and and then brine, backextracted in some EtOAc, dried over sodium sulfate, filtered, adsorbed on silica and concentrated in vacuo. It was purified by silica column chromatography (70 g, EtOAc in n-heptane 0% to 10%). The product was isolated together with tetramethyloxirane as a white solid (1.41 g, impure, 36% yield). MS (ESI): m/z=297.2 $[M+H]^+$ b) methyl 2-chloro-3-(2-methyl-6-oxo-1H-pyridin-4-yl)benzoate 4-bromo-6-methylpyridin-2(1H)-one (1 eq, 125 mg), methyl 2-chloro-3-(4,4,5,5-tetramethyl-1,3,2-dioxaborolan-2-yl)benzoate (1.1 eq, 361 mg of ca. 60% purity), (APhos)$_2PdCl_2$ (0.1 eq, 47 mg) and potassium carbonate (3 eq, 276 mg) were mixed with 3 mL dioxane and 1 mL water and degassed with argon. The mixture was then reacted in the microwave (115° C., 30 min) and then diluted with EtOAc and washed with brine. The aqueous phase was backextracted an the combined organic phases were dried over sodium sulfate, filtered and concentrated in vacuo. The crude was purified by silica column chromatography (20 g, MeOH in DCM 0% to 10%). The product was isolated as a a green-white solid (206 mg, 112%, impurities). MS (ESI): m/z=278.2 $[M+H]^+$ Intermediate 60

2-chloro-3-(2-methyl-6-oxo-1,6-dihydropyridin-3-yl)benzoic acid methyl 2-chloro-3-(6-methoxy-2-methyl-3-pyridyl)benzoate (1 eq, 106 mg) was mixed with 4 mL 7.6 M aq. HCl and the colorless mixture heated to 120° C. in a pressure vial and sandbath. After 22 h, complete monodemethylation and partial dimethylation was observed. After 30 h, the reaction was at ca. 80% conversion (UV), cooled down to RT, the flasks rinsed with some water/MeCN and the solvents evaporated with the aid of toluene to an off-white solid (56 mg, 58%) MS (ESI): m/z=264.1 $[M+H]^+$ a) methyl 2-chloro-3-(6-methoxy-2-methyl-3-pyridyl)benzoate methyl 2-chloro-3-(4,4,5,5-tetramethyl-1,3,2-dioxaborolan-2-yl)benzoate (1 eq, 232 mg of ca. 60% purity), 3-bromo-6-methoxy-2-methylpyridine (1.35 eq, 128 mg), Pd dppf DCM complex (0.1 eq, 38 mg) and potassium carbonate (3 eq, 195 mg) were suspended in 3 mL dioxane and 1 mL water, degassed with argon and reacted in the microwave (115° C., 30 min). Colling to RT the mixture was diluted with EtOAc and washed with brine. The organic phase was dried over sodium sulfate, filtered and concentrated in vacuo. The crude was then purified by silica column chromatography (20 g, EtOAc in n-heptane 0% to 50%). The product eluted at ca. 25% EtOAc partly together with impurities and was isolated as a light yellow oil (119 mg, 71% yield combined). MS (ESI): m/z=292.2 $[M+H]^+$ Intermediate 61

2-chloro-3-(4-oxo-1H-pyridazin-5-yl)benzoic acid

The crude 3-(5-benzyloxypyridazin-4-yl)-2-chloro-benzoic acid (1 eq, 45 mg) was dissolved in 2.5 mL MeOH in a 25 mL flask. The flask was purged with argon/vacuum three times. Palladium on carbon (0.1 eq, 14 mg) was added and the flask purged with argon three times again. A hydrogen balloon was added and purged three times and then stirred at RT. After 100 min, ca. 60% (by LC-UV) conversion was visible. The next morning it was filtered over celite and concentrated in vacuo to yield a green crude solid (40 mg), which was used without puriication for the next step. MS (ESI): m/z=251.1 $[M+H]^+$ a) 4-benzyloxy-5-chloro-pyridazine Work in dark. In an aluminium foil wrapped flask, 5-chloropyridazin-4(1H)-one (1 eq, 300 mg), benzyl bromide (1.2 eq, 330 uL) and silver carbonate (1.2 eq, 760 mg) were dispersed in 5 mL dry toluene and heated to 85° C. for 30 min and then to 50° C. for 1 h. It was then diluted with half-saturated brine and extracted into EtOAc three times. The combined organic phases were dried over sodium sulfate, filtered and concentrated in vacuo. It was purified by silica column chromatography (50 g, EtOAc in n-heptane 30% to 100%). The product was obtained as yellow solid (85 mg, 17%). MS (ESI): m/z=221.1 $[M+H]^+$ b) methyl 3-(5-benzyloxypyridazin-4-yl)-2-chloro-benzoate methyl 2-chloro-3-(4,4,5,5-tetramethyl-1,3,2-dioxaborolan-2-yl)benzoate (1.05 eq, 122 mg of ca. 60% purity), 4-benzyloxy-5-chloro-pyridazine (1 eq, 52 mg), 1,1'-bis(diphenylphosphino)ferrocene-palladium(II)dichloride dichloromethane complex (0.1 eq, 19 mg) and potassium carbonate (3 eq, 98 mg) were mixed with 2.4 mL dioxane and 0.8 mL water, degassed and reacted in the microwave (115° C., 30 min). It was purified by silica column chromatography (20 g, EtOAc in n-heptane 0% to 80%). The product was obtained as an orange oil (47 mg, 34%). MS (ESI): m/z=355.1 $[M+H]^+$ c) 3-(5-benzyloxypyridazin-4-yl)-2-chloro-benzoic acid methyl 3-(5-benzyloxypyridazin-4-yl)-2-chloro-benzoate (1 eq, 47 mg) was mixed with 1.5 mL 7.6 M aq. HCl and heated to 120° C. in a sandbath and pressure vial for 16 h. Cooloing to RT and acetonitrile was added to give a homogenous solution and LCMS showed full ester hydrolysis. It was concentrated in vacuo to a yellow/orange oil and was used in the next step without further purification (45 mg, 100%). MS (ESI): m/z=341.1 $[M+H]^+$ Intermediate 62

2-chloro-3-(5-cyano-1H-pyrazol-3-yl)benzoic acid

Saponification according to Intermediate 54, starting from methyl 2-chloro-3-(5-cyano-1H-pyrazol-3-yl)benzoate. MS (ESI): m/z=248.1 $[M+H]^+$ a) 5-bromo-1H-pyrazole-3-carboxamide methyl 5-bromo-1H-pyrazole-3-carboxylate (1 eq, 140 mg) was dissolved in 3 mL MeOH. Aq. ammonium hydroxide solution (10 eq, 1 ml of a 25% solution) was added and the solution heated to 60° C. After 40 min, ca. 20% re-esterification to the methyl ester but no amide bond formation was visible. After 1 h, the temperature was raised to 80° C. 18 h later, it was concentrated in vacuo to remove excess ammonia. A white solid was obtained (120 mg, 100%). MS (ESI): m/z=251.1 $[M+H]^+$ b) 5-bromo-1H-pyrazole-3-carbonitrile 5-bromo-1H-pyrazole-3-carboxamide (crude, 1 eq, 120 mg) was dissolved in 3.5 ml pyridine and cooled to 0° C. Trifluoroacetic anhydride (4 eq, 360 uL) was added dropwise. White smoke emerged immediately. 40 min later, it was diluted with EtOAc, washed with sat. aq. bicarbonate solution twice and then 1 M HCl twice, dried over sodium sulfate and concentrated in vacuo to a light brown solid (121 mg). It was purified by silica column chromatography (10 g, EtOAc in n-heptane 0% to 50%). The product was obtained as a white solid (56 mg, 51%) MS (ESI): m/z=172.0 $[M+H]^+$ c) methyl 2-chloro-3-(5-cyano-1H-pyrazol-3-yl) benzoate 5-bromo-1H-pyrazole-3-carbonitrile (1 eq, 56 mg), methyl 2-chloro-3-(4,4,5,5-tetramethyl-1,3,2-dioxaborolan-2-yl)benzoate (1.3 eq, 209 mg of ca. 60% purity), 1,1'-bis (diphenylphosphino)ferrocene-palladium(II)dichloride dichloromethane complex (0.1 eq, 26 mg) and potassium carbonate (3 eq, 135 mg) were mixed with 1.8 ml dioxane and 600 ul water, degassed and reacted in the microwave (30 min, 115° C.). Another 40 mg (0.3 eq) of methyl 2-chloro-3-(4,4,5,5-tetramethyl-1,3,2-dioxaborolan-2-yl)benzoate and a pinch of Pd cat was added, degassed and reacted again (120° C., 30 min). The reaction was cooled to RT and diluted with EtOAc, washed with water and then brine, dried over sodium sulfate, filtered and concentrated in vacuo. It was then purified by silica column chromatography (10 g, EtOAc in n-heptane 0% to 50%). The product was isolated as an orange/yellow oil (24 mg, 28%). MS (ESI): m/z=262.2 $[M+H]^+$ Intermediate 63

3-((3R,9aS)-octahydropyrazino[2,1-c][1,4]oxazin-3-yl)-6-(trifluoromethyl)pyridin-2(1H)-one hydrobromide tert-butyl (3R,9aS)-3-(2-methoxy-6-(trifluoromethyl) pyridin-3-yl)hexahydropyrazino[2,1-c][1,4]oxazine-8(1H)-carboxylate (0.160 g, 383 µmol) was dissolved in AcOH (1.92 ml) and 33% HBr in AcOH (7 mL) was added. The reaction mixture was stirred at 100° C. for 2 hrs. Then it was concentrated under vaccum and co-evaporated twice with toluene. No further purification, product was obtained as a brown powder (182 mg, crude, 100%). MS (ESI): m/z=304.1 $[M+H]^+$ a) 2-methoxy-6-(trifluoromethyl)-3-vinylpyridine 3-bromo-2-methoxy-6-(trifluoromethyl)pyridine (1 g, 3.91 mmol), potassium trifluoro(vinyl)borate (628 mg, 4.69 mmol), 1,1'-bis(diphenylphosphino)ferrocene-palladium(II) dichloride dichloromethane complex (159 mg, 195 µmol) and triethylamine (395 mg, 544 µl, 3.91 mmol) were dispersed in degassed Ethanol (29.4 ml). The reaction mixture was then heated up to 130° C. for 1 hour in a scealed tube. It was then concentrated in vacuo, diluted with EtOAc, washed with water, dried over sodium sulfate, filtered, adsorbed on silica and concentrated in vacuo. It was purified by silica column chromatography (50 g, EA in Hept 0% to 15%). Product obtained as a colourless oil, 610 mg, 77%. MS (ESI): m/z=204.0 $[M+H]^+$ b) 2-methoxy-3-(oxiran-2-yl)-6-(trifluoromethyl) pyridine 2-methoxy-6-(trifluoromethyl)-3-vinylpyridine (0.61 g, 3 mmol) was dispersed in 70 mL water and 70 mL dioxane. 1-bromopyrrolidine-2,5-dione (641 mg, 3.6 mmol) in 70 mL water and 70 mL dioxane was added dropwise. It was stirred at RT for 7 hours. According to LCMS all starting material was consumed and bromohydrin was formed. The reaction mixture was cooled down to 0° C. and 4 M NaOH solution (2.25 ml) was added dropwise. The ice-bath was removed and the RM was stirred overnight at RT. LC-MS showed complete reaction and formation of desired product. It was mixed with sat. bicarbonate solution and extracted into EtOAc twice. The combined org. phases were washed with water, brine and then dried over sodium sulfate, filtered and concentrated in vacuo. Product obtained as a colourless oil, 620 mg, 94%. $^1$H-NMR complies.

c) tert-butyl (3S)-4-(2-hydroxy-2-(2-methoxy-6-(trifluoromethyl)pyridin-3-yl)ethyl)-3-(hydroxymethyl)piperazine-1-carboxylate 2-methoxy-3-(oxiran-2-yl)-6-(trifluoromethyl)pyridine (0.62 g, 2.83 mmol) and tert-butyl (S)-3-(hydroxymethyl) piperazine-1-carboxylate (673 mg, 3.11 mmol) were dissolved in ethanol (10.7 ml) and tetrahydrofuran (10.7 ml) and heated up to 130° C. overnight in a scealed tube. It was then concentrated in vacuo and purified by silica column chromatography (20 g, MeOH in DCM 0% to 5%). Product obtained as a colourless oil, 750 mg, 61%. MS (ESI): m/z=436.2 $[M+H]^+$ d) tert-butyl (3R,9aS)-3-(2-methoxy-6-(trifluoromethyl)pyridin-3-yl)hexahydropyrazino[2,1-c][1,4] oxazine-8(1H)-carboxylate tert-butyl (3S)-4-(2-hydroxy-2-(2-methoxy-6-(trifluoromethyl)pyridin-3-yl)ethyl)-3-(hydroxymethyl)piperazine-1-carboxylate (0.75 g, 1.72 mmol) was dissolved in dry toluene (12.5 ml). 2-(tributyl-15-phosphaneylidene)acetonitrile (831 mg, 904 µl, 3.44 mmol) in dry Toluene (12.5 ml) was added and the mixture heated up to 105° C. Toluene was evaporated and the residue was purified by silica column chromatography (20 g, EA in Hept 0% to 50%). The first eluting diastereomer (less polar) was isolated and is expected to be the more active conformation and was used in the next steps. Product was obtained as a dark brown oil, 160 mg, 22%. MS (ESI): m/z=418.2 [M+H]$^+$ Intermediate 64

2-chloro-3-(5-cyano-1H-pyrrol-3-yl)-5-fluorobenzoic acid

To a solution of methyl 2-chloro-3-(5-cyano-1H-pyrrol-3-yl)-5-fluorobenzoate (1.2 g, 4.31 mmol) in THF (21.5 ml) was added aq solution of lithium hydroxide 0.5M (11.2 ml, 5.6 mmol) dropwise and the reaction was heated up to 70° C. for 2 hrs. The solvent was removed under vacuum and the residue was acidified with HCl 1 M (pH=2). It was then extracted twice with EtOAc, dried, filtered and concentrated under vacuum to get the desired product as a orange solid. MS (ESI): m/z=263.0 [M+H]$^+$ a) methyl 2-chloro-5-fluoro-3-(4,4,5,5-tetramethyl-1,3,2-dioxaborolan-2-yl)benzoate In a MW vial, methyl 3-bromo-2-chloro-5-fluorobenzoate (4.0 g, 15 mmol), 4,4,4',4',5,5,5',5'-octamethyl-2,2'-bi(1,3,2-dioxaborolane) (4.56 g, 17.9 mmol and potassium acetate (4.4 g, 44.9 mmol) were dispersed in dioxane (59.6 ml) and degassed. 1,1'-bis(diphenylphosphino)ferrocene-palladium (II)dichloride dichloromethane complex (1.83 g, 2.24 mmol) was then added. The red suspension was reacted in the heating plate (105° C., 2 hrs). The crude material was purified by flash chromatography (silica gel, 50 g, 0% to 20% EtOAc in heptane in 40 min). Product obtained as white solid, 3.52 g, 75%. $^1$H-NMR complies.

b) methyl 2-chloro-3-(5-cyano-1H-pyrrol-3-yl)-5-fluorobenzoate methyl 2-chloro-5-fluoro-3-(4,4,5,5-tetramethyl-1,3,2-dioxaborolan-2-yl)benzoate (3.5 g, 9.12 mmol), 4-bromo-1H-pyrrole-2-carbonitrile (1.72 g, 10 mmol), $(APhos)_2PdCl2$ (646 mg, 912 μmol) and $K_2CO_3$ (3.78 g, 27.4 mmol) were dispersed in dioxane (50.8 ml) and Water (9.24 ml) and degassed with argon. It was then heated at 80° C. for 2 hrs. The mixture was poured into sat. $NaHCO_3$ and extracted with EtOAc twice. The organic layers were combined, washed with brine, dried over $Na_2SO_4$ and concentrated in vacuo. The crude orange oil was purified by silica gel chromatographie (20 g, DCM/MeOH 0 to 10% in 30 min). Product was obtained as a yellow solid, 1.2 g, 47%. MS (ESI): m/z=277.1 [M−H]$^-$ Intermediate 65

2-chloro-5-fluoro-3-(3-fluoro-1H-pyrazol-4-yl)benzoic acid

Saponification was carried out as described for intermediate 64, starting from methyl 2-chloro-5-fluoro-3-(3-fluoro-1H-pyrazol-4-yl)benzoate (80 mg, 293 umol). Product obtained as white solid, 20 mg, 26%. MS (ESI): m/z=259.1 [M+H]$^+$ a) methyl 2-chloro-5-fluoro-3-(3-fluoro-1H-pyrazol-4-yl)benzoate methyl 2-chloro-5-fluoro-3-(4,4,5,5-tetramethyl-1,3,2-dioxaborolan-2-yl)benzoate (732 mg, 2.33 mmol), 4-bromo-3-fluoro-1H-pyrazole (320 mg, 1.94 mmol), $(APhos)_2PdCl_2$ (137 mg, 194 μmol) and $K_2CO_3$ (804 mg, 5.82 mmol) were dispersed in dioxane (9.57 ml) and Water (3.19 ml) and degassed with argon.(yellow suspension). It was then heated at 60° C. for 30 min and at 110° C. for 3 hours. The mixture was poured into sat. $NaHCO_3$ and extracted with EtOAc twice. The organic layers were combined, washed with brine, dried over $Na_2SO_4$ and concentrated in vacuo. The crude yellow oil was purified by silica gel chromatography (n-heptane and EtOAc 0 to 70% in 40 min) to get the desired product as a light yellow oil (80 mg, 15%). MS (ESI): m/z=273.1 [M+H]$^+$ Intermediate 66

3-chloro-2-fluoro-5-((3R,9aS)-octahydropyrazino[2,1-c][1,4]oxazin-3-yl)benzonitrile trifluoroacetate tert-butyl (3R,9aS)-3-(3-chloro-5-cyano-4-fluorophenyl)hexahydropyrazino[2,1-c][1,4]oxazine-8(1H)-carboxylate (0.160 g, 404 μmol) was dissolved in DCM (8.79 ml). Trifluoroacetic acid (1.38 g, 928 μl, 12.1 mmol) was added and the orange solution stirred at RT. The mixture was concentrated in vacuo, redissolved in toluene and concentrated in vacuo again to obtain an orange oil. The crude was used in the next step without further purification. (200 mg, 100%). MS (ESI): m/z=290.2 [M+H]$^+$ a) tert-butyl (3S)-4-(2-(3-chloro-5-cyano-4-fluorophenyl)-2-hydroxyethyl)-3-(hydroxymethyl)piperazine-1-carboxylate 3-chloro-2-fluoro-5-(oxiran-2-yl)benzonitrile (1.3 g, 6.58 mmol) and tert-butyl (S)-3-(hydroxymethyl)piperazine-1-carboxylate (1.57 g, 7.24 mmol) were dissolved in EtOH (15 ml) and THF (15 ml) and heated up to 130° C. overnight in a scealed tube. It was then concentrated in vacuo and purified by silica column chromatography (50 g, MeOH in DCM 0% to 5%). Product obtained as a yellow oil, 1.68 g, 62%. MS (ESI): m/z=414.3 [M+H]$^+$ b) tert-butyl (3R,9aS)-3-(3-chloro-5-cyano-4-fluorophenyl)hexahydropyrazino[2,1-c][1,4]oxazine-8(1H)-carboxylate tert-butyl (3S)-4-(2-(3-chloro-5-cyano-4-fluorophenyl)-2-hydroxyethyl)-3-(hydroxymethyl)piperazine-1-carboxylate (1.68 g, 4.06 mmol) was dissolved in dry toluene (29.4 ml). 2-(tributyl-15-phosphaneylidene)acetonitrile (1.96 g, 8.12 mmol) in dry Toluene (29.4 ml) was added dropwise and the mixture heated up to 110° C. overnight. Toluene was evaporated and the residue was purified by silica column chromatography (50 g, EA in Hept 0% to 50%). The 2 diastereomers came out as a single spot and were collected together. Product obtained as red oil (160 mg, 10%). MS (ESI): m/z=396.2 [M+H]$^+$ Intermediate 67

5-((3R,9aS)-octahydropyrazino[2,1-c][1,4]oxazin-3-yl)-2-(trifluoromethyl)pyridin-4(1H)-one hydrobromide tert-butyl (3R,9aS)-3-(4-methoxy-6-(trifluoromethyl)pyridin-3-yl)hexahydropyrazino[2,1-c][1,4]oxazine-8(1H)-carboxylate (0.674 g, 1.61 mmol) was dissolved in AcOH (8.07 ml) and 33% HBr in AcOH (28 mL) was added. The mixture was stirred at 100° C. for 3 hrs. Then it was concentrated under vacuum and co-evaporated twice with toluene. Used without any further purification, product obtained as a dark brown foam (1 g, crude, 100%). MS (ESI): m/z=304.1 $[M+H]^+$ a) 4-methoxy-2-(trifluoromethyl)-5-vinylpyridine 5-bromo-4-methoxy-2-(trifluoromethyl)pyridine (1.3 g, 5.08 mmol), potassium trifluoro(vinyl)borate (816 mg, 6.09 mmol), 1,1'-bis(diphenylphosphino)ferrocene-palladium(II) dichloride dichloromethane complex (207 mg, 254 μmol, Eq) and triethylamine (514 mg, 708 μl, 5.08 mmol) were dispersed in degassed Ethanol (38.2 ml). The reation mixture was then heated up to 130° C. for 1 hour in a sealed tube. It was then concentrated in vacuo, diluted with EtOAc, washed with water, dried over sodium sulfate, filtered, adsorbed on silica and concentrated in vacuo. It was purified by silica column chromatography (50 g, EA in Hept 0% to 15%). Product obtained as a light yellow oil (838 mg, 81%). MS (ESI): m/z=204.0 $[M+H]^+$ b) 4-methoxy-5-(oxiran-2-yl)-2-(trifluoromethyl) pyridine 4-methoxy-2-(trifluoromethyl)-5-vinylpyridine (0.838 g, 4.12 mmol) was dispersed in 8 mL water and 8 mL dioxane. 1-bromopyrrolidine-2,5-dione (881 mg, 4.95 mmol) in 8 mL water and 8 mL dioxane was added dropwise. It was stirred at RT for 4 hours (and then cooled down to 0° C. and 4 M NaOH solution was added dropwise. The ice-bath was removed, the mixture was stirred overnight at RT and mixed with sat. bicarbonate solution and extracted into EtOAc twice. The combined org. phases were washed with water, brine and then dried over sodium sulfate, filtered and concentrated in vacuo. It was purified by silica column chromatography (20 g, EA in Hept 0% to 50%). Product obtained as a colorless oil (554 mg, 61%). MS (ESI): m/z=220.1 $[M+H]^+$ c) tert-butyl (3S)-4-(2-hydroxy-2-(4-methoxy-6-(trifluoromethyl)pyridin-3-yl)ethyl)-3-(hydroxymethyl)piperazine-1-carboxylate 4-methoxy-5-(oxiran-2-yl)-2-(trifluoromethyl)pyridine (0.550 g, 2.51 mmol,) and tert-butyl (S)-3-(hydroxymethyl) piperazine-1-carboxylate (597 mg, 2.76 mmol) were dissolved in Ethanol (9.51 ml) and Tetrahydrofuran (9.51 ml)) and heated up to 130° C. overnight in a sealed tube. It was then concentrated in vacuo and purified by silica column chromatography (20 g, MeOH in DCM 0% to 5%). Product was obtained as a colorless oil (1.05 g, 96%). MS (ESI): m/z=436.3 $[M+H]^+$ d) tert-butyl (3R,9aS)-3-(4-methoxy-6-(trifluoromethyl)pyridin-3-yl)hexahydropyrazino[2,1-c][1,4] oxazine-8(1H)-carboxylate tert-butyl (3S)-4-(2-hydroxy-2-(4-methoxy-6-(trifluoromethyl)pyridin-3-yl)ethyl)-3-(hydroxymethyl)piperazine-1-carboxylate (1.05 g, 2.41 mmol) was dissolved in dry Toluene (17.5 ml). 2-(tributyl-15-phosphaneylidene)acetonitrile (1.16 g, 4.82 mmol) in dry Toluene (17.5 ml) was added and the mixture heated up to 100° C. Toluene was evaporated and the residue was purified by silica column chromatography (50 g, EA in Heptane 0% to 90%). Yield 734 mg, 73%, mixture of both diastereomers. MS (ESI): m/z=418.2 $[M+H]^+$ Intermediate 68

(3S,9aS)-3-(5-chloro-6-(trifluoromethyl)pyridin-2-yl)octahydropyrazino[2,1-c][1,4]oxazine trifluoroacetate Boc-deprotection as described for example 66, starting from tert-butyl (3S,9aS)-3-(5-chloro-6-(trifluoromethyl) pyridin-2-yl)hexahydropyrazino[2,1-c][1,4]oxazine-8(1H)-carboxylate (200 mg, 474 umol). Product was obtained as a orange oil (274 mg, crude, 100%). MS (ESI): m/z=322.1 $[M+H]^+$ a) 3-chloro-2-(trifluoromethyl)-6-vinylpyridine Vinylation as described for intermediate 67, step a, starting from 3,6-dichloro-2-(trifluoromethyl)pyridine (2 g, 9.26 mmol). Product was obtained as a colorless oil (1.28 g, 67%). MS (ESI): m/z=207.9 $[M+H]^+$ b) 3-chloro-6-(oxiran-2-yl)-2-(trifluoromethyl)pyridine Epoxidation as described for intermediate 67, step b, starting from 3-chloro-2-(trifluoromethyl)-6-vinylpyridine (1.28 g, 6.17 mmol). Product was obtained as a colorless oil (0.5 g, 36%). MS (ESI): m/z=224.2 $[M+H]^+$ c) tert-butyl (3S)-4-(2-(5-chloro-6-(trifluoromethyl) pyridin-2-yl)-2-hydroxyethyl)-3-(hydroxymethyl) piperazine-1-carboxylate Reaction of 3-chloro-6-(oxiran-2-yl)-2-(trifluoromethyl) pyridine (0.53 g, 2.37 mmol) and tert-butyl (S)-3-(hydroxymethyl)piperazine-1-carboxylate (564 mg, 2.61 mmol) as described for Intermediate 66, step a. Product was obtained as a light yellow oil (1.04 g, 99%). MS (ESI): m/z=440.3 $[M+H]^+$ d) tert-butyl (3S,9aS)-3-(5-chloro-6-(trifluoromethyl)pyridin-2-yl)hexahydropyrazino[2,1-c][1,4] oxazine-8(1H)-carboxylate Ring closure as described for Intermediate 66, step b, starting from tert-butyl (3S)-4-(2-(5-chloro-6-(trifluoromethyl)pyridin-2-yl)-2-hydroxyethyl)-3-(hydroxymethyl)piperazine-1-carboxylate (1.05 g, 2.39 mmol). Product was obtained as a red oil (200 mg, 20%). MS (ESI): m/z=422.3 $[M+H]^+$ Intermediate 69

2-chloro-3-(4-fluoro-1H-pyrazol-3-yl)benzoic acid

Saponification was carried out as described for intermediate 64, starting from methyl 2-chloro-3-(4-fluoro-1H-pyrazol-3-yl)benzoate (227 mg, 891 umol). Product obtained as yellow oil, 193 mg, 90%. MS (ESI): m/z=241.0 $[M+H]^+$ a) methyl 2-chloro-3-(4-fluoro-1H-pyrazol-3-yl) benzoate Cross coupling as described for intermediate 65, step a, starting from methyl 2-chloro-3-(4,4,5,5-tetramethyl-1,3,2-dioxaborolan-2-yl)benzoate (420 mg, 1.42 mmol) and 3-bromo-4-fluoro-1H-pyrazole (100 mg, 1.56 mmol). Product obtained as yellow oil, 227 mg, 63%. $^1$H-NMR complies.

Intermediate 70

2-bromo-1-(2-(6-methoxypyridin-3-yl)thiazol-4-yl) ethan-1-one

Intermediate 70 was synthesized starting from 6-Methoxypyridine-carbothioamide and 1,4-Dibromo-2,3-butanedione, The reactants were dissolved in DMF and 2,6-di-tert.butylpyridin was added. The mixture was stirred at room temperature before the product was isolated.

General Methods and Columns Used for Reversed Phase HPLC and SFC Purifications:

HPLC Prep Method A:

Gemini NX, 12 nm, 5 μm, 100×30 mm, 15 min run time, gradient 30-50-65-100 ACN in water+0.10% HCOOH HPLC Prep Method B:

Gemini NX, 12 nm, 5 μm, 100×30 mm, 15 min run time, gradient 20-40-55-100 ACN in water+0.10% HCOOH HPLC Prep Method C:

Gemini NX, 12 nm, 5 μm, 100×30 mm, 15 min run time, 40 ml/min, gradient 30-80 ACN in water+0.1% HCOOH HPLC Prep Method D:

YMC-Triart $C_{18}$, 12 nm, 5 μm, 100×30 mm, 15 min run time, gradient 20-40-60-100 ACN in water+0.10% HCOOH HPLC Prep Method E:

Gemini NX, 12 nm, 5 μm, 100×30 mm, 15 min run time, 40 ml/min, gradient 30-80 ACN in water+0.10% TEA HPLC Prep Method F:

YMC-Triart $C_{18}$, 12 nm, 5 μm, 100×30 mm, 11 min run time, gradient 30-50-65-100 ACN in water+0.1% HCOOH HPLC Prep Method G:

Gemini NX, 12 nm, 5 μm, 100×30 mm, 11 min run time, gradient 10-25-40-100 ACN in water+0.10% HCOOH HPLC Prep Method H:

Gemini NX, 12 nm, 5 μm, 100×30 mm, 11 min run time, gradient 15-35-50-100 ACN in water+0.1% HCOOH HPLC Prep Method J:

Gemini NX, 12 nm, 5 μm, 100×30 mm, 15 min run time, gradient 20-40-55-100 ACN in water+0.1% TEA HPLC Prep Method K:

YMC-Triart $C_{18}$, 12 nm, 5 μm, 100×30 mm, 11 min run time, gradient 20-98 ACN in water+0.1% TEA HPLC Prep Method L:

Gemini NX, 12 nm, 5 μm, 100×30 mm, 15 min run time, gradient 5-50-100 ACN in water+0.1% HCOOH SFC Method A ChiralPak IB, 12 nm, 5 μm, 250×4.6 mm, 25% MeOH SFC Method B ChiralPak AY-H, 12 nm, 5 μm, 250×4.6 mm, Gradient 30-40% EtOAC SFC Method C ChiralPak OD-H, 12 nm, 5 μm, 250×4.6 mm, 35% MeOH SFC Method D ChiralPak IC, 12 nm, 5 μm, 250×4.6 mm, 40% MeOH+0.2% Diethylamine SFC Method E ChiralPak AY-H, 12 nm, 5 μm, 250×4.6 mm, 25% MeOH Example 47

[3-(3-bicyclo[4.2.0]octa-1,3,5-trienyl)-3,4,6,7,9,9a-hexahydro-1H-pyrazino[2,1-c][1,4]oxazin-8-yl]-(2-chloro-3-methoxy-phenyl)methanone i) (2-chloro-3-methoxyphenyl)(3-(hydroxymethyl)piperazin-1-yl)methanone (Intermediate 1, 695 umol, 198 mg, dissolved in 2 mL MeOH) was added to 2-(3-bicyclo[4.2.0]octa-1(6),2,4-trienyl)oxirane (Intermediate 36, 94 mg, 580 umol) in a microwave vial. The vial was sealed and the mixture was heated in a 100 min at 120° C. It was concentrated in vacuo and purified by silica column chromatography (0% to 20% MeOH in DCM). The product eluted together with an impurity. It was purified again in EtOAc/Heptanes and the product eluted as a very broad peak at 100% EtOAc. The product was obtained as a colorless oil (45 mg, 18%). ESI (MS) m/z=431.3 [M+H]$^+$ ii) (4-(2-(bicyclo[4.2.0]octa-1,3,5-trien-3-yl)-2-hydroxyethyl)-3-(hydroxymethyl)piperazin-1-yl)(2-chloro-3-methoxyphenyl)methanone (104 umol, 45 mg) was dissolved in 0.9 ml dry Toluene and 0.2 ml dry THF to aid solution, cyanomethylenetributylphosphorane (125 umol, 36 mg) in 100 uL dry Toluene was added to the microwave vial. The vial was capped, degassed with argon and heated at 100° C. under argon while stirring. LCMS showed only little conversion to product, therefore 3 additional portions of cyanomethylenetributylphosphorane (in total 90 mg, 208 umol) were added over the next 30 hours while stirring at 100° C. continued. The solvent was partly evaporated and the orange-brown solution was subjected to silica column purification (0%-15% MeOH in DCM). Additional SFC purification to remove the co-eluting Tributylphosphinoxid yielded the pure product as a colorless oil (mixture of all four stereoisomers, 3.7 mg, 7.8%) ESI (MS) m/z=413.3 [M+H]$^+$ Example 48

(2-chloro-3-methoxy-phenyl)-[3-[4-(difluoromethyl)phenyl]-3,4,6,7,9,9a-hexahydro-1H-pyrazino[2,1-c][1,4]oxazin-8-yl]methanone Example 48 was obtained from Intermediate 1 (104 mg, 365 umol) and 2-(4-(difluoromethyl)phenyl)oxirane (CAS 1546906-13-1, 82 mg, 482 umol), using the same procedure as described for Example 47. Colorless oil, mixture of all four stereoisomers 6.9 mg (18%). ESI (MS) m/z=437.3 [M+H]$^+$ Example 9

[(3R,9aS)-3-(3-chloro-4-fluoro-phenyl)-3,4,6,7,9,9a-hexahydro-1H-pyrazino[2,1-c][1,4]oxazin-8-yl]-(2-fluoro-3-methoxy-phenyl)methanone A mixture of (9aS)-3-(3-chloro-4-fluorophenyl)octahydropyrazino[2,1-c][1,4]oxazine (Intermediate 2, 0.080 g, 295 μmol), 2-fluoro-3-methoxybenzoic acid (55.3 mg, 325 μmol) and HATU (124 mg, 325 μmol) was dissolved in DMF (2 ml) and then DIPEA (115 mg, 155 μl, 886 μmol) was added to the solution. The reaction mixture was stirred at RT for 1 hour. The crude product was purified by prep. HPLC (method C) to get the pure product as a white, lyophilized powder. 41 mg (32.8%). ESI (MS) m/z=423.13 [M+H]$^+$ The following examples were prepared following the same procedure as described for Example 9:

| Ex. | Building Blocks | ESI(MS) |
|---|---|---|
| 17 | Intermediate 2<br>2-chloro-3,5-dimethoxybenzoic acid<br>Minor isomer (cis, major: Example 18), separated with HPLC (Method A) | m/z = 469.1 [M + H]$^+$ |

-continued

| Ex. | Building Blocks | ESI(MS) |
|---|---|---|
| 18 | Intermediate 2<br>2-chloro-3,5-dimethoxybenzoic acid<br>Major isomer (trans), separated with HPLC (Method A) | m/z = 469.1 $[M + H]^+$ |
| 19 | Intermediate 2<br>2-chloro-3,4-dimethoxybenzoic acid<br>Major isomer (trans), separated with HPLC (Method B) | m/z = 469.1 $[M + H]^+$ |
| 20 | Intermediate 2<br>2-cyano-3-methylbenzoic acid<br>Major isomer (trans), separated with HPLC (Method B) | m/z = 414.1 $[M + H]^+$ |
| 21 | Intermediate 2<br>2-fluoro-3-trifluoromethoxybenzoic acid<br>Major isomer (trans), separated with HPLC (Method A) | m/z = 477.1 $[M + H]^+$ |
| 25 | Intermediate 2<br>2-chloro-3-difluoromethoxybenzoic acid<br>Major isomer (trans), separated with HPLC (Method C) | m/z = 475.1 $[M + H]^+$ |
| 26 | Intermediate 2<br>Intermediate 13<br>Major isomer (trans), separated with HPLC (Method D) | m/z = 489.1 $[M + H]^+$ |
| 27 | Intermediate 2<br>Intermediate 14<br>Major isomer (trans), separated with HPLC (Method B) | m/z = 500.1 $[M + H]^+$ |
| 28 | Intermediate 2<br>Intermediate 15<br>Major isomer (trans), separated with HPLC (Method B) | m/z = 500.1 $[M + H]^+$ |
| 29 | Intermediate 2<br>Intermediate 16<br>Major isomer (trans), separated with HPLC (Method B) | m/z = 487.1 $[M + H]^+$ |
| 30 | Intermediate 2<br>Intermediate 17<br>Major isomer (trans), separated with HPLC (Method E) | m/z = 486.1 $[M + H]^+$ |
| 31 | Intermediate 2<br>Intermediate 18<br>Major isomer (trans), separated with HPLC (Method E) | m/z = 487.1 $[M + H]^+$ |
| 34 | Intermediate 2<br>Intermediate 19<br>Major isomer (trans), separated with HPLC (Method B) | m/z = 501.1 $[M + H]^+$ |
| 35 | Intermediate 2<br>Intermediate 20<br>Major isomer (trans), separated with HPLC (Method B) | m/z = 501.1 $[M + H]^+$ |
| 36 | Intermediate 2<br>Intermediate 21<br>Major isomer (trans), separated with HPLC (Method B) | m/z = 475.1 $[M + H]^+$ |
| 37 | Intermediate 2<br>Intermediate 22<br>Major isomer (trans), separated with HPLC (Method B) | m/z = 500.1 $[M + H]^+$ |
| 38 | Intermediate 2<br>Intermediate 23<br>Major isomer (trans), separated with HPLC (Method B) | m/z = 475.1 $[M + H]^+$ |
| 39 | Intermediate 2<br>Intermediate 24<br>Major isomer (trans), separated with HPLC (Method B) | m/z = 503.1 $[M + H]^+$ |
| 40 | Intermediate 2<br>Intermediate 25<br>Major isomer (trans), separated with HPLC (Method B) | m/z = 490.3 $[M + H]^+$ |
| 41 | Intermediate 2<br>CAS: 1895008-64-6<br>Major isomer (trans), separated with HPLC (Method D) and subsequent SFC (Method A) | m/z = 463.1 $[M + H]^+$ |

-continued

| Ex. | Building Blocks | ESI(MS) |
|---|---|---|
| 42 | Intermediate 2<br>Intermediate 26<br>Major isomer (trans), separated with HPLC (Method B) | m/z = 506.3 $[M + H]^+$ |
| 43 | Intermediate 2<br>Intermediate 27<br>Major isomer (trans), separated with HPLC (Method B) | m/z = 494.3 $[M + H]^+$ |
| 44 | Intermediate 2<br>Intermediate 28<br>Major isomer (trans), separated with HPLC (Method B) | m/z = 476.3 $[M + H]^+$ |
| 49 | Intermediate 2<br>Intermediate 29<br>Major isomer (trans), separated with HPLC (Method F) | m/z = 493.3 $[M + H]^+$ |
| 50 | Intermediate 2<br>Intermediate 29<br>Minor isomer (cis, major: example 49), separated with HPLC (Method F) | m/z = 493.3 $[M + H]^+$ |
| 1 | Intermediate 2<br>CAS: 33234-36-5<br>Major isomer (trans), separated by flash column chromatography ($SiO_2$, EtOAc/Heptan 0-100%). Contains ca. 25% cis isomer. | m/z = 439.1 $[M + H]^+$ |
| 2 | Intermediate 2<br>CAS: 88377-29-1<br>Major isomer (trans), separated by flash column chromatography ($SiO_2$, EtOAc/Heptan 0-100%). Contains ca. 25% cis isomer. | m/z = 485.1 $[M + H]^+$ |
| 5 | Intermediate 2<br>CAS: 700844-19-5<br>Major isomer (trans), separated with HPLC (Method C) | m/z = 466.1 $[M + H]^+$ |
| 8 | Intermediate 2<br>CAS: 1780768-22-0<br>Major isomer (trans), separated with HPLC (Method E) and subsequent SFC (Method B) | m/z = 450.1 $[M + H]^+$ |
| 16 | Intermediate 2<br>CAS: 179024-66-9<br>Major isomer (trans), separated with HPLC (Method C) | m/z = 460.1 $[M + H]^+$ |
| 22 | Intermediate 2<br>CAS: 19240-62-1<br>Major isomer (trans), separated with HPLC (Method C) | m/z = 485.1 $[M + H]^+$ |
| 23 | Intermediate 2<br>Intermediate 30<br>Major isomer (trans), separated with HPLC (Method C) | m/z = 515.1 $[M + H]^+$ |
| 72 | Intermediate 7<br>Intermediate 29<br>Isomer (trans), separated with HPLC (Method B) | m/z = 482.3 $[M - H]^-$ |
| 76 | Intermediate 6<br>Intermediate 32<br>Purified by flash chromatography ($SiO_2$, MeOH in DCM 0% to 10%) | m/z = 492.2 $[M + H]^+$ |
| 108 | Intermediate 2<br>Intermediate 31<br>Major isomer (trans), separated with HPLC (Method B) | m/z = 480.2 $[M + H]^+$ |
| 110 | Intermediate 53<br>CAS: 33234-36-5<br>Purified by flash chromatography ($SiO_2$, EtOAc in Heptane 0% to 100%) | m/z = 501.2 $[M + H]^+$ |
| 111 | Intermediate 2<br>CAS: 886499-40-7<br>Major diastereomer (trans), purified by HPLC (Method B) | m/z = 457.2 $[M + H]^+$ |
| 112 | Intermediate 63<br>Intermediate 64<br>Purified by preparative HPLC (Method D). | m/z = 550.2 $[M + H]^+$ |
| 113 | Intermediate 10<br>Intermediate 55<br>Purified by flash chromatography ($SiO_2$, MeOH in DCM 0% to 10%) | m/z = 499.1 $[M + H]^+$ |

-continued

| Ex. | Building Blocks | ESI(MS) |
|---|---|---|
| 115 | Intermediate 49<br>Intermediate 64<br>Major diastereomer (trans), purified by HPLC (Method B) | m/z =<br>516.2<br>[M + H]$^+$ |
| 116 | Intermediate 6<br>CAS: 886499-40-7<br>Major diastereomer (trans), purified by HPLC (Method F) | m/z =<br>473.1<br>[M + H]$^+$ |
| 117 | Intermediate 49<br>Intermediate 55<br>Purified by flash chromatography ($SiO_2$, MeOH in DCM 0% to 10%) | m/z =<br>498.2<br>[M + H]$^+$ |
| 118 | Intermediate 51b<br>Intermediate 58<br>Purified by flash chromatography ($SiO_2$, MeOH in DCM 0% to 10%) | m/z =<br>508.3<br>[M + H]$^+$ |
| 121 | Intermediate 2<br>Intermediate 58<br>Major isomer (trans), separated with HPLC (Method H) | m/z =<br>492.3<br>[M + H]$^+$ |
| 122 | Intermediate 51a<br>Intermediate 58<br>Purified by flash chromatography ($SiO_2$, MeOH in DCM 0% to 10%) | m/z =<br>526.3<br>[M + H]$^+$ |
| 123 | Intermediate 2<br>Intermediate 59<br>Purified by flash chromatography ($SiO_2$, MeOH in DCM 0% to 10%) | m/z =<br>516.5<br>[M + H]$^+$ |
| 124 | Intermediate 2<br>Intermediate 60<br>Purified by flash chromatography ($SiO_2$, MeOH in DCM 0% to 10%) | m/z =<br>516.3<br>[M + H]$^+$ |
| 126 | Intermediate 2<br>Intermediate 54<br>Purified by flash chromatography ($SiO_2$, MeOH in DCM 0% to 10%) | m/z =<br>507.3<br>[M + H]$^+$ |
| 132 | Intermediate 67<br>Intermediate 64<br>Trans diastereomer, isolated with HPLC (Method D). Second diastereomer is Example 151 | m/z =<br>550.2<br>[M + H]$^+$ |
| 133 | Intermediate 49<br>Intermediate 65<br>Major isomer (trans), separated with HPLC (Method B) | m/z =<br>510.2<br>[M + H]$^+$ |
| 134 | Intermediate 2<br>Intermediate 57<br>Major isomer (trans), separated with HPLC (Method H) | m/z =<br>493.2<br>[M + H]$^+$ |
| 135 | Intermediate 66<br>CAS 33234-36-5<br>Diastereomer (trans), isolated by HPLC (Method B) | m/z =<br>464.3<br>[M + H]$^+$ |
| 138 | Intermediate 2<br>Intermediate 62<br>Purified by flash chromatography ($SiO_2$, MeOH in DCM 0% to 10%) | m/z =<br>500.3<br>[M + H]$^+$ |
| 140 | Intermediate 49<br>Intermediate 69<br>Purified by preparative HPLC (Method L) | m/z =<br>492.2<br>[M + H]$^+$ |
| 147 | Intermediate 49<br>CAS 886499-40-7<br>Purified by preparative HPLC (Method K) | m/z =<br>456.1<br>[M + H]$^+$ |
| 148 | Intermediate 68<br>CAS 33234-36-5<br>Major diastereomer, isolated by preparative HPLC (Method A) | m/z =<br>490.2<br>[M + H]$^+$ |
| 151 | Intermediate 67<br>Intermediate 64<br>Cis diastereomer, isolated with HPLC (Method D). Second diastereomer is Example 132 | m/z =<br>550.2<br>[M + H]$^+$ |
| 152 | Intermediate 10<br>Intermediate 56<br>Purified by flash chromatography ($SiO_2$, MeOH in DCM 0% to 0%) | m/z =<br>500.3<br>[M + H]$^+$ |
| 155 | Intermediate 63<br>CAS 33234-36-5<br>Purified by preparative HPLC (Method B) | m/z =<br>472.2<br>[M + H]$^+$ |

-continued

| Ex. | Building Blocks | ESI(MS) |
|---|---|---|
| 158 | Intermediate 2<br>Intermediate 61<br>Major isomer (trans), separated with HPLC (Method H) | m/z =<br>503.3<br>[M + H]$^+$ |
| 159 | Intermediate 2<br>CAS: 886499-40-7<br>Minor diastereomer (cis), purified by HPLC (Method B)<br>(Major isomer is example 111) | m/z =<br>457.2<br>[M + H]$^+$ |

Example 6

[(3R,9aS)-3-(3-bromo-4-fluoro-phenyl)-3,4,6,7,9,9a-hexahydro-1H-pyrazino[2,1-c][1,4]oxazin-8-yl]-(2-chloro-3-methoxy-phenyl)methanone A mixture of (9aS)-3-(3-bromo-4-fluorophenyl)octahydropyrazino[2,1-c][1,4]oxazine (Intermediate 3, 1.36 g, 3.87 mmol), 2-chloro-3-methoxybenzoic acid (722 mg, 3.87 mmol) and HATU (1.4 g, 3.67 mmol) was dissolved in DMF (15 ml) and then DIPEA (1.5 mg, 2.03 ml, 11.6 mmol) was added to the solution. The reaction mixture was stirred at RT for 30 minutes. The crude product was purified by prep. HPLC (method C) to get the pure product as a white, lyophilized powder. 1.46 g (78%). ESI (MS) m/z=485.1 [M+H]$^+$

Example 10

(2-chloro-3-methoxy-phenyl)-[(3R,9aS)-3-[4-fluoro-3-[rac-(E)-prop-1-enyl]phenyl]-3,4,6,7,9,9a-hexahydro-1H-pyrazino[2,1-c][1,4]oxazin-8-yl]methanone In a microwave vial [(3R,9aS)-3-(3-bromo-4-fluoro-phenyl)-3,4,6,7,9,9a-hexahydro-TH-pyrazino[2,1-c][1,4]oxazin-8-yl]-(2-chloro-3-methoxy-phenyl)methanone (example 6, 54 mg, 112 µmol), sodium carbonate (29.6 mg, 279 µmol) and (E)-prop-1-en-1-ylboronic acid (14.4 mg, 167 µmol) in Dioxane (1.2 ml)/Water (120 µl) was degassed with argon. Tetrakis(triphenylphosphine)palladium (0) (25.8 mg, 22.3 µmol) was added and the mixture was heated at 110° C. for 35 min in the microwave. The mixture was diluted with water and extracted 3 with DCM. The combined organic layers were washed with sat. bicarb solution and brine, dried ($Na_2SO_4$), filtered and concentrated. The residue was purified via flash chromatography on silica gel to yield the desired product as an off-white powder. 26 mg (52%). ESI (MS) m/z=445.2 [M+H]$^+$ The following examples were prepared as described for example 10:

| Ex. | Building Blocks | ESI(MS) |
|---|---|---|
| 11 | Example 6<br>phenylboronic acid<br>Major isomer (trans) isolated by SFC (method C) | m/z =<br>481.2<br>[M + H]$^+$ |
| 12 | Example 6<br>phenylboronic acid<br>Minor isomer (cis, major: example 11), isolated by SFC (Method C) | m/z =<br>481.2<br>[M + H]$^+$ |

Example 13

[(3R,9aS)-3-(4-fluoro-3-prop-1-ynyl-phenyl)-3,4,6,7,9,9a-hexahydro-1H-pyrazino[2,1-c][1,4]oxazin-8-yl]-(2-chloro-3-methoxy-phenyl)methanone In a microwave vial [(3R,9aS)-3-(3-bromo-4-fluoro-phenyl)-3,4,6,7,9,9a-hexahydro-1H-pyrazino[2,1-c][1,4]oxazin-8-yl]-(2-chloro-3-methoxy-phenyl)methanone (example 6, 43 mg, 88.9 μmol), TEA (27 mg, 37.2 μl, 267 μmol), trimethyl(prop-1-yn-1-yl)silane (39.9 mg, 52.7 μl, 356 μmol), PdCl2(DPPF)-CH2Cl2 adduct (7.26 mg, 8.89 μmol), copper(I) iodide (2.5 mg, 13.3 umol) in DMF (0.75 ml) was degassed with argon. Subsequently TBAF 1M in THF (133 μl, 133 μmol) was added. Reaction mixture was then heated in the microwave at 120° C. for 2.5 h. The mixture was diluted with water and extracted 3× with DCM. The combined organic layers were washed with sat. bicarb solution and brine, dried ($Na_2SO_4$), filtered and concentrated. The residue was purified by SFC (method C). 5 mg (10.5%). ESI (MS) m/z=443.2 $[M+H]^+$ Example 14

[(3R,9aS)-3-(3-cyano-4-fluoro-phenyl)-3,4,6,7,9,9a-hexahydro-1H-pyrazino[2,1-c][1,4]oxazin-8-yl]-(2-chloro-3-methoxy-phenyl)methanone A microwave vial was charged with [(3R,9aS)-3-(3-bromo-4-fluoro-phenyl)-3,4,6,7,9,9a-hexahydro-1H-pyrazino[2,1-c][1,4]oxazin-8-yl]-(2-chloro-3-methoxy-phenyl)methanone (example 6, 62 mg, 128 μmol), dicyanozinc (10.1 mg, 85.9 μmol), TMEDA (4.47 mg, 5.8 μl, 38.4 μmol) and was placed under argon. DMF anhydrous (1 ml) was added and the mixture was degassed for 5 min. Pd2(dba)3 (11.7 mg, 12.8 μmol) and xantphos (11.1 mg, 19.2 μmol) were added and the mixture was degassed for 5 min. The vial was sealed and irradiated at 110° C. in the microwave for 40 min. The reaction mixture was diluted with DCM, poured into 5% $NaHCO_3$ and extracted thrice with DCM. The organic layers were washed with brine, dried over Na2SO4, filtered and concentrated in vacuo. This was then purified by prep.HPLC (method C) to get the final compound as a white lyoph powder (34 mg, 59.2%). ESI (MS) m/z=430.1 $[M+H]^+$ Example 24

[(3R,9aS)-3-(3-cyclopropyl-4-fluoro-phenyl)-3,4,6,7,9,9a-hexahydro-1H-pyrazino[2,1-c][1,4]oxazin-8-yl]-(2-chloro-3-methoxy-phenyl)methanone A microwave vial was charged with ((3R,9aS)-3-(3-bromo-4-fluorophenyl)hexahydropyrazino[2,1-c][1,4]oxazin-8(1H)-yl)(2-chloro-3-methoxyphenyl)methanone (example 6, 67 mg, 138 μmol), potassium cyclopropyltrifluoroborate (26.6 mg, 180 μmol) and cesium carbonate (135 mg, 415 μmol) in toluene (1.0 ml)/Water (100 μl) and was degassed with argon. cataCXium A Pd G2 (9.26 mg, 13.8 μmol) was added and the mixture was heated to 100° C. for 16 hr. Extracted with EtOAc/water (3×), dried over $Na_2SO_4$, conc. in vacuo. Pre-purified by SiO2 flash chromatography, product isolated by preparative HPLC (method C) as a white, lyophilized powder (2 mg, 3.2%). ESI (MS) m/z=445.2 $[M+H]^+$ Example 32 and Example 33

(2-chloro-3-methoxy-phenyl)-[(rel-3R,9aS)-3-(3-chloro-4-fluoro-phenyl)-9a-methyl-1,3,4,6,7,9-hexahydropyrazino[2,1-c][1,4]oxazin-8-yl]methanone and (2-chloro-3-methoxy-phenyl)-[(rel-3S,9aR)-3-(3-chloro-4-fluoro-phenyl)-9a-methyl-1,3,4,6,7,9-hexahydropyrazino[2,1-c][1,4]oxazin-8-yl]methanone A mixture of 2-chloro-3-methoxybenzoic acid (56.6 mg, 304 μmol), 3-(3-chloro-4-fluorophenyl)-9a-methyloctahydropyrazino[2,1-c][1,4]oxazine hydrochloride (intermediate 4, 75 mg, 233 μmol) and HATU (133 mg, 350 μmol) was dissolved in DMF (2.08 ml) and then DIPEA (151 mg, 204 μl, 1.17 mmol) was added to the solution and the reaction mixture was stirred at rt for 30 min. The reaction mixture was extracted with EtOAc/sat. $NaHCO_3$ (3×30 ml), brine, dried over $Na_2SO_4$, filtered, and concentrated in vacuo. Purification by SFC (method C) and HPLC (method A) yielded the two products.

Example 32: lyophilized, white powder (21 mg, 18%), ESI (MS) m/z=453.1 $[M+H]^+$ Example 33: lyophilized, white powder (10 mg, 9%), ESI (MS) m/z=453.1 $[M+H]^+$ Example 45 and Example 46

(2-chloro-3-methoxy-phenyl)-[(3R,9aS)-3-(3-chloro-4-fluoro-phenyl)-3-hydroxy-1,4,6,7,9,9a-hexahydro-pyrazino[2,1-c][1,4]oxazin-8-yl]methanone and (2-chloro-3-methoxy-phenyl)-[(3S,9aR)-3-(3-chloro-4-fluoro-phenyl)-3-hydroxy-1,4,6,7,9,9a-hexahydro-pyrazino[2,1-c][1,4]oxazin-8-yl]methanone In a 25 mL round-bottomed flask, (2-chloro-3-methoxy-phenyl)(3-(hydroxymethyl)piperazin-1-yl)methanone (intermediate 1, 143 mg, 502 μmol) was combined with Tetrahydrofuran (2.5 ml) to give a colorless solution. DIPEA (84.4 mg, 114 μl, 653 μmol) and 2-bromo-1-(3-chloro-4-fluorophenyl)ethan-1-one (126 mg, 502 μmol) were added. The reaction mixture was stirred at room temperature for 2 hours. The reaction was diluted with EtOAc, washed with sat. $NaHCO_3$ solution, dried over NaSO4, filtered and concentrated. The solvent was removed in vacuo and the crude product was purified by flash chromatography. (DCM/MeOH 0-20%). 222 mg of product were isolated, they were submitted to chiral SFC (method E) to separate the isomers.

Example 45 85 mg (37%), light-brown solid. ESI (MS) m/z=455.3 $[M+H]^+$

Example 46 81 mg (35%), light-brown solid. ESI (MS) m/z=455.3 $[M+H]^+$

Example 51 and Example 52

(2-chloro-3-methoxy-phenyl)-[rel-(3S,9aS)-3-(2,4-dimethylthiazol-5-yl)-3,4,6,7,9,9a-hexahydro-1H-pyrazino[2,1-c][1,4]oxazin-8-yl]methanone and (2-chloro-3-methoxy-phenyl)-[rel-(3R,9aR)-3-(2,4-dimethylthiazol-5-yl)-3,4,6,7,9,9a-hexahydro-1H-pyrazino[2,1-c][1,4]oxazin-8-yl]methanone i) (2-chloro-3-methoxyphenyl)(3-(hydroxymethyl)piperazin-1-yl)methanone (intermediate 1, 164 mg, 577 umol) and 2-bromo-1-(2,4-dimethylthiazol-5-yl)ethan-1-one (135 mg, 0.577 umol) were dissolved/dispersed in 8 mL THF. DIPEA (130 uL, 750 umol) was added dropwise over 10 min. The dark green reaction mixture was stirred at room temperature. After 18 h, the reaction was diluted with EtOAc, washed with sat. $NaHCO_3$ solution, the aqueous phase backextracted with EtOAc and the combined org. phases dried over $NaSO_4$, filtered, adsorbed on silica and concentrated in vacuo. The crude was purified by silica column chromatography ($SiO_2$, DCM:MeOH 100:0 to 90:10). rac-(2-chloro-3-methoxyphenyl)((3R,9aS)-3-(2,4-dimethylthiazol-5-yl)-3-hydroxyhexahydropyrazino[2,1-c][1,4]oxazin-8(1H)-yl)methanone was isolated as racemate (100 mg, 40%).

ii) rac-(2-chloro-3-methoxyphenyl)((3R,9aS)-3-(2,4-dimethylthiazol-5-yl)-3-hydroxyhexahydropyrazino[2,1-c][1,4]oxazin-8(1H)-yl)methanone (60 mg, 137 umol) was dissolved in 4.4 mL DCM and 2.2 mL TFA. Triethylsilane (66 uL, 411 umol) was added and the mixture stirred at 45° C. After 48 h, additional TFA (1 mL) and silane (30 uL) was added and the mixture heated to 65° C. After another 72 h, the mixture was concentrated in vacuo and purified by silica column chromatography (DCM/MeOH). Chiral SFC (method A) yielded the two separate enantiomers (1.8 mg, 2.4%; 2.1 mg, 3%). ESI (MS) m/z=422.2 $[M+H]^+$ Example 53 and Example 54

(2-chloro-3-methoxy-phenyl)-[rac-(3R,9aR)-3-(5-bromo-2-pyridyl)-3,4,6,7,9,9a-hexahydro-TH-pyrazino[2,1-c][1,4]oxazin-8-yl]methanone and (2-chloro-3-methoxy-phenyl)-[rac-(3S,9aR)-3-(5-bromo-2-pyridyl)-3,4,6,7,9,9a-hexahydro-TH-pyrazino[2,1-c][1,4]oxazin-8-yl]methanone i) 2-chloro-3-methoxyphenyl)(3-(hydroxymethyl) piperazin-1-yl)methanone (intermediate 1, 218 mg, 765 umol) and 5-bromo-2-(oxiran-2-yl)pyridine (CAS 1335050-95-7, 153 mg, 765 umol) were dissolved in 2 mL MeOH in a microwave vial and heated in the microwave for 85 min at 120° C. It was then purified by silica column chromatography (DCM/MeOH) to yield (4-(2-(5-bromopyridin-2-yl)-2-hydroxyethyl)-3-(hydroxymethyl)piperazin-1-yl)(2-chloro-3-methoxyphenyl)methanone as a dark red oil (262 mg, 71%). ESI (MS) m/z=486.2 $[M+H]^+$ ii) (4-(2-(5-bromopyridin-2-yl)-2-hydroxyethyl)-3-(hydroxymethyl)piperazin-1-yl)(2-chloro-3-methoxyphenyl) methanone (73 mg, 151 umol) was dissolved in 1.2 mL dry toluene. 2-(tributyl-15-phosphaneylidene)acetonitrile (127 mg, 527 umol) in 0.3 mL toluene was added and the mixture degassed with argon and then heated up to 100° C. for 4 h. The mixture was concentrated in vacuo. It was purified by silica column chromatography (DCM/MeOH 100/0 to 90/10). The still impure compound was obtained as a brown viscous oil (66 mg) and submitted to SFC to separate the two diastereomers.

Example 53 (trans) 1.7 mg, 2.4%; ESI (MS) m/z=468.1 $[M+H]^+$

Example 54 (cis) 4.7 mg, 6.7%; ESI (MS) m/z=468.1 $[M+H]^+$

Example 58 and Example 59

(2-chloro-3-methoxy-phenyl)-[rac-(3S,9aS)-3-(5-chloro-3-pyridyl)-3,4,6,7,9,9a-hexahydro-1H-pyrazino[2,1-c][1,4]oxazin-8-yl]methanone and (2-chloro-3-methoxy-phenyl)-[rac-(3R,9aS)-3-(5-chloro-3-pyridyl)-3,4,6,7,9,9a-hexahydro-1H-pyrazino[2,1-c][1,4]oxazin-8-yl]methanone Examples 58 and 59 was synthesized according to the procedure as described for examples 53 and 54, starting from 3-chloro-5-(oxiran-2-yl)pyridine (CAS 1335057-62-9, 72 mg, 464 umol) and intermediate 1 (120 mg, 0.42 mmol).

Example 58 (cis), 5.4 mg, ESI (MS) m/z=422.2 $[M+H]^+$

Example 59 (trans), 5.8 mg, ESI (MS) m/z=422.2 $[M+H]^+$

Example 60 and Example 61

(2-chloro-3-methoxy-phenyl)-[rel-(3S,9aS)-3-(1H-benzimidazol-2-yl)-3-hydroxy-1,4,6,7,9,9a-hexahydropyrazino[2,1-c][1,4]oxazin-8-yl]methanone and (2-chloro-3-methoxy-phenyl)-[rel-(3R,9aR)-3-(1H-benzimidazol-2-yl)-3-hydroxy-1,4,6,7,9,9a-hexahydropyrazino[2,1-c][1,4]oxazin-8-yl]methanone (2-chloro-3-methoxyphenyl)(3-(hydroxymethyl)piperazin-1-yl)methanone (intermediate 1, 96 mg, 337 umol) and DIPEA (65 uL, 371 umol) were dispersed in 2 mL dry THF and cooled down in an ice bath. 1-(1H-benzo[d]imidazol-2-yl)-2-chloroethan-1-one (79 mg, 405 umol) was dissolved in 1 mL dry THF and added dropwise to the solution over 10 min. It was then heated up to 70° C. overnight. It was concentrated in vacuo and then purified by silica column chromatography (DCM:MeOH 100:0 to 90:10). The compound was obtained as a yellow solid (47 mg, 24%), the two enantiomers were separated by chiral SFC (method D).

Example 60 (enantiomer A) 10.9 mg, ESI (MS) m/z=443.2 $[M+H]^+$

Example 61 (enantiomer B) 16.2 mg, ESI (MS) m/z=443.2 $[M+H]^+$

Example 63

(2-chloro-3-methoxy-phenyl)-[rel-(3S,9aS)-3-[6-(trifluoromethyl)-2-pyridyl]-3,4,6,7,9,9a-hexahydro-1H-pyrazino[2,1-c][1,4]oxazin-8-yl]methanone Example 63 was synthesized according to the procedure as described for examples 53 and 54, starting from 2-(oxiran-2-yl)-6-(trifluoromethyl)pyridine (CAS 1346534-02-8, 187 mg, 989 umol) and intermediate 1 (262 mg, 920 umol). Purification by SFC (twice, methods C and E) yielded the 4 stereoisomers enantiopure.

Example 63 (major stereoisomer, trans, Enantiomer A), 13.8 mg (6.4%), colorless oil, ESI (MS) m/z=456.2 $[M+H]^+$ Example 66 and Example 67

(2-chloro-3-methoxy-phenyl)-[rel-(3R,9aR)-3-(4,5-dichloro-2-pyridyl)-3,4,6,7,9,9a-hexahydro-1H-pyrazino[2,1-c][1,4]oxazin-8-yl]methanone and (2-chloro-3-methoxy-phenyl)-[rel-(3S,9aS)-3-(4,5-dichloro-2-pyridyl)-3,4,6,7,9,9a-hexahydro-1H-pyrazino[2,1-c][1,4]oxazin-8-yl]methanone Examples 66 and 67 was synthesized according to the procedure as described for examples 53 and 54, starting from 4,5-dichloro-2-(oxiran-2-yl)pyridine (Intermediate 37, 159 mg, 669 umol) and intermediate 1 (170 mg, 284 umol). Product was isolated as two separate enantiomers (both trans) after chiral SFC.

Example 66 (enantiomer A) 8.7 mg, 4.6%, ESI (MS) m/z=456.1 $[M+H]^+$

Example 67 (enantiomer B) 9.6 mg, 5.4%, ESI (MS) m/z=456.1 $[M+H]^+$

Example 65

[(3R,9aS)-3-hydroxy-3-[6-(trifluoromethyl)pyridin-3-yl]-1,4,6,7,9,9a-hexahydropyrazino[2,1-c][1,4]oxazin-8-yl]-[2-chloro-3-(3-fluoro-1H-pyrazol-4-yl)phenyl]methanone (S)-(2-chloro-3-(3-fluoro-1H-pyrazol-4-yl)phenyl)(3-(hydroxymethyl)piperazin-1-yl)methanone (intermediate 5, 40 mg, 118 umol) and DIPEA (16.8 mg, 130 umol) were dispersed in 0.8 mL dry THF and cooled down to 0° C. 2-bromo-1-(6-(trifluoromethyl)pyridin-2-yl)ethan-1-one (CAS 1379332-23-6, 32 mg, 118 umol) was dissolved in 0.5 mL dry THF and added dropwise to the solution over 10 min. After 5 h the reaction was allowed to warm to RT and stirred overnight. The mixture was diluted with water and extracted into EtOAc twice. The combined organic phases were dried over sodium sulfate, concentrated in vacuo and purified by silica column chromatography (MeOH in DCM 0% to 10%). The product was obtained as a white solid, 30.8 mg, 48%. ESI (MS) m/z=526.2 $[M+H]^+$

Example 68

[(9aS)-3-[6-(trifluoromethyl)-3-pyridyl]-3,4,6,7,9,9a-hexahydro-1H-pyrazino[2,1-c][1,4]oxazin-8-yl]-[2-chloro-3-(3-fluoro-1H-pyrazol-4-yl)phenyl]methanone

[(3R,9aS)-3-hydroxy-3-[6-(trifluoromethyl)pyridin-3-yl]-1,4,6,7,9,9a-hexahydropyrazino[2,1-c][1,4]oxazin-8-yl]-[2-chloro-3-(3-fluoro-1H-pyrazol-4-yl)phenyl]methanone (example 65, 5.7 mg, 10.8 umol) was dissolved in 0.3 mL dry DCM and 0.15 mL TFA. TES (5.2 uL, 32.5 umol) was added to the yellowish solution and it was stirred at 60° C. for 64 h upon which the solution turned red. The reaction mixture was concentrated in vacuo and the residual TFA coevaporated with toluene. The crude was then purified by reverse phase HPLC (method B) to obtain the target compound as a white solid (2.5 mg, 45%). Mixture of two diastereomers (trans/cis 2:1). ESI (MS) m/z=510.2 $[M+H]^+$

Example 69

[2-chloro-3-(3-fluoro-1H-pyrazol-4-yl)phenyl]-[(3R,9aS)-3-[4-(difluoromethoxy)phenyl]-3-hydroxy-1,4,6,7,9,9a-hexahydropyrazino[2,1-c][1,4]oxazin-8-yl]methanone (S)-(2-chloro-3-(3-fluoro-1H-pyrazol-4-yl)phenyl)(3-(hydroxymethyl)piperazin-1-yl)methanone (intermediate 5, 37 mg, 109 umol) and DIPEA (23 uL, 131 umol) were dispersed in 1.1 mL dry THF and cooled down to 0° C. 2-bromo-1-(4-(difluoromethoxy)phenyl)ethan-1-one (CAS 141134-24-9, 32 mg, 120 umol) was dissolved in 0.3 mL dry THF and added dropwise to the solution over 10 min. After stirring overnight at RT, the reaction was cooled down again and another 6 uL DIPEA and 10 mg of 2-bromo-1-(4-(difluoromethoxy)phenyl)ethan-1-one in 0.3 mL dry THF were added. After 30 min, it was warmed up to RT. 3.5 h later, it was diluted with water and extracted into EtOAc twice. The combined organic phases were dried over sodium sulfate, concentrated in vacuo and purified by silica column chromatography (MeOH in DCM 0% to 10%). The product was isolated as yellow solid (28.8 mg, 50%). ESI (MS) m/z=523.2 $[M+H]^+$

Example 73

(2-chloro-3-(3-fluoro-1H-pyrazol-4-yl)phenyl)((9aS)-3-(4-(difluoromethoxy)phenyl)hexahydropyrazino[2,1-c][1,4]oxazin-8(1H)-yl)methanone Example 73 was prepared as described for example 68, starting from example 69 (10.9 mg, 20.8 umol). Reaction was complete after 3 hours, yielding the product as a white solid (10.3 mg, 97%). Mixture of diastereomers trans/cis 3:1. ESI (MS) m/z=507.2 $[M+H]^+$

Example 70

[2-chloro-3-(3-fluoro-1H-pyrazol-4-yl)phenyl]-[(9aS)-3-(6-bromo-3-pyridyl)-3,4,6,7,9,9a-hexahydro-1H-pyrazino[2,1-c][1,4]oxazin-8-yl]methanone (9aS)-3-(5-bromopyridin-2-yl)octahydropyrazino[2,1-c][1,4]oxazine hydrochloride (intermediate 38, 25 mg, 74.7 umol), 2-chloro-3-(3-fluoro-1H-pyrazol-4-yl)benzoic acid (intermediate 29, 24.3 mg, 101 umol) and HATU (38.3 mg, 101 umol) were dissolved in 800 uL DMF. DIPEA (46 uL, 261 umol) was added and the reaction stirred at RT. After 3 h, it was concentrated in vacuo and separated by preparative HPLC. 2.7 mg (6%) of desired product were obtained as a white, lyophilized solid. Mixture of both diastereomers. ESI (MS) m/z=522.2 $[M+H]^+$

Example 71

[(3S,9aS)-3-hydroxy-3-(1-methylbenzimidazol-2-yl)-1,4,6,7,9,9a-hexahydropyrazino[2,1-c][1,4]oxazin-8-yl]-(2-chloro-3-methoxy-phenyl)methanone Example 71 was synthesized as described for example 65, starting from intermediate 1S and 2-bromo-1-(1-methyl-1H-benzo[d]imidazol-2-yl)ethan-1-one. Yield 203 mg, 80.1%. ESI (MS) m/z=457.3 $[M+H]^+$

Example 74

3-[(3S,9aS)-8-(2-chloro-3-methoxy-benzoyl)-3,4,6,7,9,9a-hexahydro-1H-pyrazino [2,1-c][1,4]oxazin-3-yl]-5-chloro-1H-pyridin-2-one ((3S,9aS)-3-(2-(benzyloxy)-5-chloropyridin-3-yl)hexahydropyrazino[2,1-c][1,4]oxazin-8(1H)-yl)(2-chloro-3-methoxyphenyl)methanone (intermediate 35B, 31.6 mg, 59.8 umol) was dissolved in 1 mL dry DCM and 1 mL TFA was added dropwise. After 1.5 h, the mixture was concentrated in vacuo, dissolved in EtOAc and washed with sat. bicarbonate solution. The organic phase was dried over sodium sulfate, filtered and concentrated in vacuo. It was then purified by silica chromatography (MeOH in DCM 0% to 10%). The desired product was obtained as an orange-brown solid (19.3 mg, 66%). ESI (MS) m/z=438.2 $[M+H]^+$ Example 75

3-[(3R,9aS)-8-(2-chloro-3-methoxy-benzoyl)-3,4,6,7,9,9a-hexahydro-1H-pyrazino[2,1-c][1,4]oxazin-3-yl]-5-chloro-1H-pyridin-2-one ((3S,9aS)-3-(2-(benzyloxy)-5-chloropyridin-3-yl)hexahydropyrazino[2,1-c][1,4]oxazin-8(1H)-yl)(2-chloro-3-methoxyphenyl)methanone (intermediate 35A, 44.7 mg, 84.6 umol) was dissolved in 1.3 mL dry DCM and 1.3 mL TFA was added dropwise. After 1.5 h, the mixture was concentrated in vacuo, dissolved in EtOAc and washed with sat. bicarbonate solution. The organic phase was dried over sodium sulfate, filtered and concentrated in vacuo. It was then purified by silica chromatography (MeOH in DCM 0% to 10%). The desired product was obtained as a light brown solid (34.3 mg, 93%). ESI (MS) m/z=438.2 $[M+H]^+$ Example 77

3-[(3R,9aS)-8-[2-chloro-3-(3-fluoro-1H-pyrazol-4-yl)benzoyl]-3,4,6,7,9,9a-hexahydro-1H-pyrazino[2,1-c][1,4]oxazin-3-yl]-5-chloro-1H-pyridin-2-one Example 77 was prepared as described for example 70, starting from 5-chloro-3-((3R,9aS)-octahydropyrazino[2,1-c][1,4]oxazin-3-yl)pyridin-2-ol 2,2,2-trifluoroacetate (intermediate 49, 24 mg, 62.5 umol) and intermediate 29 (24.5 mg, 101 umol). Purified by preparatice HPLC (method G), product obtained as white, lyophilized solid (5.4 mg, 14.6%). ESI (MS) m/z=492.2 $[M+H]^+$ Example 83 and Example 84

(2-chloro-3-methoxyphenyl)((3S,9aS)-3-(5-chloro-4-methylpyridin-2-yl)hexahydropyrazino[2,1-c][1,4]oxazin-8(1H)-yl)methanone and (2-chloro-3-methoxyphenyl)((3R,9aS)-3-(5-chloro-4-methylpyridin-2-yl)hexahydropyrazino[2,1-c][1,4]oxazin-8(1H)-yl)methanone Examples 83 and 84 were synthesized according to the procedure as described for examples 53 and 54, starting from 5-chloro-4-methyl-2-(oxiran-2-yl)pyridine (intermediate 39, 130 mg, 766 umol) and intermediate 1S (291 mg, 0.92 mmol). Purification by preparatice HPLC yielded the two diastereomers separately.

Example 83 (major stereoisomer, trans), yellow solid, 47 mg, ESI (MS) m/z=436.2 $[M+H]^+$ Example 84 (minor stereoisomer, cis, contains ca. 30% trans), yellow solid, 25.8 mg (9.8%), ESI (MS) m/z=436.2 $[M+H]^+$ Example 89

(2-chloro-3-methoxy-phenyl)-[(3S,9aS)-3-[6-(trifluoromethyl)pyridazin-3-yl]-3,4,6,7,9,9a-hexahydro-1H-pyrazino[2,1-c][1,4]oxazin-8-yl]methanone Example 89 was synthesized according to the procedure as described for examples 53 and 54, starting from 3-(oxiran-2-yl)-6-(trifluoromethyl)pyridazine (see intermediate 11, steps a+b, 72 mg, 379 umol) and intermediate 1S (178 mg, 530 umol). Purification by preparatice HPLC yielded the two diastereomers separately.

Example 89 (major stereoisomer, trans), white lyophilized solid, 5.3 mg (4.0%), ESI (MS) m/z=457.2 $[M+H]^+$ Example 90 and Example 91

[(3R,9aS)-3-(4-chloro-2-pyridyl)-3,4,6,7,9,9a-hexahydro-1H-pyrazino[2,1-c][1,4]oxazin-8-yl]-(2-chloro-3-methoxy-phenyl)methanone and [(3S,9aS)-3-(4-chloro-2-pyridyl)-3,4,6,7,9,9a-hexahydro-1H-pyrazino[2,1-c][1,4]oxazin-8-yl]-(2-chloro-3-methoxy-phenyl)methanone Examples 90 and 91 were synthesized according to the procedure as described for examples 53 and 54, starting from 4-chloro-2-(oxiran-2-yl)pyridine (CAS 115548-57-7, 90 mg, 578 umol) and intermediate 1S (220 mg, 694 umol). Purification by preparatice HPLC yielded the two diastereomers separately.

Example 90 (minor stereoisomer, cis), light brown solid, 17.2 mg, ESI (MS) m/z=422.1 $[M+H]^+$ Example 91 (major stereoisomer, trans), light brown solid, 18.7 mg, ESI (MS) m/z=422.1 $[M+H]^+$ Example 98

(2-chloro-3-methoxy-phenyl)-[(3S,9aS)-3-[5-chloro-4-(trifluoromethyl)-2-pyridyl]-3,4,6,7,9,9a-hexahydro-1H-pyrazino[2,1-c][1,4]oxazin-8-yl]methanone Example 98 was synthesized according to the procedure as described for examples 53 and 54, starting from 5-chloro-2-(oxiran-2-yl)-4-(trifluoromethyl)pyridine (intermediate 40, 192 mg, 859 umol) and intermediate 1S (353 mg, 1.12 mmol). Purification by preparatice HPLC yielded the two diastereomers separately.

Example 98 (major stereoisomer, trans), white lyophilized solid, 22.8 mg (9.1%) ESI (MS) m/z=490.2 $[M+H]^+$ Example 99

(2-chloro-3-methoxy-phenyl)-[(3S,9aS)-3-[4-(trifluoromethoxy)-2-pyridyl]-3,4,6,7,9,9a-hexahydro-1H-pyrazino[2,1-c][1,4]oxazin-8-yl]methanone Example 99 was synthesized according to the procedure as described for examples 53 and 54, starting from 2-(oxiran-2-yl)-4-(trifluoromethoxy)pyridine (intermediate 41, 218 mg, 1.06 mmol) and intermediate 1S (403 mg, 1.28 mmol). Purification by preparatice HPLC yielded the two diastereomers separately.

Example 99 (major stereoisomer, trans), light yellow lyophilized solid, 51.1 mg (16%) ESI (MS) m/z=472.2 $[M+H]^+$ Example 101

(2-chloro-3-methoxy-phenyl)-[(3S,9aS)-3-[5-fluoro-4-(trifluoromethyl)-2-pyridyl]-3,4,6,7,9,9a-hexahydro-1H-pyrazino[2,1-c][1,4]oxazin-8-yl]methanone Example 101 was synthesized according to the procedure as described for examples 53 and 54, starting from 5-fluoro-2-(oxiran-2-yl)-4-(trifluoromethyl)pyridine (intermediate 42, 308 mg, 1.49 mmol) and intermediate 1S (508 mg, 1.78 mmol). Purification by preparatice HPLC yielded the two diastereomers separately.

Example 101 (major stereoisomer, trans), off-white lyophilized solid, 30.6 mg (12.8%) ESI (MS) m/z=474.2 $[M+H]^+$ Example 104

(2-chloro-3-methoxy-phenyl)-[(3S,9aS)-3-[5-chloro-4-(difluoromethyl)-2-pyridyl]-3,4,6,7,9,9a-hexahydro-1H-pyrazino[2,1-c][1,4]oxazin-8-yl]methanone Example 104 was synthesized according to the procedure as described for examples 53 and 54, starting from 5-chloro-4-(difluoromethyl)-2-(oxiran-2-yl)pyridine (intermediate 43, 350 mg, 1.53 mmol) and intermediate 1S (524 mg, 1.84 mmol). Purification by preparatice HPLC yielded the two diastereomers separately.

Example 104 (major stereoisomer, trans), off-white lyophilized solid, 68.2 mg (14.1%) ESI (MS) m/z=472.2 $[M+H]^+$ Example 107

(2-chloro-3-methoxy-phenyl)-[(3S,9aS)-3-[5-chloro-4-bromo-2-pyridyl]-3,4,6,7,9,9a-hexahydro-1H-pyrazino[2,1-c][1,4]oxazin-8-yl]methanone Example 107 was synthesized according to the procedure as described for examples 53 and 54, starting from 4-bromo-5-chloro-2-(oxiran-2-yl)pyridine (intermediate 44, 304 mg, 908 umol, 70% pure) and intermediate 1S (315 mg, 1.22 mmol). Purification by preparative HPLC yielded the two diastereomers separately.

Example 107 (major stereoisomer, trans), off-white lyophilized solid, 23 mg (8.4%) ESI (MS) m/z=502.1 $[M+H]^+$ Example 102

[(3R,9aS)-3-(3-chloro-4-fluoro-phenyl)-3,4,6,7,9,9a-hexahydro-TH-pyrazino[2,1-c][1,4]oxazin-8-yl]-[2-fluoro-3-[5-(trifluoromethyl)-1H-pyrazol-4-yl]phenyl]methanone (3R,9aS)-3-(3-chloro-4-fluorophenyl)octahydropyrazino[2,1-c][1,4]oxazine (intermediate 2, 26.5 mg, 97.9 umol), 2-fluoro-3-(5-(trifluoromethyl)-1H-pyrazol-4-yl)benzoic acid (intermediate 45, 33.5 mg, 97.9 umol) and DIPEA (56 uL, 323 umol) were mixed with 1 mL dry THF and cooled to 0° C. T3P (93 mg of a 50% wt/wt solution in EtOAc, 147 umol) in 0.2 mL dry THF was added dropwise over 10 min. After 20 min, it was warmed to RT. 30 min later, it was diluted with EtOAc, washed with sat. bicarbonate solution and then brine, dried over sodium sulfate, filtered and concentrated in vacuo. The crude was purified by silica column chromatography (MeOH in DCM 0% to 10%). The compound was obtained as a yellow solid (30.5 mg, 51%). ESI (MS) m/z=527.2 $[M+H]^+$ Example 103

[(3R,9aS)-3-(3-chloro-4-fluoro-phenyl)-3,4,6,7,9,9a-hexahydro-1H-pyrazino[2,1-c][1,4]oxazin-8-yl]-[3-[5-(trifluoromethyl)-1H-pyrazol-4-yl]phenyl]methanone Example 103 was prepared as described for example 102, starting from intermediate 2 (22.9 mg, 84.6 umol) and 3-(5-(trifluoromethyl)-1H-pyrazol-4-yl)benzoic acid (intermediate 46, 26 mg, 102 umol). The crude was purified by silica column chromatography (MeOH in DCM 0% to 10%). The compound was obtained as a white solid (19.9 mg, 37.4%). ESI (MS) m/z=509.2 $[M+H]^+$ Example 105

4-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]-1H-pyridin-2-one Example 105 was prepared as described for example 102, starting from intermediate 2 (40 mg, 148 umol) and lithium 2-chloro-3-(2-oxo-1,2-dihydropyridin-4-yl)benzoate (intermediate 47, 37.8 mg, 148 umol). The crude was purified by silica column chromatography (MeOH in DCM 0% to 10%). The compound was obtained as a off-white solid (14.7 mg, 17.2%). ESI (MS) m/z=502.2 $[M+H]^+$ Example 106

5-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]-1H-pyridin-2-one Example 106 was prepared as described for example 102, starting from intermediate 2 (60 mg, 222 umol) and 2-chloro-3-(6-oxo-1,6-dihydropyridin-3-yl)benzoic acid (intermediate 48, 55 mg, 222 umol). The crude was purified by silica column chromatography (MeOH in DCM 0% to 10%). The compound was obtained as a white solid (12.8 mg, 10.8%). ESI (MS) m/z=502.2 $[M+H]^+$ Example 78

[(3R,9aS)-3-hydroxy-3-[6-(trifluoromethyl)-3-pyridyl]-1,4,6,7,9,9a-hexahydropyrazino[2,1-c][1,4]oxazin-8-yl]-[2-fluoro-3-(3-fluoro-1H-pyrazol-4-yl)phenyl]methanone Example 78 was prepared as described for example 102, starting from intermediate 8 (33.8 mg, 89.2 umol) and 2-fluoro-3-(3-fluoro-1H-pyrazol-4-yl)benzoic acid (intermediate 33, 20 mg, 89.2 umol). The crude was purified by silica column chromatography (MeOH in DCM 0% to 10%). The compound was obtained as a off-white solid (14.7 mg, 29.8%). ESI (MS) m/z=510.2 $[M+H]^+$ Example 80

4-[3-[(3R,9aS)-3-hydroxy-3-[6-(trifluoromethyl)-3-pyridyl]-1,4,6,7,9,9a-hexahydropyrazino[2,1-c][1,4]oxazine-8-carbonyl]-2-chloro-phenyl]-1H-pyrazole-3-carbonitrile Example 80 was prepared as described for example 102, starting from intermediate 8 (23.3 mg, 68.6 umol) and 2-chloro-3-(3-cyano-1H-pyrazol-4-yl)benzoic acid (intermediate 34, 17 mg, 68.6 umol). The crude was purified by silica column chromatography (MeOH in DCM 0% to 10%). The compound was obtained as a off-white solid (15.1 mg, 31%). ESI (MS) m/z=533.2 $[M+H]^+$

Example 81

[(3R,9aS)-3-hydroxy-3-[6-(trifluoromethyl)-3-pyridyl]-1,4,6,7,9,9a-hexahydropyrazino[2,1-c][1,4]oxazin-8-yl]-[3-(3-fluoro-1H-pyrazol-4-yl)phenyl]methanone Example 81 was prepared as described for example 102, starting from intermediate 8 (188 mg, 554 umol) and 2-chloro-3-(3-fluoro-1H-pyrazol-4-yl)benzoic acid (intermediate 29, 127 mg, 528 umol). The crude was purified by silica column chromatography (MeOH in DCM 0% to 10%). Dechlorinated example 81 was isolated as a byproduct (major product was example 65). The compound was obtained as a off-white solid (23.2 mg, 8.1%). ESI (MS) m/z=492.3 $[M+H]^+$

Example 85

[(3S,9aS)-3-hydroxy-3-[5-(trifluoromethyl)-2-pyridyl]-1,4,6,7,9,9a-hexahydropyrazino[2,1-c][1,4]oxazin-8-yl]-[2-chloro-3-(3-fluoro-1H-pyrazol-4-yl)phenyl]methanone Example 85 was prepared as described for example 102, starting from intermediate 9 (33.8 mg, 99.5 umol) and 2-chloro-3-(3-fluoro-1H-pyrazol-4-yl)benzoic acid (intermediate 29, 22.8 mg, 94.8 umol). The crude was purified by silica column chromatography (MeOH in DCM 0% to 10%). Dechlorinated example 81 was isolated as a byproduct (major product was example 65). The compound was obtained as a off-white solid (6.9 mg, 13.8%). ESI (MS) m/z=526.2 $[M+H]^+$

Example 86

[(3S,9aS)-3-hydroxy-3-[5-(trifluoromethyl)-2-pyridyl]-1,4,6,7,9,9a-hexahydropyrazino[2,1-c][1,4]oxazin-8-yl]-(2-chloro-3-oxazol-4-yl-phenyl)methanone Example 86 was prepared as described for example 102, starting from intermediate 9 (41 mg, 121 umol) and 2-chloro-3-(oxazol-5-yl)benzoic acid (intermediate 32, 27 mg, 121 umol). The crude was purified by silica column chromatography (MeOH in DCM 0% to 10%). The compound was obtained as a white solid (7 mg, 11.4%). ESI (MS) m/z=509.2 $[M+H]^+$

Example 97

[(3S,9aS)-3-[6-(trifluoromethyl)pyridazin-3-yl]-3,4,6,7,9,9a-hexahydro-1H-pyrazino[2,1-c][1,4]oxazin-8-yl]-[2-chloro-3-(3-fluoro-1H-pyrazol-4-yl)phenyl]methanone Example 97 was prepared as described for example 102, starting from intermediate 11 (22 mg, 76.3 umol) and 2-chloro-3-(3-fluoro-TH-pyrazol-4-yl)benzoic acid (intermediate 29, 27.5 mg, 91.6 umol). The crude was purified by reversed phase chromatography (Method B). The compound was obtained as a white solid (8.2 mg, 20.5%). ESI (MS) m/z=511.2 $[M+H]^+$

Example 82

[(3R,9aS)-3-hydroxy-3-[6-(trifluoromethyl)-3-pyridyl]-1,4,6,7,9,9a-hexahydropyrazino[2,1-c][1,4]oxazin-8-yl]-[2-chloro-3-(1H-pyrazol-4-yl)phenyl]methanone A microwave vial was charged with (2-chloro-3-(4,4,5,5-tetramethyl-1,3,2-dioxaborolan-2-yl)phenyl)((3R,9aS)-3-hydroxy-3-(6-(trifluoromethyl)pyridin-3-yl)hexahydropyrazino[2,1-c][1,4]oxazin-8(1H)-yl)methanone (0.064 g, 113 μmol, crude), 4-bromo-TH-pyrazole (18.2 mg, 124 μmol), K2CO3 (46.7 mg, 338 μmol) and combined with Dioxane (1.5 ml) and Water (0.5 ml). The reaction mixture was degassed and Bis(di-tert-butyl(4-dimethylaminophenyl)phosphine)dichloropalladium(II) (7.98 mg, 11.3 μmol) was added. It was then heated at 115° C. for 30 min. The reaction mixture was poured into 2 mL sat $NaHCO_3$ and extracted with EtOAc (2×5 mL). The organic layers were combined, washed with brine, dried over $Na_2SO_4$ and concentrated in vacuo. The crude material was purified by flash chromatography (silica gel, 0% to 10% MeOH in DCM): 10 mg of a mixture desired product+impurity. The yellow oil was purified by preparative HPLC (method B), to yield the product as a white lyophilized powder (2.1 mg, 3%). ESI (MS) m/z=506.31 $[M-H]^-$ a) (3-bromo-2-chlorophenyl)((3R,9aS)-3-hydroxy-3-(6-(trifluoromethyl)pyridin-3-yl)hexahydropyrazino[2,1-c][1,4]oxazin-8(1H)-yl)methanone In a 25 mL two-necked flask, (3R,9aS)-3-(6-(trifluoromethyl)pyridin-3-yl)octahydropyrazino[2,1-c][1,4]oxazin-3-ol hydrochloride (intermediate 8, 0.100 g, 294 μmol), 3-bromo-2-chlorobenzoic acid (83.2 mg, 353 μmol) and HATU (134 mg, 353 μmol) were combined with DMF (3 ml) to give a yellow solution. DIPEA (114 mg, 154 μl, 883 μmol) was added. The reaction mixture was stirred at RT for 1 h.

The reaction mixture was poured into 5 mL H2O and extracted with EtOAc (2×10 mL). The organic layers were combined, washed with brine, dried over $Na_2SO_4$ and concentrated in vacuo. The crude material was purified by flash chromatography (silica gel, 0% to 100% EtOAc in heptane). The product was obtained as a colorless oil (132 mg, 86%). ESI (MS) m/z=522.1 $[M+H]^+$ b) (2-chloro-3-(4,4,5,5-tetramethyl-1,3,2-dioxaborolan-2-yl)phenyl)((3R,9aS)-3-hydroxy-3-(6-(trifluoromethyl)pyridin-3-yl)hexahydropyrazino[2,1-c][1,4]oxazin-8(H)-yl)methanone In a microwave vial, Bis(pinacolato)diboron (83.7 mg, 330 μmol), (3-bromo-2-chlorophenyl)((3R,9aS)-3-hydroxy-3-(6-(trifluoromethyl)pyridin-3-yl)hexahydropyrazino[2,1-c][1,4]oxazin-8(1H)-yl)methanone (0.132 g, 253 μmol) and potassium acetate (74.6 mg, 760 μmol) were dispersed in Dioxane (1 ml) and degassed. [1,1'-Bis(diphenylphosphino)ferrocene]dichloropalladium(II) (31.1 mg, 38 μmol) was then added. It was reacted in the MW (100, 60 min). It was then mixed with water and extracted with EtOAc twice. The combined org. phases were washed with brine, dried over Na2SO4 and concentrated in vacuo. The crude material was attempted to purify by flash chromatography twice (silica gel, 50% to 100% EtOAc in heptane; silica gel, 0% to 10% MeOH in DCM) both leading to no separation. The crude product (brown oil, 64 mg, 44.5%) was used accordingly for the step directly. ESI (MS) m/z=568.3 $[M+H]^+$ Example 87

[3-(1,3-benzothiazol-2-yl)-6,7,9,9a-tetrahydro-1H-pyrazino[2,1-c][1,4]oxazin-8-yl]-(2-chloro-3-methoxy-phenyl)methanone (3-(benzo[d]thiazol-2-yl)-3-hydroxyhexahydropyrazino[2,1-c][1,4]oxazin-8(1H)-yl)(2-chloro-3-methoxyphenyl)methanone (150 mg, 326 umol) was dissolved in 9 mL DCM and 4.5 mL TFA. TES (420 uL, 2.61 mmol) was added and the reddish mixture stirred at RT under argon in a closed pressure vial. After 2 h, it was heated up to 60° C. After two days, the reaction was concentrated in vacuo, poured into EtOAc, washed with sat. bicarbonate solution, filtered, adsorbed on silica and purified by silica column chromatography (Hept:EtOAc 80:20 to 10:90). The described product after elimination was the main product and obtained as a yellow solid (40 mg, 28%). ESI (MS) m/z=442.2 $[M+H]^+$ a) (3-(benzo[d]thiazol-2-yl)-3-hydroxyhexahydropyrazino[2,1-c][1,4]oxazin-8(1H)-yl)(2-chloro-3-methoxyphenyl)methanone (2-chloro-3-methoxyphenyl)(3-(hydroxymethyl)piperazin-1-yl)methanone (intermediate 1, 96 mg, 337 umol) and DIPEA (65 uL, 371 umol) were dissolved in 2 mL dry THF and cooled down in an ice bath. 1-(benzo[d]thiazol-2-yl)-2-bromoethan-1-one (88 mg, 345 umol) was dissolved in 1 mL dry THF and added dropwise to the solution over 10 min. After 4 h, it was concentrated in vacuo. The red foam was dissolved in EtOAc and washed with sat. aq. bicarbonate solution and then water, dried ($Na_2SO_4$) and concentrated in vacuo. The compound was obtained as a slightly impure yellow-golden oil, 153 mg. It was used without further purification in the next step.

Example 88

[2-chloro-3-(3-fluoro-1H-pyrazol-4-yl)phenyl]-[(3S,9aS)-3-fluoro-3-[6-(trifluoromethyl)-3-pyridyl]-1,4,6,7,9,9a-hexahydropyrazino[2,1-c][1,4]oxazin-8-yl]methanone (2-chloro-3-(3-fluoro-1H-pyrazol-4-yl)phenyl)((3R,9aS)-3-hydroxy-3-(6-(trifluoromethyl)pyridin-3-yl)hexahydropyrazino[2,1-c][1,4]oxazin-8(1H)-yl)methanone (Example 65, 16.7 mg, 31.8 umol) was dissolved in 0.7 mL dry DCM and cooled to −78° C. DAST (6.6 mg, 41.3 umol) dissolved in 0.3 mL dry DCM was added dropwise. After 40 min, the white suspension was warmed up to room temperature. After overnight stirring, ca 20-30% conversion was visible so the flask was cooled down to −78° C. again and DAST (12 mg, 64 umol) in 0.2 mL dry DCM were added. Two hours later, it was warmed up to room temperature. Not much more progress was visible, so the mixture was cooled to −78° C. again and DAST (19 mg, 95 umol) in 0.2 mL dry DCM were added. 40 min later, it was warmed up to room temperature. 2 h later, it was concentrated in vacuo, diluted with sat. bicarbonate solution and extracted into EtOAc twice. The combined organic phases were dried over sodium sulfate, filtered and concentrated in vacuo and then purified by silica column chromatography (silica gel, 0% to 10% MeOH in DCM). The product was obtained as a slightly orange solid (13.9 mg, 68%). ESI (MS) m/z=528.2 $[M+H]^+$ Example 92 and Example 93

[(3R,9aS)-3-(3,4-difluorophenyl)-3-hydroxy-1,4,6,7,9,9a-hexahydropyrazino[2,1-c][1,4]oxazin-8-yl]-[2-chloro-3-(3-fluoro-1H-pyrazol-4-yl)phenyl]methanone and [(3R,9aS)-3-(3,4-difluorophenyl)-3-hydroxy-1,4,6,7,9,9a-hexahydropyrazino[2,1-c][1,4]oxazin-8-yl]-[3-(3-fluoro-1H-pyrazol-4-yl)phenyl]methanone (3R,9aS)-3-(3,4-difluorophenyl)octahydropyrazino[2,1-c][1,4]oxazin-3-ol hydrochloride (intermediate 10, 134 mg, 436 μmol), 2-chloro-3-(3-fluoro-1H-pyrazol-4-yl)benzoic acid (intermediate 29, 100 mg, 416 umol) and DIPEA (231 mg, 312 μl, 1.79 mmol) were mixed with 3.5 mL dry THF and cooled to 0° C. T3P (410 mg, 644 μmol) dissolved in 1 mL dry THF was added dropwise over 15 min. After 20 min, it was warmed up to RT and an hour later, it was concentrated in vacuo, diluted with EtOAc, washed with sat. ammonium chloride solution, dried over sodium sulfate, filtered and concentrated in vacuo. The crude was purified by silica column chromatography (MeOH in DCM 0% to 10%). It was then purified by prep HPLC (method B) to separate the 2 products.

Example 92 32.2 mg (13.8%), white lyophilized powder, ESI (MS) m/z=493.1 $[M+H]^+$ Example 93 11.4 mg (5.4%), white lyophilized powder, ESI (MS) m/z=459.2 $[M+H]^+$ Example 94

[(9aS)-3-[5-(trifluoromethyl)-2-pyridyl]-6,7,9,9a-tetrahydro-1H-pyrazino[2,1-c][1,4]oxazin-8-yl]-[2-chloro-3-(3-fluoro-1H-pyrazol-4-yl)phenyl]methanone (S)-3-(5-(trifluoromethyl)pyridin-2-yl)-1,6,7,8,9,9a-hexahydropyrazino[2,1-c][1,4]oxazine (23 mg, 80.6 umol), 2-chloro-3-(3-fluoro-1H-pyrazol-4-yl)benzoic acid (intermediate 29, 24.2 mg, 80.6 umol) and DIPEA (42 uL, 242 umol) were dissolved in 0.6 mL DMSO-d6 and 0.2 mL dry THF and cooled to 0° C. T3P (1.5 eq, 77 mg of a 50% wt/wt solution in EtOAc) in 0.2 mL dry THF was added dropwise. After 20 min, it was warmed up to RT. It was partly solid because of the frozen DMSO, but turned into a yellow solution quickly upon removing from the ice bath. The next morning, the reaction had still not gone to completion, so another 20 uL (1.5 eq) of DIPEA and 38 mg (0.75 eq) of T3P were added. 2 h later, it was diluted with sat. bicarbonate solution, extracted twice into EtOAc, dried over sodium sulfate, filtered and concentrated in vacuo. Purification by reversed phase HPLC (method B) lead to the product which was obtained as a bright yellow solid (7.5 mg, 18.3%). ESI (MS) m/z=508.2 $[M+H]^+$ a) S)-3-(5-(trifluoromethyl)pyridin-2-yl)-1,6,7,8,9,9a-hexahydropyrazino[2,1-c][1,4]oxazine (3S,9aS)-3-(5-(trifluoromethyl)pyridin-2-yl)octahydropyrazino[2,1-c][1,4]oxazin-3-ol hydrochloride (intermediate 9, 130 mg, 383 umol) was dissolved in 5.3 mL TFA and 10.6 mL dry DCM upon which TES (183 uL, 1.15 mmol) were added and the yellow solution was stirred at room temperature. After heating at 70° C. for 2.5 days, the bright yellow solution was concentrated in vacuo, diluted with 1 M HCl and washed with diethyl ether twice. The ether phase was then backextracted with brine. The yellow aqeuous solution was basified with 4 M NaOH, treated with sodium chloride, extracted into excess EtOAc, dried over sodium sulfate, filtered and concentrated in vacuo. The product was obtained as a neon yellow solid (24 mg, 22%). In contrast to the desired dehydroxylated product, dehydratation occurred, leading to the unsaturated product. ESI (MS) m/z=286.2 $[M+H]^+$ Example 95 and Example 96

[(3R,9aS)-3-(3,4-difluorophenyl)-3,4,6,7,9,9a-hexahydro-1H-pyrazino[2,1-c][1,4]oxazin-8-yl]-[2-chloro-3-(3-fluoro-1H-pyrazol-4-yl)phenyl]methanone and [(3S,9aS)-3-(3,4-difluorophenyl)-3,4,6,7,9,9a-hexahydro-1H-pyrazino[2,1-c][1,4]oxazin-8-yl]-[2-chloro-3-(3-fluoro-1H-pyrazol-4-yl)phenyl]methanone (2-chloro-3-(3-fluoro-1H-pyrazol-4-yl)phenyl)((3R,9aS)-3-(3,4-difluorophenyl)-3-hydroxyhexahydropyrazino[2,1-c][1,4]oxazin-8(1H)-yl)methanone (example 92, 18 mg, 36.5 μmol) was dissolved in 1 mL dry DCM. 2,2,2-trifluoroacetic acid (750 mg, 506 μl, 6.57 mmol) and triethylsilane (12.7 mg, 17.5 μl, 110 μmol) were added. The colorless solution was stirred at room temperature for 3 hours. The crude was diluted with EtOAc, washed with sat. $NaHCO_3$ solution, filtered and concentrated in vacuo. The crude material was purified by preparative HPLC (method B):

Example 95, major isomer (trans), 8.6 mg (49.4%), white lyophilized powder, ESI (MS) m/z=477.1 $[M+H]^+$ Example 96, minor isomer (cis), 1.5 mg (8.6%), white lyophilized powder, ESI (MS) m/z=477.2 $[M+H]^+$ Example 100

3-[(3R,9aS)-8-[2-chloro-3-(3-fluoro-1H-pyrazol-4-yl)benzoyl]-3-hydroxy-1,4,6,7,9,9a-hexahydropyrazino[2,1-c][1,4]oxazin-3-yl]-6-(trifluoromethyl)-1H-pyridin-2-one 3-((3R,9aS)-3-hydroxyoctahydropyrazino[2,1-c][1,4]oxazin-3-yl)-6-(trifluoromethyl)pyridin-2(1H)-one (intermediate 12, 15 mg, 47 umol), 2-chloro-3-(3-fluoro-1H-pyrazol-4-yl)benzoic acid (intermediate 29, 12.5 mg, 51.7 umol), EDC hydrochloride (13.5 mg, 70.5 umol) and HOBT monohydrate (8 mg, 51.7 umol) were mixed with 0.6 mL dry DMF upon which DIPEA (25 uL, 141 umol) was added. The yellow mixture was stirred at room temperature. After 4.5 h the mixture was diluted with EtOAc and washed with sat. bicarbonate solution and then brine. The organic phase was dried over sodium sulfate, filtered and concentrated in vacuo. The yellow crude material was purified by silica column chromatography (MeOH in DCM 0% to 10%). The obtained solid was still impure and further purified by reversed phase HPLC (Method B).

The product was obtained as a light yellow solid (2.5 mg, 9%), ESI (MS) m/z=542.2 $[M+H]^+$ Example 109

4-[3-[(3R,9aS)-3-(3-chloro-4-fluoro-phenyl)-3-hydroxy-1,4,6,7,9,9a-hexahydropyrazino[2,1-c][1,4]oxazine-8-carbonyl]-2-chloro-phenyl]-1H-pyrrole-2-carbonitrile Synthesis of example 109 was carried out as described for example 127, starting from Intermediate 52 and 4-bromo-1H-pyrrole-2-carbonitrile. Purification by preparative HPLC (Method B). Yield 2.4 mg, 4%. ESI (MS) m/z=515.3 $[M+H]^+$ Example 114

4-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-5-fluoro-phenyl]-1H-pyridin-2-one (3-bromo-2-chloro-5-fluorophenyl)((3R,9aS)-3-(3-chloro-4-fluorophenyl)hexahydropyrazino[2,1-c][1,4]oxazin-8(1H)-yl)methanone (intermediate 50, 1 eq, 50 mg), (2-oxo-1,2-dihydropyridin-4-yl)boronic acid (1.2 eq, 16.5 mg), potassium carbonate (3 eq, 41 mg) and 1,1'-bis(diphenylphosphino)ferrocene-palladium(II)dichloride dichloromethane complex (0.1 eq, 8 mg) were mixed with 0.9 ml dioxane and 0.1 ml water, degassed with argon and reacted in the microwave (115° C., 25 min). Another 30 mg of (2-oxo-1,2-dihydropyridin-4-yl)boronic acid and 30 uL DIPEA were added and the mixture reacted again (115° C., 30 min).

The reaction was still not complete but the boronate consumed again, so another 40 mg (2-oxo-1,2-dihydropyridin-4-yl)boronic acid and 30 uL DIPEA was added and the mixture reacted again (115° C., 30 min). The reaction was still not complete but the boronate consumed again, so another 60 mg boronic acid and 30 uL DIPEA was added and the mixture reacted again (115° C., 30 min). The reaction was still not complete but was worked up anyway: It was diluted with EtOAc and washed with water and then sat. aq. bicarbonate solution, dried over sodium sulfate, filtered and concentrated in vacuo. It was purified by silica column chromatography (10 g, MeOH in DCM 0% to 10%). The crude product was submitted to HPLC purification (Method B) and obtained as a white solid. (10 mg, 19%). ESI (MS) m/z=520.3 $[M+H]^+$ Example 119

[(3R,9aS)-3-hydroxy-3-[4-(trifluoromethyl)phenyl]-1,4,6,7,9,9a-hexahydropyrazino[2,1-c][1,4]oxazin-8-yl]-(2-chloro-3-methoxy-phenyl)methanone Example 119 was synthesized as described for example 65, starting from intermediate 1S and 2-bromo-1-(4-(trifluoromethyl)phenyl)ethan-1-one (CAS 383-53-9). Yield 145 mg, 78%. ESI (MS) m/z=471.3 $[M+H]^+$ Example 120

[(3R,9aS)-3-(4-chloro-3-fluoro-phenyl)-3-hydroxy-1,4,6,7,9,9a-hexahydropyrazino[2,1-c][1,4]oxazin-8-yl]-(2-chloro-3-methoxy-phenyl)methanone Example 120 was synthesized as described for example 65, starting from intermediate 1S and 2-bromo-1-(4-chloro-3-fluorophenyl)ethan-1-one (CAS 63529-30-6). Yield 165 mg, 82%. ESI (MS) m/z=455.2 $[M+H]^+$ Example 125

[(3R,9aS)-3-(3-bromo-5-chloro-phenyl)-3-hydroxy-1,4,6,7,9,9a-hexahydropyrazino[2,1-c][1,4]oxazin-8-yl]-(2-chloro-3-methoxy-phenyl)methanone Example 125 was synthesized as described for example 65, starting from intermediate 1S and 2-bromo-1-(3-bromo- 5-chlorophenyl)ethan-1-one (CAS 41011-01-2). Yield 119 mg, 66%. ESI (MS) m/z=517.2 $[M+H]^+$ Example 127

[(3R,9aS)-3-(3-chloro-4-fluoro-phenyl)-3-hydroxy-1,4,6,7,9,9a-hexahydropyrazino[2,1-c][1,4]oxazin-8-yl]-(2-chloro-3-isothiazol-4-yl-phenyl)methanone (2-chloro-3-(4,4,5,5-tetramethyl-1,3,2-dioxaborolan-2-yl)phenyl)((3R,9aS)-3-(3-chloro-4-fluorophenyl)-3-hydroxyhexahydropyrazino[2,1-c][1,4]oxazin-8(1H)-yl) methanone (Intermediate 52, 0.060 g, 109 μmol), 4-bromoisothiazole (19.6 mg, 120 μmol), $K_2CO_3$ (45.1 mg, 327 μmol) were combined with Dioxane (1.5 ml) and Water (250 μl) in a microwave vial.

The reaction mixture was degassed and bis(di-tert-butyl (4-dimethylaminophenyl)phosphine)dichloropalladium(II) ($APhos_2$ $PdCl_2$, 7.71 mg, 10.9 μmol) was added. The vial was sealed and heated at 80° C. for 2 hours. The reaction mixture was poured into 2 mL sat $NaHCO_3$ and extracted with EtOAc (2×5 mL). The organic layers were combined, washed with brine, dried over $Na_2SO_4$ and concentrated in vacuo. The crude material was purified by flash chromatography (silica gel, 20 g, 0% to 10% MeOH in DCM) to yield a crude product, which was further purified by preparative HPLC (Method J). Eventually the product was obtained as 4 mg (7%) of white lyophilized powder. ESI (MS) m/z=508.1 $[M+H]^+$ Example 128

[(3R,9aS)-3-(2,4,5-trifluorophenyl)-3,4,6,7,9,9a-hexahydro-1H-pyrazino[2,1-c][1,4]oxazin-8-yl]-(2-chloro-3-methoxy-phenyl)methanone (2-chloro-3-methoxyphenyl)((3R,9aS)-3-hydroxy-3-(2,4,5-trifluorophenyl)hexahydropyrazino[2,1-c][1,4]oxazin-8(1H)-yl)methanone (Example 144, 1 eq, 37 mg) was dissolved in 1 mL dry DCM and 0.5 mL TFA at room temperature. TES (3 eq, 35 uL) was added and the yellowish solution stirred at 40° C. for 5 h and then at room temperature overnight. It was then concentrated in vacuo and purified by silica column chromatography (10 g, MeOH in DCM 0% to 10%). The product was obtained as a yellow oil (28 mg, 80%). ESI (MS) m/z=441.2 $[M+H]^+$ Example 129

[(3R,9aS)-3-(2,4-dichlorophenyl)-3-hydroxy-1,4,6,7,9,9a-hexahydropyrazino[2,1-c][1,4]oxazin-8-yl]-(2-chloro-3-methoxy-phenyl)methanone Example 129 was synthesized as described for example 65, starting from intermediate 1S and 2-bromo-1-(2,4-dichlorophenyl)ethan-1-one (CAS 2631-72-3). Yield 163 mg, 82%. ESI (MS) m/z 20=473.2 $[M+H]^+$ Example 130

[(3R,9aS)-3-hydroxy-3-(2,3,4-trifluorophenyl)-1,4,6,7,9,9a-hexahydropyrazino[2,1-c][1,4]oxazin-8-yl]-(2-chloro-3-methoxy-phenyl)methanone Example 130 was synthesized as described for example 65, starting from intermediate 1S and 2-bromo-1-(2,3,4-trifluorophenyl)ethan-1-one (CAS 1214345-02-4). Yield 109 mg, 55%. ESI (MS) m/z=457.3 $[M+H]^+$ Example 131

[(3S,9aS)-3-(4-bromo-5-methoxy-2-thienyl)-3-hydroxy-1,4,6,7,9,9a-hexahydropyrazino[2,1-c][1,4]oxazin-8-yl]-(2-chloro-3-methoxy-phenyl)methanone Example 131 was synthesized as described for example 65, starting from intermediate 1S and 2-bromo-1-(4-bromo-5-methoxythiophen-2-yl)ethan-1-one (CAS 882748-05-2). Purification by HPLC, Method J. Yield 22.6 mg, 22%. ESI (MS) m/z=519.2 $[M+H]^+$ Example 136

3-[(3R,9aS)-8-(2-chloro-3-methoxy-benzoyl)-3-hydroxy-1,4,6,7,9,9a-hexahydropyrazino[2,1-c][1,4]oxazin-3-yl]-6-(trifluoromethyl)-1H-pyridin-2-one Example 136 was synthesized as described for example 65, starting from intermediate 1S and 3-(2-bromoacetyl)-6-(trifluoromethyl)pyridin-2(1H)-one (CAS 1000931-76-9). Purification by HPLC, Method B. Yield 10.4 mg, 7.5%. ESI (MS) m/z=488.3 $[M+H]^+$ Example 137

[(3R,9aS)-3-(3-chloro-4-oxazol-5-yl-phenyl)-3,4,6,7,9,9a-hexahydro-1H-pyrazino[2,1-c][1,4]oxazin-8-yl]-(2-chloro-3-methoxy-phenyl)methanone ((3R,9aS)-3-(4-bromo-3-chlorophenyl)hexahydropyrazino[2,1-c][1,4]oxazin-8(1H)-yl)(2-chloro-3-methoxyphenyl)methanone (Example 110, 0.075 g, 150 μmol), oxazole (20.7 mg, 300 μmol, Eq: 2), $Pd(OAc)_2$ (1.68 mg, 7.5 μmol), potassium carbonate (62.2 mg, 450 μmol), pivalic acid (6.13 mg, 60 μmol) and di-tert-butyl(2',4',6'-triisopropyl-3,4,5,6-tetramethyl-[1,1'-biphenyl]-2-yl)phosphane (7.21 mg, 15 μmol) were dispersed in DMA (2 ml), degassed and heated to 110° C. in a thermoblock for 2 hours. It was then cooled down to RT, diluted with water and extracted with EtOAc twice. The organic phases were combined, washed with brine (×2), dried over sodium sulfate, filtered and conc. in vacuo. The crude material was purified by flash chromatography (silica gel, 20 g, 0% to 10% MeOH in DCM). Yield 29 mg, 35%. ESI (MS) m/z=488.3 $[M+H]^+$ Example 139

[(3S,9aS)-3-[2-(4-fluorophenyl)thiazol-4-yl]-3-hydroxy-1,4,6,7,9,9a-hexahydropyrazino[2,1-c][1,4]oxazin-8-yl]-(2-chloro-3-methoxy-phenyl)methanone Example 139 was synthesized as described for example 65, starting from intermediate 1S and 2-bromo-1-(2-(4-fluorophenyl)thiazol-4-yl)ethan-1-one (CAS 937079-09-9). Yield 68 mg, 75%. ESI (MS) m/z=504.3 $[M+H]^+$ Example 141

[(3R,9aS)-3-hydroxy-3-[3-(trifluoromethyl)phenyl]-1,4,6,7,9,9a-hexahydropyrazino[2,1-c][1,4]oxazin-8-yl]-(2-chloro-3-methoxy-phenyl)methanone Example 141 was synthesized as described for example 65, starting from intermediate 1S and 2-bromo-1-(3-(trifluoromethyl)phenyl)ethan-1-one (CAS 2003-10-3). Yield 135 mg, 71%. ESI (MS) m/z=471.3 $[M+H]^+$ Example 142

[(3R,9aS)-3-(2,3-difluorophenyl)-3-hydroxy-1,4,6,7,9,9a-hexahydropyrazino[2,1-c][1,4]oxazin-8-yl]-(2-chloro-3-methoxy-phenyl)methanone Example 142 was synthesized as described for example 65, starting from intermediate 1S and 2-bromo-1-(2,3-difluorophenyl)ethan-1-one (CAS 886762-77-2). Yield 150 mg, 72%. ESI (MS) m/z=439.2 $[M+H]^+$ Example 143

[(3S,9aS)-3-hydroxy-3-(3-phenylisoxazol-5-yl)-1,4,6,7,9,9a-hexahydropyrazino[2,1-c][1,4]oxazin-8-yl]-(2-chloro-3-methoxy-phenyl)methanone Example 143 was synthesized as described for example 65, starting from intermediate 1S and 2-bromo-1-(3-phenylisoxazol-5-yl)ethan-1-one (CAS 14731-14-7). Yield 124 mg, 70%. ESI (MS) m/z=470.3 $[M+H]^+$ Example 144

[(3R,9aS)-3-hydroxy-3-(2,4,5-trifluorophenyl)-1,4,6,7,9,9a-hexahy dropyrazino[2,1-c][1,4]oxazin-8-yl]-(2-chloro-3-methoxy-phenyl)methanone Example 144 was synthesized as described for example 65, starting from intermediate 1S and 2-bromo-1-(2,4,5-trifluorophenyl)ethan-1-one (CAS 193977-34-3). Yield 58 mg, 36%. ESI (MS) m/z=457.2 $[M+H]^+$ Example 145

[(9aS)-3-(4-fluoro-3-oxazol-5-yl-phenyl)-3,4,6,7,9,9a-hexahydro-1H-pyrazino[2,1-c][1,4]oxazin-8-yl]-(2-chloro-3-methoxy-phenyl)methanone ((9aS)-3-(3-bromo-4-fluorophenyl)hexahydropyrazino[2,1-c][1,4]oxazin-8(1H)-yl)(2-chloro-3-methoxyphenyl)methanone (Example 6, 0.075 g, 155 μmol), oxazole (21.4 mg, 310 μmol), $Pd(OAc)_2$ (1.74 mg, 7.75 μmol), potassium carbonate (64.3 mg, 465 μmol), pivalic acid (6.33 mg, 7.2 μl, 62 μmol) and di-tert-butyl(2',4',6'-triisopropyl-3,4,5,6-tetramethyl-[1,1'-biphenyl]-2-yl)phosphine (tBuXPhos) (7.45 mg, 15.5 μmol) were dispersed in DMA (2 ml), degassed and heated to 110° C. in a thermoblock for 2 hours. It was then cooled down to RT, diluted with water and extracted with EtOAc twice. The organic phases were combined, washed with brine (×2), dried over sodium sulfate, filtered and concentrated in vacuo. The crude material was purified by flash chromatography (silica gel, 20 g, 0% to 10% MeOH in DCM). Yield 38 mg, 48%, light brown oil. ESI (MS) m/z=472.3 $[M+H]^+$ Example 146

[(3S,9aS)-3-(1,3-benzothiazol-2-yl)-3-hydroxy-1,4,6,7,9,9a-hexahydropyrazino[2,1-c][1,4]oxazin-8-yl]-(2-chloro-3-methoxy-phenyl)methanone Example 146 was synthesized as described for example 65, starting from intermediate 1S and 1-(1,3-Benzothiazol-2-yl)-2-bromoethan-1-one (CAS 54223-20-0). Yield 118 mg, 68%. ESI (MS) m/z=460.3 $[M+H]^+$ Example 149

[(3R,9aS)-3-(2,3-difluorophenyl)-3,4,6,7,9,9a-hexahydro-1H-pyrazino[2,1-c][1,4]oxazin-8-yl]-(2-chloro-3-methoxy-phenyl)methanone

[(3R,9aS)-3-(2,3-difluorophenyl)-3-hydroxy-1,4,6,7,9,9a-hexahydropyrazino[2,1-c][1,4]oxazin-8-yl]-(2-chloro-3-methoxy-phenyl)methanone (Example 142, 50 mg, 114 umol) was dissolved in 575 ul dry DCM and 262 ul TFA at room temperature. TES (55 uL, 342 umol) was added and the yellowish solution stirred at 45° C. for 2 h. It was then concentrated in vacuo and purified by silica column chromatography (10 g, MeOH in DCM 0% to 10%) and subsequently by preparative HPLC (Method B). The product was obtained as a yellow oil (20 mg, 39%). ESI (MS) m/z=423.2 $[M+H]^+$ Example 150

[(3R,9aS)-3-(2-chlorophenyl)-3-hydroxy-1,4,6,7,9,9a-hexahydropyrazino[2,1-c][1,4]oxazin-8-yl]-(2-chloro-3-methoxy-phenyl)methanone Example 150 was synthesized as described for example 65, starting from intermediate 1S and 2-bromo-1-(2-chlorophenyl)ethan-1-one (CAS 5000-66-8). Yield 128 mg, 62%. ESI (MS) m/z=437.3 $[M+H]^+$ Example 153

[(3R,9aS)-3-hydroxy-3-[2-methyl-6-(trifluoromethyl)-3-pyridyl]-1,4,6,7,9,9a-hexahydropyrazino[2,1-c][1,4]oxazin-8-yl]-(2-chloro-3-methoxy-phenyl)methanone Example 153 was synthesized as described for example 65, starting from intermediate 1S and 2-bromo-1-(2-methyl-6-(trifluoromethyl)pyridin-3-yl)ethan-1-one, bromide salt (CAS 1377962-47-4). Yield 63 mg, 67%. ESI (MS) m/z=486.3 $[M+H]^+$ Example 154

[(3R,9aS)-3-(3-chloro-5-oxazol-5-yl-phenyl)-3-hydroxy-1,4,6,7,9,9a-hexahydropyrazino[2,1-c][1,4]oxazin-8-yl]-(2-chloro-3-methoxy-phenyl)methanone Synthesis was performed as described for example 145, starting from [(3R,9aS)-3-(3-bromo-5-chloro-phenyl)-3-hydroxy-1,4,6,7,9,9a-hexahydropyrazino[2,1-c][1,4]oxazin-8-yl]-(2-chloro-3-methoxy-phenyl)methanone (Example 125, 91 mg, 176 umol) and oxazole (24.3 mg, 252 umol). Yellow oil, Yield 46 mg, 51%. ESI (MS) m/z=504.3 $[M+H]^+$ Example 156

[(9aS)-3-[4-fluoro-3-(1-methylpyrrol-3-yl)phenyl]-3,4,6,7,9,9a-hexahydro-1H-pyrazino[2,1-c][1,4]oxazin-8-yl]-(2-chloro-3-methoxy-phenyl)methanone ((9aS)-3-(3-bromo-4-fluorophenyl)hexahydropyrazino[2,1-c][1,4]oxazin-8(1H)-yl)(2-chloro-3-methoxyphenyl)

methanone (Example 6, 0.075 g, 155 μmol),1-methyl-3-(4,4,5,5-tetramethyl-1,3,2-dioxaborolan-2-yl)-1H-pyrrole (32.1 mg, 155 μmol), $K_2CO_3$ (64.3 mg, 465 μmol) were combined with Dioxane (1.5 ml) and Water (0.25 ml) in a microwave vial. The reaction mixture was degassed and bis(di-tert-butyl(4-dimethylaminophenyl)phosphine)dichloropalladium(II) (11 mg, 15.5 μmol) was added. The reaction was heated at 80° C. for 2 hours and then poured into 2 mL sat $NaHCO_3$ and extracted with EtOAc (2×5 mL). The organic layers were combined, washed with brine, dried over $Na_2SO_4$ and concentrated in vacuo. The crude material was purified by flash chromatography (silica gel, 20 g, 0% to 10% MeOH in DCM), yielding 77 mg of a crude product, which was further purified by preparative HPLC (Method B). The product was obtained as a yellow lyophilized powder. Yield 28 mg, 36%. ESI (MS) m/z=484.4 $[M+H]^+$

Example 157

[(3S,9aS)-3-(3-bromoisoxazol-5-yl)-3-hydroxy-1,4,6,7,9,9a-hexahydropyrazino[2,1-c][1,4]oxazin-8-yl]-(2-chloro-3-methoxy-phenyl)methanone Example 157 was synthesized as described for example 65, starting from intermediate 1S and 2-bromo-1-(3-bromoisoxazol-5-yl)ethan-1-one (CAS 76596-54-8). Yield 13.6 mg, 15%. ESI (MS) m/z=474.2 $[M+H]^+$

Example 160

[(3S,9aS)-3-hydroxy-3-[2-(6-methoxy-3-pyridyl)thiazol-4-yl]-1,4,6,7,9,9a-hexahydropyrazino[2,1-c][1,4]oxazin-8-yl]-(2-chloro-3-methoxy-phenyl)methanone Example 160 was synthesized as described for example 65, starting from intermediate 1S and 2-bromo-1-(2-(6-methoxypyridin-3-yl)thiazol-4-yl)ethan-1-one (Intermediate 70). Yield 10 mg, 19%. ESI (MS) m/z=517.3 $[M+H]^+$

Example 161 & Example 162

[(9aS)-3-(3-chloro-4-fluoro-phenyl)-3,4,6,7,9,9a-hexahydro-1H-pyrazino[2,1-c][1,4]thiazin-8-yl]-(2-chloro-3-methoxy-phenyl)methanone In a 25 ml glass tube under argon, S-(((2S)-1-(2-chloro-2-(3-chloro-4-fluorophenyl)ethyl)-4-(2-chloro-3-methoxybenzoyl)piperazin-2-yl)methyl) ethanethioate (100 mg, 187 μmol) in THF (10 ml) was treated with sodium methoxide 25% in methanol (121 mg, 129 μl, 562 μmol). The yellow mixture was stirred at 20-22° C. under argon for lhr. LCMS showed the formation of the desired product as a pair of diastereomers. The reaction mixture was concentrated and partitioned between ethyl acetat and water. The organic layer was separated and washed with brine, dried and evaporated to dryness get the crude product as a yellow oil (95 mg). The crude product was purified by SFC, Reprospher 100 PEI, 10% MeOH.

Example 161, first eluting diastereomer, 23 mg (26%), ESI (MS) m/z=455.2 $[M+H]^+$ Example 162, second eluting diastereomer, 24 mg (27%), ESI (MS) m/z=455.2 $[M+H]^+$ a) (2-chloro-3-methoxyphenyl)(4-(2-(3-chloro-4-fluorophenyl)-2-hydroxyethyl)-3-(hydroxymethyl)piperazin-1-yl)methanone 2-(3-chloro-4-fluorophenyl)oxirane (210 mg, 1.22 mmol) and (S)-(2-chloro-3-methoxyphenyl)(3-(hydroxymethyl)piperazin-1-yl)methanone (intermediate 1S, 440 mg, 1.54 mmol) were dissolved in 7 mL MeOH and reacted in the microwave (120° C., 60 min). It was concentrated in vacuo and purified by silica column chromatography (70 g, MeOH in DCM 0% to 10%). Product was obtained as an yellow oil (206 mg, 37%). ESI (MS) m/z=457.2 $[M+H]^+$ b) S-(((2S)-4-(2-chloro-3-methoxybenzoyl)-1-(2-(3-chloro-4-fluorophenyl)-2-hydroxyethyl)piperazin-2-yl)methyl) ethanethioate In a 25 ml glass tube under argon, (2-chloro-3-methoxyphenyl)(4-(2-(3-chloro-4-fluorophenyl)-2-hydroxyethyl)-3-(hydroxymethyl)piperazin-1-yl)methanone (175 mg, 383 μmol) was dissolved in THF (3.8 ml) and cooled to 0° C. TEA (46.5 mg, 64 μl, 459 μmol) was added followed by addition of methanesulfonyl chloride (48.2 mg, 32.8 μl, 421 μmol), and DMAP (4.68 mg, 38.3 μmol). The ice bath was removed and stirring was continued for 2 hr. The reaction mixture was then concentrated under reduced pressure. The resulting material was re-dissolved in DMSO 3 ml and treaded with potassium thioacetate (58.1 mg, 509 μmol). The reaction mixture ws stirred at RT under argon overnight. The mixture was diluted with ethyl acetate and washed with water (3 times) and brine, dried ($Na_2SO_4$), filtered and concentrated. The crude product was purified by flash chromatography (silica gel, 100% heptane to 80% EtOAc/heptane) to give the desired product as a light brown oil (110 mg, 50%). ESI (MS) m/z=515.3 $[M+H]^+$ c) S-(((2S)-1-(2-chloro-2-(3-chloro-4-fluorophenyl)ethyl)-4-(2-chloro-3-methoxybenzoyl)piperazin-2-yl)methyl) ethanethioate In a 2 5 ml glass tube under argon, to S-(((2S)-4-(2-chloro-3-methoxybenzoyl)-1-(2-(3-chloro-4-fluorophenyl)-2-hydroxyethyl)piperazin-2-yl)methyl) ethanethioate (110 mg, 213 μmol) in DCM (2.5 ml) was added thionyl chloride (76.2 mg, 46.7 μl, 640 μmol). The mixture was cooled with an ice bath and pyridine (67.5 mg, 69 μl, 854 μmol) was added in 0.5 ml DCM dropwise. The reaction mixture was stirred at 0-2° C. for 20 min, and then allowed to warm to room temperature over a hour and finally stirred over night at room temperature. The reaction mixture was concentrated and the residue was diluted with ethyl acetate, washed with 2×10 ml water and brine. The organic layer was separated, dried with Na2SO4, filtered and concentrated in vacuum. Product obtained as a Product obtained as a yellow oil, used directly in the next step (105 mg, crude). ESI (MS) m/z=535.3 $[M+H]^+$

Example 163

A compound of formula (I) can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example 164

A compound of formula (I) can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

The invention claimed is:

1. A compound of formula (I):

(I)

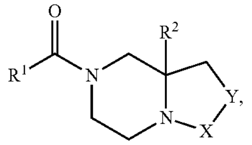

or a pharmaceutically acceptable salt thereof, wherein:

X is —$CH_2CR^3R^4$— or —CH═$CR^3$—;

Y is —O— or —S;

$R^1$ is (a) 5- to 10-membered heteroaryl substituted with 1 substituent selected from halogen; or (b) a group

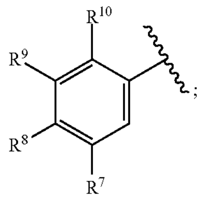

$R^2$ is hydrogen or $C_1$-$C_6$-alkyl;

$R^3$ is a group

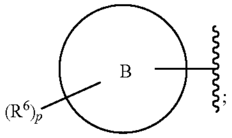

$R^4$ is hydrogen, halogen or hydroxy;

$R^5$ is hydrogen, halogen, hydroxy, halo-$C_1$-$C_6$-alkyl, $C_1$-$C_6$-alkoxy, $C_1$-$C_6$-alkyl, halo-$C_1$-$C_6$-alkoxy, cyano or oxo;

$R^6$ is hydrogen, halogen, $C_6$-$C_{10}$-aryl, 5- to 10-membered heteroaryl, halo-$C_1$-$C_6$-alkoxy, halo-$C_1$-$C_6$-alkyl, oxo, $C_1$-$C_6$-alkyl, $C_1$-$C_6$-alkoxy, $C_2$-$C_6$-alkenyl, $C_2$-$C_6$-alkynyl, $C_3$-$C_{14}$-cycloalkyl or cyano; wherein said 5- to 10-membered heteroaryl or $C_6$-$C_{10}$-aryl is optionally substituted with 1-2 substituents selected from halogen, cyano, -amino, hydroxy, $C_1$-$C_6$-alkyl and $C_1$-$C_6$-alkoxy;

$R^7$ is hydrogen or $C_1$-$C_6$-alkoxy;

$R^8$ is hydrogen or $C_1$-$C_6$-alkoxy;

$R^9$ is hydrogen, $C_1$-$C_6$-alkyl, $C_1$-$C_6$-alkoxy, halo-$C_1$-$C_6$-alkoxy or a group

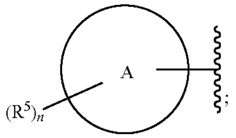

$R^{10}$ is hydrogen, halogen, or cyano;

A and B are each independently 5- to 10-membered heteroaryl, $C_6$-$C_{10}$-aryl or 3- to 14-membered heterocyclyl; and n and p are each independently 1, 2, 3, 4 or 5.

2. The compound of claim 1, or a pharmaceutically acceptable salt thereof, wherein X is —$CH_2CR^3R^4$—.

3. The compound of claim 1, or a pharmaceutically acceptable salt thereof, wherein Y is —O—.

4. The compound of claim 1, or a pharmaceutically acceptable salt thereof, wherein $R^1$ is phenyl substituted with 2-3 substituents independently selected from chloro, fluoro, methoxy, and a group

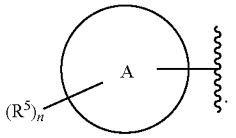

5. The compound of claim 1, or a pharmaceutically acceptable salt thereof, wherein $R^2$ is hydrogen.

6. The compound of claim 1, or a pharmaceutically acceptable salt thereof, wherein $R^4$ is hydrogen or hydroxy.

7. The compound of claim 1, or a pharmaceutically acceptable salt thereof, wherein $R^5$ is hydrogen, halogen, cyano, hydroxy or oxo.

8. The compound of claim 1, or a pharmaceutically acceptable salt thereof, wherein $R^5$ is hydrogen, fluoro, cyano, hydroxy or oxo.

9. The compound of claim 1, or a pharmaceutically acceptable salt thereof, wherein $R^6$ is hydrogen, halogen, $C_6$-$C_{10}$-aryl, 5- to 10-membered heteroaryl, halo-$C_1$-$C_6$-alkoxy, halo-$C_1$-$C_6$-alkyl, oxo, $C_1$-$C_6$-alkyl, $C_1$-$C_6$-alkoxy, $C_2$-$C_6$-alkenyl, $C_2$-$C_6$-alkynyl, $C_3$-$C_{14}$-cycloalkyl or cyano, wherein said 5- to 10-membered heteroaryl or $C_6$-$C_{10}$-aryl is optionally substituted with a substituent selected from halogen, $C_1$-$C_6$-alkyl and $C_1$-$C_6$-alkoxy.

10. The compound of claim 1, or a pharmaceutically acceptable salt thereof, wherein $R^6$ is halogen, oxo, halo-$C_1$-$C_6$-alkyl or halo-$C_1$-$C_6$-alkoxy.

11. The compound of claim 1, or a pharmaceutically acceptable salt thereof, wherein $R^6$ is chloro, fluoro, oxo, trifluoromethyl or difluoromethoxy.

12. The compound of claim 1, or a pharmaceutically acceptable salt thereof, wherein n is 1 or 2.

13. The compound of claim 1, or a pharmaceutically acceptable salt thereof, wherein p is 1, 2 or 3.

14. The compound of claim 1, or a pharmaceutically acceptable salt thereof, wherein p is 1 or 2.

15. The compound of claim 1, or a pharmaceutically acceptable salt thereof, wherein A is 5- to 10-membered heteroaryl, phenyl or 3- to 14-membered heterocyclyl.

16. The compound of claim 1, or a pharmaceutically acceptable salt thereof, wherein A is 5- to 10-membered heteroaryl or 3- to 14-membered heterocyclyl.

17. The compound of claim 1, or a pharmaceutically acceptable salt thereof, wherein A is imidazolyl, pyrazolyl, pyrrolyl, or 1,2-dihydropyridinyl.

18. The compound of claim 1, or a pharmaceutically acceptable salt thereof, wherein B is phenyl, 5- to 10-membered heteroaryl or 3- to 14-membered heterocyclyl.

19. The compound of claim 1, or a pharmaceutically acceptable salt thereof, wherein B is phenyl, 1,2-dihydropyridinyl or pyridyl.

20. The compound of claim 1, or a pharmaceutically acceptable salt thereof, wherein:

X is $—CH_2CR^3R^4—$;

Y is —O—;

$R^1$ is phenyl substituted with 2-3 substituents independently selected from chloro, fluoro, methoxy, and a group

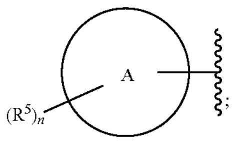

$R^2$ is hydrogen;

$R^4$ is hydrogen or hydroxy;

$R^5$ is hydrogen, halogen, hydroxy, halo-$C_1$-$C_6$-alkyl, $C_1$-$C_6$-alkoxy, $C_1$-$C_6$-alkyl, cyano or oxo;

$R^6$ is hydrogen, halogen, $C_6$-$C_{10}$-aryl, 5- to 10-membered heteroaryl, halo-$C_1$-$C_6$-alkoxy, halo-$C_1$-$C_6$-alkyl, oxo, $C_1$-$C_6$-alkyl, $C_1$-$C_6$-alkoxy, $C_2$-$C_6$-alkenyl, $C_2$-$C_6$-alkynyl, $C_3$-$C_{14}$-cycloalkyl or cyano, wherein said 5- to 10-membered heteroaryl or $C_6$-$C_{10}$-aryl is optionally substituted with a substituent selected from halogen, $C_1$-$C_6$-alkyl and $C_1$-$C_6$-alkoxy;

n is 1 or 2;

p is 1, 2 or 3;

A is 5- to 10-membered heteroaryl or 3- to 14-membered heterocyclyl; and

B is phenyl, 5- to 10-membered heteroaryl or 3- to 14-membered heterocyclyl.

21. A compound selected from the group consisting of:

[(3R,9aS)-3-(3-chloro-4-fluoro-phenyl)-3,4,6,7,9,9a-hexahydro-1H-pyrazino[2,1-c][1,4]oxazin-8-yl]-(2-chloro-3-methoxy-phenyl)methanone;

(2-bromo-3-methoxy-phenyl)-[rac-(3R,9aS)-3-(3-chloro-4-fluoro-phenyl)-3,4,6,7,9,9a-hexahydro-1H-pyrazino [2,1-c][1,4]oxazin-8-yl]methanone;

(4-chlorothieno[2,3-b]pyridin-5-yl)-[(3R,9aS)-3-(3-chloro-4-fluoro-phenyl)-3,4,6,7,9,9a-hexahydro-1H-pyrazino[2,1-c][1,4]oxazin-8-yl]methanone;

[(3R,9aS)-3-(3-bromo-4-fluoro-phenyl)-3,4,6,7,9,9a-hexahydro-1H-pyrazino[2,1-c][1,4]oxazin-8-yl]-(2-chloro-3-methoxy-phenyl)methanone;

[(3R,9aS)-3-(3-chloro-4-fluoro-phenyl)-3,4,6,7,9,9a-hexahydro-1H-pyrazino[2,1-c][1,4]oxazin-8-yl]-(4-chloro-1H-pyrazolo[3,4-b]pyridin-5-yl)methanone;

[(3R,9aS)-3-(3-chloro-4-fluoro-phenyl)-3,4,6,7,9,9a-hexahydro-1H-pyrazino[2,1-c][1,4]oxazin-8-yl]-(2-fluoro-3-methoxy-phenyl)methanone;

(2-chloro-3-methoxy-phenyl)-[(3R,9aS)-3-[4-fluoro-3-[rac-(E)-prop-1-enyl]phenyl]-3,4,6,7,9,9a-hexahydro-1H-pyrazino[2,1-c][1,4]oxazin-8-yl]methanone;

[(3R,9aS)-3-(4-fluoro-3-phenyl-phenyl)-3,4,6,7,9,9a-hexahydro-1H-pyrazino[2,1-c][1,4]oxazin-8-yl]-(2-chloro-3-methoxy-phenyl)methanone;

[(3S,9aS)-3-(4-fluoro-3-phenyl-phenyl)-3,4,6,7,9,9a-hexahydro-1H-pyrazino[2,1-c][1,4]oxazin-8-yl]-(2-chloro-3-methoxy-phenyl)methanone;

[(3R,9aS)-3-(4-fluoro-3-prop-1-ynyl-phenyl)-3,4,6,7,9,9a-hexahydro-1H-pyrazino[2,1-c][1,4]oxazin-8-yl]-(2-chloro-3-methoxy-phenyl)methanone;

[(3,9aS)-3-(3-cyano-4-fluoro-phenyl)-3,4,6,7,9,9a-hexahydro-1H-pyrazino[2,1-c][1,4]oxazin-8-yl]-(2-chloro-3-methoxy-phenyl)methanone;

[(3R,9aS)-3-(3-chloro-4-fluoro-phenyl)-3,4,6,7,9,9a-hexahydro-1H-pyrazino[2,1-c][1,4]oxazin-8-yl]-(4-chloro-3-quinolyl)methanone;

[(3S,9aS)-3-(3-chloro-4-fluoro-phenyl)-3,4,6,7,9,9a-hexahydro-1H-pyrazino[2,1-c][1,4]oxazin-8-yl]-(2-chloro-3,5-dimethoxy-phenyl)methanone;

[(3R,9aS)-3-(3-chloro-4-fluoro-phenyl)-3,4,6,7,9,9a-hexahydro-1H-pyrazino[2,1-c][1,4]oxazin-8-yl]-(2-chloro-3,5-dimethoxy-phenyl)methanone;

[(3R,9aS)-3-(3-chloro-4-fluoro-phenyl)-3,4,6,7,9,9a-hexahydro-1H-pyrazino[2,1-c][1,4]oxazin-8-yl]-(2-chloro-3,4-dimethoxy-phenyl)methanone;

2-[(3R,9aS)-3-(3-chloro-4-fluoro-phenyl)-3,4,6,7,9,9a-hexahydro-1H-pyrazino[2,1-c][1,4]oxazine-8-carbonyl]-6-methyl-benzonitrile;

[(3R,9aS)-3-(3-chloro-4-fluoro-phenyl)-3,4,6,7,9,9a-hexahydro-1H-pyrazino[2,1-c][1,4]oxazin-8-yl]-[2-fluoro-3-(trifluoromethoxy)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-(2-chloro-3-phenyl-phenyl)methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(2-methoxyphenyl)phenyl]methanone;

[(3R,9aS)-3-(3-cyclopropyl-4-fluoro-phenyl)-3,4,6,7,9,9a-hexahydro-1H-pyrazino[2,1-c][1,4]oxazin-8-yl]-(2-chloro-3-methoxy-phenyl)methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(difluoromethoxy)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(5-methyl-1H-pyrazol-4-yl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(4-methyl-3-pyridyl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(3-methyl-4-pyridyl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-(2-chloro-3-pyridazin-4-yl-phenyl)methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(2-pyridyl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-(2-chloro-3-pyridazin-3-yl-phenyl)methanone;

(2-chloro-3-methoxy-phenyl)-[(rel-3R,9aS)-3-(3-chloro-4-fluoro-phenyl)-9a-methyl-1,3,4,6,7,9-hexahydropyrazino[2,1-c][1,4]oxazin-8-yl]methanone;

(2-chloro-3-methoxy-phenyl)-[(rel-3S,9aR)-3-(3-chloro-4-fluoro-phenyl)-9a-methyl-1,3,4,6,7,9-hexahydropyrazino[2,1-c][1,4]oxazin-8-yl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(4-methylpyridazin-3-yl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(5-methylpyrimidin-4-yl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(1H-imidazol-5-yl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(3-methyl-2-pyridyl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(1H-pyrazol-4-yl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(1,5-dimethylpyrazol-4-yl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(3-methylisoxazol-4-yl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-(4-chloro-3-methyl-1H-indazol-5-yl)methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(2-oxa-6-azaspiro[3.3]heptan-6-yl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-(2-chloro-3-morpholino-phenyl)methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(1H-triazol-5-yl)phenyl]methanone;

[(3R,9aS)-3-(3-chloro-4-fluoro-phenyl)-3-hydroxy-1,4,6,7,9,9a-hexahydropyrazino[2,1-c][1,4]oxazin-8-yl]-(2-chloro-3-methoxy-phenyl)methanone;

[(3S,9aR)-3-(3-chloro-4-fluoro-phenyl)-3-hydroxy-1,4,6,7,9,9a-hexahydropyrazino[2,1-c][1,4]oxazin-8-yl]-(2-chloro-3-methoxy-phenyl)methanone;

[3-(3-bicyclo[4.2.0]octa-1,3,5-trienyl)-3,4,6,7,9,9a-hexahydro-1H-pyrazino[2,1-c][1,4]oxazin-8-yl]-(2-chloro-3-methoxy-phenyl)methanone;

(2-chloro-3-methoxy-phenyl)-[3-[4-(difluoromethyl)phenyl]-3,4,6,7,9,9a-hexahydro-1H-pyrazino[2,1-c][1,4]oxazin-8-yl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(3-fluoro-1H-pyrazol-4-yl)phenyl]methanone;

[(3S,9aS)-3-(3-chloro-4-fluoro-phenyl)-3,4,6,7,9,9a-hexahydro-1H-pyrazino[2,1-c][1,4]oxazin-8-yl]-[2-chloro-3-(3-fluoro-1H-pyrazol-4-yl)phenyl]methanone;

(2-chloro-3-methoxy-phenyl)-[rel-(3S,9aS)-3-(2,4-dimethylthiazol-5-yl)-3,4,6,7,9,9a-hexahydro-1H-pyrazino[2,1-c][1,4]oxazin-8-yl]methanone;

(2-chloro-3-methoxy-phenyl)-[rel-(3R,9aR)-3-(2,4-dimethylthiazol-5-yl)-3,4,6,7,9,9a-hexahydro-1H-pyrazino[2,1-c][1,4]oxazin-8-yl]methanone;

(2-chloro-3-methoxy-phenyl)-[rac-(3R,9aR)-3-(5-bromo-2-pyridyl)-3,4,6,7,9,9a-hexahydro-1H-pyrazino[2,1-c][1,4]oxazin-8-yl]methanone;

(2-chloro-3-methoxy-phenyl)-[rac-(3S,9aR)-3-(5-bromo-2-pyridyl)-3,4,6,7,9,9a-hexahydro-1H-pyrazino[2,1-c][1,4]oxazin-8-yl]methanone;

(2-chloro-3-methoxy-phenyl)-[rac-(3S,9aS)-3-(5-chloro-3-pyridyl)-3,4,6,7,9,9a-hexahydro-1H-pyrazino[2,1-c][1,4]oxazin-8-yl]methanone;

(2-chloro-3-methoxy-phenyl)-[rac-(3R,9aS)-3-(5-chloro-3-pyridyl)-3,4,6,7,9,9a-hexahydro-1H-pyrazino[2,1-c][1,4]oxazin-8-yl]methanone;

(2-chloro-3-methoxy-phenyl)-[rel-(3S,9aS)-3-(1H-benzimidazol-2-yl)-3-hydroxy-1,4,6,7,9,9a-hexahydropyrazino[2,1-c][1,4]oxazin-8-yl]methanone;

(2-chloro-3-methoxy-phenyl)-[rel-(3R,9aR)-3-(1H-benzimidazol-2-yl)-3-hydroxy-1,4,6,7,9,9a-hexahydropyrazino[2,1-c][1,4]oxazin-8-yl]methanone;

(2-chloro-3-methoxy-phenyl)-[rel-(3S,9aS)-3-[6-(trifluoromethyl)-2-pyridyl]-3,4,6,7,9,9a-hexahydro-1H-pyrazino[2,1-c][1,4]oxazin-8-yl]methanone;

[(3R,9aS)-3-hydroxy-3-[6-(trifluoromethyl)pyridin-3-yl]-1,4,6,7,9,9a-hexahydropyrazino[2,1-c][1,4]oxazin-8-yl]-[2-chloro-3-(3-fluoro-1H-pyrazol-4-yl)phenyl]methanone;

(2-chloro-3-methoxy-phenyl)-[rel-(3R,9aR)-3-(4,5-dichloro-2-pyridyl)-3,4,6,7,9,9a-hexahydro-1H-pyrazino[2,1-c][1,4]oxazin-8-yl]methanone;

(2-chloro-3-methoxy-phenyl)-[rel-(3S,9aS)-3-(4,5-dichloro-2-pyridyl)-3,4,6,7,9,9a-hexahydro-1H-pyrazino[2,1-c][1,4]oxazin-8-yl]methanone;

[(9aS)-3-[6-(trifluoromethyl)-3-pyridyl]-3,4,6,7,9,9a-hexahydro-1H-pyrazino[2,1-c][1,4]oxazin-8-yl]-[2-chloro-3-(3-fluoro-1H-pyrazol-4-yl)phenyl]methanone;

[2-chloro-3-(3-fluoro-1H-pyrazol-4-yl)phenyl]-[(3R,9aS)-3-[4-(difluoromethoxy)phenyl]-3-hydroxy-1,4,6,7,9,9a-hexahydropyrazino[2,1-c][1,4]oxazin-8-yl]methanone;

[2-chloro-3-(3-fluoro-1H-pyrazol-4-yl)phenyl]-[(9aS)-3-(6-bromo-3-pyridyl)-3,4,6,7,9,9a-hexahydro-1H-pyrazino[2,1-c][1,4]oxazin-8-yl]methanone;

[(3S,9aS)-3-hydroxy-3-(1-methylbenzimidazol-2-yl)-1,4,6,7,9,9a-hexahydropyrazino[2,1-c][1,4]oxazin-8-yl]-(2-chloro-3-methoxy-phenyl)methanone;

5-[(3R,9aS)-8-[2-chloro-3-(3-fluoro-1H-pyrazol-4-yl)benzoyl]-3,4,6,7,9,9a-hexahydro-1H-pyrazino[2,1-c][1,4]oxazin-3-yl]-2-fluoro-benzonitrile;

(2-chloro-3-(3-fluoro-1H-pyrazol-4-yl)phenyl)((9aS)-3-(4-(difluoromethoxy)phenyl)hexahydropyrazino[2,1-c][1,4]oxazin-8(1H)-yl)methanone;

3-[(3 S,9aS)-8-(2-chloro-3-methoxy-benzoyl)-3,4,6,7,9,9a-hexahydro-1H-pyrazino[2,1-c][1,4]oxazin-3-yl]-5-chloro-1H-pyridin-2-one;

3-[(3R,9aS)-8-(2-chloro-3-methoxy-benzoyl)-3,4,6,7,9,9a-hexahydro-1H-pyrazino[2,1-c][1,4]oxazin-3-yl]-5-chloro-1H-pyridin-2-one;

[(3R,9aS)-3-(3-chloro-4-fluoro-phenyl)-3-hydroxy-1,4,6,7,9,9a-hexahydropyrazino[2,1-c][1,4]oxazin-8-yl]-(2-chloro-3-oxazol-5-yl-phenyl)methanone;

3-[(3R,9aS)-8-[2-chloro-3-(3-fluoro-1H-pyrazol-4-yl)benzoyl]-3,4,6,7,9,9a-hexahydro-1H-pyrazino[2,1-c][1,4]oxazin-3-yl]-5-chloro-1H-pyridin-2-one;

[(3R,9aS)-3-hydroxy-3-[6-(trifluoromethyl)-3-pyridyl]-1,4,6,7,9,9a-hexahydropyrazino[2,1-c][1,4]oxazin-8-yl]-[2-fluoro-3-(3-fluoro-1H-pyrazol-4-yl)phenyl]methanone;

4-[3-[(3R,9aS)-3-hydroxy-3-[6-(trifluoromethyl)-3-pyridyl]-1,4,6,7,9,9a-hexahydropyrazino[2,1-c][1,4]oxazine-8-carbonyl]-2-chloro-phenyl]-1H-pyrazole-3-carbonitrile;

[(3R,9aS)-3-hydroxy-3-[6-(trifluoromethyl)-3-pyridyl]-1,4,6,7,9,9a-hexahydropyrazino[2,1-c][1,4]oxazin-8-yl]-[3-(3-fluoro-1H-pyrazol-4-yl)phenyl]methanone;

[(3R,9aS)-3-hydroxy-3-[6-(trifluoromethyl)-3-pyridyl]-1,4,6,7,9,9a-hexahydropyrazino[2,1-c][1,4]oxazin-8-yl]-[2-chloro-3-(1H-pyrazol-4-yl)phenyl]methanone;

(2-chloro-3-methoxyphenyl)((3S,9aS)-3-(5-chloro-4-methylpyridin-2-yl)hexahydropyrazino[2,1-c][1,4]oxazin-8(1H)-yl)methanone;

(2-chloro-3-methoxyphenyl)((3R,9aS)-3-(5-chloro-4-methylpyridin-2-yl)hexahydropyrazino[2,1-c][1,4]oxazin-8(1H)-yl)methanone;

[(3S,9aS)-3-hydroxy-3-[5-(trifluoromethyl)-2-pyridyl]-1,4,6,7,9,9a-hexahydropyrazino[2,1-c][1,4]oxazin-8-yl]-[2-chloro-3-(3-fluoro-1H-pyrazol-4-yl)phenyl]methanone;

[(3S,9aS)-3-hydroxy-3-[5-(trifluoromethyl)-2-pyridyl]-1,4,6,7,9,9a-hexahydropyrazino[2,1-c][1,4]oxazin-8-yl]-(2-chloro-3-oxazol-4-yl-phenyl)methanone;

[3-(1,3-benzothiazol-2-yl)-6,7,9,9a-tetrahydro-1H-pyrazino[2,1-c][1,4]oxazin-8-yl]-(2-chloro-3-methoxy-phenyl)methanone;

[2-chloro-3-(3-fluoro-1H-pyrazol-4-yl)phenyl]-[(3S,9aS)-3-fluoro-3-[6-(trifluoromethyl)-3-pyridyl]-1,4,6,7,9,9a-hexahydropyrazino[2,1-c][1,4]oxazin-8-yl]methanone;

(2-chloro-3-methoxy-phenyl)-[(3S,9aS)-3-[6-(trifluoromethyl)pyridazin-3-yl]-3,4,6,7,9,9a-hexahydro-1H-pyrazino[2,1-c][1,4]oxazin-8-yl]methanone;

[(3R,9aS)-3-(4-chloro-2-pyridyl)-3,4,6,7,9,9a-hexahydro-1H-pyrazino[2,1-c][1,4]oxazin-8-yl]-(2-chloro-3-methoxy-phenyl)methanone;

[(3S,9aS)-3-(4-chloro-2-pyridyl)-3,4,6,7,9,9a-hexahydro-1H-pyrazino[2,1-c][1,4]oxazin-8-yl]-(2-chloro-3-methoxy-phenyl)methanone;

[(3R,9aS)-3-(3,4-difluorophenyl)-3-hydroxy-1,4,6,7,9,9a-hexahydropyrazino[2,1-c][1,4]oxazin-8-yl]-[2-chloro-3-(3-fluoro-1H-pyrazol-4-yl)phenyl]methanone;

[(3R,9aS)-3-(3,4-difluorophenyl)-3-hydroxy-1,4,6,7,9,9a-hexahydropyrazino[2,1-c][1,4]oxazin-8-yl]-[3-(3-fluoro-1H-pyrazol-4-yl)phenyl]methanone;

[(9aS)-3-[5-(trifluoromethyl)-2-pyridyl]-6,7,9,9a-tetrahydro-1H-pyrazino[2,1-c][1,4]oxazin-8-yl]-[2-chloro-3-(3-fluoro-1H-pyrazol-4-yl)phenyl]methanone;

[(3R,9aS)-3-(3,4-difluorophenyl)-3,4,6,7,9,9a-hexahydro-1H-pyrazino[2,1-c][1,4]oxazin-8-yl]-[2-chloro-3-(3-fluoro-1H-pyrazol-4-yl)phenyl]methanone;

[(3S,9aS)-3-(3,4-difluorophenyl)-3,4,6,7,9,9a-hexahydro-1H-pyrazino[2,1-c][1,4]oxazin-8-yl]-[2-chloro-3-(3-fluoro-1H-pyrazol-4-yl)phenyl]methanone;

[(3S,9aS)-3-[6-(trifluoromethyl)pyridazin-3-yl]-3,4,6,7,9,9a-hexahydro-1H-pyrazino[2,1-c][1,4]oxazin-8-yl]-[2-chloro-3-(3-fluoro-1H-pyrazol-4-yl)phenyl]methanone;

(2-chloro-3-methoxy-phenyl)-[(3S,9aS)-3-[5-chloro-4-(trifluoromethyl)-2-pyridyl]-3,4,6,7,9,9a-hexahydro-1H-pyrazino[2,1-c][1,4]oxazin-8-yl]methanone;

(2-chloro-3-methoxy-phenyl)-[(3S,9aS)-3-[4-(trifluoromethoxy)-2-pyridyl]-3,4,6,7,9,9a-hexahydro-1H-pyrazino[2,1-c][1,4]oxazin-8-yl]methanone;

3-[(3R,9aS)-8-[2-chloro-3-(3-fluoro-1H-pyrazol-4-yl)benzoyl]-3-hydroxy-1,4,6,7,9,9a-hexahydropyrazino[2,1-c][1,4]oxazin-3-yl]-6-(trifluoromethyl)-1H-pyridin-2-one;

(2-chloro-3-methoxy-phenyl)-[(3S,9aS)-3-[5-fluoro-4-(trifluoromethyl)-2-pyridyl]-3,4,6,7,9,9a-hexahydro-1H-pyrazino[2,1-c][1,4]oxazin-8-yl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-fluoro-3-[5-(trifluoromethyl)-1H-pyrazol-4-yl]phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-[3-[5-(trifluoromethyl)-1H-pyrazol-4-yl]phenyl]methanone;

(2-chloro-3-methoxy-phenyl)-[(3S,9aS)-3-[4-(difluoromethyl)-5-fluoro-2-pyridyl]-3,4,6,7,9,9a-hexahydro-1H-pyrazino[2,1-c][1,4]oxazin-8-yl]methanone;

4-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]-1H-pyridin-2-one;

5-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]-1H-pyridin-2-one;

(2-chloro-3-methoxy-phenyl)-[(3S,9aS)-3-[5-chloro-4-bromo-2-pyridyl]-3,4,6,7,9,9a-hexahydro-1H-pyrazino[2,1-c][1,4]oxazin-8-yl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(3-hydroxyazetidin-1-yl)phenyl]methanone;

4-[3-[(3R,9aS)-3-(3-chloro-4-fluoro-phenyl)-3-hydroxy-1,4,6,7,9,9a-hexahydropyrazino[2,1-c][1,4]oxazine-8-carbonyl]-2-chloro-phenyl]-1H-pyrrole-2-carbonitrile;

[(3R,9aS)-3-(4-bromo-3-chloro-phenyl)-3,4,6,7,9,9a-hexahydro-1H-pyrazino[2,1-c][1,4]oxazin-8-yl]-(2-chloro-3-methoxy-phenyl)methanone;

[(3R,9aS)-3-(3-chloro-4-fluoro-phenyl)-3,4,6,7,9,9a-hexahydro-1H-pyrazino[2,1-c][1,4]oxazin-8-yl]-(2-chloro-6-fluoro-3-methoxy-phenyl)methanone;

4-[3-[(3R,9aS)-3-[2-oxo-6-(trifluoromethyl)-1H-pyridin-3-yl]-3,4,6,7,9,9a-hexahydro-1H-pyrazino[2,1-c][1,4]oxazine-8-carbonyl]-2-chloro-5-fluoro-phenyl]-1H-pyrrole-2-carbonitrile;

4-[3-[(3R,9aS)-3-(3,4-difluorophenyl)-3-hydroxy-1,4,6,7,9,9a-hexahydropyrazino[2,1-c][1,4]oxazine-8-carbonyl]-2-chloro-phenyl]-1H-pyrrole-2-carbonitrile;

4-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-5-fluoro-phenyl]-1H-pyridin-2-one;

4-[3-[(3R,9aS)-3-(5-chloro-2-oxo-1H-pyridin-3-yl)-3,4,6,7,9,9a-hexahydro-1H-pyrazino[2,1-c][1,4]oxazine-8-carbonyl]-2-chloro-5-fluoro-phenyl]-1H-pyrrole-2-carbonitrile;

[(3R,9aS)-3-(3-chloro-4-fluoro-phenyl)-3-hydroxy-1,4,6,7,9,9a-hexahydropyrazino[2,1-c][1,4]oxazin-8-yl]-(2-chloro-6-fluoro-3-methoxy-phenyl)methanone;

4-[3-[(3R,9aS)-3-(5-chloro-2-oxo-1H-pyridin-3-yl)-3,4,6,7,9,9a-hexahydro-1H-pyrazino[2,1-c][1,4]oxazine-8-carbonyl]-2-chloro-phenyl]-1H-pyrrole-2-carbonitrile;

5-[3-[(3R,9aS)-3-(3,4-dichlorophenyl)-3,4,6,7,9,9a-hexahydro-1H-pyrazino[2,1-c][1,4]oxazine-8-carbonyl]-2-chloro-phenyl]-3H-oxazol-2-one;

[(3R,9aS)-3-hydroxy-3-[4-(trifluoromethyl)phenyl]-1,4,6,7,9,9a-hexahydropyrazino[2,1-c][1,4]oxazin-8-yl]-(2-chloro-3-methoxy-phenyl)methanone;

[(3R,9aS)-3-(4-chloro-3-fluoro-phenyl)-3-hydroxy-1,4,6,7,9,9a-hexahydropyrazino[2,1-c][1,4]oxazin-8-yl]-(2-chloro-3-methoxy-phenyl)methanone;

5-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]-3H-oxazol-2-one;

5-[3-[(3R,9aS)-3-(3,4-dichlorophenyl)-3-hydroxy-1,4,6,7,9,9a-hexahydropyrazino[2,1-c][1,4]oxazine-8-carbonyl]-2-chloro-phenyl]-3H-oxazol-2-one;

4-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]-6-methyl-1H-pyridin-2-one;

5-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]-6-methyl-1H-pyridin-2-one;

[(3R,9aS)-3-(3-bromo-5-chloro-phenyl)-3-hydroxy-1,4,6,7,9,9a-hexahydropyrazino[2,1-c][1,4]oxazin-8-yl]-(2-chloro-3-methoxy-phenyl)methanone;

4-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]piperazin-2-one;

[(3R,9aS)-3-(3-chloro-4-fluoro-phenyl)-3-hydroxy-1,4,6,7,9,9a-hexahydropyrazino[2,1-c][1,4]oxazin-8-yl]-(2-chloro-3-isothiazol-4-yl-phenyl)methanone;

[(3R,9aS)-3-(2,4,5-trifluorophenyl)-3,4,6,7,9,9a-hexahydro-1H-pyrazino[2,1-c][1,4]oxazin-8-yl]-(2-chloro-3-methoxy-phenyl)methanone;

[(3R,9aS)-3-(2,4-dichlorophenyl)-3-hydroxy-1,4,6,7,9,9a-hexahydropyrazino[2,1-c][1,4]oxazin-8-yl]-(2-chloro-3-methoxy-phenyl)methanone;

[(3R,9aS)-3-hydroxy-3-(2,3,4-trifluorophenyl)-1,4,6,7,9,9a-hexahydropyrazino[2,1-c][1,4]oxazin-8-yl]-(2-chloro-3-methoxy-phenyl)methanone;

[(3S,9aS)-3-(4-bromo-5-methoxy-2-thienyl)-3-hydroxy-1,4,6,7,9,9a-hexahydropyrazino[2,1-c][1,4]oxazin-8-yl]-(2-chloro-3-methoxy-phenyl)methanone;

4-[3-[(3R,9aS)-3-[4-oxo-6-(trifluoromethyl)-1H-pyridin-3-yl]-3,4,6,7,9,9a-hexahydro-1H-pyrazino[2,1-c][1,4]oxazine-8-carbonyl]-2-chloro-5-fluoro-phenyl]-1H-pyrrole-2-carbonitrile;

3-[(3R,9aS)-8-[2-chloro-5-fluoro-3-(3-fluoro-1H-pyrazol-4-yl)benzoyl]-3,4,6,7,9,9a-hexahydro-1H-pyrazino[2,1-c][1,4]oxazin-3-yl]-5-chloro-1H-pyridin-2-one;

5-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]-3H-1,3,4-oxadiazol-2-one;

5-[(3R,9aS)-8-(2-chloro-3-methoxy-benzoyl)-3,4,6,7,9,9a-hexahydro-1H-pyrazino[2,1-c][1,4]oxazin-3-yl]-3-chloro-2-fluoro-benzonitrile;

3-[(3R,9aS)-8-(2-chloro-3-methoxy-benzoyl)-3-hydroxy-1,4,6,7,9,9a-hexahydropyrazino[2,1-c][1,4]oxazin-3-yl]-6-(trifluoromethyl)-1H-pyridin-2-one;

[(3R,9aS)-3-(3-chloro-4-oxazol-5-yl-phenyl)-3,4,6,7,9,9a-hexahydro-1H-pyrazino[2,1-c][1,4]oxazin-8-yl]-(2-chloro-3-methoxy-phenyl)methanone;

3-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]-1H-pyrazole-5-carbonitrile;

[(3S,9aS)-3-[2-(4-fluorophenyl)thiazol-4-yl]-3-hydroxy-1,4,6,7,9,9a-hexahydropyrazino[2,1-c][1,4]oxazin-8-yl]-(2-chloro-3-methoxy-phenyl)methanone;

3-[(3R,9aS)-8-[2-chloro-3-(4-fluoro-1H-pyrazol-3-yl)benzoyl]-3,4,6,7,9,9a-hexahydro-1H-pyrazino[2,1-c][1,4]oxazin-3-yl]-5-chloro-1H-pyridin-2-one;

[(3R,9aS)-3-hydroxy-3-[3-(trifluoromethyl)phenyl]-1,4,6,7,9,9a-hexahydropyrazino[2,1-c][1,4]oxazin-8-yl]-(2-chloro-3-methoxy-phenyl)methanone;

[(3R,9aS)-3-(2,3-difluorophenyl)-3-hydroxy-1,4,6,7,9,9a-hexahydropyrazino[2,1-c][1,4]oxazin-8-yl]-(2-chloro-3-methoxy-phenyl)methanone;

[(3S,9aS)-3-hydroxy-3-(3-phenylisoxazol-5-yl)-1,4,6,7,9,9a-hexahydropyrazino[2,1-c][1,4]oxazin-8-yl]-(2-chloro-3-methoxy-phenyl)methanone;

[(3R,9aS)-3-hydroxy-3-(2,4,5-trifluorophenyl)-1,4,6,7,9,9a-hexahydropyrazino[2,1-c][1,4]oxazin-8-yl]-(2-chloro-3-methoxy-phenyl)methanone;

[(9aS)-3-(4-fluoro-3-oxazol-5-yl-phenyl)-3,4,6,7,9,9a-hexahydro-1H-pyrazino[2,1-c][1,4]oxazin-8-yl]-(2-chloro-3-methoxy-phenyl)methanone;

[(3S,9aS)-3-(1,3-benzothiazol-2-yl)-3-hydroxy-1,4,6,7,9,9a-hexahydropyrazino[2,1-c][1,4]oxazin-8-yl]-(2-chloro-3-methoxy-phenyl)methanone;

3-[(3R,9aS)-8-(2-chloro-6-fluoro-3-methoxy-benzoyl)-3,4,6,7,9,9a-hexahydro-1H-pyrazino[2,1-c][1,4]oxazin-3-yl]-5-chloro-1H-pyridin-2-one;

[(3S,9aS)-3-[5-chloro-6-(trifluoromethyl)-2-pyridyl]-3,4,6,7,9,9a-hexahydro-1H-pyrazino[2,1-c][1,4]oxazin-8-yl]-(2-chloro-3-methoxy-phenyl)methanone;

[(3R,9aS)-3-(2,3-difluorophenyl)-3,4,6,7,9,9a-hexahydro-1H-pyrazino[2,1-c][1,4]oxazin-8-yl]-(2-chloro-3-methoxy-phenyl)methanone;

[(3R,9aS)-3-(2-chlorophenyl)-3-hydroxy-1,4,6,7,9,9a-hexahydropyrazino[2,1-c][1,4]oxazin-8-yl]-(2-chloro-3-methoxy-phenyl)methanone;

4-[3-[(3S,9aS)-3-[4-oxo-6-(trifluoromethyl)-1H-pyridin-3-yl]-3,4,6,7,9,9a-hexahydro-1H-pyrazino[2,1-c][1,4]oxazine-8-carbonyl]-2-chloro-5-fluoro-phenyl]-1H-pyrrole-2-carbonitrile;

5-[3-[(3R,9aS)-3-(3,4-difluorophenyl)-3-hydroxy-1,4,6,7,9,9a-hexahydropyrazino[2,1-c][1,4]oxazine-8-carbonyl]-2-chloro-phenyl]-1H-imidazole-2-carbonitrile;

[(3R,9aS)-3-hydroxy-3-[2-methyl-6-(trifluoromethyl)-3-pyridyl]-1,4,6,7,9,9a-hexahydropyrazino[2,1-c][1,4]oxazin-8-yl]-(2-chloro-3-methoxy-phenyl)methanone;

[(3R,9aS)-3-(3-chloro-5-oxazol-5-yl-phenyl)-3-hydroxy-1,4,6,7,9,9a-hexahydropyrazino[2,1-c][1,4]oxazin-8-yl]-(2-chloro-3-methoxy-phenyl)methanone;

3-[(3R,9aS)-8-(2-chloro-3-methoxy-benzoyl)-3,4,6,7,9,9a-hexahydro-1H-pyrazino[2,1-c][1,4]oxazin-3-yl]-6-(trifluoromethyl)-1H-pyridin-2-one;

[(9aS)-3-[4-fluoro-3-(1-methylpyrrol-3-yl)phenyl]-3,4,6,7,9,9a-hexahydro-1H-pyrazino[2,1-c][1,4]oxazin-8-yl]-(2-chloro-3-methoxy-phenyl)methanone;

[(3S,9aS)-3-(3-bromoisoxazol-5-yl)-3-hydroxy-1,4,6,7,9,9a-hexahydropyrazino[2,1-c][1,4]oxazin-8-yl]-(2-chloro-3-methoxy-phenyl)methanone;

5-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]-1H-pyridazin-4-one;

[(3S,9aS)-3-(3-chloro-4-fluoro-phenyl)-3,4,6,7,9,9a-hexahydro-1H-pyrazino[2,1-c][1,4]oxazin-8-yl]-(2-chloro-6-fluoro-3-methoxy-phenyl)methanone;

[(3S,9aS)-3-hydroxy-3-[2-(6-methoxy-3-pyridyl)thiazol-4-yl]-1,4,6,7,9,9a-hexahydropyrazino[2,1-c][1,4]oxazin-8-yl]-(2-chloro-3-methoxy-phenyl)methanone;

[(9aS)-3-(3-chloro-4-fluoro-phenyl)-3,4,6,7,9,9a-hexahydro-1H-pyrazino[2,1-c][1,4]thiazin-8-yl]-(2-chloro-3-methoxy-phenyl)methanone; and

[(9aS)-3-(3-chloro-4-fluoro-phenyl)-3,4,6,7,9,9a-hexahydro-1H-pyrazino[2,1-c][1,4]thiazin-8-yl]-(2-chloro-3-methoxy-phenyl)methanone;

or a pharmaceutically acceptable salt thereof.

22. A pharmaceutical composition comprising a compound of claim 1, or a pharmaceutically acceptable salt thereof, and a therapeutically inert carrier.

23. A pharmaceutical composition comprising a compound of claim 21, or a pharmaceutically acceptable salt thereof, and a therapeutically inert carrier.

24. A process of manufacturing a compound of claim 1, comprising:

(a) reacting a diol 5, wherein $R^1$ and $R^3$ are as defined in claim 1,

5

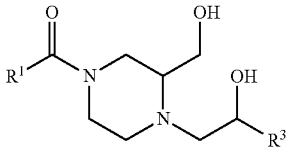

with an etherification reagent to yield the compound of claim 1, wherein X is $—CH_2CHR^3—$, Y is —O—, $R^1$ and $R^3$ are as defined in claim 1, and $R^2$ is hydrogen; or (b) reacting an amine 8a, wherein Y, $R^2$ and $R^3$ are as defined in claim 1, 8a

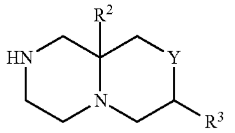

with a carboxylic acid 1, wherein $R^1$ is as defined in claim 1,

1

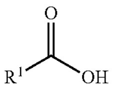

in the presence of a base and a coupling reagent to yield said compound of claim 1, wherein X is $—CH_2CHR^3—$, Y, $R^1$ and $R^3$ are as defined in claim 1, and $R^2$ is hydrogen; or (c) submitting a compound of formula (I), wherein Y is as defined in claim 1, X is $—CH_2CR^3R^4—$, $R^1$ to $R^3$ are as defined in claim 1, and $R^4$ is hydroxy, to dehydrating conditions to yield: a compound of formula (I) wherein Y is as defined in claim 1, X is $—CH_2CR^3—$ and $R^1$ to $R^3$ are as defined in claim 1, or to yield a compound of formula (I) wherein Y is as defined in claim 1, X is $—CH{=}CR^3—$ and $R^1$ to $R^3$ are as defined in claim 1; or (d) reacting a compound of claim 1 wherein Y is as defined in claim 1, X is $—CH_2CR^3R^4—$, $R^1$ to $R^3$ are as defined in claim 1, and $R^4$ is hydroxy, with a nucleophilic fluorinating agent to yield a compound of claim 1 wherein X is $—CH_2CFR^3—$ and $R^1$ to $R^3$ are as defined in claim 1; or (e) submitting a compound of formula (I),

I

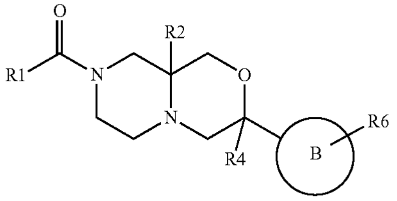

wherein $R^1$, $R^2$, $R^4$, and B are as defined in claim 1, and $R^6$ is bromo, to a transition metal catalyzed cross-coupling reaction to afford compound of formula (I)

I

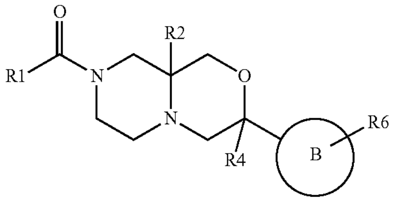

wherein $R^1$, $R^2$, $R^4$, and B are as defined in claim 1, and $R^6$ is selected from aryl, alkenyl, alkynyl, alkyl, cyano, cycloalkyl, and heteroaryl; or (f) submitting a compound 12, wherein $R^1$ is aryl or heteroaryl optionally substituted with 1-4 substituents independently selected from $C_1$-$C_6$-alkyl, $C_1$-$C_6$-alkoxy, halo-$C_1$-$C_6$-alkyl, halo-$C_1$-$C_6$-alkoxy, halogen, and cyano; and $R^2$ to $R^4$ are as defined in claim 1,

12

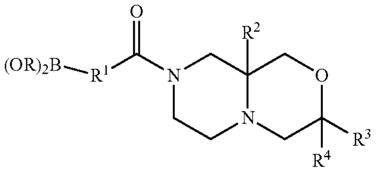

$B(OR_2) = B(OH)_2$ or boronate pinacol ester to a Suzuki-Miyaura cross coupling reaction with a compound 13, wherein A, $R^5$, and n are as defined in claim 1

13

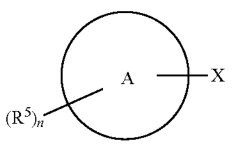

X = Cl, Br, I, OTf in the presence of a transition metal catalyst and an organic or inorganic base; to afford said compound of formula (I), wherein $R^1$ is aryl or heteroaryl optionally substituted with 1-4 substituents independently selected from $C_1$-$C_6$-alkyl, $C_1$-$C_6$-alkoxy, halo-$C_1$-$C_6$-alkyl, halo-$C_1$-$C_6$-alkoxy, halogen, and cyano; and $R^2$ to $R^5$ and n are as defined in claim 1

I

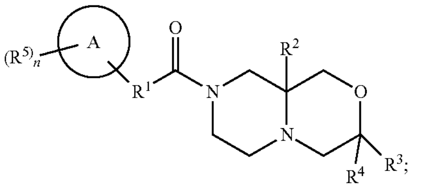

or (g) reacting a compound of formula (I), wherein Y is sulfur and $R^1$, $R^2$, and $R^3$ are as defined in claim 1,

I

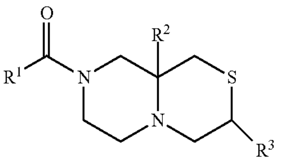

with an oxidizing agent, to afford a compound of formula (I), wherein Y is a sulfoxide or a sulfone and $R^1$, $R^2$, and $R^3$ are as defined in claim 1:

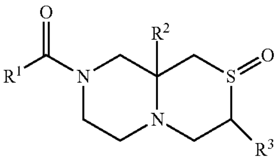

I

+

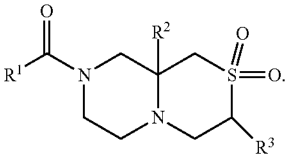

I

25. A method, comprising administering an effective amount of a compound of claim 1, or a pharmaceutically acceptable salt thereof, to a mammal, wherein the method is for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain, or spasticity associated with pain in the mammal.

26. The compound of claim 1, wherein the compound is:

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(5-methyl-1H-pyrazol-4-yl)phenyl]methanone;

or is a pharmaceutically acceptable salt thereof.

27. The compound of claim 1, selected from the group consisting of:

4-(2-chloro-3-((3R,9aS)-3-(5-chloro-2-oxo-1,2-dihydropyridin-3-yl)octahydropyrazino[2,1-c][1,4]oxazine-8-carbonyl)phenyl)-1H-pyrrole-2-carbonitrile;

4-(2-chloro-3-((3R,9aS)-3-(3-chloro-4-fluorophenyl)-3-hydroxyoctahydropyrazino[2,1-c][1,4]oxazine-8-carbonyl)phenyl)-1H-pyrrole-2-carbonitrile;

4-(2-chloro-3-((3R,9aS)-3-(3-chloro-4-fluorophenyl)octahydropyrazino[2,1-c][1,4]oxazine-8-carbonyl)-5-fluorophenyl)pyridin-2(1H)-one;

4-(2-chloro-3-((3R,9aS)-3-(5-chloro-2-oxo-1,2-dihydropyridin-3-yl)octahydropyrazino[2,1-c][1,4]oxazine-8-carbonyl)-5-fluorophenyl)-1H-pyrrole-2-carbonitrile;

4-(2-chloro-5-fluoro-3-((3R,9aS)-3-(2-oxo-6-(trifluoromethyl)-1,2-dihydropyridin-3-yl)octahydropyrazino[2,1-c][1,4]oxazine-8-carbonyl)phenyl)-1H-pyrrole-2-carbonitrile;

((3R,9aS)-3-(3-chloro-4-fluorophenyl)hexahydropyrazino[2,1-c][1,4]oxazin-8(1H)-yl)(2-chloro-6-fluoro-3-methoxyphenyl)methanone;

[2-chloro-3-(3-fluoro-1H-pyrazol-4-yl)phenyl]-[rac-(3R,9aS)-3-(3-chloro-4-fluoro-phenyl)-3,4,6,7,9,9a-hexahydro-1H-pyrazino[2,1-c][1,4]oxazin-8-yl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(1H-pyrazol-4-yl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(1H-imidazol-5-yl)phenyl]methanone;

[(3R,9aS)-3-(3,4-difluorophenyl)-3,4,6,7,9,9a-hexahydro-1H-pyrazino[2,1-c][1,4]oxazin-8-yl]-[2-chloro-3-(3-fluoro-1H-pyrazol-4-yl)phenyl]methanone;

[(3S,9aS)-3-(4,5-dichloro-2-pyridyl)-3,4,6,7,9,9a-hexahydro-1H-pyrazino[2,1-c][1,4]oxazin-8-yl]-(2-chloro-3-methoxy-phenyl)methanone;

4-[3-[(3R,9aS)-3-(3-chloro-4-fluoro-phenyl)-3,4,6,7,9,9a-hexahydro-1H-pyrazino[2,1-c][1,4]oxazine-8-carbonyl]-2-chloro-phenyl]-1H-pyridin-2-one;

[(3R,9aS)-3-(3,4-difluorophenyl)-3-hydroxy-1,4,6,7,9,9a-hexahydropyrazino[2,1-c][1,4]oxazin-8-yl]-[2-chloro-3-(3-fluoro-1H-pyrazol-4-yl)phenyl]methanone;

[(3R,9aS)-3-(3-chloro-4-fluoro-phenyl)-3,4,6,7,9,9a-hexahydro-1H-pyrazino[2,1-c][1,4]oxazin-8-yl]-[2-chloro-3-(3-hydroxyazetidin-1-yl)phenyl]methanone;

[(3R,9aS)-3-hydroxy-3-[6-(trifluoromethyl)-3-pyridyl]-1,4,6,7,9,9a-hexahydropyrazino[2,1-c][1,4]oxazin-8-yl]-[2-chloro-3-(3-fluoro-1H-pyrazol-4-yl)phenyl]methanone;

[2-chloro-3-(3-fluoro-1H-pyrazol-4-yl)phenyl]-[rac-(9aS)-3-[6-(trifluoromethyl)-3-pyridyl]-3,4,6,7,9,9a-hexahydro-1H-pyrazino[2,1-c][1,4]oxazin-8-yl]methanone;

[(3R,9aS)-3-(3-chloro-4-fluoro-phenyl)-3,4,6,7,9,9a-hexahydro-1H-pyrazino[2,1-c][1,4]oxazin-8-yl]-(2-chloro-3-methoxy-phenyl)methanone;

[(3R,9aS)-3-(3-chloro-4-fluoro-phenyl)-3-hydroxy-1,4,6,7,9,9a-hexahydropyrazino[2,1-c][1,4]oxazin-8-yl]-(2-chloro-3-methoxy-phenyl)methanone; and

[2-chloro-3-(3-fluoro-1H-pyrazol-4-yl)phenyl]-[rac-(9aS)-3-[4-(difluoromethoxy)phenyl]-3,4,6,7,9,9a-hexahydro-1H-pyrazino[2,1-c][1,4]oxazin-8-yl]methanone, or is a pharmaceutically acceptable salt thereof.

28. A pharmaceutical composition comprising a compound of claim 27, or a pharmaceutically acceptable salt thereof, and a therapeutically inert carrier.

* * * * *